(12) United States Patent
Glaser et al.

(10) Patent No.: US 8,021,661 B2
(45) Date of Patent: Sep. 20, 2011

(54) CRIPTO BINDING MOLECULES

(75) Inventors: Scott Glaser, San Diego, CA (US);
Herman Van Vlijmen, Mechelen (BE);
Alexey Alexandrovich Lugovskoy,
Woburn, MA (US); Michele Sanicola-Nadel, Winchester, MA (US);
Xiufeng Wu, San Diego, CA (US); Ellen Garber, Cambridge, MA (US); Jose William Saldanha, Enfield (GB)

(73) Assignee: Biogen Idec MA Inc., Cambridge, MA (US)

(*) Notice: Subject to any disclaimer, the term of this patent is extended or adjusted under 35 U.S.C. 154(b) by 928 days.

(21) Appl. No.: 11/825,305

(22) Filed: Jul. 3, 2007

(65) Prior Publication Data
US 2010/0008906 A1    Jan. 14, 2010

Related U.S. Application Data

(63) Continuation of application No. PCT/US2006/000502, filed on Jan. 5, 2006.

(60) Provisional application No. 60/641,691, filed on Jan. 5, 2005.

(51) Int. Cl.
*C07K 16/00* (2006.01)

(52) U.S. Cl. .............. 424/133.1; 530/387.1; 530/387.3; 530/391.3; 530/391.7

(58) Field of Classification Search ............... 424/133.1; 530/387.1, 387.3, 391.3, 391.7
See application file for complete search history.

(56) References Cited

U.S. PATENT DOCUMENTS

| | | | |
|---|---|---|---|
| 5,208,020 A | 5/1993 | Chari et al. | |
| 5,256,643 A | 10/1993 | Persico et al. | |
| 5,264,557 A | 11/1993 | Salomon et al. | |
| 5,530,101 A | 6/1996 | Queen et al. | |
| 5,650,285 A | 7/1997 | Salomon et al. | |
| 5,654,140 A | 8/1997 | Persico et al. | |
| 5,792,616 A | 8/1998 | Persico et al. | |
| 5,854,399 A | 12/1998 | Salomon et al. | |
| 5,981,215 A | 11/1999 | Meissner et al. | |
| 6,207,153 B1 | 3/2001 | Dan et al. | |
| 6,333,410 B1 | 12/2001 | Chari et al. | |
| 6,335,170 B1 | 1/2002 | Orntoft | |
| 6,949,245 B1 | 9/2005 | Sliwkowski | |
| 6,989,145 B2 | 1/2006 | Shitara et al. | |
| 7,318,924 B2 | 1/2008 | McKenzie et al. | |
| 7,531,174 B2 | 5/2009 | Sanicola-Nadel et al. | |
| 2003/0232755 A1 | 12/2003 | Williams et al. | |
| 2004/0014690 A1 | 1/2004 | Ma et al. | |
| 2004/0082762 A1 | 4/2004 | Basi et al. | |
| 2004/0146940 A1 | 7/2004 | Sanicola-Nadel et al. | |
| 2004/0176576 A1 | 9/2004 | McKenzie et al. | |
| 2005/0163782 A1 | 7/2005 | Glaser et al. | |
| 2005/0163783 A1 | 7/2005 | Braslawsky et al. | |
| 2005/0208045 A1 | 9/2005 | Vale et al. | |
| 2005/0255117 A1 | 11/2005 | Sanicola-Nadel et al. | |
| 2008/0166341 A1 | 7/2008 | Sanicola-Nadel et al. | |
| 2009/0285818 A1 | 11/2009 | Sanicola-Nadel et al. | |
| 2010/0041032 A1 | 2/2010 | Orozco et al. | |
| 2010/0202962 A1 | 8/2010 | Sanicola-Nadel et al. | |

FOREIGN PATENT DOCUMENTS

| | | |
|---|---|---|
| JP | 2001-46066 | 2/2001 |
| WO | WO-94/09817 A1 | 5/1994 |
| WO | WO-99/15549 A2 | 4/1999 |
| WO | WO-00/06723 A1 | 2/2000 |
| WO | WO-00/63693 A1 | 10/2000 |
| WO | WO-01/40309 A2 | 6/2001 |
| WO | WO-01/64754 A1 | 9/2001 |
| WO | WO-02/16413 A2 | 2/2002 |
| WO | WO-02/22808 A2 | 3/2002 |
| WO | WO-02/059620 A2 | 8/2002 |
| WO | WO-02/060955 A2 | 8/2002 |
| WO | WO-02/077033 A1 | 10/2002 |
| WO | WO-02/088170 A2 | 11/2002 |
| WO | WO-02/096948 A2 | 12/2002 |
| WO | WO-03/024392 A2 | 3/2003 |
| WO | WO-03/083041 A2 | 10/2003 |
| WO | 2004/003019 * | 6/2004 |
| WO | WO-2005/000898 A2 | 1/2005 |
| WO | WO-2005/000899 A2 | 1/2005 |
| WO | WO-2006/074397 A2 | 7/2006 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Lo, B.K.C., "Antibody Humanization by CDR Grafting" in *Antibody Engineering, Methods and Protocols*, Lo, B.K.C. ed., Humana Press, Totowa, NJ, pp. 135-159 (2004).
Adkins, Heather J. et al., "Antibody blockade of the Cripto CFC domain suppresses tumor cell growth in vivo," *The Journal of Clinical Investigation*, vol. 112(4):575-587 (2003).

(Continued)

*Primary Examiner* — Lynn Bristol
(74) *Attorney, Agent, or Firm* — Sterne, Kessler, Goldstein & Fox P.L.L.C.

(57) ABSTRACT

The invention pertains to humanized forms of an anti-CRIPTO antibody and portions thereof. In one embodiment, the variable regions of these antibodies or polypeptides comprising them (e.g., full-length antibodies or domain deleted antibodies) can be used to treat disorders, such as cancer.

29 Claims, 39 Drawing Sheets

OTHER PUBLICATIONS

Alt, M. et al., "Novel tetravalent and bispecific IgG-like antibody molecules combining signal-chain diabodies with the immunoglobulin gamma1 Fc or CH3 region," *FEBS Letters*, vol. 454(1-2):90-94 (1999).

Angal, S. et al., "A Single Amino Acid Substitution Abolishes the Heterogeneity of Chimeric Mouse/Human (IgG4) Antibody," *Molecular Immunology*, vol. 30(1):105-108 (1993).

Bera, Tapan K. et al., "A Bivalent Disulfide-stabilized Fv with Improved Antigen Binding to erbB2," *J. Mol. Biol.*, vol. 281:475-483 (1998).

Bianco, Caterina et al., "Cripto-1 Indirectly Stimulates the Tyrosine Phosphorylation of *erb* B-4 through a Novel Receptor," *The Journal of Biological Chemistry*, vol. 274(13):8624-8629 (1999).

Bloom, James W. et al., "Intrachain disulfide bond in the core hinge region of human IgG4," *Protein Science*, vol. 6:407-415 (1997).

Brandt, Ralf et al., "Identification and Biological Characterization of an Epidermal Growth Factor-related Protein: Cripto-1," *The Journal of Biological Chemistry*, vol. 269(25):17320-17328 (1994).

Brekke, Ole Henrik et al., "The structural requirements for complement activation by IgG: does it hinge on the hinge?" *Immunology Today*, vol. 16(2):85-90 (1995).

Campbell, Ailsa M., "General properties and applications of monoclonal antibodies," *Laboratory Techniques in Biochemistry and Molecular Biology, Monoclonal Antibody Technology*, Chapter 1, vol. 13:1-32 (1984).

Carter, Paul et al., "Engineering antibodies for imaging and therapy," *Current Opinion in Biotechnology*, vol. 8:449-454 (1997).

Ciardiello, Fortunato et al., "Inhibition of CRIPTO expression and tumorigenicity in human colon cancer cells by antisense RNA and oligodeoxynucleotides," *Oncogene*, vol. 9:291-298 (1994).

Ciccodicola, Alfredo et al., "Molecular characterization of a gene of the 'EGF family' expressed in undifferentiated human NTERA2 teratocarcinoma cells," *The EMBO Journal*, vol. 8(7):1987-1991 (1989).

Dorai, Haimanti et al., "Role of Inter-Heavy and Light Chain Disulfide Bonds in the Effector Functions of Human Immunoglobulin IgG1," *Molecular Immunology*, vol. 29(12):1487-1491 (1992).

Dublin, Edwin A. et al., "Amphiregulin and cripto overexpression in breast cancer: relationship with prognosis and clinical and molecular variables," *International Journal of Oncology*, vol. 7:617-622 (1995).

Ebert, Andreas D. et al., "Cripto-1 Induces Phosphatidylinositol 3'-Kinase-dependent Phosphorylation of AKT and Glycogen Synthase Kinase 3β in Human Cervical Carcinoma Cells," *Cancer Research*, vol. 59:4502-4505 (1999).

Gillies, Stephen D. et al., "Antigen binding and biological activities of engineered mutant chimeric antibodies with human tumor specificities," *Hum. Antibod. Hybridomas*, vol. 1(1):47-54 (1990).

Hu, Shi-zhen et al., "Minobody: A Novel Engineered Anti-Carcinoembryonic Antigen Antibody Fragment (Single-Chain Fv-$C_{H}3$) Which Exhibits Rapid, High-Level Targeting of Xenografts," *Cancer Research*, vol. 56:3055-3061 (1996).

Hu, Xiu Feng et al., "Cripto Monoclonal Antibodies," *Drug News Perspect.*, vol. 18(5):293-303 (2005).

Hudson, Peter J., "Recombinant antibody constructs in cancer therapy," *Current Opinion in Immunology*, vol. 11:548-557 (1999).

Kannan, Subha et al., "Cripto Enhances the Tyrosine Phosphorylation of Shc and Activates Mitogen-activated Protein Kinase (MAPK) in Mammary Epithelial Cells," *The Journal of Biological Chemistry*, vol. 272(6):3330-3335 (1997).

Lee, Hyun-Sil et al., "Generation and characterization of a novel single-gene-encoded single-chain immunoglobulin molecule with antigen binding activity and effector functions," *Molecular Immunology*, vol. 36:61-71 (1999).

LePage, Doreen J. et al., "Inhibition of human tumor xenografts by anti-Cripto antibodies," *Proceedings of the American Association for Cancer Research*, vol. 44, 2nd Ed., No. 749, p. 145 (2003).

Normanno, Nicola et al., "Expression of amphiregulin, cripto-1, and heregulin α in human breast cancer cells," *International Journal of Oncology*, vol. 2:903-911 (1993).

Panico, Luigi et al., "Differential Immunohistochemical Detection of Transforming Growth Factor α, Amphiregulin and Cripto in Human Normal and Malignant Breast Tissues," *Int. J. Cancer*, vol. 65:51-56 (1996).

Paul, William E., Fundamental Immunology, Third Edition, Raven Press, Chpt. 9, pp. 292-295 (1993).

Qi, C.-F. et al., "Expression of transforming growth factor α, amphiregulin and cripto-1 in human breast carcinomas," *Br. J. Cancer*, vol. 69:903-910 (1994).

Reff, Mitchell E. et al., "A review of modifications to recombinant antibodies: attempt to incrase efficacy in oncology applications," *Critical Reviews in Oncology/Hematology*, vol. 40:25-35 (2001).

Saeki, Toshiaki et al., "Expression of cripto-1 in human colorectal adenomas and carcinomas is related to the degree of dysplasia," *International Journal of Oncology*, vol. 5:445-451 (1994).

Saeki, Toshiaki et al., "Immunohistochemical detection of cripto-1, amphiregulin and transforming growth factor alpha in human gastric carcinomas and intestinal metaplasias," *International Journal of Oncology*, vol. 5:215-223 (1994).

Salomon, D.S. et al., "The EGF-CFC family: novel epidermal growth factor-related proteins in development and cancer," *Endocrine-Related Cancer*, vol. 7:199-226 (2000).

Schlom, Jeffrey, "Monoclonal Antibodies: They're More and Less Than You Think," *Molecular Foundations of Oncology*, Eds. Broder et al., pp. 95-134 (1991).

Schuurman, Janine et al., "The inter-heavy chain disulfide bonds of IgG4 are in equilibrium with intra-chain disulfide bonds," *Molecular Immunology*, vol. 38:1-8 (2001).

Shopes, Bob, "A Genetically Engineered Human IgG with Limited Flexibility Fully INitiates Cytolysis via Complement," *Molecular Immunology*, vol. 30(6):603-609 (1993).

Slavin-Chiorini, Dale C. et al., "Biological Properties of Chimeric Domain-deleted Anticarcinoma Immunoglobulins," *Cancer Research*, vol. 55(Suppl.):5957s-5967s (1995).

Xing, Pei Xiang et al., "Cripto: A Novel Target for Antibody-Based Cancer Immunotherapy," *Cancer Research*, vol. 64:4018-4023 (2004).

Yazaki, Paul J. et al., "Mammalian expression and hollow fiber bioreactor production of recombinant anti-CEA diabody and minibody for clinical applications," *Journal of Immunological Methods*, vol. 253:195-208 (2001).

International Search Report for Application No. PCT/US2004/020945, dated Jun. 24, 2005.

International Search Report for Application No. PCT/US02/11950, dated Sep. 5, 2003.

International Search Report for Application No. PCT/US2006/000502, dated Aug. 2, 2006.

Champier, Jacques et al., "Identification of differentially expressed genes in human pineal parenchymal tumors by microarray analysis," *Acta Neuropathol.*, vol. 109:306-313 (2005).

Ciardiello, Fortunato et al., "Antitumor Activity of Combined Blockade of Epidermal Growth Factor Receptor and Protein Kinase A," *Journal of National Cancer Institute*, vol. 88(23):1770-1776 (1996).

Dono, Rosanna et al., "Isolation and Characterization of the CRIIPTO Autosomal Gene and its X-linked Related Sequence," *Am. J. Hum. Genet.*, vol. 49:555-565 (1991).

Friess, Helmut et al., "CRIPTO, a Member of the Epidermal Growth Factor Family, is Over-expressed in Human Pancreatic Cancer and Chronic Pancreatitis," *Int. J. Cancer*, vol. 56:668-674 (1994).

Hentschke, Moritz et al., "Germ Cell Nuclear Factor is a Repressor of *CRIPTO-1* and *CRIPTO-3*," *The Journal of Biological Chemistry*, vol. 281(44):33497-33504 (2006).

Hu, X.F. et al., "Anti-Cripto Mab inhibit tumour growth and overcome MDR in a human leukaemia MDR cell line by inhibition of Akt and activation of JNK/SAPK and bad death pathways," *British Journal of Cancer*, vol. 96:918-927 (2007).

Rudikoff, Stuart et al., "Single amino acid substitution altering antigen-binding specificity," *Proc. Natl. Acad. Sci. USA*, vol. 79:1979-1983 (1982).

Schiffer, Susan G. et al., "Fucosylation of Cripto is Required for its Ability to Facilitate Nodal Signaling," *The Journal of Biological Chemistry*, vol. 276(41):37769-37778 (2001).

Sugino, Yukio, "Biotechnology Series, Monoclonal Antibody," (1986).

Weiss, Thomas et al., "Molecular basis of basal cell carcinoma: Analysis of differential gene expression by differential display PCR and expression array," *Int. J. Cancer*, vol. 104:66-72 (2003).

Sebolt-Leopold, Judith S. et al., "Development of anticancer drugs targeting the MAP kinase pathway," Oncogene, vol. 19:6594-6599 (2000).

Ueda, Yutaka, et al., "Signal Transduction Inhibitor," Cancer and Chemotherapy (Gan to Kagaku Ryoho), vol. 28 (5):591-600 (2001).

Weinstein-Oppenheimer, Caroline R. et al., "The Raf signal transduction cascade as a target for chemotherapeutic intervention in growth factor-responsive tumors," Pharmacology & Therapeutics, vol. 88:229-279 (2000).

Yeo, Chang-Yeol et al., "Nodal Signals to Smads through Cripto-Dependent and Cripto-Independent Mechanisms," Molecular Cell, vol. 7:949-957 (2001).

Japanese Office Action for Application No. 2003-580477, dated Sep. 24, 2009.

Co-pending U.S. Appl. No. 12/317,477, inventors Sanicola-Nadel et al., filed Dec. 22, 2008 (Not Published).

Co-pending U.S. Appl. No. 12/602,625, inventors Sanicola-Nadel et al., filed Jun. 2, 2008 (Not Published).

NCBI Entrez, GenBank Report, Accession No. BAC01733, Akahori, Y. et al. (2002).

NCBI Entrez, GenBank Report, Accession No. AAK57792, Salcedo, I. et al. (2002).

* cited by examiner

Figure 1A

Nucleic acid sequence of heavy chain CH2 domain-deleted chB3F6 containing G1/G3/Pro243Ala244Pro245 + [Gly/Ser] hinge connecting peptide CAGGTCCAACTGCAGCAGGTTGGGGCTGAACTGGTGAAGCCTGGGGCTTCAGTGA
AGCTGTCCTGCAAGGCTTCTGGCTACACCTTCACCAGCTACTGGATACACTGGGT
GAAGCAGAGGCCTGGACAGGGCCTTGAGTGGATTGGAGAGAATGATCCTAGCAAC
GGTCGTACTAACTACAATGAGAAGTTCAAGAACAAGGCCACACTGACTGTAGACA
AATCCTCCAGCACAGCCTACATGCATCTCAGCAGCCTGACATCTGAGGACTCTGC
GGTCTATTACTGTTCAAGGGGCCCTAATTACTTCTATTCTTGGACTACTGGGGTC
AAGGAACCTCAGTCACCGTCTCCTCAGCTAGCACCAAGGGCCCATCGGTCTTCCC
CCTGGCACCCTCCTCAAGAGCACCTCTGGGGGCACAGCGGCCCTGGGCTGCCTG
GTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCT
CAGCAGCGTGGTGACCGTGCCCTCCAGCAGCTTGGGCACCCAGACCTACATCTGC
AACGTGAATCACAAGCCCAGCAACACCAAGGTGGACAAGAAAGTTGAGCCCAAAT
CTTGTGACAAAACTCACACATGCCCACCGTGCCCAGAGCCCAAATCTTGTGACAC
ACCTCCCCCATGCCCACGGTGCCCAGCACCTGGAGGTGGCTCGAGTGGAGGCGGT
TCCGGAGGGCAGCCCCGAGAACCACAGGTGTACACCCTGCCCCCATCCCGGGATG
AGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACC
ACGCCTCCCGTGCTGGACTCCGACGGCTCCTTCTTCCTCTACAGCAAGCTCACCG
TGGACAAGAGCAGGTGGCAGCAGGGGAACGTCTTCTCATGCTCCGTGATGCATGA
GGCTCTGCACAACCACTACACGCAGAAGAGCCTCTCCCTGTCTCCGGGT (SEQ. ID NO#: 1)

Figure 1B

Nucleic acid sequence of light chain CH2 domain-deleted chB3F6

GATTTTTTGATGACCCAAACTCCACTCTCCCTGCCTGTCAGTCTTGGAGATCAAG
CCTCCATCTCTTGCAGATCAAGTCAGAGCATTGTACATAGTAATGGAAACACCTA
TTTCGAATGGTACCTGCAGAAACCAGGCCAGTCTCCAAAGCTCCTCATCTACAAA
GTTTCCAACCGATTTTCTGGGGTCCCAGACAGGTTCAGTGGCAGTGGATCAGGGA
CAGATTTCACACTCAAGATCAGCAGAGTGGAGGCTGAGGATCTGGGAGTTTATTA
CTGCTTTCAAGGTTCACATGTTCCTCTCACGTTCGGTGCTGGGACAAGCTGGAGC
TGAAGCGTACGGTGGCTGCACCATCTGTCTTCATCTTCCCGCCATCTGATGAGCA
GTTGAAATCTGGAACTGCCTCTGTTGTGTGCCTGCTGAATAACTTCTATCCCAGA
GAGGCCAAAGTACAGTGGAAGGTGGATAACGCCCTCCAATCGGGTAACTCCCAGG
AGAGTGTCACAGAGCAGGACAGCAAGGACAGCACCTACAGCCTCAGCAGCACCCT
GACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGT (SEQ. ID NO#: 2)

Figure 2A

Amino acid sequence of heavy chain CH2 domain-deleted chB3F6 containing G1/G3:Pro243Ala244Pro245 + [Gly/Ser] hinge connecting peptide QVQLQQVGAELVKPGASVKLSCKASGYTFTSYWIHWVKQRPGQGLEWIGENDPSN
GRTNYNEKFKNKATLTVDKSSSTAYMHLSSLTSEDSAVYYCSRGPNYFYSMDYWG
QGTSVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPK
SCDKTHTCPPCPEPKSCDTPPPCPRCPAPGGGSSGGGSGGQPREPQVYTLPPSRD
ELTKNQVSLTCLVKGFYPSDIAVEWESNGQPENNYKTTPPVLDSDGSFFLYSKLT
VDKSRWQQGNVFSCSVMHEALHNHYTQKSLSLSPG     (SEQ. ID NO#: 3)

Figure 2B

Amino acid sequence of light chain CH2 domain-deleted chB3F6

DFLMTQTPLSLPVSLGDQASISCRSSQSIVHSNGNTYLEWYLQKPGQSPKLLIYK
VSNRFSGVPDRFSGSGSGTDFTLKISRVEAEDLGVYYCFQGSHVPLTFGAGTKLE
LKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC
                                        (SEQ. ID NO#: 4)

1. Mark 12 standards
2. ChB3F6ΔCH2 G1/G3:PAP (reduced)
3. Blank
4. ChB3F6ΔCH2 G1/G3:PAP (non- reduced)

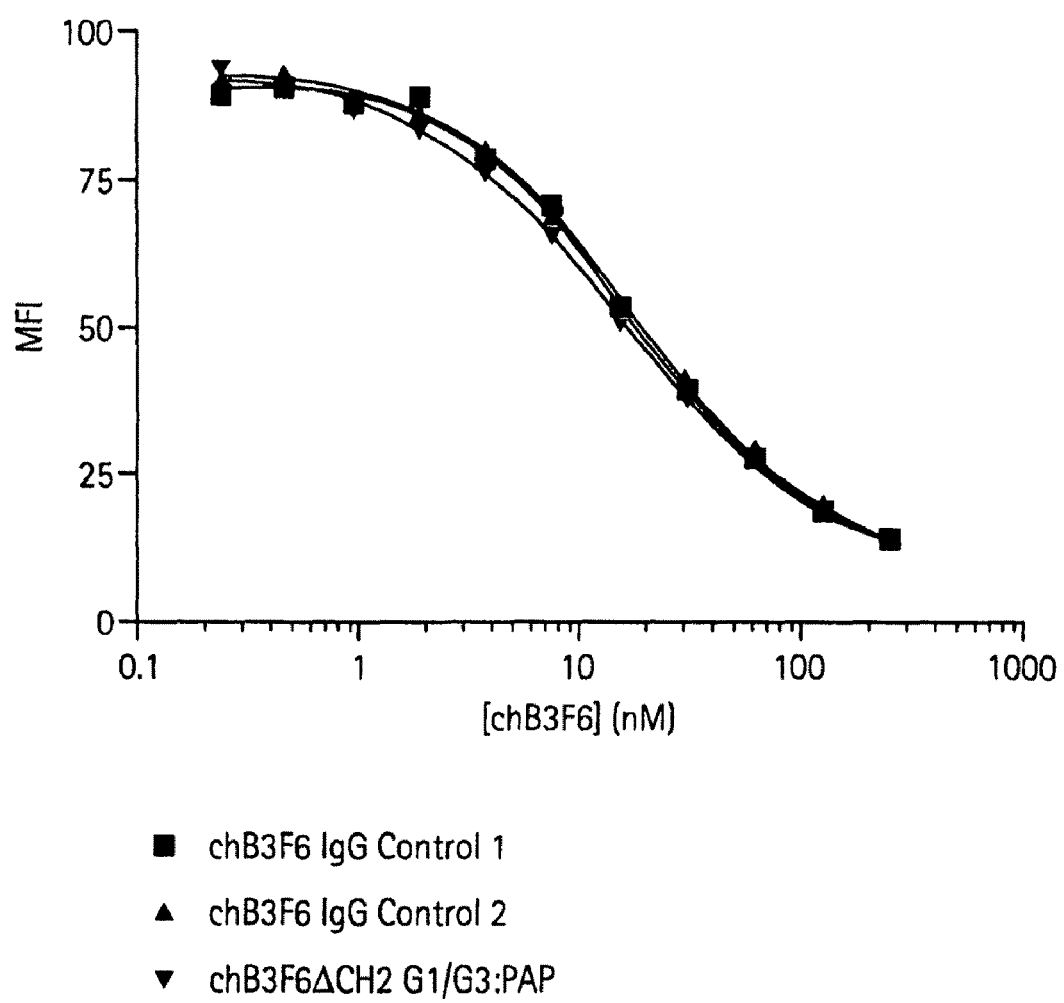

Figure 5

```
                  Kabat No.
                         2                           29
VL muB3F6              DFLMTQTPLSLPVSLGDQASISCRSSQSIVHSNGNTYLE
VL BAC01733            DVVMTQSPLSLPVTPGEPASISCRSSQSLLHSNGYNYLD
VL huB3F6 CDR MKLPVRLLVLMFWIPASSSDVVMTQSPLSLPVTPGEPASISCRSSQSIVHSNGNTYLE
VL huB3F6.L1  MKLPVRLLVLMFWIPASSSDEVMTQSPLSLPVTPGEPASISCRSSQSIVHSNGNTYLE
VL huB3F6.L2  MKLPVRLLVLMFWIPASSSDEVMTQSPLSLPVTPGEPASISCRSSQSIVHSNGNTYLE
              Signal peptide              FR1                      CDR L1

VL muB3F6     WYLQKPGQSPKLLIYKVSNRFSGVPDRFSGSGSGTDFTLKISRVEAEDLGVYYC
VL BAC01733   WYLQKPGQSPQLLIYLGSNRASGVPDRFSGSGSGTDFTLKISRVEAEDVGVYYC
VL huB3F6 CDR WYLQKPGQSPQLLIYKVSNRFSGVPDRFSGSGSGTDFTLKISRVEAEDVGVYYC
VL huB3F6.L1  WYLQKPGQSPQLLIYKVSNRFSGVPDRFSGSGSGTDFTLKISRVEAEDVGVYYC
VL huB3F6.L2  WYLQKPGQSPQLLIYKVSNRFSGVPDRFSGSGSGTDFTLKISRVEAEDVGVYYC
                    FR2          CDR L2                FR3

93        100
VL muB3F6     FQGSHVPLTFGAGTKLELK    SEQ ID NO:39
VL BAC01733   MQALQTPYTFGQGTKLEIK    SEQ ID NO:45
VL huB3F6 CDR FQGSHVPLTFGQGTKLEIK    SEQ ID NO:63
VL huB3F6.L1  FQGSHVPLTFGQGTKLEIK    SEQ ID NO:64
VL huB3F6.L2  FQGSHVPLTFGaGTKLEIK    SEQ ID NO:65
                 CDR L3      FR4
```

A. Day 58

A. Day 70

B. Day 107

A. Day 70

```
                        SEQUENCE LISTING

<160> NUMBER OF SEQ ID NOS: 71

<210> SEQ ID NO 1
<211> LENGTH: 1095
<212> TYPE: DNA
<213> ORGANISM: Artificial Sequence
<220> FEATURE:
<223> OTHER INFORMATION: synthetic construct

<400> SEQUENCE: 1
caggtccaac tgcagcaggt tggggctgaa ctggtgaagc ctggggcttc agtgaagctg      60
tcctgcaagg cttctggcta caccttcacc agctactgga tacactgggt gaagcagagg     120
cctggacagg gccttgagtg gattggagag aatgatccta gcaacggtcg tactaactac     180
aatgagaagt tcaagaacaa ggccacactg actgtagaca atcctccag cacagcctac      240 atgcatctca gcagcctgac atctgaggac tctgcggtct attactgttc aaggggccct     300
aattacttct attctatgga ctactggggt caaggaacct cagtcaccgt ctcctcagct     360
agcaccaagg gcccatcggt cttccccctg gcacctcct ccaagagcac ctctgggggc      420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagagc ccaaatcttg tgacacacct    720
cccccatgcc cacggtgccc agcacctgga ggtggctcga gtggaggcgg ttccggaggg    780
cagccccgag aaccacaggt gtacaccctg cccccatccc gggatgagct gaccaagaac    840
caggtcagcc tgacctgcct ggtcaaaggc ttctatccca gcgacatcgc cgtggagtgg    900
gagagcaatg ggcagccgga gaacaactac aagaccacgc ctcccgtgct ggactccgac    960
ggctccttct cctctacag caagctcacc gtggacaaga gcaggtggca gcaggggaac   1020
gtcttctcat gctccgtgat gcatgaggct ctgcacaacc actacacgca gaagagcctc   1080
tccctgtctc cgggt                                                   1095

<210> SEQ ID NO 2
<211> LENGTH: 657
<212> TYPE: DNA
<213> ORGANISM: Artificial Sequence
<220> FEATURE:
<223> OTHER INFORMATION: synthetic construct

<400> SEQUENCE: 2 gatttttga tgacccaaac tccactctcc ctgcctgtca gtcttggaga tcaagcctcc       60
atctcttgca gatcaagtca gagcattgta catagtaatg gaaacaccta tttagaatgg    120
tacctgcaga aaccaggcca gtctccaaag ctcctcatct acaaagtttc caaccgattt    180
```

-continued

```
tctggggtcc cagacaggtt cagtggcagt ggatcaggga cagatttcac actcaagatc    240
agcagagtgg aggctgagga tctgggagtt tattactgct ttcaaggttc acatgttcct    300
ctcacgttcg gtgctgggac caagctggag ctgaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

```
<210> SEQ ID NO 3
<211> LENGTH: 365
<212> TYPE: PRT
<213> ORGANISM: Artificial Sequence
<220> FEATURE:
<223> OTHER INFORMATION: synthetic construct

<400> SEQUENCE: 3

Gln Val Gln Leu Gln Gln Val Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ser Arg Gly Pro Asn Tyr Phe Tyr Ser Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Glu Pro Lys Ser Cys Asp Thr Pro
225                 230                 235                 240

Pro Pro Cys Pro Arg Cys Pro Ala Pro Gly Gly Ser Ser Gly Gly
                245                 250                 255

Gly Ser Gly Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285
```

```
Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
                340                 345                 350

Asn His Tyr Thr Gln Lys Ser Leu Ser Leu Ser Pro Gly
                355                 360                 365

<210> SEQ ID NO 4
<211> LENGTH: 219
<212> TYPE: PRT
<213> ORGANISM: Artificial Sequence
<220> FEATURE:
<223> OTHER INFORMATION: synthetic construct

<400> SEQUENCE: 4

Asp Phe Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 42
<212> TYPE: PRT
<213> ORGANISM: Artificial Sequence
<220> FEATURE:
<223> OTHER INFORMATION: synthetic construct

<400> SEQUENCE: 5

Glu Pro Lys Ser Cys Asp Lys Thr His Thr Cys Pro Pro Cys Pro Glu
1               5                   10                  15
```

```
Pro Lys Ser Cys Asp Thr Pro Pro Cys Pro Arg Cys Pro Ala Pro
            20                  25                  30
Gly Gly Gly Ser Ser Gly Gly Gly Ser Gly
            35                  40
```

<210> SEQ ID NO 6
<211> LENGTH: 188
<212> TYPE: PRT
<213> ORGANISM: Artificial Sequence
<220> FEATURE:
<223> OTHER INFORMATION: synthetic construct

<400> SEQUENCE: 6

```
Met Asp Cys Arg Lys Met Ala Arg Phe Ser Tyr Ser Val Ile Trp Ile
1               5                   10                  15
Met Ala Ile Ser Lys Val Phe Glu Leu Gly Leu Val Ala Gly Leu Gly
                20                  25                  30
His Gln Glu Phe Ala Arg Pro Ser Arg Gly Tyr Leu Ala Phe Arg Asp
            35                  40                  45
Asp Ser Ile Trp Pro Gln Glu Glu Pro Ala Ile Arg Pro Arg Ser Ser
    50                  55                  60
Gln Arg Val Pro Pro Met Gly Ile Gln His Ser Lys Glu Leu Asn Arg
65                  70                  75                  80
Thr Cys Cys Leu Asn Gly Gly Thr Cys Met Leu Gly Ser Phe Cys Ala
                85                  90                  95
Cys Pro Pro Ser Phe Tyr Gly Arg Asn Cys Glu His Asp Val Arg Lys
            100                 105                 110
Glu Asn Cys Gly Ser Val Pro His Asp Thr Trp Leu Pro Lys Lys Cys
        115                 120                 125
Ser Leu Cys Lys Cys Trp His Gly Gln Leu Arg Cys Phe Pro Gln Ala
    130                 135                 140
Phe Leu Pro Gly Cys Asp Gly Leu Val Met Asp Glu His Leu Val Ala
145                 150                 155                 160
Ser Arg Thr Pro Glu Leu Pro Pro Ser Ala Arg Thr Thr Thr Phe Met
                165                 170                 175
Leu Val Gly Ile Cys Leu Ser Ile Gln Ser Tyr Tyr
            180                 185
```

<210> SEQ ID NO 7
<211> LENGTH: 188
<212> TYPE: PRT
<213> ORGANISM: Artificial Sequence
<220> FEATURE:
<223> OTHER INFORMATION: synthetic construct

<400> SEQUENCE: 7

```
Met Asp Cys Arg Lys Met Val Arg Phe Ser Tyr Ser Val Ile Trp Ile
1               5                   10                  15
Met Ala Ile Ser Lys Ala Phe Glu Leu Gly Leu Val Ala Gly Leu Gly
                20                  25                  30
His Gln Glu Phe Ala Arg Pro Ser Arg Gly Asp Leu Ala Phe Arg Asp
            35                  40                  45
Asp Ser Ile Trp Pro Gln Glu Glu Pro Ala Ile Arg Pro Arg Ser Ser
    50                  55                  60
Gln Arg Val Leu Pro Met Gly Ile Gln His Ser Lys Glu Leu Asn Arg
65                  70                  75                  80
Thr Cys Cys Leu Asn Gly Gly Thr Cys Met Leu Glu Ser Phe Cys Ala
                85                  90                  95
```

```
Cys Pro Pro Ser Phe Tyr Gly Arg Asn Cys Glu His Asp Val Arg Lys
            100                 105                 110
Glu Asn Cys Gly Ser Val Pro His Asp Thr Trp Leu Pro Lys Lys Cys
        115                 120                 125
Ser Leu Cys Lys Cys Trp His Gly Gln Leu Arg Cys Phe Pro Gln Ala
    130                 135                 140
Phe Leu Pro Gly Cys Asp Gly Leu Val Met Asp Glu His Leu Val Ala
145                 150                 155                 160
Ser Arg Thr Pro Glu Leu Pro Pro Ser Ala Arg Thr Thr Thr Phe Met
                165                 170                 175
Leu Ala Gly Ile Cys Leu Ser Ile Gln Ser Tyr Tyr
                180                 185

<210> SEQ ID NO 8
<211> LENGTH: 10
<212> TYPE: PRT
<213> ORGANISM: Artificial Sequence
<220> FEATURE:
<223> OTHER INFORMATION: synthetic construct

<400> SEQUENCE: 8

Gly Gly Gly Ser Ser Gly Gly Ser Gly
1               5                   10

<210> SEQ ID NO 9
<211> LENGTH: 16
<212> TYPE: PRT
<213> ORGANISM: Artificial Sequence
<220> FEATURE:
<223> OTHER INFORMATION: synthetic construct

<400> SEQUENCE: 9

Arg Ser Ser Gln Ser Ile Val His Ser Asn Gly Asn Thr Tyr Leu Glu
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: synthetic construct

<400> SEQUENCE: 10

Lys Val Ser Asn Arg Phe Ser
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic construct

<400> SEQUENCE: 11

Phe Gln Gly Ser His Val Pro Leu Thr
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic construct

<400> SEQUENCE: 12
```

```
Ser Tyr Trp Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: synthetic construct

<400> SEQUENCE: 13

Glu Asn Asp Pro Ser Asn Gly Arg Thr Asn Tyr Asn Glu Lys Phe Lys
1               5                   10                  15

Asn

<210> SEQ ID NO 14
<211> LENGTH: 10
<212> TYPE: PRT
<213> ORGANISM: Artificial Sequence
<220> FEATURE:
<223> OTHER INFORMATION: synthetic construct

<400> SEQUENCE: 14

Gly Pro Asn Tyr Phe Tyr Ser Met Asp Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic construct

<400> SEQUENCE: 15

Ile Gly Lys Thr Ile Ser Lys Lys Ala Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: synthetic construct

<400> SEQUENCE: 16

Cys Pro Glu Pro Lys Ser Cys Asp Thr Pro Pro Cys Pro Arg
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: synthetic construct

<400> SEQUENCE: 17

Glu Pro Lys Ser Cys Asp Lys Thr His Thr
1               5                   10

<210> SEQ ID NO 18
<211> LENGTH: 5
<212> TYPE: PRT
<213> ORGANISM: Artificial Sequence
<220> FEATURE:
<223> OTHER INFORMATION: synthetic construct

<400> SEQUENCE: 18
```

```
Cys Pro Pro Cys Pro
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic construct

<400> SEQUENCE: 19

Ala Pro Glu Leu Leu Gly Gly Pro
1               5

<210> SEQ ID NO 20
<211> LENGTH: 12
<212> TYPE: PRT
<213> ORGANISM: Artificial Sequence
<220> FEATURE:
<223> OTHER INFORMATION: synthetic construct

<400> SEQUENCE: 20

Glu Leu Lys Thr Pro Leu Gly Asp Thr Thr His Thr
1               5                   10

<210> SEQ ID NO 21
<211> LENGTH: 20
<212> TYPE: PRT
<213> ORGANISM: Artificial Sequence
<220> FEATURE:
<223> OTHER INFORMATION: synthetic construct

<400> SEQUENCE: 21

Cys Pro Arg Cys Pro Glu Pro Lys Ser Cys Asp Thr Pro Pro Pro Cys
1               5                   10                  15

Pro Arg Cys Pro
            20

<210> SEQ ID NO 22
<211> LENGTH: 7
<212> TYPE: PRT
<213> ORGANISM: Artificial Sequence
<220> FEATURE:
<223> OTHER INFORMATION: synthetic construct

<400> SEQUENCE: 22

Glu Ser Lys Tyr Gly Pro Pro
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic construct

<400> SEQUENCE: 23

Cys Pro Ser Cys Pro
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 24

Ala Pro Glu Phe Leu Gly Gly Pro
1               5

<210> SEQ ID NO 25
<211> LENGTH: 24
<212> TYPE: PRT
<213> ORGANISM: Artificial Sequence
<220> FEATURE:
<223> OTHER INFORMATION: synthetic construct

<400> SEQUENCE: 25

Glu Pro Lys Ser Cys Asp Lys Thr His Thr Cys Pro Pro Cys Gly Gly
1               5                   10                  15

Gly Ser Ser Gly Gly Gly Ser Gly
            20

<210> SEQ ID NO 26
<211> LENGTH: 40
<212> TYPE: PRT
<213> ORGANISM: Artificial Sequence
<220> FEATURE:
<223> OTHER INFORMATION: synthetic construct

<400> SEQUENCE: 26

Glu Pro Lys Ser Cys Asp Lys Thr His Thr Cys Pro Pro Cys Pro Glu
1               5                   10                  15

Pro Lys Ser Cys Asp Thr Pro Pro Cys Pro Arg Cys Pro Gly Gly
            20                  25                  30

Gly Ser Ser Gly Gly Gly Ser Gly
            35                  40

<210> SEQ ID NO 27
<211> LENGTH: 24
<212> TYPE: PRT
<213> ORGANISM: Artificial Sequence
<220> FEATURE:
<223> OTHER INFORMATION: Synthetic construct

<400> SEQUENCE: 27

Glu Pro Lys Ser Cys Asp Lys Thr His Thr Cys Pro Pro Cys Gly Gly
1               5                   10                  15

Gly Ser Ser Gly Gly Gly Ser Gly
            20

<210> SEQ ID NO 28
<211> LENGTH: 25
<212> TYPE: PRT
<213> ORGANISM: Artificial Sequence
<220> FEATURE:
<223> OTHER INFORMATION: synthetic construct

<400> SEQUENCE: 28

Glu Pro Lys Ser Cys Asp Lys Thr His Thr Ser Pro Pro Cys Pro Gly
1               5                   10                  15

Gly Gly Ser Ser Gly Gly Gly Ser Gly
            20                  25

<210> SEQ ID NO 29
<211> LENGTH: 27
<212> TYPE: PRT
<213> ORGANISM: Artificial Sequence
<220> FEATURE:
<223> OTHER INFORMATION: synthetic construct
```

```
<400> SEQUENCE: 29

Glu Pro Lys Ser Cys Asp Lys Thr His Thr Ser Pro Pro Cys Pro Ala
1               5                   10                  15

Pro Gly Gly Gly Ser Ser Gly Gly Gly Ser Gly
            20                  25

<210> SEQ ID NO 30
<211> LENGTH: 25
<212> TYPE: PRT
<213> ORGANISM: Artificial Sequence
<220> FEATURE:
<223> OTHER INFORMATION: synthetic construct

<400> SEQUENCE: 30

Glu Pro Lys Ser Cys Asp Lys Thr His Thr Cys Pro Pro Ser Pro Gly
1               5                   10                  15

Gly Gly Ser Ser Gly Gly Gly Ser Gly
            20                  25

<210> SEQ ID NO 31
<211> LENGTH: 27
<212> TYPE: PRT
<213> ORGANISM: Artificial Sequence
<220> FEATURE:
<223> OTHER INFORMATION: synthetic construct

<400> SEQUENCE: 31

Glu Pro Lys Ser Cys Asp Lys Thr His Thr Cys Pro Pro Ser Pro Ala
1               5                   10                  15

Pro Gly Gly Gly Ser Ser Gly Gly Gly Ser Gly
            20                  25

<210> SEQ ID NO 32
<211> LENGTH: 27
<212> TYPE: PRT
<213> ORGANISM: Artificial Sequence
<220> FEATURE:
<223> OTHER INFORMATION: synthetic construct

<400> SEQUENCE: 32

Glu Pro Lys Ser Cys Asp Lys Thr His Thr Cys Pro Pro Cys Pro Ala
1               5                   10                  15

Pro Gly Gly Gly Ser Ser Gly Gly Gly Ser Gly
            20                  25

<210> SEQ ID NO 33
<211> LENGTH: 25
<212> TYPE: PRT
<213> ORGANISM: Artificial Sequence
<220> FEATURE:
<223> OTHER INFORMATION: synthetic construct

<400> SEQUENCE: 33

Glu Pro Lys Ser Cys Asp Lys Thr His Thr Cys Pro Pro Cys Pro Gly
1               5                   10                  15

Gly Gly Ser Ser Gly Gly Gly Ser Gly
            20                  25

<210> SEQ ID NO 34
<211> LENGTH: 29
<212> TYPE: PRT
<213> ORGANISM: Artificial Sequence
<220> FEATURE:
<223> OTHER INFORMATION: synthetic construct
```

-continued

```
<400> SEQUENCE: 34

Glu Ser Lys Tyr Gly Pro Pro Cys Pro Ser Pro Glu Pro Lys Ser
1               5                   10                  15

Cys Asp Thr Pro Pro Pro Cys Pro Arg Cys Pro Ala Pro
            20                  25

<210> SEQ ID NO 35
<211> LENGTH: 15
<212> TYPE: PRT
<213> ORGANISM: Artificial Sequence
<220> FEATURE:
<223> OTHER INFORMATION: synthetic construct

<400> SEQUENCE: 35

Cys Pro Glu Pro Lys Ser Cys Asp Thr Pro Pro Cys Pro Arg
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: synthetic construct

<400> SEQUENCE: 36

Glu Pro Lys Ser Cys Asp Lys Thr His Thr Cys Pro Pro Cys Pro Ala
1               5                   10                  15

Pro

<210> SEQ ID NO 37
<211> LENGTH: 5
<212> TYPE: PRT
<213> ORGANISM: Artificial Sequence
<220> FEATURE:
<223> OTHER INFORMATION: synthetic construct

<400> SEQUENCE: 37

Glu Ser Lys Tyr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic construct

<400> SEQUENCE: 38

Pro Pro Cys Pro Ser
1               5

<210> SEQ ID NO 39
<211> LENGTH: 112
<212> TYPE: PRT
<213> ORGANISM: Artificial Sequence
<220> FEATURE:
<223> OTHER INFORMATION: synthetic construct

<400> SEQUENCE: 39

Asp Phe Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
            100                 105                 110
```

<210> SEQ ID NO 40
<211> LENGTH: 121
<212> TYPE: PRT
<213> ORGANISM: Artificial Sequence
<220> FEATURE:
<223> OTHER INFORMATION: synthetic construct

<400> SEQUENCE: 40

```
Gln Val Gln Leu Gln Gln Val Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Ile His Trp Val Lys Gln Arg Pro Gly Gln Gly Leu Glu Trp Ile
            35                  40                  45

Gly Glu Asn Asp Pro Ser Asn Gly Arg Thr Asn Tyr Asn Glu Lys Phe
 50                  55                  60

Lys Asn Lys Ala Thr Leu Thr Val Ala Ser Pro Lys Ser Ser Ser Thr
 65                  70                  75                  80

Ala Tyr Met His Leu Ser Ser Leu Thr Ser Glu Asp Ser Ala Val Tyr
                 85                  90                  95

Tyr Cys Ser Arg Gly Pro Asn Tyr Phe Tyr Ser Met Asp Tyr Trp Gly
            100                 105                 110

Gln Gly Thr Ser Val Thr Val Ser Ser
            115                 120
```

<210> SEQ ID NO 41
<211> LENGTH: 113
<212> TYPE: PRT
<213> ORGANISM: Artificial Sequence
<220> FEATURE:
<223> OTHER INFORMATION: synthetic construct

<400> SEQUENCE: 41

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Thr His Val Pro Pro Tyr Thr Phe Gly Gly Gly Thr Lys Leu Glu Ile
            100                 105                 110

Lys
```

```
<210> SEQ ID NO 42
<211> LENGTH: 129
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (108)..(109)
<223> OTHER INFORMATION: Xaa = Any Amino Acid
<220> FEATURE:
<221> NAME/KEY: misc_feature
<222> LOCATION: (112)..(112)
<223> OTHER INFORMATION: Xaa = Any Amino Acid

<400> SEQUENCE: 42

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile Asp Pro Asn Ser Gly Gly Thr Asn Tyr Asn Glu Lys Phe
    50                  55                  60

Lys Ser Lys Ala Thr Leu Thr Val Ala Ser Pro Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Tyr Tyr Tyr Gly Gly Ser Ser Xaa Xaa Val Tyr Xaa
            100                 105                 110

Tyr Trp Tyr Phe Asp Tyr Trp Gly Gln Gly Thr Thr Val Thr Val Ser
        115                 120                 125

Ser

<210> SEQ ID NO 43
<211> LENGTH: 114
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (33)..(33)
<223> OTHER INFORMATION: Xaa = Any Amino Acid
<220> FEATURE:
<221> NAME/KEY: VARIANT
<222> LOCATION: (100)..(100)
<223> OTHER INFORMATION: Xaa = Any Amino Acid
<220> FEATURE:
<221> NAME/KEY: misc_feature
<222> LOCATION: (103)..(103)
<223> OTHER INFORMATION: Xaa = Any Amino Acid

<400> SEQUENCE: 43

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Xaa Asp Gly Asn Asn Tyr Leu Asn Trp Tyr Leu Gln Lys Pro Gly Gln
        35                  40                  45

Ser Pro Gln Leu Leu Ile Tyr Leu Val Ser Asn Arg Ala Ser Gly Val
    50                  55                  60

Pro Asp Arg Phe Ser Gly Ser Gly Ser Gly Thr Asp Phe Thr Leu Lys
65                  70                  75                  80
```

```
Ile Ser Arg Val Glu Ala Glu Asp Val Gly Val Tyr Tyr Cys Met Gln
                85                  90                  95

Ala Leu Gln Xaa Pro Arg Xaa Thr Phe Gly Gln Gly Thr Lys Val Glu
            100                 105                 110

Ile Lys
```

<210> SEQ ID NO 44
<211> LENGTH: 131
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (117)..(117)
<223> OTHER INFORMATION: Xaa = Any Amino Acid

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile Ser Trp Val Arg Gly Gln Ala Pro Gly Gln Gly Leu Glu
            35                  40                  45

Trp Met Gly Trp Ile Asn Pro Tyr Gly Asn Gly Asp Thr Asn Tyr Ala
50                  55                  60

Gln Lys Phe Gln Gly Arg Val Thr Ile Thr Ala Asp Thr Ser Thr Ser
65                  70                  75                  80

Thr Ala Tyr Met Glu Leu Ser Ser Leu Arg Ser Glu Asp Thr Ala Val
                85                  90                  95

Tyr Tyr Cys Ala Arg Ala Pro Gly Tyr Gly Ser Gly Gly Cys Tyr
            100                 105                 110

Arg Gly Asp Tyr Xaa Phe Asp Tyr Trp Gly Gln Gly Thr Leu Val Thr
            115                 120                 125

Val Ser Ser
    130
```

<210> SEQ ID NO 45
<211> LENGTH: 112
<212> TYPE: PRT
<213> ORGANISM: Artificial Sequence
<220> FEATURE:
<223> OTHER INFORMATION: synthetic construct

<400> SEQUENCE: 45

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 46
<211> LENGTH: 122
<212> TYPE: PRT
<213> ORGANISM: Artificial Sequence
<220> FEATURE:
<223> OTHER INFORMATION: synthetic construct

<400> SEQUENCE: 46

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Phe Met His Trp Val Ala Arg Gly Gln Ala Pro Gly Gln Gly Leu Glu
        35                  40                  45

Trp Met Gly Arg Ile Asn Pro Asn Ser Gly Gly Thr Asn Tyr Ala Gln
    50                  55                  60

Lys Phe Gln Gly Arg Val Thr Leu Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Leu Asp Thr Ala Ile Asp Ala Phe Asp Ile Trp Gly
            100                 105                 110

Gln Gly Thr Met Val Thr Val Cys Ser Asn
        115                 120

<210> SEQ ID NO 47
<211> LENGTH: 112
<212> TYPE: PRT
<213> ORGANISM: Artificial Sequence
<220> FEATURE:
<223> OTHER INFORMATION: synthetic construct

<400> SEQUENCE: 47

Asp Phe Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 48
<211> LENGTH: 119
<212> TYPE: PRT
<213> ORGANISM: Artificial Sequence
<220> FEATURE:
<223> OTHER INFORMATION: synthetic construct

<400> SEQUENCE: 48

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                20                  25                  30
Trp Ile His Trp Val Arg Gln Ala Pro Gly Gln Gly Leu Glu Trp Ile
            35                  40                  45

Gly Glu Asn Asp Pro Ser Asn Gly Arg Thr Asn Tyr Asn Glu Lys Phe
        50                  55                  60

Lys Asn Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Gly Pro Asn Tyr Phe Tyr Ser Met Asp Tyr Trp Gly Gln Gly
            100                 105                 110

Thr Met Val Thr Val Ser Ser
            115

<210> SEQ ID NO 49
<211> LENGTH: 119
<212> TYPE: PRT
<213> ORGANISM: Artificial Sequence
<220> FEATURE:
<223> OTHER INFORMATION: synthetic construct

<400> SEQUENCE: 49

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Met
            35                  40                  45

Gly Glu Asn Asp Pro Ser Asn Gly Arg Thr Asn Tyr Asn Glu Lys Phe
        50                  55                  60

Lys Asn Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Ser Ser
            115

<210> SEQ ID NO 50
<211> LENGTH: 112
<212> TYPE: PRT
<213> ORGANISM: Artificial Sequence
<220> FEATURE:
<223> OTHER INFORMATION: synthetic construct

<400> SEQUENCE: 50

Asp Phe Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

```
                    85                  90                  95

Ser His Val Pro Leu Thr Phe Gly Ala Gly Thr Lys Leu Glu Ile Lys
            100                 105                 110
```

<210> SEQ ID NO 51
<211> LENGTH: 119
<212> TYPE: PRT
<213> ORGANISM: Artificial Sequence
<220> FEATURE:
<223> OTHER INFORMATION: synthetic construct

<400> SEQUENCE: 51

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Arg Val Thr Leu Thr Val Asp Thr Ser Ile Ser Thr Ala Tyr
65                  70                  75                  80

Met His Leu Ser Ser Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Ser Ser
        115
```

<210> SEQ ID NO 52
<211> LENGTH: 223
<212> TYPE: PRT
<213> ORGANISM: Artificial Sequence
<220> FEATURE:
<223> OTHER INFORMATION: synthetic construct

<400> SEQUENCE: 52

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Leu Ala Ala Pro Ser Val Phe Ile Phe Pro Pro Ser
        115                 120                 125

Asp Glu Gln Leu Lys Ser Gly Thr Ala Ser Val Cys Leu Leu Asn
    130                 135                 140

Asn Phe Tyr Pro Arg Glu Ala Lys Val Gln Trp Lys Val Ala Ser Pro
145                 150                 155                 160

Asn Ala Leu Gln Ser Gly Asn Ser Gln Glu Ser Val Thr Glu Gln Asp
```

```
                165                 170                 175
Ser Lys Asp Ser Thr Tyr Ser Leu Ser Ser Thr Leu Thr Leu Ser Lys
        180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220

<210> SEQ ID NO 53
<211> LENGTH: 223
<212> TYPE: PRT
<213> ORGANISM: Artificial Sequence
<220> FEATURE:
<223> OTHER INFORMATION: synthetic construct

<400> SEQUENCE: 53

Asp Phe Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Leu Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Ala Ser Pro
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220

<210> SEQ ID NO 54
<211> LENGTH: 223
<212> TYPE: PRT
<213> ORGANISM: Artificial Sequence
<220> FEATURE:
<223> OTHER INFORMATION: synthetic construct

<400> SEQUENCE: 54

Asp Phe Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
```

```
                35                  40                  45
Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Ala Gly Thr Lys Leu Glu Ile Lys
                100                 105                 110

Arg Thr Val Ala Leu Ala Ala Pro Ser Val Phe Ile Phe Pro Pro Ser
            115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Ala Ser Pro
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220

<210> SEQ ID NO 55
<211> LENGTH: 448
<212> TYPE: PRT
<213> ORGANISM: Artificial Sequence
<220> FEATURE:
<223> OTHER INFORMATION: synthetic construct

<400> SEQUENCE: 55

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Trp Ile His Trp Val Arg Gln Ala Pro Gly Gln Gly Leu Glu Trp Met
         35                  40                  45

Gly Glu Asn Asp Pro Ser Asn Gly Arg Thr Asn Tyr Asn Glu Lys Phe
     50                  55                  60

Lys Asn Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Pro Asn Tyr Phe Tyr Ser Met Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 56
<211> LENGTH: 448
<212> TYPE: PRT
<213> ORGANISM: Artificial Sequence
<220> FEATURE:
<223> OTHER INFORMATION: synthetic construct

<400> SEQUENCE: 56

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Gly Pro Asn Tyr Phe Tyr Ser Met Asp Tyr Trp Gly Gln Gly
            100                 105                 110

```
Thr Met Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 57
<211> LENGTH: 448
<212> TYPE: PRT
<213> ORGANISM: Artificial Sequence
<220> FEATURE:
<223> OTHER INFORMATION: synthetic construct

<400> SEQUENCE: 57

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Met
```

```
            35                  40                  45
Gly Glu Asn Asp Pro Ser Asn Gly Arg Thr Asn Tyr Asn Glu Lys Phe
 50                  55                  60

Lys Asn Arg Val Thr Leu Thr Val Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Gly Pro Asn Tyr Phe Tyr Ser Met Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 58
<211> LENGTH: 448
```

<212> TYPE: PRT
<213> ORGANISM: Artificial Sequence
<220> FEATURE:
<223> OTHER INFORMATION: synthetic construct

<400> SEQUENCE: 58

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Arg Val Thr Leu Thr Val Asp Thr Ser Ile Ser Thr Ala Tyr
65                  70                  75                  80

Met His Leu Ser Ser Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 59
<211> LENGTH: 373
<212> TYPE: PRT
<213> ORGANISM: Artificial Sequence
<220> FEATURE:
<223> OTHER INFORMATION: synthetic construct

<400> SEQUENCE: 59

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Ala Arg Gly Gln Ala Pro Gly Gln Gly Leu Glu
        35                  40                  45

Trp Met Gly Glu Asn Asp Pro Ser Asn Gly Arg Thr Asn Tyr Asn Glu
    50                  55                  60

Lys Phe Lys Asn Arg Val Thr Leu Thr Arg Asp Thr Ser Ile Ser Thr
65                  70                  75                  80

Ala Tyr Met Glu Leu Ser Arg Leu Arg Ser Asp Thr Ala Val Tyr
                85                  90                  95

Tyr Cys Ala Arg Gly Pro Asn Tyr Phe Tyr Ser Met Asp Tyr Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Ala Ser
        195                 200                 205

Asn His Lys Pro Ser Asn Thr Lys Val Ala Ser Pro Lys Lys Val Glu
    210                 215                 220

Pro Lys Ser Cys Asp Lys Thr His Thr Cys Pro Pro Cys Pro Glu Pro
225                 230                 235                 240

Lys Ser Cys Asp Thr Pro Pro Cys Pro Arg Cys Pro Ala Pro Gly
                245                 250                 255

Gly Gly Ser Ser Gly Gly Gly Ser Gly Gly Gln Pro Arg Glu Pro Gln
            260                 265                 270

Val Tyr Thr Leu Pro Pro Ser Arg Asp Glu Leu Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320
```

```
Pro Val Leu Asp Ser Asp Gly Ser Phe Phe Leu Tyr Ser Lys Leu Thr
            325                 330                 335

Val Ala Ser Pro Lys Ser Arg Trp Gln Gln Gly Asn Val Phe Ser Cys
            340                 345                 350

Ser Val Met His Glu Ala Leu His Asn His Tyr Thr Gln Lys Ser Leu
            355                 360                 365

Ser Leu Ser Pro Gly
            370

<210> SEQ ID NO 60
<211> LENGTH: 365
<212> TYPE: PRT
<213> ORGANISM: Artificial Sequence
<220> FEATURE:
<223> OTHER INFORMATION: synthetic construct

<400> SEQUENCE: 60

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Gly Pro Asn Tyr Phe Tyr Ser Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Glu Pro Lys Ser Cys Asp Thr Pro
225                 230                 235                 240

Pro Pro Cys Pro Arg Cys Pro Ala Pro Gly Gly Ser Ser Gly Gly
                245                 250                 255

Gly Ser Gly Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300
```

```
Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
            325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
            355                 360                 365

<210> SEQ ID NO 61
<211> LENGTH: 365
<212> TYPE: PRT
<213> ORGANISM: Artificial Sequence
<220> FEATURE:
<223> OTHER INFORMATION: synthetic construct

<400> SEQUENCE: 61

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Asn Asp Pro Ser Asn Gly Arg Thr Asn Tyr Asn Glu Lys Phe
    50                  55                  60

Lys Asn Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Glu Pro Lys Ser Cys Asp Thr Pro
225                 230                 235                 240

Pro Pro Cys Pro Arg Cys Pro Ala Pro Gly Gly Ser Ser Gly Gly
                245                 250                 255

Gly Ser Gly Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
```

```
                        305                 310                 315                 320
Gly Ser Phe Phe Leu Tyr Ser Lys Leu Thr Val Asp Lys Ser Arg Trp
                    325                 330                 335

Gln Gln Gly Asn Val Phe Ser Cys Ser Val Met His Glu Ala Leu His
                340                 345                 350

Asn His Tyr Thr Gln Lys Ser Leu Ser Leu Ser Pro Gly
            355                 360                 365

<210> SEQ ID NO 62
<211> LENGTH: 365
<212> TYPE: PRT
<213> ORGANISM: Artificial Sequence
<220> FEATURE:
<223> OTHER INFORMATION: synthetic construct

<400> SEQUENCE: 62

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Asn Asp Pro Ser Asn Gly Arg Thr Asn Tyr Asn Glu Lys Phe
    50                  55                  60

Lys Asn Arg Val Thr Leu Thr Val Asp Thr Ser Ile Ser Thr Ala Tyr
65                  70                  75                  80

Met His Leu Ser Ser Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Glu Pro Lys Ser Cys Asp Thr Pro
225                 230                 235                 240

Pro Pro Cys Pro Arg Cys Pro Ala Pro Gly Gly Ser Ser Gly Gly
                245                 250                 255

Gly Ser Gly Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320
```

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
        355                 360                 365

<210> SEQ ID NO 63
<211> LENGTH: 133
<212> TYPE: PRT
<213> ORGANISM: Artificial Sequence
<220> FEATURE:
<223> OTHER INFORMATION: synthetic construct

<400> SEQUENCE: 63

Met Lys Leu Pro Val Ala Arg Gly Leu Leu Val Leu Met Phe Trp Ile
1               5                   10                  15

Pro Ala Ser Ser Ser Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Ile Val His Ser Asn Gly Asn Thr Tyr Leu Glu Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Leu Thr Phe Gly Gln Gly Thr
        115                 120                 125

Lys Leu Glu Ile Lys
    130

<210> SEQ ID NO 64
<211> LENGTH: 133
<212> TYPE: PRT
<213> ORGANISM: Artificial Sequence
<220> FEATURE:
<223> OTHER INFORMATION: synthetic construct

<400> SEQUENCE: 64

Met Lys Leu Pro Val Ala Arg Gly Leu Leu Val Leu Met Phe Trp Ile
1               5                   10                  15

Pro Ala Ser Ser Ser Asp Phe Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Ile Val His Ser Asn Gly Asn Thr Tyr Leu Glu Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Leu Thr Phe Gly Gln Gly Thr
        115                 120                 125

Lys Leu Glu Ile Lys
    130

<210> SEQ ID NO 65
<211> LENGTH: 133
<212> TYPE: PRT
<213> ORGANISM: Artificial Sequence
<220> FEATURE:
<223> OTHER INFORMATION: synthetic construct

<400> SEQUENCE: 65

Met Lys Leu Pro Val Ala Arg Gly Leu Leu Val Leu Met Phe Trp Ile
1               5                   10                  15

Pro Ala Ser Ser Ser Asp Phe Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Ile Val His Ser Asn Gly Asn Thr Tyr Leu Glu Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Leu Thr Phe Gly Ala Gly Thr
        115                 120                 125

Lys Leu Glu Ile Lys
    130

<210> SEQ ID NO 66
<211> LENGTH: 140
<212> TYPE: PRT
<213> ORGANISM: Artificial Sequence
<220> FEATURE:
<223> OTHER INFORMATION: synthetic construct

<400> SEQUENCE: 66

Met Gly Trp Ser Leu Ile Leu Leu Phe Leu Val Ala Val Ala Thr Arg
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile His Trp Val Ala Arg Gln Ala Pro Gly Gln
    50                  55                  60

Gly Leu Glu Trp Met Gly Glu Asn Asp Pro Ser Asn Gly Arg Thr Asn
65                  70                  75                  80

Tyr Asn Glu Lys Phe Lys Asn Arg Val Thr Leu Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Gly Pro Asn Tyr Phe Tyr Ser Met Asp
        115                 120                 125

Tyr Trp Gly Gln Gly Thr Met Val Thr Val Ser Ser
    130                 135                 140

<210> SEQ ID NO 67

```
<211> LENGTH: 138
<212> TYPE: PRT
<213> ORGANISM: Artificial Sequence
<220> FEATURE:
<223> OTHER INFORMATION: synthetic construct

<400> SEQUENCE: 67

Met Gly Trp Ser Leu Ile Leu Leu Phe Leu Val Ala Val Ala Thr Arg
1               5                   10                  15

Val Leu Ser Glu Val Gln Leu Val Glu Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile His Trp Val Arg Gln Ala Pro Gly Gln Gly Leu
    50                  55                  60

Glu Trp Ile Gly Glu Asn Asp Pro Ser Asn Gly Arg Thr Asn Tyr Asn
65                  70                  75                  80

Glu Lys Phe Lys Asn Arg Ala Thr Leu Thr Val Asp Lys Ser Ile Ser
                85                  90                  95

Thr Ala Tyr Met Glu Leu Ser Arg Leu Arg Ser Asp Asp Thr Ala Val
            100                 105                 110

Tyr Tyr Cys Ser Arg Gly Pro Asn Tyr Phe Tyr Ser Met Asp Tyr Trp
        115                 120                 125

Gly Gln Gly Thr Met Val Thr Val Ser Ser
    130                 135

<210> SEQ ID NO 68
<211> LENGTH: 138
<212> TYPE: PRT
<213> ORGANISM: Artificial Sequence
<220> FEATURE:
<223> OTHER INFORMATION: synthetic construct

<400> SEQUENCE: 68

Met Gly Trp Ser Leu Ile Leu Leu Phe Leu Val Ala Val Ala Thr Arg
1               5                   10                  15

Val Leu Ser Glu Val Gln Leu Val Glu Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile His Trp Val Arg Gln Ala Pro Gly Gln Gly Leu
    50                  55                  60

Glu Trp Met Gly Glu Asn Asp Pro Ser Asn Gly Arg Thr Asn Tyr Asn
65                  70                  75                  80

Glu Lys Phe Lys Asn Arg Val Thr Leu Thr Val Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Pro Asn Tyr Phe Tyr Ser Met Asp Tyr Trp
        115                 120                 125

Gly Gln Gly Thr Met Val Thr Val Ser Ser
    130                 135

<210> SEQ ID NO 69
<211> LENGTH: 138
<212> TYPE: PRT
<213> ORGANISM: Artificial Sequence
<220> FEATURE:
<223> OTHER INFORMATION: synthetic construct
```

-continued

<400> SEQUENCE: 69

Met Gly Trp Ser Leu Ile Leu Leu Phe Leu Val Ala Val Ala Thr Arg
1               5                   10                  15

Val Leu Ser Gln Val Gln Leu Val Glu Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile His Trp Val Arg Gln Ala Pro Gly Gln Gly Leu
    50                  55                  60

Glu Trp Ile Gly Glu Asn Asp Pro Ser Asn Gly Arg Thr Asn Tyr Asn
65                  70                  75                  80

Glu Lys Phe Lys Asn Arg Val Thr Leu Thr Val Asp Thr Ser Ile Ser
                85                  90                  95

Thr Ala Tyr Met His Leu Ser Ser Leu Arg Ser Asp Asp Thr Ala Val
            100                 105                 110

Tyr Tyr Cys Ala Arg Gly Pro Asn Tyr Phe Tyr Ser Met Asp Tyr Trp
        115                 120                 125

Gly Gln Gly Thr Met Val Thr Val Ser Ser
    130                 135

<210> SEQ ID NO 70
<211> LENGTH: 251
<212> TYPE: PRT
<213> ORGANISM: Artificial Sequence
<220> FEATURE:
<223> OTHER INFORMATION: synthetic construct

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Ala Ser Asn His Lys Pro Ser Asn Thr Lys Val
                85                  90                  95

Ala Ser Pro Lys Lys Val Glu Pro Lys Ser Cys Asp Lys Thr His Thr
            100                 105                 110

Cys Pro Pro Cys Pro Glu Pro Lys Ser Cys Asp Thr Pro Pro Pro Cys
        115                 120                 125

Pro Arg Cys Pro Ala Pro Gly Gly Ser Gly Gly Gly Ser Gly
        115                 120                 125

Pro Arg Cys Pro Ala Pro Gly Gly Ser Gly Gly Gly Ser Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Ala Ser Pro Lys Ser Arg Trp Gln Gln
    210                 215                 220

-continued

Gly Asn Val Phe Ser Cys Ser Val Met His Glu Ala Leu His Asn His
225                 230                 235                 240

Tyr Thr Gln Lys Ser Leu Ser Leu Ser Pro Gly
                245                 250

<210> SEQ ID NO 71
<211> LENGTH: 329
<212> TYPE: PRT
<213> ORGANISM: Artificial Sequence
<220> FEATURE:
<223> OTHER INFORMATION: synthetic construct

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

CRIPTO BINDING MOLECULES

RELATED APPLICATIONS

This application is a continuation application of International Patent Application No. PCT/US2006/000502, filed Jan. 5, 2006, titled "Cripto Binding Molecules" which claims the benefit of U.S. Ser. No. 60/641,691, titled "Purification and Preferential Synthesis of Binding Molecules," filed on Jan. 5, 2005.

This application is related to U.S. Ser. No. 60/483,877, titled "Purification and Preferential Synthesis of Polypeptides," filed on Jun. 27, 2003 and to U.S. Ser. No. 60/508,810, titled "Purification and Preferential Synthesis of Antigen Binding Polypeptides," filed Oct. 3, 2003. This application is also related to U.S. Ser. No. 10/880,320, titled "Purification and Preferential Synthesis of Binding Molecules" filed on Jun. 28, 2004. This application is also related to U.S. Ser. No. 10/945,853, titled "Cripto-Specific Antibodies," filed Sep. 20, 2004, to U.S. Ser. No. 10/693,538, titled "Cripto Blocking Antibodies and Uses Thereof," filed Oct. 23, 2003, and to U.S. Application Nos. 60/367,002, titled "Antibodies Directed to the Ligand Binding Domain of Cripto," filed Mar. 22, 2002; 60/301,091, titled "Cripto Blocking Antibodies and Uses Thereof," filed Jun. 26, 2001; 60/293,020, titled "Antibodies Directed to the Ligand Binding Domain of Cripto," filed May 17, 2001; and 60/286,782, titled "Antibodies Directed to the Ligand Binding Domain of Cripto," filed Apr. 26, 2001.

The contents of each of the above-identified applications are incorporated in their entirety by this reference.

BACKGROUND OF THE INVENTION

Antibodies, and various engineered forms thereof, are effective therapeutic agents currently being used to treat patients suffering from a variety of disorders. Some of these antibodies recognize antigens present on the surface of tumor cells. Cripto is a 188-amino-acid cell surface protein overexpressed by many tumor cells. Cripto was isolated in a cDNA screen of a human embryonic carcinoma library (Ciccodicola et al., 1989, *EMBO J.* 8:1987-91). Cripto was originally classified as a member of the EGF family (Ciccodicola et al., supra); however, subsequent analysis showed that Cripto did not bind any of the known EGF receptors and its EGF-like domain was actually divergent from the EGF family (Bianco et al., 1999, *J. Biol. Chem.* 274:8624-29).

Overexpression of the Cripto protein is associated with tumors in many tissues (including, but not limited to brain, breast, testicular, colon, lung, ovary, bladder, uterine, cervical, pancreatic and stomach). Panico et al., 1996, *Int. J. Cancer* 65:51-56; Byrne et al., 1998, *J. Pathology* 185:108-11; De Angelis et al., 1999, *Int. J. Oncology* 14:437-40.

Murine antibodies that bind to Cripto have been described. However, while murine antibodies do have applicability as therapeutic agents in humans, because they are not of human origin they may be immunogenic. Administration of such antibodies may result in a neutralizing antibody response (human anti-murine antibody (HAMA) response), which is particularly problematic if the antibodies are desired to be administered repeatedly, e.g., in treatment of a chronic or recurrent disease condition. Also, because they contain murine constant domains they may not exhibit human effector functions.

In an effort to alleviate the immunogenicity concerns, "humanized" antibodies are often produced. In one protocol, CDRs from an antibody of mouse origin are transferred onto human framework regions resulting in a "CDR grafted" antibody. Frequently, amino acid residues which could potentially affect antigen binding in the framework region are backmuated the corresponding mouse residue.

However, while humanized antibodies are desirable because of their potential low immunogenicity in humans, their production is unpredictable. For example, sequence modification of antibodies may result in substantial or even total loss of antigen binding affinity, or loss of binding specificity. In addition, despite sequence modification "humanized antibodies" may still exhibit immunogenicity in humans. The development of humanized anti-Cripto antibodies would be of great benefit in inhibiting the consequences of Cripto expression in the cells of patients. In addition, the development of such antibodies would provide a means for targeting Cripto positive tumor cells in order to deliver anti-tumor agents, such as toxins, radiolabels, and the like.

SUMMARY OF THE INVENTION

The invention is based, at least in part, on the development of CDR grafted and other humanized anti-Cripto antibodies. As described in more detail below, multiple forms of humanized anti-Cripto antibodies were developed and conjugated to maytansoids for testing in animal models for tumor growth. The results presented in the instant examples demonstrate the utility of these antibodies for the inhibition of tumor cell growth in vivo. These humanized anti-Cripto antibodies are more suited than mouse antibodies for use in human subjects.

Both humanized full-length antibodies and humanized antibodies lacking CH2 domains have been made. Compositions of CH2 domain deleted antibodies comprise a mixture of dimeric binding molecules comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B)). One form or the other can be preferentially obtained, e.g., by separation using hydrophobic interaction chromatography or by inclusion of synthetic connecting peptides which result in the preferential biosynthesis of either Form A or Form B. The connecting peptides of the invention can be included in any dimeric molecule that tends to form both Form A and Form B, e.g., antibody molecules, domain deleted antibody molecules (e.g., lacking all or part of a CH2 domain), minibodies, diabodies, fusion proteins, etc. In a preferred embodiment, the formation of Form A is enhanced. Form A polypeptide dimers show enhanced stability in vitro and enhanced biodistribution in vivo.

Accordingly, in one aspect, the invention pertains to a binding molecule comprising at least one CDR sequence selected from the group consisting of:

| | | |
|---|---|---|
| CDR L1: | RSSQSIVHSNGNTYLE, | (SEQ ID NO: 9) |
| CDR L2: | KVSNRFS, | (SEQ ID NO: 10) |
| CDR L3: | FQGSHVPLT, | (SEQ ID NO: 11) |
| CDR H1: | SYWIH, | (SEQ ID NO: 12) |
| CDR H2: | ENDPSNGRTNYNEKFKN, and | (SEQ ID NO: 13) |
| CDR H3: | GPNYFYSMDY | (SEQ ID NO: 14) | and a variable framework region sequence from a human acceptor immunoglobulin sequence, wherein the binding molecule binds specifically to a human Cripto antigen.

In one embodiment, the binding molecule comprises the CDR H3 sequence GPNYFYSMDY (SEQ ID NO:14).

In another embodiment, the CDR H2 sequence ENDPSNGRTNYNEKFKN (SEQ ID NO:13).

In one embodiment, the binding molecule comprises the CDR H1 sequence SYWIH (SEQ ID NO:12).

In one embodiment, the binding molecule comprises the CDR L3 sequence FQGSHVPLT (SEQ ID NO:11).

In one embodiment, the binding molecule comprises the CDR L2 sequence KVSNRFS (SEQ ID NO:10).

In one embodiment, the binding molecule comprises the CDR L1 sequence RSSQSIVHSNGNTYLE (SEQ ID NO:9).

In one embodiment, at least one framework residue of the variable framework region sequence is substituted with the corresponding amino acid residue from a corresponding mouse B3F6 variable region sequence.

In another aspect, the invention pertains to a binding molecule comprising: a light chain variable region comprising CDRs 1-3 of SEQ ID NO:39 and a variable framework region from a human acceptor immunoglobulin light chain sequence, and a heavy chain variable region comprising CDRs 1-3 of SEQ ID NO: 40 and a variable framework region from a human acceptor immunoglobulin heavy chain, wherein the binding molecule binds specifically to a human CRIPTO antigen.

In one embodiment, the variable framework region from a human acceptor immunoglobulin heavy chain is at least about 50% identical to the framework and CDR regions of SEQ ID NO:40.

In one embodiment, the variable framework region from a human acceptor immunoglobulin heavy chain is derived from a human subgroup 1 sequence, a human subgroup 1 consensus sequence, or a human germline sequence.

In one embodiment, the variable framework region from a human acceptor immunoglobulin heavy chain comprises the amino acid sequence shown in SEQ ID NO: 46.

In one embodiment, the variable framework region from a human acceptor immunoglobulin light chain sequence is at least about 60% identical to the framework and CDR regions of SEQ ID NO:39.

In one embodiment, the variable framework region from a human acceptor immunoglobulin light chain sequence is derived from a human subgroup Kappa 2 sequence, a human subgroup Kappa 2 consensus sequence, or a human germline sequence.

In one embodiment, the variable framework region from a human acceptor immunoglobulin light chain sequence comprises the amino acid sequence shown in SEQ ID NO: 45.

In one embodiment, at least one framework residue of the variable framework region from a human acceptor immunoglobulin heavy chain is substituted with the corresponding amino acid residue from the mouse amino acid sequence shown in SEQ ID NO: 40, wherein the at least one amino acid residue is
  a) a canonical residue,
  b) an interface packing residue,
  c) an unusual or rare residues that is close to the binding site,
  d) a residue having a side chain atom within about 3 angstrom units of some atom in a CDR.

In one embodiment, at least one framework residue is selected from the group consisting of H1, H48, H67, H71, H73, H81, H82b, H93, and H112 (Kabat numbering convention).

In one embodiment, the at least one framework residue includes H48, H67, H71, H73, H93, and H112.

In one embodiment, the at least one framework residue is H71 and H112.

In one embodiment, the at least one framework residue includes H1, H48, H71, H81, H82b, and H112.

In one embodiment, at least one framework residue of the variable framework region from a human acceptor immunoglobulin light chain sequence is substituted with the corresponding amino acid residue from the mouse sequence shown in SEQ ID NO: 39, wherein the at least one amino acid residue is
  a) a canonical residue,
  b) an interface packing residue,
  c) an unusual or rare residues that is close to the binding site,
  d) a residue having a side chain atom within about 3 angstrom units of some atom in a CDR.

In one embodiment, the variable framework region from a human acceptor immunoglobulin light chain sequence is L2 or L100 (Kabat numbering convention).

In one embodiment, the variable framework region from a human acceptor immunoglobulin light chain sequence is L2.

In one embodiment, the variable framework region from a human acceptor immunoglobulin light chain sequence includes L2 and L100.

In another aspect, the invention pertains to a binding molecule comprising: a light chain comprising the CDR and framework amino acid sequences shown in a VL sequence selected from the group consisting of SEQ ID NO: 47, SEQ ID NO:50, and amino acid residues 1-112 of SEQ ID NO: 52; and, optionally, a signal sequence and a heavy chain comprising the CDR and framework amino acid sequences shown in a VH sequence selected from the group consisting of SEQ ID NO: 48, SEQ ID NO:49, SEQ ID NO:51, and amino acid residues 1-121 of SEQ ID NO: 55; and, optionally, a signal sequence; wherein the binding molecule binds specifically to a human Cripto antigen.

In one embodiment, the binding molecule comprises a light chain comprising the framework and CDR amino acid sequences shown in amino acids 1-112 of SEQ ID NO: 52 and, optionally, a signal sequence and a heavy chain comprising the framework and CDR amino acid sequences shown in amino acids 1-121 of SEQ ID NO: 55 and, optionally, a signal sequence.

In one embodiment, the binding molecule comprises a light chain comprising the framework and CDR amino acid sequences shown in SEQ ID NO: 47 and, optionally, a signal sequence and a heavy chain comprising the framework and CDR amino acid sequences shown in SEQ ID NO: 48 and, optionally, a signal sequence.

In one embodiment, the binding molecule comprises a light chain comprising the framework and CDR amino acid sequences shown in SEQ ID NO: 47 and, optionally, a signal sequence a heavy chain comprising the framework and CDR amino acid sequences shown in SEQ ID NO:49 and, optionally, a signal sequence.

In one embodiment, the binding molecule comprises a light chain the framework and CDR amino acid sequences shown in SEQ ID NO: 47 and, optionally, a signal sequence, a heavy chain comprising the framework and CDR amino acid sequences shown in SEQ ID NO:51 and, optionally, a signal sequence.

In one embodiment, the binding molecule comprises a light chain comprising the framework and CDR amino acid sequences shown in SEQ ID NO:50 and, optionally, a signal sequence, a heavy chain comprising the framework and CDR amino acid sequences shown in SEQ ID NO: 48 and, optionally, a signal sequence.

In one embodiment, the binding molecule comprises a light chain comprising the framework and CDR amino acid sequences shown in SEQ ID NO:50 and, optionally, a signal sequence and a heavy chain comprising the framework and CDR amino acid sequences shown in and SEQ ID NO: 49 and, optionally, a signal sequence.

In one embodiment, the binding molecule comprises a light chain comprising the framework and CDR amino acid sequences shown in SEQ ID NO:50 and, optionally, a signal sequence; a heavy chain comprising the framework and CDR amino acid sequences shown in SEQ ID NO: 51 and, optionally, a signal sequence.

In one embodiment, the binding molecule heavy chain comprises a CH3 domain genetically fused to a VH, VL, or CH1 domain via a synthetic connecting peptide.

In one embodiment, the binding molecule heavy chains lack all or part of a CH2 domain.

In one embodiment, the binding molecule comprises a constant region derived from an antibody of an isotype selected from the group consisting of: IgG1, IgG2, IgG3, and IgG4.

In one embodiment, the binding molecule comprises an amino acid sequence derived from a hinge region selected from the group consisting of: a γ1 hinge, a γ2 hinge a γ3 hinge, and a γ4 hinge.

In one embodiment, the binding molecule comprises a chimeric hinge.

In one embodiment, the binding molecule comprises at least a portion of an IgG1 hinge domain, at least a portion of an IgG3 hinge domain.

In one embodiment, the binding molecule comprises a heavy chain constant region comprising a cysteine residue at position 239 or 242 (Kabat numbering system).

In one embodiment, the binding molecule comprises a heavy chain constant region comprising at least one amino acid modification as compared to a wild type Fc region. In one embodiment, the modification comprises an amino acid substitution in any of EU positions 297-299 such that the variant is substantially aglycosylated when expressed in a mammalian cell.

In one embodiment, the binding molecule comprises has a reduced effector function as compared to a binding molecule having a wild-type Fc region.

In one embodiment, the binding molecule has reduced antigen-dependent cytotoxicity.

In one embodiment, the binding molecule has an enhanced half-life.

In one embodiment, the modified Fc region has at least one engineered cysteine residue. In one embodiment, the engineered cysteine residue is in the CH3 domain of the Fc region.

In one embodiment, the invention pertains to a binding molecule which is conjugated to an effector moiety. In one embodiment, the effector moiety is selected from the group consisting of a cytotoxin, a prodrug, a biological toxin, and a radioisotope.

In one embodiment, the effector moiety is conjugated via an amide bond.

In one embodiment, the effector moiety is a maytansinoid.

In one embodiment, the light chain comprises the framework and CDR amino acid sequences shown in SEQ ID NO: 53 and the heavy chain comprises the framework and CDR amino acid sequences shown in SEQ ID NO:56.

In one embodiment, the light chain comprises the framework and CDR amino acid sequences shown in SEQ ID NO: 53 and the heavy chain comprises the framework and CDR amino acid sequences shown in sequence set forth as SEQ ID NO:57.

In one embodiment, a binding molecule comprises a heavy chain constant region of the γ1 isotype In one embodiment, a binding molecule comprises heavy chain constant region sequence shown in SEQ ID NO:71.

In another aspect, the invention pertains to a humanized anti-Cripto monoclonal antibody produced by the cell line deposited with the ATCC under Accession Number PTA-7284.

In one embodiment, a binding molecule comprises a light chain comprising sequence set forth as SEQ ID NO: 53 and the heavy chain sequence set forth as SEQ ID NO:58.

In one embodiment, a binding molecule comprises a light chain comprising the sequence set forth as SEQ ID NO: 54 and the heavy chain has the sequence set forth as SEQ ID NO:56.

In one embodiment, a binding molecule comprises a light chain comprising the sequence set forth as SEQ ID NO: 54 and the heavy chain sequence set forth as SEQ ID NO:57.

In one embodiment, a binding molecule of the invention comprises a light chain comprising the sequence set forth as SEQ ID NO: 54 and the heavy chain sequence set forth as SEQ ID NO:58.

In one embodiment, a binding molecule of the invention comprises a light chain comprising the sequence set forth as SEQ ID NO: 52 and the heavy chain has the sequence set forth as SEQ ID NO:55.

In another aspect, the invention pertains to a CH2 domain-deleted binding molecule comprising: a light chain comprising a light chain variable region (VL) sequence selected from the group consisting of SEQ ID NO: 52, SEQ ID NO: 53, and SEQ ID NO:54; a heavy chain comprising a heavy chain variable region (VH) sequence selected from the group consisting of SEQ ID NO: 55; SEQ ID NO: 56, SEQ ID NO:57, and SEQ ID NO:58; wherein the binding molecule binds specifically to a human CRIPTO antigen.

In one embodiment, the light chain has the sequence set forth as SEQ ID NO: 53 and the heavy chain has the sequence set forth as SEQ ID NO:60.

In one embodiment, wherein the light chain has the sequence set forth as SEQ ID NO: 53 and the heavy chain has the sequence set forth as SEQ ID NO:61.

In one embodiment, the light chain has the sequence set forth as SEQ ID NO: 53 and the heavy chain has the sequence set forth as SEQ ID NO:62.

In one embodiment, the light chain has the sequence set forth as SEQ ID NO: 54 and the heavy chain has the sequence set forth as SEQ ID NO:60.

In one embodiment, the light chain has the sequence set forth as SEQ ID NO: 54 and the heavy chain has the sequence set forth as SEQ ID NO:61.

In one embodiment, the light chain has the sequence set forth as SEQ ID NO: 54 and the heavy chain has the sequence set forth as SEQ ID NO:62.

In one embodiment, the light chain has the sequence set forth as SEQ ID NO: 52 and the heavy chain has the sequence set forth as SEQ ID NO:59.

In one embodiment, the binding molecule is altered to comprise at least one conservative amino acid substitution in at least one CDR of the binding molecule.

In one embodiment, a binding molecule of the invention is bispecific.

In one embodiment, a binding molecule of the invention is tetravalent.

In one embodiment, a binding molecule of the invention is a full-length antibody.

In one embodiment, a binding molecule of the invention is an antibody fragment.

In another aspect, the invention pertains to a composition comprising polypeptide dimers having at least two binding sites and at least two polypeptide chains, wherein at least one of the at least two binding sites comprises a humanized B3F6 variable region and wherein the at least two polypeptide chains comprise at least one heavy chain portion and a synthetic connecting peptide, wherein greater than about 70% of the polypeptide dimers comprise polypeptide chains that are linked via at least one interchain disulfide linkage and wherein the connecting peptide comprises a proline residue at position 243 of the Kabat numbering system.

In one embodiment, greater than 90% of the polypeptide dimers are linked via at least one interchain disulfide linkage.

In one embodiment, the synthetic connecting peptide further comprises a cysteine residue at position 239 or 242 of the Kabat numbering system.

In one embodiment, at least one of the polypeptide chains comprises a CH3 domain linked to a VL, VH or CH1 domain via the connecting peptide.

In one embodiment, the synthetic connecting peptide further comprises an alanine residue at position 244 and a proline residue at position 245 of the Kabat numbering system.

In another aspect, the invention pertains to a humanized anti-Cripto antibody comprising the light chain amino acid sequence shown in SEQ ID NO: 53 and the heavy chain amino acid sequence shown in SEQ ID NO: 57, wherein the antibody is conjugated to a maytansoid.

In another aspect, the invention pertains to a composition comprising a binding molecule and a pharmaceutically acceptable carrier.

In one embodiment, the binding molecule is a variant of the a humanized anti-Cripto antibody comprising the light chain amino acid sequence shown in SEQ ID NO: 53 and the heavy chain amino acid sequence shown in SEQ ID NO: 57, wherein the variant comprises at least one conservative amino acid substitution, wherein the variant retains the ability to specifically bind human Cripto.

In another embodiment, the invention pertains to an isolated nucleic acid molecule comprising a nucleotide sequence encoding a heavy or light chain of a binding molecule or a nucleic acid molecule which hybridizes to the complement thereof under high stringency conditions. In one embodiment, the nucleic acid molecule is in a vector.

In one embodiment, the invention pertains to a host cell comprising such a vector.

In another embodiment, the invention pertains to a method of producing a binding molecule, comprising culturing a host cell under conditions such that a binding molecule is produced and isolating the binding molecule from the host cell or culture.

In another embodiment, the invention pertains to a method of treating a subject that would benefit from treatment with a binding molecule of the invention comprising administering the binding molecule to the subject such that treatment occurs.

In another embodiment, the invention pertains to a method of treating a malignancy comprising administering a nucleic acid molecule that encodes a binding molecule of any one of claims 1-29 to a patient having a malignancy under conditions such that the binding molecule is expressed, such that the malignancy is treated in the patient.

In one embodiment, the subject is suffering from cancer.

In one embodiment, the method further comprises administering an additional agent.

In one embodiment, the additional agent is a chemotherapeutic agent.

In one embodiment, the additional agent is selected from the group consisting of natalizumab, trastuzumab, bevacizumab, infliximab, rituximab, ibritumomab tiuxetan, cetuximab, levamisole hydrochloride, tositumomab, alemtuzumab, IMC-C225, imatinib mesylate, fulvestrant, anastrozole, exemestane, letrozole, tamoxifen, interferon alpha, denileukin diftitox, oblimersen, erlotinib HCl, bortezomib, thalidomide, and endostatin.

In another aspect, the invention pertains to a method of inhibiting the effects of Cripto expression in a cell of a patient comprising administering to the patient an effective dosage of a binding molecule of the invention.

In one embodiment, the effective dosage of binding molecule is at least about 5 mg/kg.

In another embodiment, the effective dosage of binding molecule is at least about 10 mg/kg.

In one embodiment, the binding molecule is administered intraperitoneally, orally, intranasally, subcutaneously, intramuscularly, topically, or intravenously.

In one embodiment, the patient is suffering from a cancer in an organ selected from the group consisting of brain, breast, testicular, colon, lung, ovary, bladder, uterine, cervical, pancreatic and stomach.

BRIEF DESCRIPTION OF THE DRAWINGS

FIG. 1A (SEQ ID NO: 1) shows the DNA sequence of heavy chain CH2 domain-deleted chimeric anti-CRIPTO monoclonal antibody consisting of murine heavy and light chain variable domains fused to human heavy and light chain constant domains, respectively (chB3F6) containing G1/G3/Pro243Ala244Pro245+[GlySer] hinge connecting peptide. FIG. 1B (SEQ ID NO: 2) shows the DNA sequence of light chain CH2 domain-deleted chB3F6.

FIG. 2A (SEQ ID NO: 3) shows the amino acid sequence of heavy chain CH2 domain-deleted chB3F6 containing G1/G3/Pro243Ala244Pro245+[GlySer] hinge connecting peptide. FIG. 2B (SEQ ID NO: 4) shows the amino acid sequence of light chain CH2 domain-deleted chB3F6.

FIG. 4 shows that chimeric B3F6 (chB3F6) and chimeric B3F6 domain deleted antibody comprising a connecting peptide (B3F6ΔCH2 G1/G3/Pro243Ala244Pro245) compete equally for binding to GEO tumor cells.

FIG. 5 shows an alignment of the light chains of donor murine B3F6 light chain variable region, the human acceptor, and the various humanized forms made. CDR sequences are shaded. The differences in FR amino acid residues between the donor and acceptor are bolded. The backmuations made are indicated in bold and lower case letters. Kabat numbers are indicated along the top of the alignment.

$^a$ On Day 44 only three mice whose tumors were showing progressive growth were dosed.

Figure 23A:
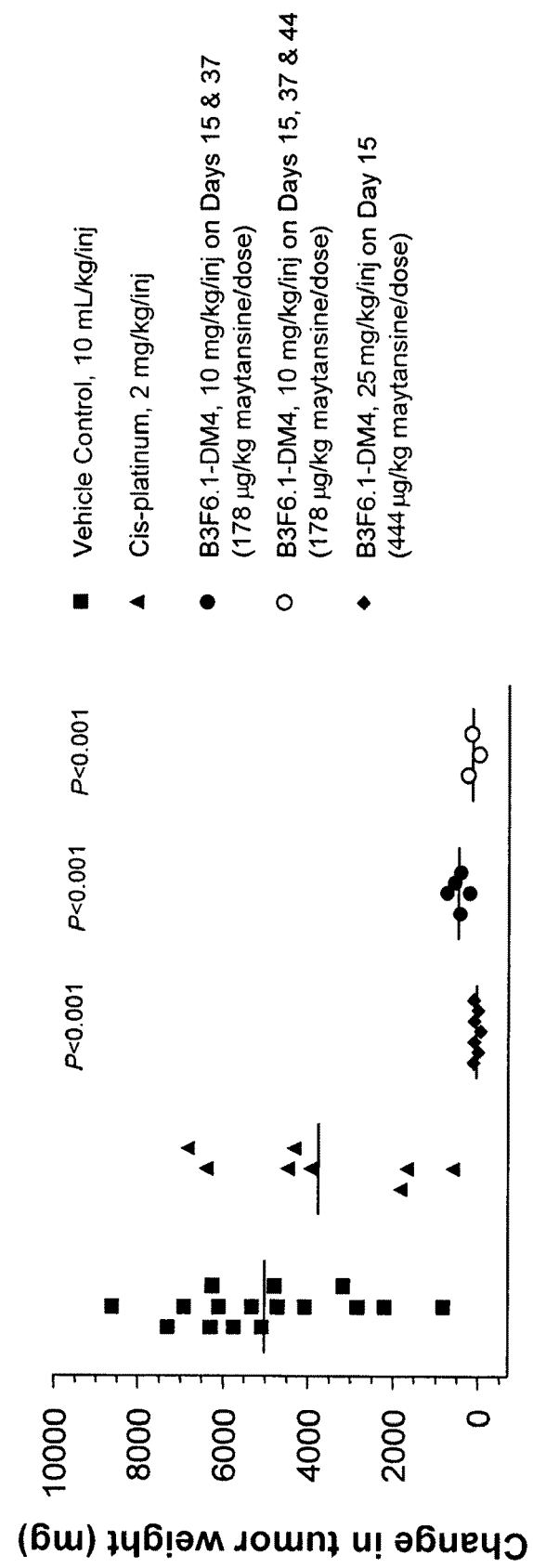
Figure 23B:
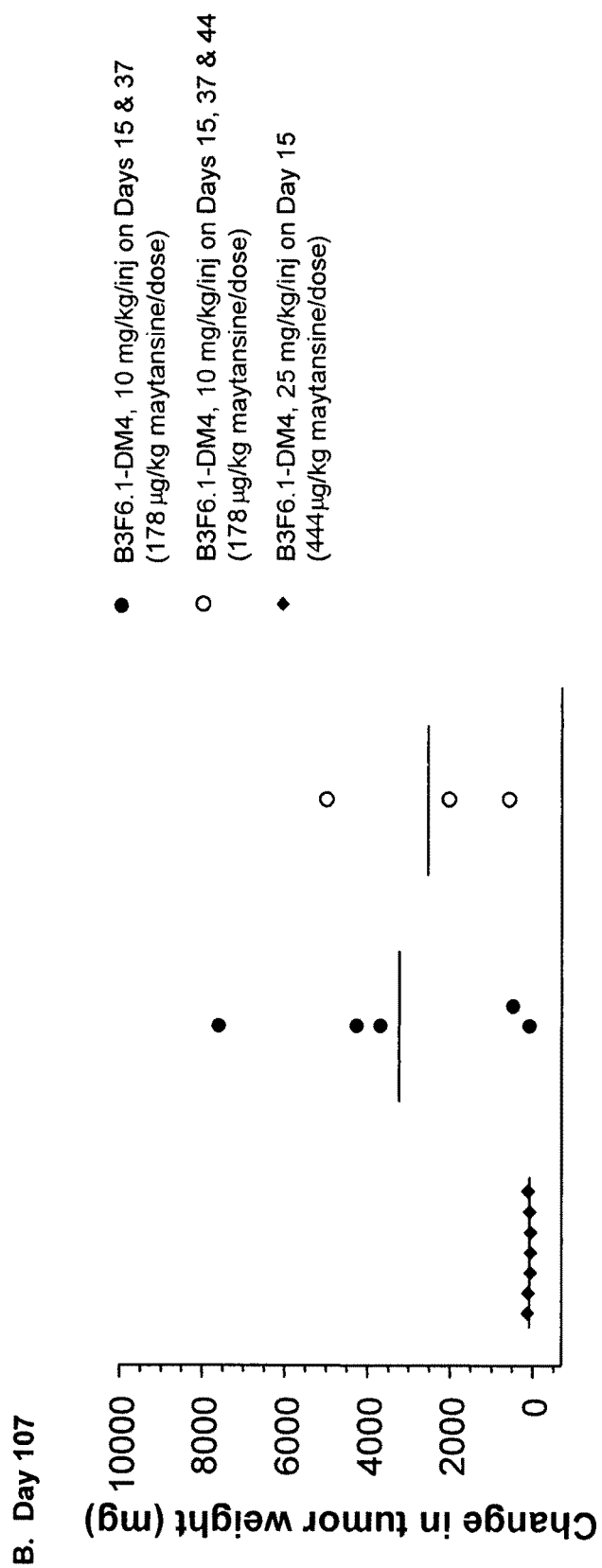

FIG. 23 panels A and B show the effect of full-length B3F6.1-DM4 on tumors in nude mice as measured by a change in tumor weight. Mice bearing established NCCIT human testicular tumors were treated with B3F6.1-DM4 at 25 (n=8) mg/kg IV once on Day 15, B3F6.1-DM4 at 10 (n=8) mg/kg IV on Day 15, 37, and 44$^a$, vehicle (n=16) IV q7d×3, and cis-platinum (n=8) SC 2 mg/kg 3×/wk×6 starting on Day 15. Panel A shows individual tumor weights on Day 70. Panel B shows the individual tumor weights of the remaining treatment groups on Day 107. Each point represents the tumor weight of a single mouse, and bars represent the mean tumor weight for each group.

Figure 24A:
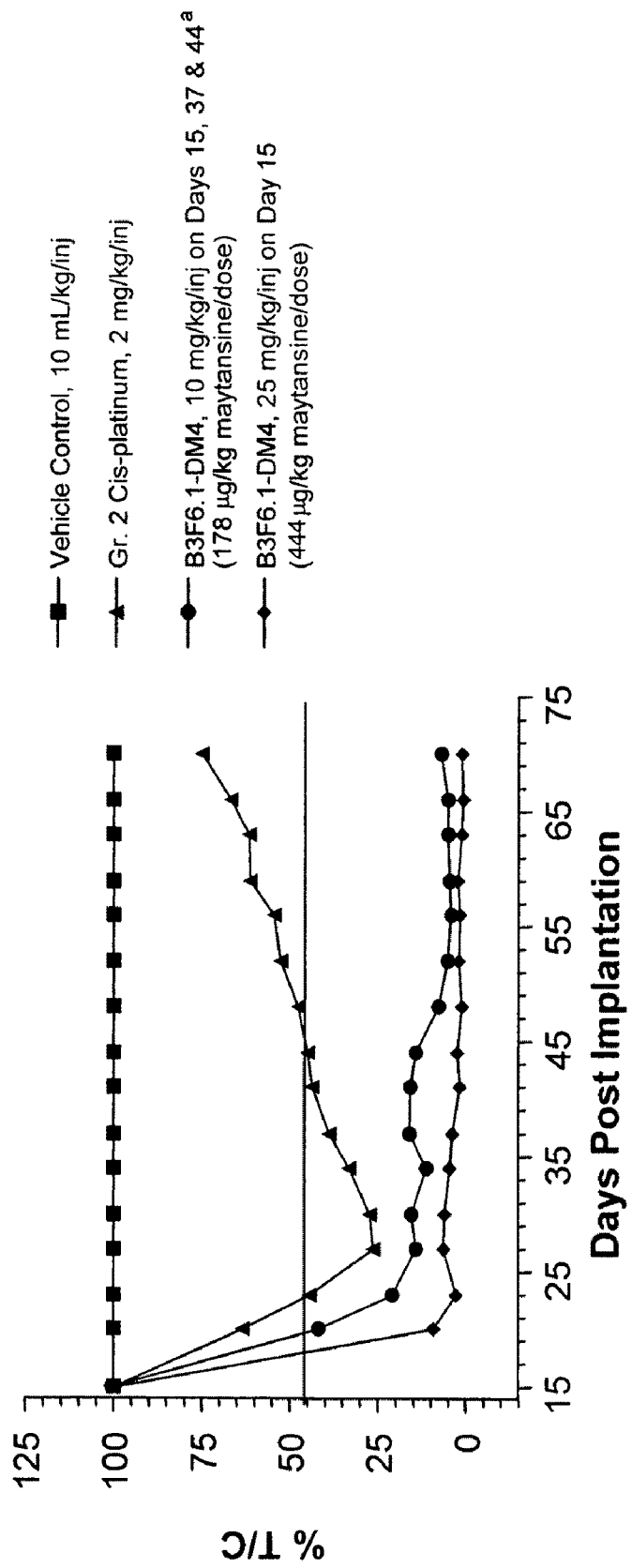
Figure 24B:
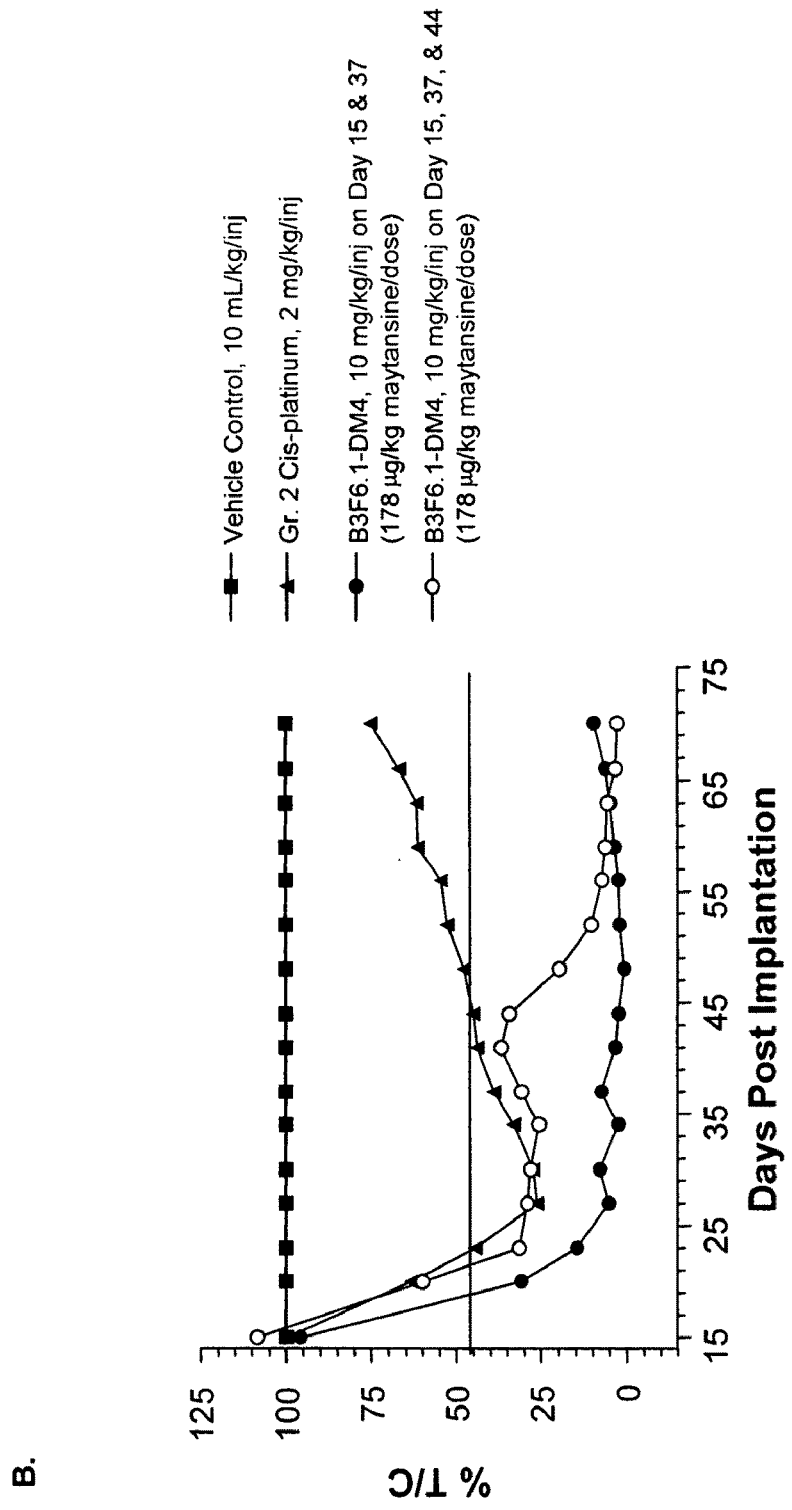

FIG. 24 panels A and B show the effect of full-length B3F6 conjugated to DM4 or cis-platinum on established NCCIT xenograft tumors in nude mice. The figure shows a comparison of test group mean change in tumor size as a percentage of the mean vehicle control change in tumor size. Nude mice bearing established NCCIT human testicular tumors were treated with B3F6.1-DM4 at 25 (n=8) mg/kg IV once on Day 15, B3F6.1-DM4 at 10 (n=8) mg/kg IV on Day 15, 37, and 44[a], vehicle (n=16) IV q7dx3, and cis-platinum (n=8) SC 2 mg/kg 3×/wk×6 starting on Day 15. Panel A shows the combined data for all mice dosed at 10 mg/kg. Panel B shows the data for the mice (n=5) dosed at 10 m/kg/inj on Day 15 and 37 separated out from the data for mice (n=3) dosed at 10 mg/kg/inj on Day 15, 37, and 44. The horizontal bar represents the National Cancer Institute's criteria for activity (42%).

Figure 25A:
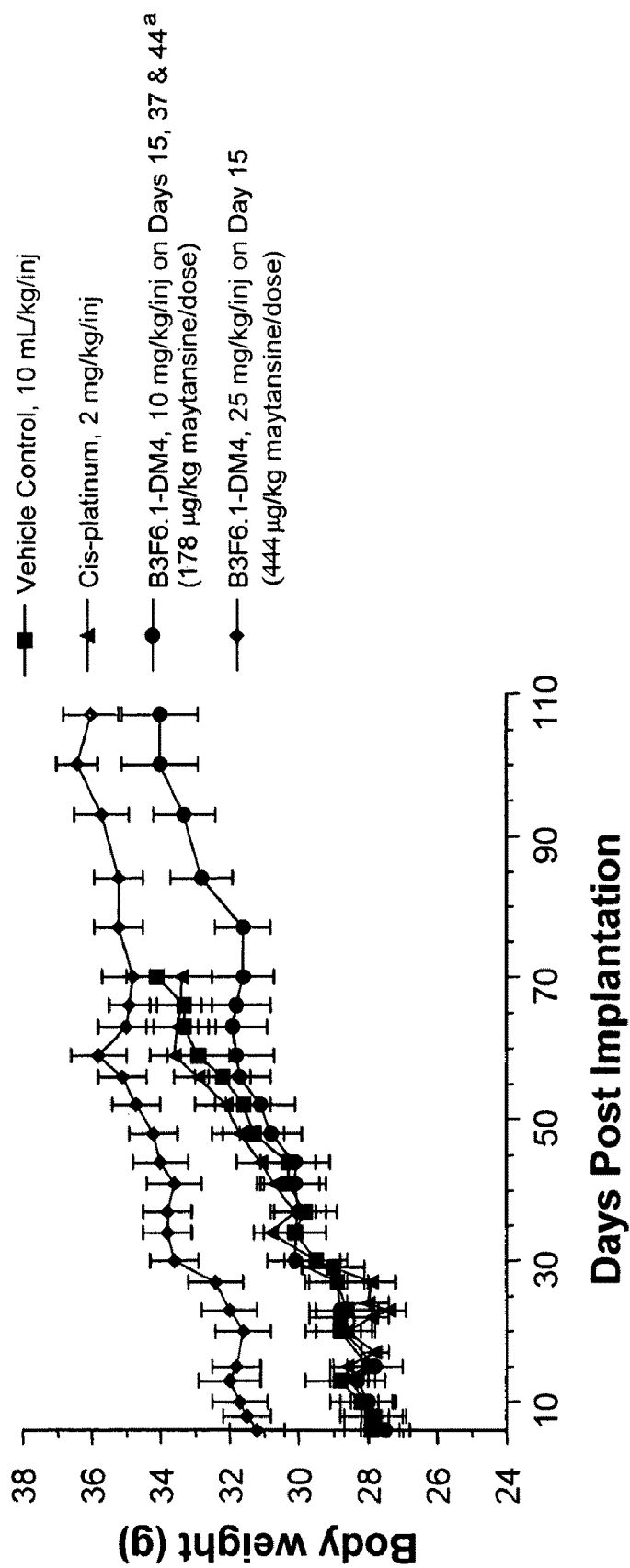
Figure 25B:
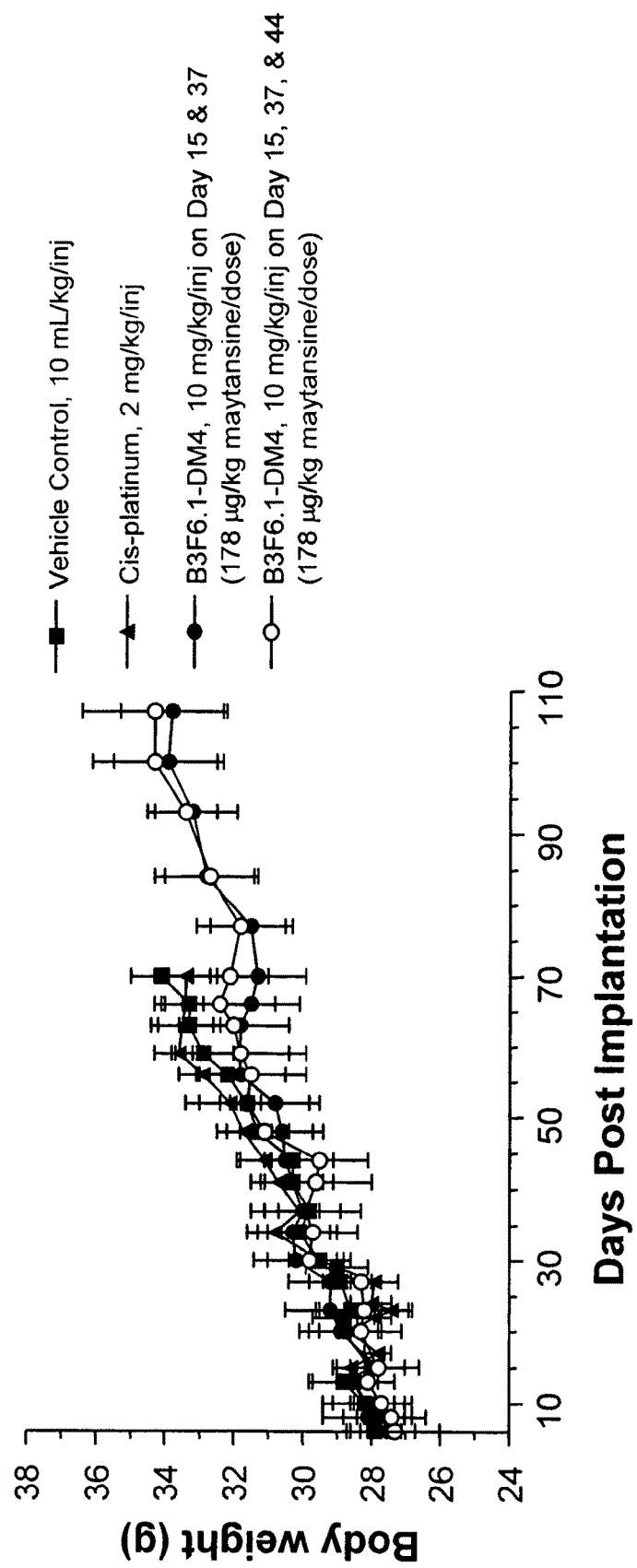

[a]On Day 44 only three mice, whose tumors showed progressive growth, were dosed at 10 mg/kg FIG. 25 panels A and B show mean Body weight of nude mice bearing established NCCIT human testicular tumors and treated with full-length B3F6.1-DM4 at 25 (n=8) mg/kg IV once on Day 15, B3F6.1-DM4 at 10 (n=8) mg/kg IV on Day 15, 37, and 44[a], vehicle (n=16) IV q7dx3, and cis-platinum (n=8) SC 2 mg/kg 3×/wk×6 starting on Day 15. Panel A shows the combined data for all mice dosed at 10 mg/kg. Panel B shows the data for the mice (n=5) dosed at 10 m/kg/inj on Days 15 and 37 separated out from the data for mice (n=3) dosed at 10 mg/kg/inj on Days 15, 37, and 44.

Figure 26:
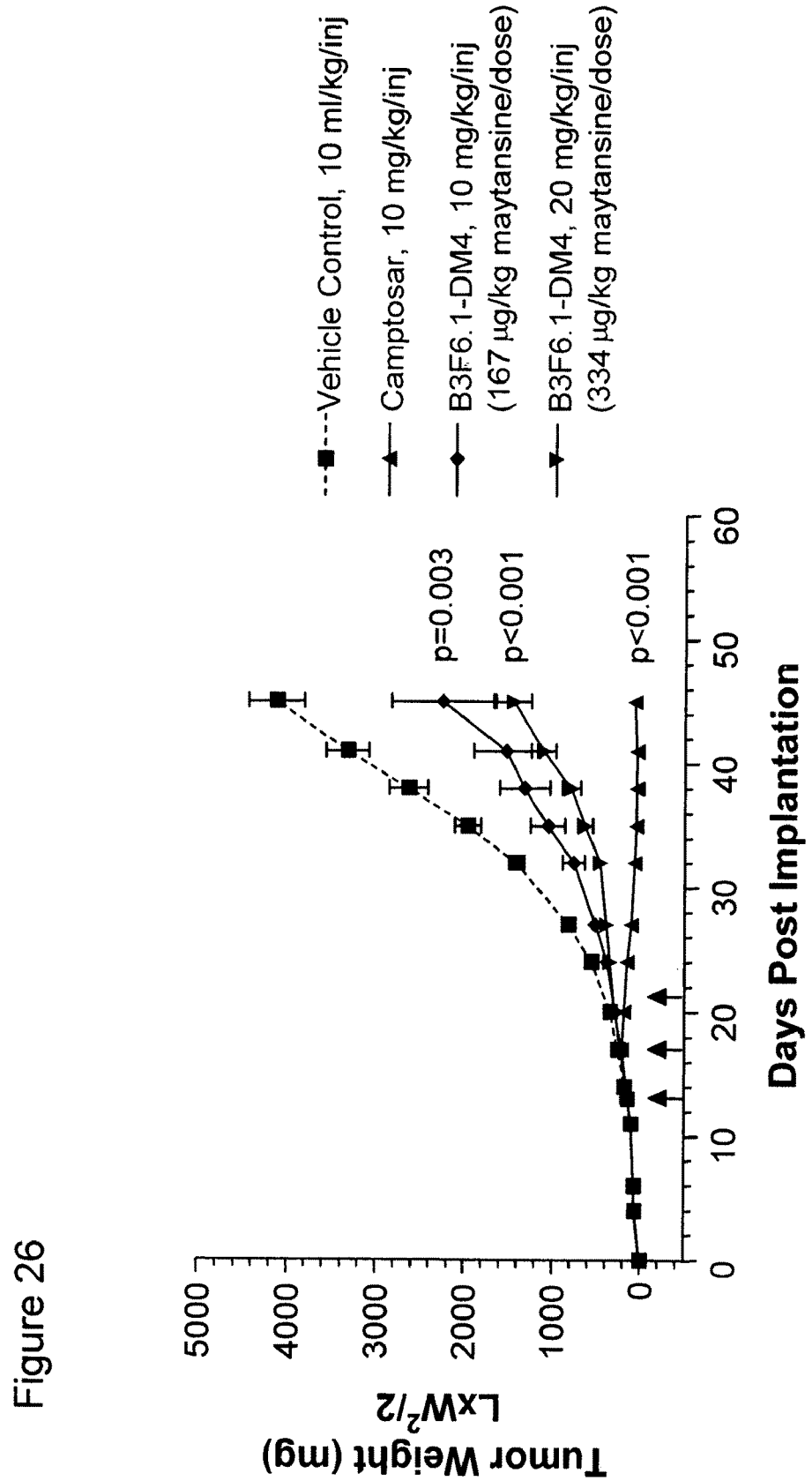

[a]On Day 44 only three mice, whose tumors showed progressive growth, were dosed at 10 mg/kg FIG. 26 shows the effect of full-length B3F6.1-DM4 at 10 (n=8) and 20 (n=8) mg/kg administered IV on Day 13, 17, and 21 (as indicated by the arrows), vehicle (n=16) administered IV 3×/wk×4 starting on Day 14, and Camptosar (n=8) 10 mg/kg administered SC on Day 13-14, 17-21, 24-26, on change in tumor weight of established Calu-6 xenograft tumors in nude mice. Vertical bars represent the standard error of the means.

Figure 27:
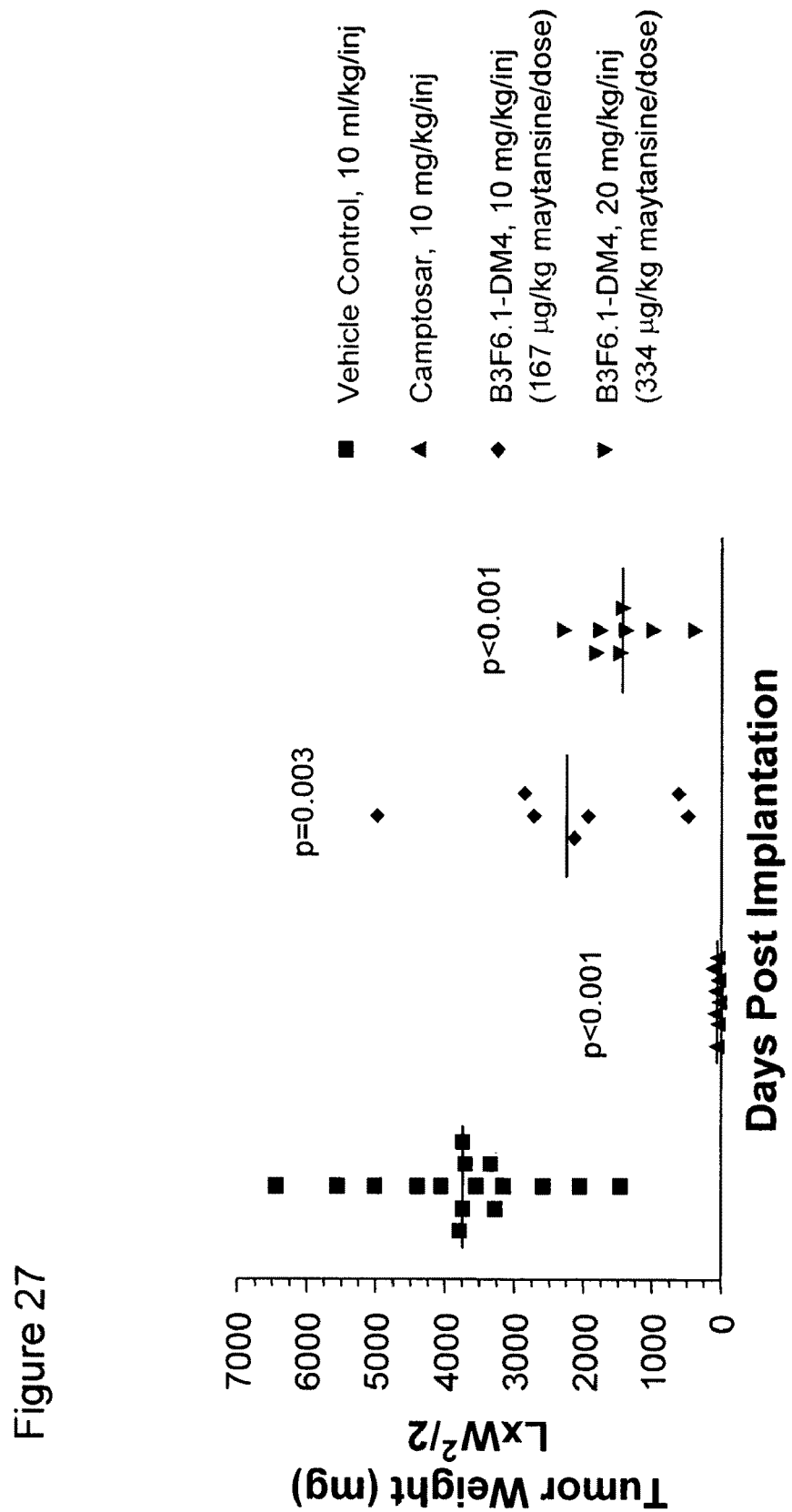

FIG. 27 shows the effect of full-length B3F6 conjugated to DM4 on established Calu-6 xenograft tumors in nude mice. The mice were treated with B3F6.1-DM4 at 10 (n=8) and 20 (n=8) mg/kg IV on Day 13, 17, and 21, vehicle (n=16) IV 3×/wk×4 starting on Day 14, and Camptosar (n=8) 10 mg/kg SC on Day 13-14, 17-21, 24-26. Each point represents the tumor weight of a single mouse, and bars represent the mean tumor weight for each group.

Figure 28:
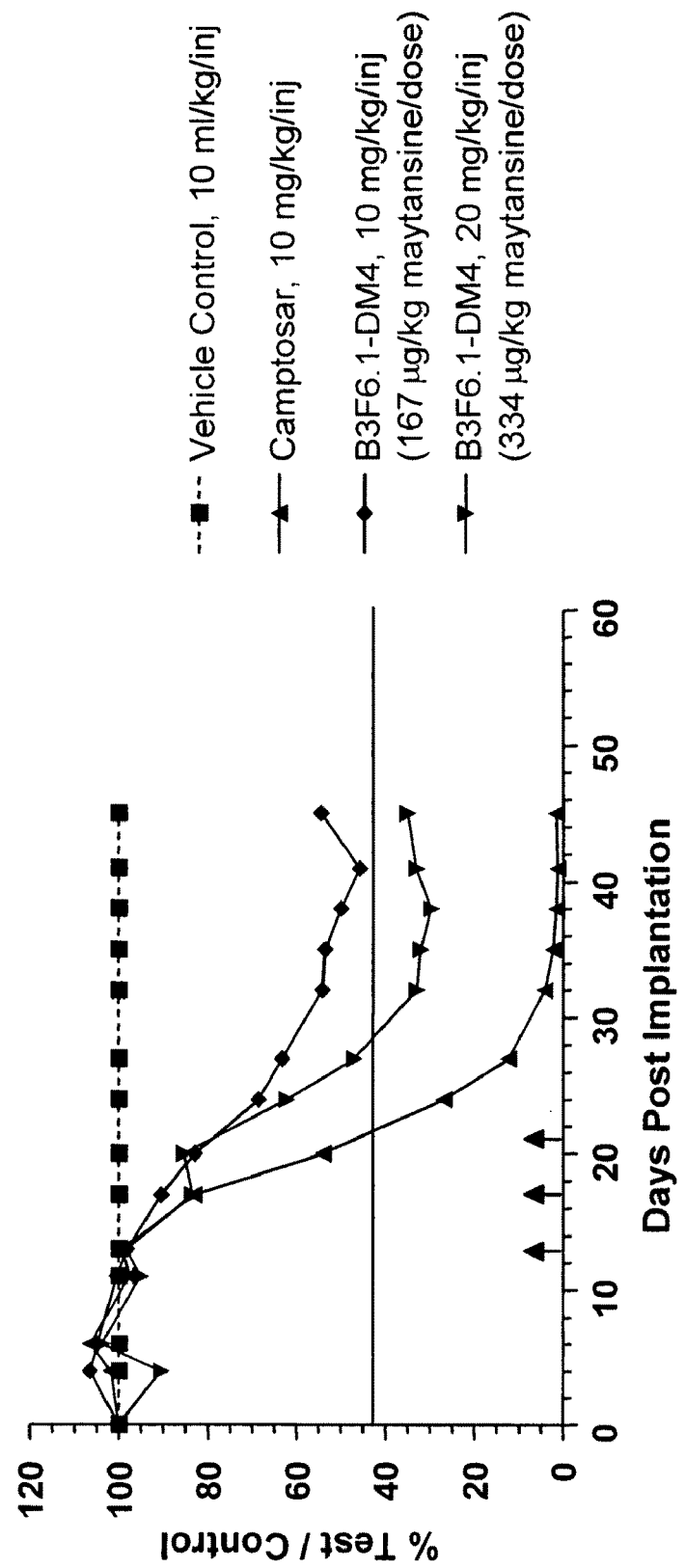

FIG. 28 shows the effect of full-length B3F6 conjugated to DM4 or Camptosar on established Calu-6 xenograft tumors in nude mice. The figure shows a comparison of test group mean tumor sizes as a percentage of the mean vehicle control tumor size. Nude mice bearing established Calu-6 xenograft tumors were treated with B3F6.1-DM4 at 10 (n=8) and 20 (n=8) mg/kg IV on Day 13, 17, and 21, vehicle (n=16) IV 3×/wk×4 starting on Day 14, and Camptosar (n=8) 10 mg/kg SC on Day 13-14, 17-21, 24-26. The bar indicates the National Cancer Institute's criteria for activity (42%).

Figure 29:
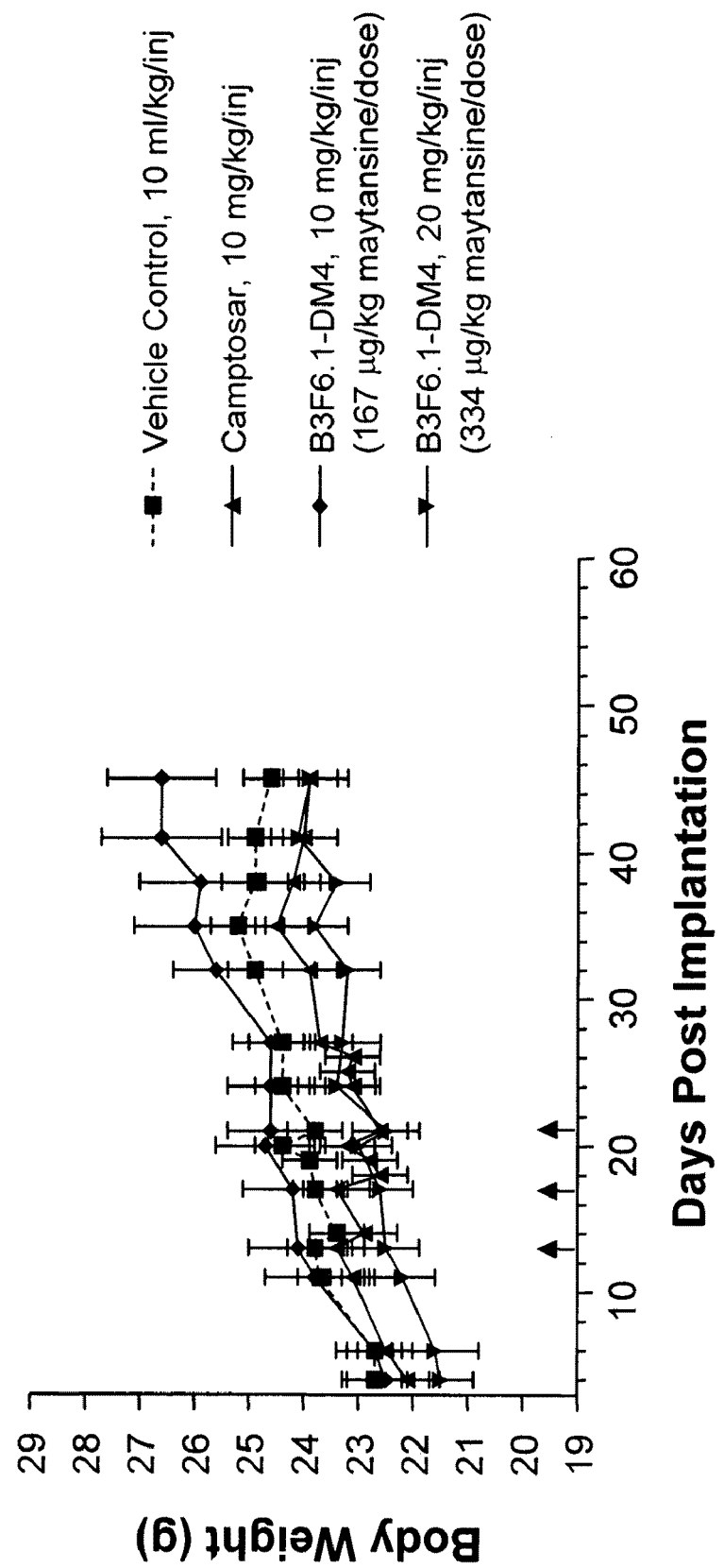

FIG. 29 shows mean body weights of nude mice bearing established Calu-6 xenograft tumors and treated with full-length B3F6 conjugated to DM4. The mice were treated with B3F6.1-DM4 at 10 (n=8) and 20 (n=8) mg/kg IV on Day 13, 17, and 21 (as indicated by arrows), vehicle (n=16) IV 3×/wk×4 starting on Day 14, and Camptosar (n=8) 10 mg/kg SC on Day 13-14, 17-21, 24-26. Vertical bars represent the standard error of the means.

Figure 30:
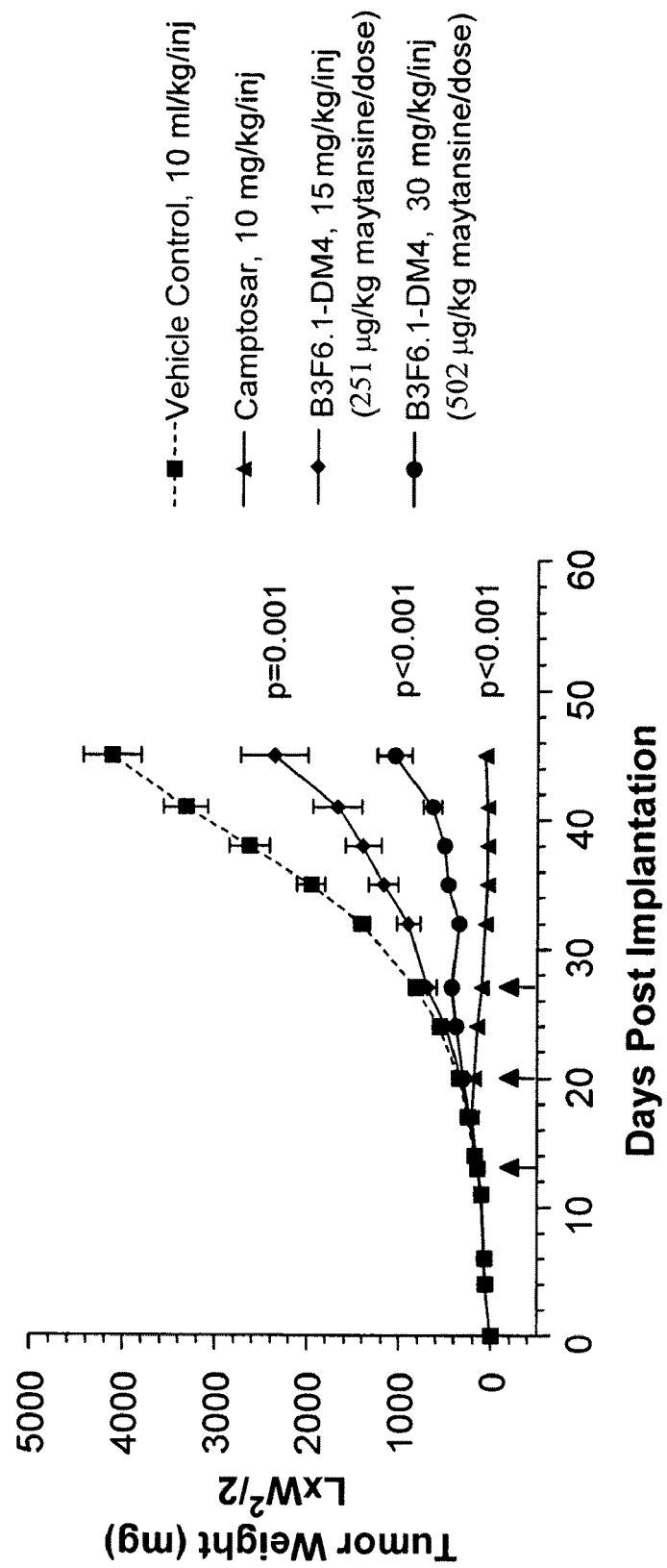

FIG. 30 shows the effects of full length B3F6 conjugated to DM4 or Camptosar on established Calu-6 xenograft tumors in nude mice. B3F6.1-DM4 at 15 (n=8) and 30 (n=8) mg/kg was administered IV q7dx3 (as indicated by the arrows), vehicle (n=16) administered IV 3×/wk×4 starting on Day 14, and Camptosar (n=8) 10 mg/kg administered SC on Day 13-14, 17-21, 24-26. The change in tumor weight of established Calu-6 xenograft tumors is shown. Vertical bars represent the standard error of the means.

Figure 31:
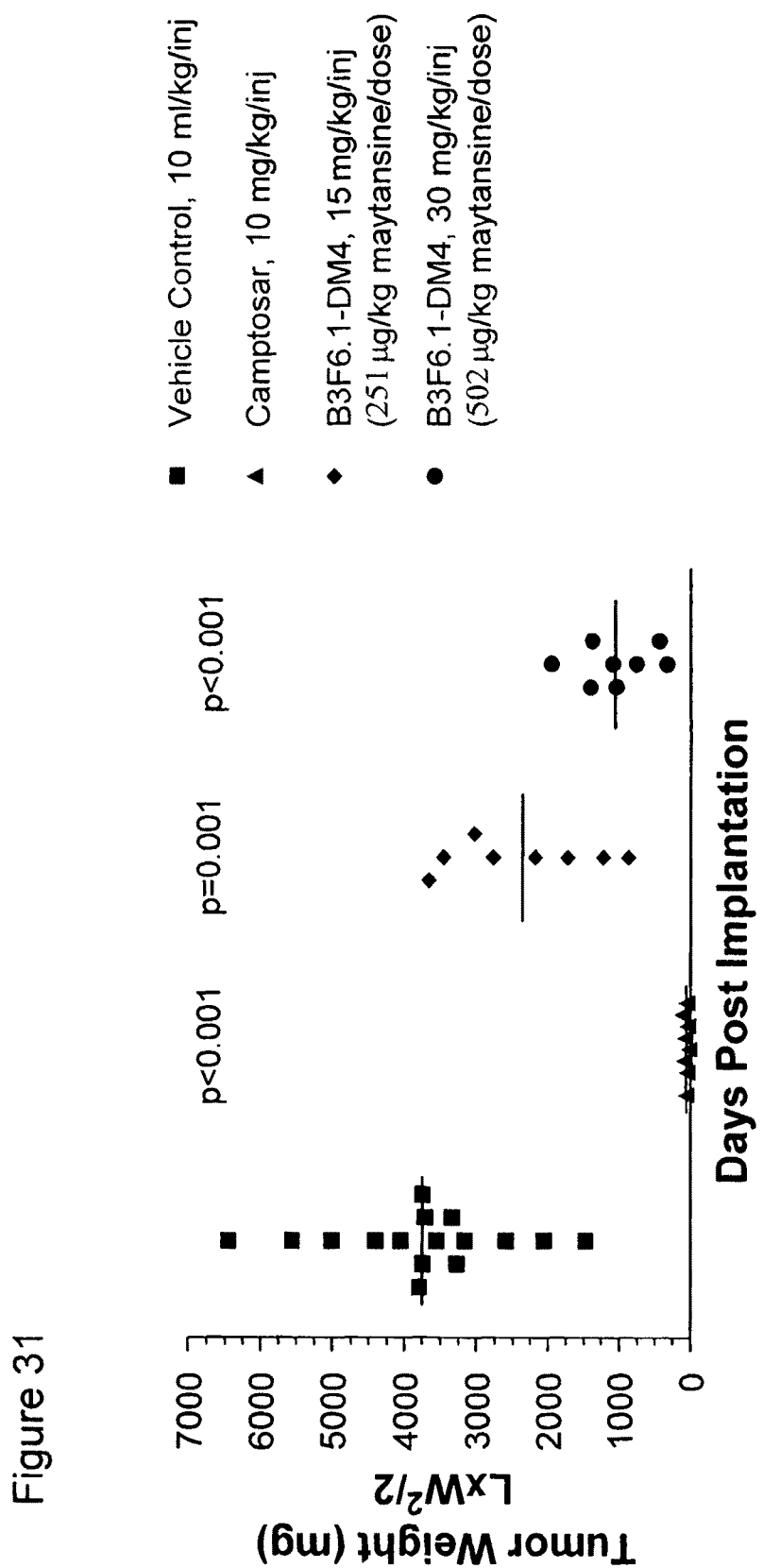

FIG. 31 shows the effect of full length B3F6.1-DM4 on established Calu-6 xenograft tumors in nude mice. Nude mice bearing established Calu-6 xenograft tumors were treated with B3F6.1-DM4 at 15 (n=8) and 30 (n=8) mg/kg IV q7dx3, vehicle (n=16) IV 3×/wk×4 starting on Day 14, and Camptosar (n=8) 10 mg/kg SC on Day 13-14, 17-21, 24-26. Each point represents the tumor weight of a single mouse, and bars represent the mean tumor weight for each group.

Figure 32:
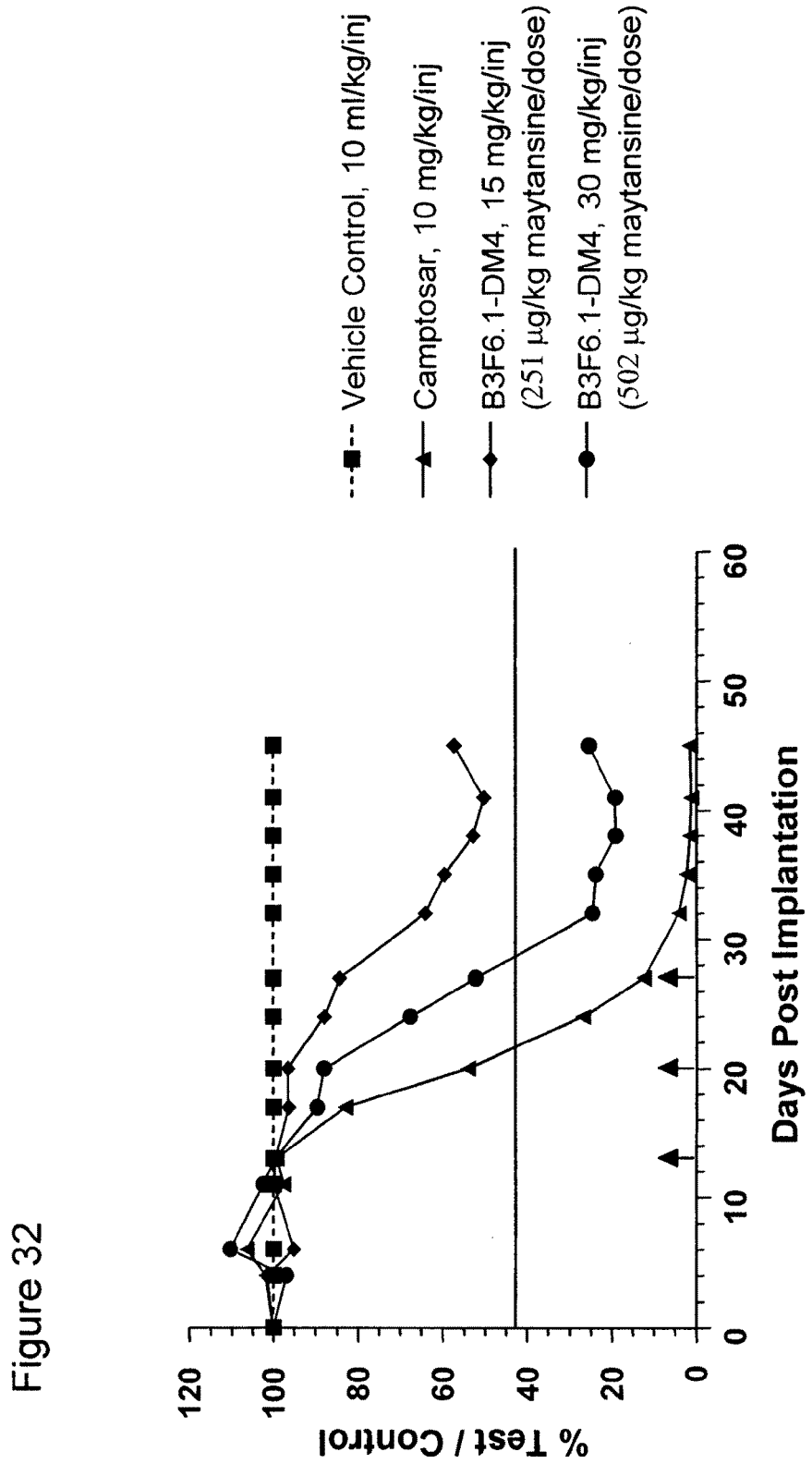

FIG. 32 shows the effect of full-length B3F6 conjugated to DM4 or Camptosar on established Calu-6 xenograft tumors in mice. The date are shown as a comparison of test group mean tumor sizes as a percentage of the mean vehicle control tumor size. Nude mice bearing established Calu-6 xenograft tumors were treated with B3F6.1-DM4 at 15 (n=8) and 30 (n=8) mg/kg IV q7dx3, vehicle (n=16) IV 3×/wk×4 starting on Day 14, and Camptosar (n=8) 10 mg/kg SC on Day 13-14, 17-21, 24-26. The bar indicates the National Cancer Institute's criteria for activity (42%).

Figure 33:
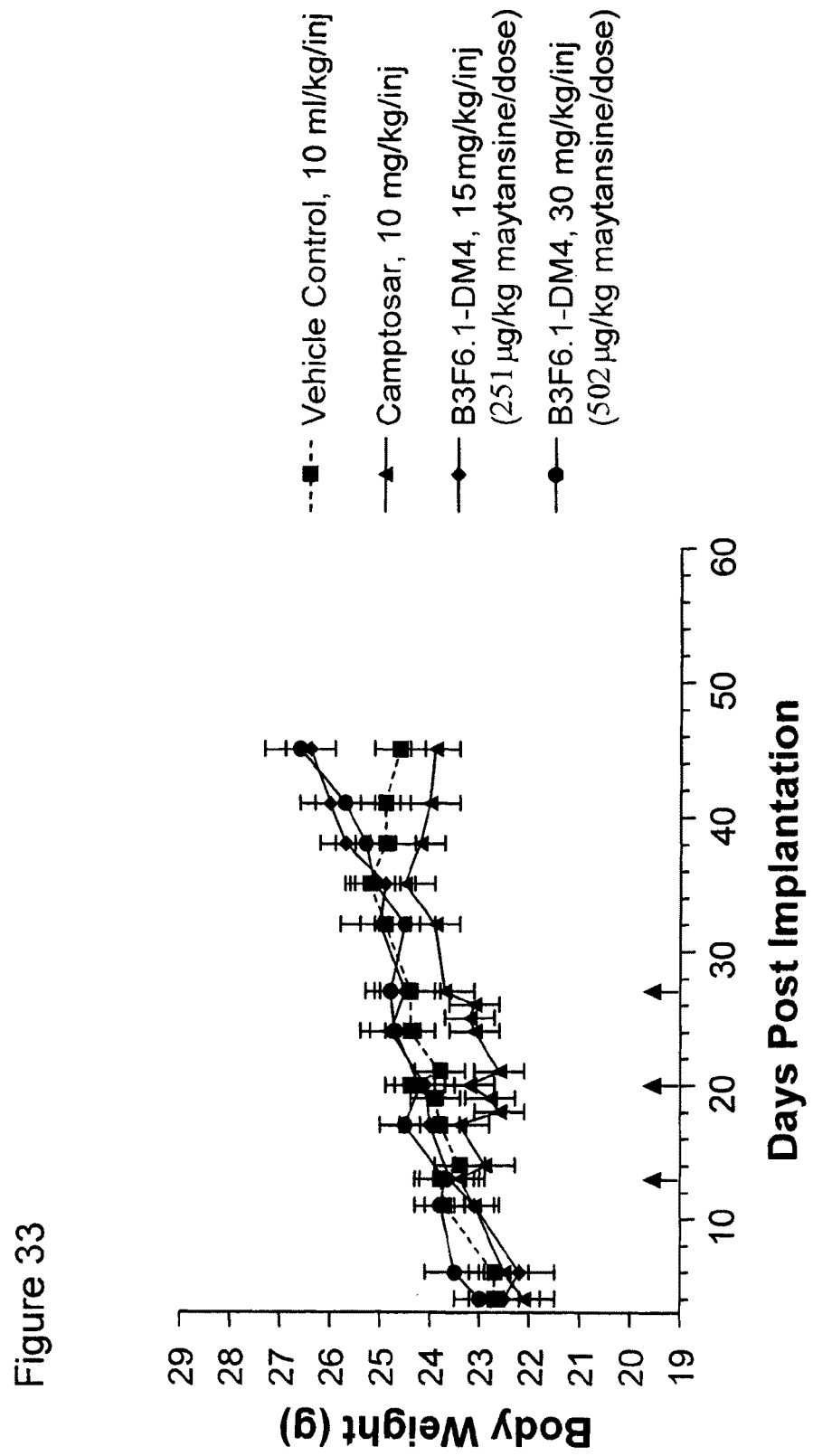

FIG. 33 shows body weights of nude mice bearing established Calu-6 human lung anaplastic tumors and treated with full length B3F6.1-DM4 at 15 (n=8) and 30 (n=8) mg/kg IV q7dx3 9 as indicated by the arrows), vehicle (n=16) IV 3×/wk×4 starting on Day 14, and irinotecan (n=8) 10 mg/kg SC on Day 13-14, 17-21, 24-26. Vertical bars represent the standard error of the means.

DETAILED DESCRIPTION OF THE INVENTION

The invention is based, at least in part, on the development of CDR grafted and other humanized anti-Cripto antibodies. More specifically, these antibodies are derived from the mouse antibody B3F6. As described herein, multiple forms of humanized anti-Cripto antibodies were developed and conjugated to maytansoids for testing in tumor cell models. The results demonstrate the utility of these antibodies for the inhibition of tumor cell growth in vivo. These humanized anti-Cripto antibodies are more suited than mouse antibodies for use in human subjects.

Both humanized full-length antibodies and humanized antibodies lacking CH2 domains have been made. Typically, recombinant CH2 domain deleted antibodies produced in cell cultures result in hinge heterogeneity, which leads to the presence of two forms of the antibody in solution. In native solutions, both of these forms are present as dimeric proteins (each monomer comprising one heavy chain and one light chain). One immunoglobulin molecule comprises a stable four chain construct of approximately 150-160 kDa in which the dimers are held together by an interchain heavy chain disulfide bond (Form A) and one comprises a form in which the dimers are not linked via interchain disulfide bonds (Form B). Form B also forms a stable dimer under native conditions, but can be identified under denaturing, non-reducing conditions, in which the heavy chains dissociate yielding a 75-80 kDa molecule. These forms have been extremely difficult to separate, even after MAb affinity purification.

The frequency of appearance of the B form in various intact IgG isotypes is due to, but not limited to, structural differences associated with the hinge region isotype of the MAb molecule. In fact, a single amino acid substitution in the hinge region of the human IgG4 hinge can significantly reduce the appearance of the B form (Angal et al. 1993. Molecular Immunology 30:105) to levels typically observed using a human IgG1 hinge. However, applying this same amino acid substitution to CH2 domain deleted antibodies does not eliminate Form B from preparations.

As described herein, inclusion of certain connecting peptides in the humanized Cripto binding molecules of the invention results in the preferential biosynthesis of polypeptide dimers that are linked via at least one interchain disulfide linkage or that are not linked via at least one interchain disulfide linkage.

Before further description of the invention, for convenience, certain terms are described below:

I. DEFINITIONS

The binding molecules of the invention are polypeptide molecules that comprise at least one binding domain which comprises a binding site that specifically binds to a human Cripto molecule. Exemplary sequences of human Cripto are shown in SEQ ID NO:6 (CR-1) and SEQ ID NO:7 (CR-3). CR-1 corresponds to the structural gene encoding the human Cripto protein expressed in the undifferentiated human teratocarcinoma cells and CR-3 corresponds to a complete copy of the mRNA containing seven base substitutions in the coding region representing both silent and replacement substitutions. CR-1 maps to chromosome 3, and CR-3 maps to Xq21-q22. Dono et al. 1991. *Am J Hum Genet*. 1991 49:555.

The binding molecules of the invention comprise at least one CDR derived from the murine B3F6 antibody. The murine B3F6 antibody binds to an epitope in the domain spanning amino acid residues 46-62 of Cripto. The hybridoma that makes the murine B3F6 antibody (also referred to B3F6.17) was deposited with the ATCC under ACCESSION NO. PTA-3319). The antibody was made by immunizing mice with a Cripto fusion protein expressed in CHO cells. The fusion protein used for immunization comprised amino acid residues 1 to 169 of Cripto [amino acids 1-169 of SEQ ID NO: 6], fused to a human IgG$_1$ Fc domain (the construct is referred to as CR(del C)-Fc). The methods for making the B3F6 antibody are described in more detail, e.g., in WO 02/088170.

As used herein the term "derived from" a designated protein refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, wherein the variant CDR sequences maintain Cripto binding activity.

It will also be understood by one of ordinary skill in the art that the binding molecules of the invention may be modified such that they vary in amino acid sequence from the B3F6 molecule from which they were derived. For example, nucleotide or amino acid substitutions leading to conservative substitutions or changes at "non-essential" amino acid residues may be made (e.g., in CDR and/or framework residues). The binding molecules of the invention maintain the ability to bind to Cripto.

An isolated nucleic acid molecule encoding a non-natural variant of a polypeptide can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence.

In one embodiment, the binding molecules comprise one binding site. In another embodiment, the binding molecules comprise at least two binding sites. In one embodiment, the binding molecules comprise two binding sites. In one embodiment, the binding molecules comprise three binding sites. In another embodiment, the binding molecules comprise four binding sites.

In one embodiment, the binding molecules of the invention are monomers. In another embodiment, the binding molecules of the invention are multimers. For example, in one embodiment, the inding molecules of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

Preferred binding molecules of the invention comprise framework and constant region amino acid sequences derived from a human amino acid sequence. However, binding polypeptides may comprise framework and/or constant region sequences derived from another mammalian species. For example, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid back mutations in which the corresponding murine amino acid residue is present. Preferred binding molecules of the invention are less immunogenic than the starting B3F6 murine antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof In one embodiment, a polypeptide of the invention comprises a polypeptide chain comprising a CH1 domain, at least a portion of a hinge domain, and a CH2 domain. In another embodiment, a polypeptide of the invention comprises a polypeptide chain comprising a CH1 domain and a CH3 domain. In another embodiment, a polypeptide of the invention comprises a polypeptide chain comprising a CH1 domain, at least a portion of a hinge domain, and a CH3 domain. In another embodiment, a polypeptide of the invention comprises a polypeptide chain comprising a CH3 domain. In one embodiment, a polypeptide of the invention lacks at least a portion of a CH2 domain (e.g., all or part of a CH2 domain). In another embodiment, a polypeptide of the invention comprises a complete Ig heavy chain. As set forth above, it will be understood by one of ordinary skill in the art that these domains (e.g., the heavy chain portions) may be modified such that they vary in amino acid sequence from the naturally occurring immunoglobulin molecule.

In one embodiment, at least two of the polypeptide chains of a binding molecule of the invention comprise at least one heavy chain portion derived from an antibody or immunoglobulin molecule. In one embodiment, at least two heavy chain portions of a polypeptide of the invention are present on different polypeptide chains and interact, e.g., via at least one disulfide linkage (Form A) or via non-covalent interactions (Form B) to form a dimeric polypeptide, each monomer of the dimer comprising at least one heavy chain portion.

In one embodiment, the heavy chain portions of one polypeptide chain of a dimer are identical to those on a second polypeptide chain of the dimer. In one embodiment, the monomers (or half-mers) of a dimer of the invention are identical to each other. In another embodiment, they are not identical. For example, each monomer may comprise a different target binding site.

In one embodiment, a dimer of the invention is held together by covalent interactions, e.g., disulfide bonds. In one embodiment, a dimer of the invention is held together by one or more disulfide bonds. In another embodiment, a dimer of the invention is held together by one or more, preferably two disulfide bonds. In another embodiment, a dimer of the invention is held together by one or more, preferably three disulfide bonds. In another embodiment, a dimer of the invention is held together by one or more, preferably four disulfide bonds. In another embodiment, a dimer of the invention is held together by one or more, preferably five disulfide bonds. In another embodiment a dimer of the invention is held together by one or more, preferably six disulfide bonds. In another embodiment, a dimer of the invention is held together by one or more, preferably seven disulfide bonds. In another embodiment, a dimer of the invention is held together by one or more, preferably eight disulfide bonds. In another embodiment, a dimer of the invention is held together by one or more, preferably nine disulfide bonds. In another embodiment, a dimer of the invention is held together by one or more, preferably ten disulfide bonds. In a further embodiment, a dimer of the invention is not held together by disulfide bonds, but is held together, e.g., by non-covalent interactions.

The heavy chain portions of a polypeptide may be derived from different immunoglobulin molecules. For example, a heavy chain portion of a polypeptide may comprise a CH1 domain derived from an IgG1 molecule and a hinge region derived from an IgG3 molecule. In another example, a heavy chain portion may comprise a hinge region derived, in part, from an IgG1 molecule and, in part, from an IgG3 molecule. In another example, a heavy chain portion may comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

In one embodiment a polypeptide of the invention comprises an amino acid sequence or one or more moieties not derived from an Ig molecule. Exemplary modifications are described in more detail below. For example, in one embodiment, a polypeptide of the invention may comprise a flexible linker sequence. In another embodiment, a polypeptide may be modified to add one or more functional moieties (e.g., PEG, a drug, a prodrug, and/or a detectable label).

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric polypeptides include fusion proteins and the chimeric hinge connecting peptides of the invention.

In one embodiment, a binding polypeptide of the invention is a fusion protein. In one embodiment, a fusion protein of the invention is a chimeric molecule that comprises a binding domain (which comprises at least one binding site) and a dimerization domain (which comprises at least one heavy chain portion). The heavy chain portion may be from any immunoglobulin, such as IgG1, IgG2, IgG3, or IgG4 subtypes, IgA, IgE, IgD or IgM. In one embodiment, a fusion protein further comprises a synthetic connecting peptide.

In another embodiment of the invention, a binding molecule is an "antibody-fusion protein chimera." Such molecules comprise a molecule which combines at least one binding domain of an antibody with at least one fusion protein. Preferably, the interface between the two polypeptides is a CH3 domain of an immunoglobulin molecule.

The term "heterologous" as applied to a polynucleotide or a polypeptide, means that the polynucleotide or polypeptide is derived from a genotypically distinct entity from that of the rest of the entity to which it is being compared. For instance, a heterologous polynucleotide or antigen may be derived from a different species, different cell type, or the same type of cell of distinct individuals.

The term "ligand binding domain" or "ligand binding portion" as used herein refers to any native receptor (e.g., cell surface receptor) or any region or derivative thereof retaining at least a qualitative ligand binding ability, and preferably the biological activity of a corresponding native receptor.

The term "receptor binding domain" or "receptor binding portion" as used herein refers to any native ligand or any region or derivative thereof retaining at least a qualitative receptor binding ability, and preferably the biological activity of a corresponding native ligand.

In one embodiment, the binding molecules of the invention are "antibody" or "immunoglobulin" molecules, e.g., naturally occurring antibody or immunoglobulin molecules (or an antiben binding fragment thereof) or genetically engineered antibody molecules that bind antigen in a manner similar to antibody molecules. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

As used herein the term "variable region CDR amino acid residues" includes amino acids in a CDR or complementarity determining region as identified using sequence or structure based methods. As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein the term "variable region framework (FR) amino acid residues" refers to those amino acids in the framework region of an Ig chain. The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments, the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains.

The term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

As used herein, the term "binding site" comprises a region of a polypeptide which is responsible for selectively binding to a target molecule of interest (e.g. an antigen, ligand, receptor, substrate or inhibitor). Binding domains comprise at least one binding site. Exemplary binding domains include an antibody variable domain, a receptor binding domain of a ligand, a ligand binding domain of a receptor or an enzymatic domain.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules have at least one binding site specific for a human Cripto molecule.

The term "specificity" refers to the ability to specifically bind (e.g., immunoreact with) a given target. A polypeptide may be monospecific and contain one or more binding sites which specifically bind a target or a polypeptide may be multispecific and contain two or more binding sites which specifically bind the same or different targets.

In one embodiment, a binding molecule of the invention is specific for more than one target. For example, in one embodiment, a multispecific binding molecule of the invention binds to Cripto and a second molecule expressed on a tumor cell. Exemplary antibodies which comprise antigen binding sites that bind to antigens expressed on tumor cells are known in the art and one or more CDRs from such antibodies can be included in a binding molecule of the invention. Exemplary antibodies include: 2B8, Lym 1, Lym 2, LL2, Her2, B1, MB1, BH3, B4, B72.3, 5 E8, and 5E10. In a preferred embodiment, a polypeptide of the invention is a C2B8 antibody which binds to CD20. In another preferred embodiment, a polypeptide of the invention is a CC49 antibody which recognizes TAG72.

In one embodiment, a binding molecule of the invention comprises a connecting peptide. The connecting peptides of the invention are synthetic. As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

Connecting peptides of the invention connect two domains (e.g., a binding domain and a dimerization domain) of a binding molecule of the invention. For example, connecting peptides connect a heavy chain portion to a binding domain comprising a binding site. In one embodiment, a connecting peptide connects two heavy chain constant region domains, such as CH1 and CH2 domains; CH1 and CH3 domains; hinge and CH1 domains; hinge and CH3 domains; VH and hinge domains, or a CH3 domain and a non-immunoglobulin polypeptide) in a linear amino acid sequence of a polypeptide chain. Preferably, such connecting peptides provide flexibility to the binding molecule and facilitate dimerization via disulfide bonding. In one embodiment, the connecting peptides of the invention are used to replace one or more heavy chain domains (e.g., at least a portion of a constant region domain (e.g., at least a portion of a CH2 domain) and/or at least a portion of the hinge region (e.g., at least a portion of the lower hinge region domain) in a domain deleted construct). For example, in one embodiment, a VH domain is fused to a CH3 domain via a connecting peptide (the C-terminus of the connecting peptide is attached to the N-terminus of the CH3 domain and the N-terminus of the connecting peptide is attached to the C-terminus of the VH domain). In another embodiment, a VL domain is fused to a CH3 domain via a connecting peptide (the C-terminus of the connecting peptide is attached to the N-terminus of the CH3 domain and the N-terminus of the connecting peptide is attached to the C-terminus of the VL domain. In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain).

In one embodiment, a synthetic connecting peptide comprises a portion of a constant region domain. For example, in one embodiment, a connecting peptide that replaces a CH2 domain may comprise a portion of the CH2 domain.

In one embodiment, a connecting peptide comprises or consists of a gly-ser linker. As used herein, the term "gly-ser linker" refers to a peptide that consists of glycine and serine residues An exemplary gly/ser linker comprises the amino acid sequence GGGSSGGGSG (SEQ ID NO:8). In one embodiment, a connecting peptide of the invention comprises at least a portion of an upper hinge region (e.g., derived from an IgG1, IgG3, or IgG4 molecule), at least a portion of a middle hinge region (e.g., derived from an IgG1, IgG3, or IgG4 molecule) and a series of gly/ser amino acid residues (e.g., a gly/ser linker such as GGGSSGGGSG (SEQ ID NO:8)). In one embodiment, the connecting peptide comprises a substitution of one or more amino acids as compared to naturally occurring IgG1 or IgG3 hinge regions. In another embodiment, a connecting peptide comprises an amino acid sequence such as described in WO 02/060955. Connecting peptides are described in more detail below.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

In one embodiment, a binding molecule of the invention comprises an antibody binding site. For example, in one embodiment, a binding molecule of the invention is a full-length antibody molecule. In another embodiment, a binding molecule of the invention is a fragment of an antibody molecule. In another embodiment, binding molecule of the invention is a modified or synthetic antibody molecule.

Binding molecules of the invention can be made using techniques that are known in the art. In one embodiment, the polypeptides of the invention are antibody molecules that have been "recombinantly produced," i.e., are produced using recombinant DNA technology. Exemplary techniques for making antibody molecules are discussed in more detail below.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a binding molecule of the invention is a fusion protein comprising at least one heavy chain portion lacking a CH2 domain and comprising a binding domain of a polypeptide comprising the binding portion of one member of a receptor ligand pair.

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. More preferably, one entire domain of the constant region of the modified antibody will be deleted and even more preferably all or part of the CH2 domain will be deleted.

In preferred embodiments, a polypeptide of the invention will not elicit a deleterious immune response in a human.

In one embodiment, a binding molecule of the invention comprises a constant region, e.g., a heavy chain constant region, which is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Exemplary modifications include additions, deletions or substitutions of one or more amino acids in one or more domains.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein the term "medium that separates polypeptides based on hydrophobic interaction" includes a medium comprising hydrophobic ligands (e.g., alkyl or aryl groups) covalently attached to a matrix. Such a medium can be used to separate polypeptides based on interaction between a solvent and accessible non-polar groups on the surface of the polypeptides and the hydrophobic ligands of the medium. An exemplary medium is Phenyl 5PW-HR available from Tosoh Bioscience.

As used herein, the term "conductivity" includes electrical conductivity of a solution as measured in microSiemens/cm (formerly micromhos/cm). The greater the ion content of a solution, the greater the conductivity of the solution. Conductivity can be readily measured using techniques that are well known in the art (e.g., by measuring the current passing between two electrodes).

The separation methods of the invention can be used with solutions having a pH ranging from acid to neutral, e.g., from about pH 3.5 to approximately neutral. As used herein, the term "approximately neutral pH" includes pH values of approximately 7. For example, in one embodiment, a separation method of the invention can be performed using a solution (e.g., a buffer) having a pH of about 3, about 4, about 5, about 6, about 7, or about 8. Preferably, the pH of the solution is about 6 or about 7. In one embodiment, the pH of the solution is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

As used herein the term "affinity matrix" includes a matrix, such as agarose, controlled pore glass, or poly (styrenedivinyl) benzene to which an affinity ligand is attached. The affinity ligand binds to the desired polypeptide and the contaminating polypeptides are not bound to the affinity ligand. The desired polypeptide can be eluted from the affinity matrix using known protocols.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the binding molecules of the invention are engineered, e.g., to express a connecting peptide of the invention.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the binding molecule can be used in unconjugated form or can be conjugated, e.g., to a drug, prodrug, or an isotope.

II. Humanization

In one embodiment, the binding molecules of the invention comprise or are derived from at least one humanized B3F6 antibody variable region, e.g., a light chain or heavy chain variable region.

The term "humanized antibody" refers to an antibody comprising at least one chain comprising variable region framework residues substantially from a human antibody chain (referred to as the "acceptor antibody") and at least one complementarity determining region ("CDR") substantially from a non-human antibody, (referred to as the "donor antibody"). The constant region(s), if present, are also substantially or entirely from a human immunoglobulin.

The CDRs of murine B3F6 are set forth below in Table 1:

TABLE 1

| B3F6 CDR Sequences (Kabat Definition) | | |
|---|---|---|
| CDR L1 | RSSQSIVHSNGNTYLE | SEQ ID NO: 9 |
| CDR L2 | KVSNRFS | SEQ ID NO: 10 |
| CDR L3 | FQGSHVPLT | SEQ ID NO: 11 |
| CDR H1 | SYWIH | SEQ ID NO: 12 |
| CDR H2 | ENDPSNGRTNYNEKFKN | SEQ ID NO: 13 |
| CDR H3 | GPNYFYSMDY | SEQ ID NO: 14 |

In one embodiment, an antigen binding molecule of the invention comprises at least one heavy or light chain CDR of a B3F6 antibody molecule. In another embodiment, an antigen binding molecule of the invention comprises at least two CDRs a B3F6 antibody molecule. In another embodiment, an antigen binding molecule of the invention comprises at least three CDRs from a B3F6 antibody molecule. In another embodiment, an antigen binding molecule of the invention comprises at least four CDRs from a B3F6 antibody molecule. In another embodiment, an antigen binding molecule of the invention comprises at least five CDRs from a B3F6 antibody molecule. In another embodiment, an antigen binding molecule of the invention comprises at least six CDRs from a B3F6 antibody molecule. In one embodiment, the at least one CDR (or at least one CDR from the greater than one B3F6 CDRs that are present in the binding molecule) is modified to vary in sequence from the CDR of a naturally occurring B3F6 molecule, yet retains the ability to bind to B3F6.

Humanized antibodies can be produced using recombinant DNA technology, see for example, e.g., Queen et al., *Proc. Natl. Acad Sci. USA*, (1989), 86:10029-10033; Jones et al., *Nature*, (1986), 321:522-25; Riechmann et al., *Nature*, (1988), 332:323-27; Verhoeyen et al., *Science*, (1988), 239: 1534-36; Orlandi et al., *Proc. Natl. Acad Sci. USA*, (1989), 86:3833-37; U.S. Pat. Nos. 5,225,539; 5,530,101; 5,585,089; 5,693,761; 5,693,762; 6,180,370.

When a preferred nonhuman donor antibody has been selected for humanization, an appropriate human acceptor antibody may be obtained, e.g., from sequence databases of expressed human antibody genes, from germline Ig sequences or a consensus sequence of several human antibodies. The substitution of nonhuman CDRs into a human variable domain framework is most likely to result in retention of their correct spatial orientation if the human variable domain framework adopts the same or similar conformation to the nonhuman variable framework from which the CDRs originated. This is achieved by obtaining the human variable domains from human acceptor antibodies whose framework sequences exhibit a high degree of sequence identity with the nonhuman variable framework domains from which the CDRs were derived. The heavy and light chain variable framework regions can be derived from the same or different human antibody sequences. Preferably the human acceptor antibody retains the canonical and interface residues of the donor antibody. Additionally, the human acceptor antibody preferably has substantial similarity in the length of CDR loops. See Kettleborough et al., *Protein Engineering* 4:773 (1991); Kolbinger et al., *Protein Engineering* 6:971 (1993) and Carter et al., WO 92/22653.

Having identified the CDRs of the donor antibody and appropriate human acceptor antibody, the next step is to determine which, if any, residues from these components should be substituted to optimize the properties of the resulting humanized antibody. Typically, some or all of the amino acids of the nonhuman, donor immunoglobulin light or heavy chain that are required for antigen binding (e.g., one or more CDRs) are used to substitute for the corresponding amino acids from the light or heavy chain of the human acceptor antibody. The human acceptor antibody retains some or all of the amino acids that are not required for antigen binding. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis.

When necessary, one or more residues in the human framework regions can be changed to residues at the corresponding positions in the murine antibody so as to preserve the binding affinity of the humanized antibody to the antigen. This change is sometimes called "back mutation." Certain amino acids from the human variable region framework residues are selected for back mutation based on their possible influence on CDR conformation and/or binding to antigen. The placement of murine CDR regions with human variable framework region can result in conformational restraints, which, unless corrected by substitution of certain amino acid residues, lead to loss of binding affinity.

In one embodiment, the selection of amino acid residues for back mutation can determined, in part, by computer modeling, using art recognized techniques. In general, molecular models are produced starting from solved structures for immunoglobulin chains or domains thereof The chains to be modeled are compared for amino acid sequence similarity with chains or domains of solved three-dimensional structures (e.g., X-ray structures) and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

In another embodiment, a knowledge based approach or database analysis may be used for humanization. For example, such humanization strategy may be based on visual inspection and analysis of V region sequences according to the methods described in Rosok et al (Rosok M J, et al., 1996. J. Biol. Chem. 271: 22611-22618). Canonical determinants, surface residues, and potential contact residues are identified. Potential contact residues are noted and broadly classified according to the structural definition of CDR loops as defined by Chothia et al. (Chothia C and Lesk A M. 1987. J. Mol. Biol. 196: 901-917), sequence hypervariability as defined by Kabat et al. (Kabat E A, Wu T T, Reid-Miller M, Parry H M, and Gottesman K S. 1987. Sequences of Protein of Immunological Interest, U.S. department of Health and Human Services, NIH, Bethesda, Md.), and potential antigen contact residues as defined by MacCallum et al. (MacCallum R M, Martin A C R, and Thorton J M. 1996. J. Mol. Biol. 262: 732-745). Murine CDR loops, according to Kabat numbering and definition, are grafted in their entirety onto the acceptor human framework. Packing residues as defined by Padlan (Padlan E A. 1991. Mol Immunol. 28: 489-498) are identified and an attempt is made to conserve the packing residues in accordance with the strategy described in Singer et al. (Singer I I et al. 1993. J. Immunol. 150: 2844-2857). Each residue in the framework sequence is assigned a low, medium, or high "risk position" for antibody humanization as described in Harris and Bajorath (Harris L and Bajorath J. 1995. Protein Science 4: 306-310).

In general, low risk positions are kept human. For many of the nonidentical medium and high risk amino acid positions reference may be made to public or proprietary collections of humanized antibody sequences. In review of previously humanized antibody sequences, whether the inclusion of a human or murine (backmutation) amino acid residue resulted in functional binding activity was noted. In those cases where a substitution is considered, reference may be made to an amino acid substitution map (D. Bordo and P. Argos. 1991. J. Mol. Biol. 217: 721-729) to confirm the functional interchangeability of the residues.

The selection of amino acid residues for substitution can also be determined, in part, by examination of the characteristics of the amino acids at particular locations, or empirical observation of the effects of substitution or mutagenesis of particular amino acids. For example, when an amino acid differs between a nonhuman variable region framework residue and a selected human variable region framework residue, the human framework amino acid should usually be substituted by the equivalent framework amino acid from the nonhuman donor antibody when the amino acid from the donor antibody is a canonical residue, an interface packing residue, or an unusual or rare residue that is close to the binding site.

In one embodiment, a binding molecule of the invention further comprises at least one backmutation of a human amino acid residue to the corresponding mouse amino acid residue where the amino acid residue is an interface packing residue. "Interface packing residues" include those residues at the interface between VL and VH as defined, for example, by Novotny and Haber, Proc. Natl. Acad. Sci. USA, 82:4592-66 (1985).

In one embodiment, a binding molecule of the invention further comprises at least one backmutation of a human amino acid residue to the corresponding mouse amino acid residue is a canonical residue. "Canonical residues" are conserved framework residues within a canonical or structural class known to be important for CDR conformation (Tramontano et al., J. Mol. Biol. 215:175 (1990), all of which are incorporated herein by reference). Canonical residues include 2, 25, 27B, 28, 29, 30, 33, 48, 51, 52, 64, 71, 90, 94 and 95 of the light chain and residues 24, 26, 27 29, 34, 54, 55, 71 and 94 of the heavy chain. Additional residues (e.g., CDR structure-determining residues) can be identified according to the methodology of Martin and Thorton (1996) J. Mol. Biol. 263:800.

In one embodiment, a binding molecule of the invention further comprises at least one backmutation of a human amino acid residue to the corresponding mouse amino acid residue where the amino acid residue is at a position capable of interacting with a CDR. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs.

Exemplary techniques for selection of framework residues for substitution are set forth, for example, in U.S. Pat. No. 5,585,089. In that patent several categories of human framework amino acids which may be altered are described. In one embodiment, a category 2 amino acid is backmutated to the corresponding murine residue. Specifically, category 2 amino acids are amino acids in the framework of the human acceptor immunoglobulin which are unusual (i.e., "rare", which as used herein indicates an amino acid occurring at that position in less than about 20% but usually less than about 10% of human heavy (respectively light) chain V region sequences in a representative data bank), and if the donor amino acid at that position is typical for human sequences (i.e., "common", which as used herein indicates an amino acid occurring in more than about 25% but usually more than about 50% of sequences in a representative data bank), then the non-human donor amino acid (e.g., murine amino acid) rather than the human acceptor amino acid may be selected. This criterion helps ensure that an atypical amino acid in the human framework does not disrupt the antibody structure. Moreover, by replacing an unusual amino acid with an amino acid from the donor antibody that happens to be typical for human antibodies, the humanized antibody may be made less immunogenic.

All human light and heavy chain variable region sequences are respectively grouped into "subgroups" of sequences that are especially homologous to each other and have the same amino acids at certain critical positions (Kabat et al., op. cit.). When deciding whether an amino acid in a human acceptor sequence is "rare" or "common" among human sequences, it will often be preferable to consider only those human sequences in the same subgroup as the acceptor sequence.

In one embodiment, a category 3 amino acid is backmutated to the corresponding murine residue. Residues in category 3 are adjacent to one or more of the 3 CDR's in the primary sequence of the humanized immunoglobulin chain, the donor amino acid(s) rather than acceptor amino acid may be selected. These amino acids are particularly likely to interact with the amino acids in the CDR's and, if chosen from the acceptor, to distort the donor CDR's and reduce affinity. Moreover, the adjacent amino acids may interact directly with the antigen (Amit et al., Science, 233, 747-753 (1986)) and selecting these amino acids from the donor may be desirable to keep all the antigen contacts that provide affinity in the original antibody.

In one embodiment, a category 4 amino acid is backmutated to the corresponding murine residue. Category 4 amino acids are those which in 3-dimensional model typically of the original donor antibody, shows that certain amino acids outside of the CDR's are close to the CDR's and have a good probability of interacting with amino acids in the CDR's by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units of some atom in the CDR's and must contain an atom that could interact with the CDR atoms according to established chemical forces, such as those listed above.

In the case of atoms that may form a hydrogen bond, the 3 angstroms is measured between their nuclei, but for atoms that do not form a bond, the 3 angstroms is measured between their Van der Waals surfaces. Hence, in the latter case, the nuclei must be within about 6 angstroms (3+sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids in the framework that are capable of interacting with amino acids in the CDR's, and which therefore belong to Category 4, may be distinguished in another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a 3-dimensional model of an antibody, using algorithms known in the art (e.g., Connolly, J. Appl. Cryst. 16, 548 (1983) and Lee and Richards, J. Mol. Biol. 55, 379 (1971)). Framework amino acids may also occasionally interact with the CDR's indirectly, by affecting the conformation of another framework amino acid that in turn contacts the CDR's.

The amino acids at several positions in the framework are known to be capable of interacting with the CDRs in many antibodies (Chothia and Lesk, J. Mol. Biol. 196, 901 (1987), Chothia et al., Nature 342, 877 (1989), and Tramontano et al., J. Mol. Biol. 215, 175 (1990), all of which are incorporated herein by reference), notably at positions 2, 48, 64 and 71 of the light chain and 26-30, 71 and 94 of the heavy chain (numbering according to Kabat, op. cit.), and therefore these amino acids will generally be in Category 4. Typically, humanized immunoglobulins of the present invention will include donor amino acids (where different) in category 4 in addition to these. The amino acids at positions 35 in the light chain and 93 and 103 in the heavy chain are also likely to interact with the CDRs. Accordingly, in one embodiment, one or more donor amino acid rather than the acceptor amino acid (when they differ) may be included in a humanized immunoglobulin. On the other hand, certain positions that may be in Category 4 such as the first 5 amino acids of the light chain may sometimes be chosen from the acceptor immunoglobulin without loss of affinity in the humanized immunoglobulin.

In addition to the above categories which describe when an amino acid in the humanized immunoglobulin may be taken from the donor, certain amino acids in the humanized immunoglobulin may be taken from neither the donor nor acceptor, if they fall into Category 5. If the amino acid at a given position in the donor immunoglobulin is "rare" for human sequences, and the amino acid at that position in the acceptor immunoglobulin is also "rare" for human sequences, as defined above, then the amino acid at that position in the humanized immunoglobulin may be chosen to be some amino acid "typical" of human sequences. A preferred choice is the amino acid that occurs most often at that position in the known human sequences belonging to the same subgroup as the acceptor sequence.

In one embodiment, a binding molecule of the invention comprises three B3F6 light chain CDRs (CDRL1, CDRL2, and CDRL3) and a human light chain framework region. In one embodiment, a binding molecule of the invention further comprises a least one backmutation of a human amino acid residue to the corresponding mouse amino acid residue at at least one position selected from the group consisting of: 2 and 100. In one embodiment, a binding molecule of the invention further comprises one backmutation of a human amino acid residue to the corresponding mouse amino acid residue at one position selected from the group consisting of: 2 and 100. In another embodiment the binding molecule comprises backmutations at positions 2 and 100 of the humanized B3F6 light chain. In another embodiment, a binding molecule of the invention comprises a backmuation at position 2 of the humanized B3F6 light chain and at least one additional backmutation. In another embodiment, a binding molecule of the invention comprises a backmuation at position 100 of the humanized B3F6 fight chain and at least one additional backmutation.

In one embodiment, a binding molecule of the invention comprises three B3F6 heavy chain CDRs (CDRH1, CDRH2, and CDRH3) and a human heavy chain framework region. In one embodiment, a binding molecule of the invention comprises a least one backmutation of a human amino acid residue to the corresponding mouse amino acid residue at at least one position selected from the group consisting of: 1, 48, 67, 71, 73, 81, 82b, 93, and 112. In one embodiment, a binding molecule of the invention comprises one backmutation of a human amino acid residue to the corresponding mouse amino acid residue at one position selected from the group consisting of: 1, 48, 67, 71, 73, 81, 82b, 93, and 112. In one embodiment, a binding molecule of the invention comprises two backmutations of a human amino acid residue to the corresponding mouse amino acid residue at two positions selected from the group consisting of: 1, 48, 67, 71, 73, 81, 82b, 93, and 112. In one embodiment, a binding molecule of the invention comprises three backmutations of a human amino acid residue to the corresponding mouse amino acid residue at three positions selected from the group consisting of: 1, 48, 67, 71, 73, 81, 82b, 93, and 112. In one embodiment, a binding molecule of the invention comprises four backmutations of a human amino acid residue to the corresponding mouse amino acid residue at four positions selected from the group consisting of: 1, 48, 67, 71, 73, 81, 82b, 93, and 112. In one embodiment, a binding molecule of the invention comprises five backmutations of a human amino acid residue to the corresponding mouse amino acid residue at five positions selected from the group consisting of: 1, 48, 67, 71, 73, 81, 82b, 93, and 112. In one embodiment, a binding molecule of the invention comprises six backmutations of a human amino acid residue to the corresponding mouse amino acid residue at six three positions selected from the group consisting of: 1, 48, 67, 71, 73, 81, 82b, 93, and 112. In one embodiment, a binding molecule of the invention comprises seven backmutations of a human amino acid residue to the corresponding mouse amino acid residue at seven positions selected from the group consisting of: 1, 48, 67, 71, 73, 81, 82b, 93, and 112. In one embodiment, a binding molecule of the invention further comprises backmutations of a human amino acid residue to the corresponding mouse amino acid residue at eight positions selected from the group consisting of: 1, 48, 67, 71, 73, 81, 82b, 93, and 112. In one embodiment, a binding molecule of the invention comprises nine backmutations of a human amino acid residue to the corresponding mouse amino acid residue at nine positions selected from the group consisting of: 1, 48, 67, 71, 73, 81, 82b, 93, and 112.

In one embodiment, the invention pertains to humanized variable regions of the B3F6 antibody and polypeptides comprising such humanized variable regions.

In one embodiment, a binding molecule of the invention comprises a CDR grafted light chain variable region sequence shown in amino acids 1-112 of SEQ ID NO:52. In one embodiment, a binding molecule of the invention comprises a CDR grafted light chain variable region sequence shown in amino acids 1-121 of SEQ ID NO:55.

In one embodiment, a binding molecule of the invention comprises a light chain version 1 variable region sequence shown in SEQ ID NO:47. In one embodiment, a binding molecule of the invention comprises a heavy chain version 1 variable region sequence shown in SEQ ID NO:48. In one embodiment, a binding molecule of the invention comprises a heavy chain version 2 variable region sequence shown in SEQ ID NO:49.

In another embodiment, a binding molecule of the invention comprises a light chain version 2 variable region sequence shown in SEQ ID NO:50. In one embodiment, a binding molecule of the invention comprises a heavy chain version 3 variable region sequence shown in SEQ ID NO:51.

In one embodiment, a binding molecule of the invention comprises a CDR grafted light chain shown in SEQ ID NO:52. In one embodiment, a binding molecule of the invention comprises a version 1 light chain shown in SEQ ID NO:53. In one embodiment, a binding molecule of the invention comprises a version 2 light chain shown in SEQ ID NO:54.

In one embodiment, a binding molecule of the invention comprises a CDR grafted heavy chain shown in SEQ ID NO:55. In one embodiment, a binding molecule of the invention comprises a version 1 heavy chain shown in SEQ ID NO:56. In one embodiment, a binding molecule of the invention comprises a version 2 heavy chain shown in SEQ ID NO:57. In one embodiment, a binding molecule of the invention comprises a version 3 heavy chain shown in SEQ ID NO:58.

In one embodiment, a binding molecule of the invention comprises a CDR grafted domain deleted heavy chain shown in SEQ ID NO:59. In one embodiment, a binding molecule of the invention comprises a version 1 domain deleted heavy chain shown in SEQ ID NO:60. In one embodiment, a binding molecule of the invention comprises a version 2 domain deleted heavy chain shown in SEQ ID NO:61. In one embodiment, a binding molecule of the invention comprises a version 3 domain deleted heavy chain shown in SEQ ID NO:62.

In one embodiment, a binding molecule of the invention comprises a CDR grafted light chain sequence shown in SEQ ID NO:63, which includes an optional signal sequence. In one embodiment, a binding molecule of the invention comprises a version 1 light chain sequence shown in SEQ ID NO:64, which includes an optional signal sequence. In one embodiment, a binding molecule of the invention comprises a version 2 light chain sequence shown in SEQ ID NO:65, which includes an optional signal sequence.

In one embodiment, a binding molecule of the invention comprises a CDR grafted heavy chain sequence shown in SEQ ID NO:66, which includes an optional signal sequence. In one embodiment, a binding molecule of the invention comprises a version 1 heavy chain sequence shown in SEQ ID NO:67, which includes an optional signal sequence. In one embodiment, a binding molecule of the invention comprises a version 2 heavy chain sequence shown in SEQ ID NO:68, which includes an optional signal sequence. In one embodiment, a binding molecule of the invention comprises a version 3 heavy chain sequence shown in SEQ ID NO:69, which includes an optional signal sequence.

In one embodiment, a light chain comprising murine B3F6 CDRs and human framework regions is combined with a heavy chain comprising murine B3F6 CDRs and human framework regions. In one embodiment, a light chain comprising murine B3F6 CDRs and human framework regions is combined with a humanized version of a B3F6 heavy chain comprising at least one backmutation of a human framework amino acid residue to the corresponding murine amino acid residue. In another embodiment, a humanized version of a B3F6 light chain comprising at least one backmutation of a human framework amino acid residue to the corresponding murine amino acid residue is combined with a humanized version of a B3F6 heavy chain comprising at least one backmutation of a human framework amino acid residue to the corresponding murine amino acid residue. In another embodiment a light chain comprising murine B3F6 CDRs and human framework regions and at least one backmutation of a human framework amino acid residue to the corresponding murine amino acid residue is combined with a humanized version of a B3F6 heavy chain. Exemplary combinations are described in more detail in the instant examples. For example, in one embodiment the humanized L1 light chain of the instant examples is combined with the H1 heavy chain of the instant examples to make the version 1 humanized B3F6 antibody. In another embodiment the humanized L1 light chain of the instant examples is combined with the H2 heavy chain of the instant examples to make the version 2 humanized B3F6 antibody. In another embodiment, the humanized L1 light chain of the instant examples is combined with the H3 heavy chain of the instant examples to make the version 3 humanized B3F6 antibody. In another embodiment the humanized L2 light chain of the instant examples is combined with the H1 heavy chain of the instant examples to make the version 4 humanized B3F6 antibody. In another embodiment the humanized L2 light chain of the instant examples is combined with the H2 heavy chain of the instant examples to make the version 5 humanized B3F6 antibody. In another embodiment the humanized L2 light chain of the instant examples is combined with the H3 heavy chain of the instant examples to make the version 6 humanized B3F6 antibody. It will be apparent to one of ordinary skill in the art that such combinations are within the scope of this invention.

In one embodiment, a binding molecule of the invention is an antibody made by the cell line deposited with the American Type Culture Collection (ATCC) 10801 University Boulevard, Manassas, Va., 20110 under ATCC ACCESSION NUMBER PTA-7284 under conditions of the Budapest treaty.

II. Forms of Binding Molecules

A. Antibodies or Portions Thereof

In one embodiment, a binding molecule of the invention is an antibody molecule. For example, in one embodiment a binding molecule of the invention is a humanized antibody or portion thereof that binds to Cripto. In another embodiment, a binding molecule of the invention comprises an antigen binding fragment of a humanized antibody that binds to Cripto and a second antigen binding fragment of an antibody.

Using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature*, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

In another embodiment of the present invention a binding site of a binding molecule of the invention may be provided by a human or substantially human antibody. Human or substantially human antibodies may be made in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the binding molecules of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis. Exemplary antibodies or fragments thereof for use in the binding molecules of the invention include antibodies that recognize the targets set forth herein.

In certain embodiments, antigen binding fragments of antibodies can be produced using techniques well known in the art.

B. Modified Antibodies

In one embodiment, a binding molecule of the invention comprises or consists of a modified antibody, i.e., and molecule that is derived from an antibody, but is not a wild-type antibody, e.g., minibodies (minibodies can be made using methods described in the art (see, e.g., see e.g., U.S. Pat. No. 5,837,821 or WO 94/09817A1)). etc.

1. Domain Deleted Antibodies

In one embodiment, a binding molecule of the invention comprises synthetic constant regions wherein one or more domains are partially or entirely deleted ("domain-deleted antibodies"). In especially preferred embodiments compatible modified antibodies will comprise domain deleted constructs or variants wherein the entire CH2 domain has been removed ($\Delta$CH2 constructs). For other preferred embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody.

In another embodiment, the modified antibodies of the invention are CH2 domain deleted antibodies. Domain deleted constructs can be derived using a vector (e.g., from IDEC Pharmaceuticals, San Diego) encoding an $IgG_1$ human constant domain (see, e.g., WO 02/060955A2 and WO02/096948A2). This exemplary vector was engineered to delete the CH2 domain and provide a synthetic vector expressing a domain deleted $IgG_1$ constant region. Genes encoding the murine variable region of the C2B8 antibody, 5E8 antibody, B3F6 antibody, or the variable region of the humanized CC49 antibody have been then inserted in the synthetic vector and cloned. When expressed in transformed cells, these vectors provided C2B8.$\Delta$CH2, 5E8.$\Delta$CH2, B3F6.$\Delta$CH2 or huCC49.$\Delta$CH2 or respectively. These constructs exhibit a number of properties that make them particularly attractive candidates for monomeric subunits. Humanized domain deleted B3F6 antibodies have also been produced and are described in more detail in the instant examples.

It will be noted that these exemplary constructs were engineered to fuse the CH3 domain directly to a hinge region of the respective polypeptides of the invention. In other constructs it may be desirable to provide a peptide spacer between the hinge region and the synthetic CH2 and/or CH3 domains. For example, compatible constructs could be expressed wherein the CH2 domain has been deleted and the remaining CH3 domain (synthetic or unsynthetic) is joined to the hinge region with a 5-20 amino acid spacer. Such a spacer may be added, for instance, to ensure that the regulatory elements of the constant domain remain free and accessible or that the hinge region remains flexible. For example, a domain deleted B3F6 construct having a short amino acid spacer GGSSGGGGSG (SEQ. ID No. 8) substituted for the CH2 domain and the lower hinge region (B3F6.$\Delta$CH2 [gly/ser]) can be used. Other exemplary connecting peptides are shown in Table 2. These connecting peptides can be used with any of the polypeptides of the invention. Preferably, the connecting peptides are used with a polypeptide lacking a CH2 heavy chain domain. Preferably, any linker compatible with the instant invention will be relatively non-immunogenic and not inhibit the non-covalent association of the polypeptides of the invention.

In one embodiment, a polypeptide of the invention comprises an immunoglobulin heavy chain having deletion or substitution of a few or even a single amino acid as long as it permits the desired covalent or non-covalent association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

It is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, effector functions may be eliminated or reduced by using a constant region of an IgG4 antibody, which is thought to be unable to deplete target cells, or making Fc variants, wherein residues in the Fc region critical for effector function(s) are mutated using techniques known in the art, for example, U.S. Pat. No. 5,585,097. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, modified forms of antibodies can be made from a whole precursor or parent antibody using techniques known in the art. Exemplary techniques are discussed in more detail below A polypeptide comprising a heavy chain portion may or may not comprise other amino acid sequences or moieties not derived from an immunoglobulin molecule. Such modifications are described in more detail below. For example, in one embodiment, a polypeptide of the invention may comprise a flexible linker sequence. In another embodiment, a polypeptide may be modified to add a functional moiety such as a drug or PEG.

2. Bispecific Binding Molecules

In one embodiment, a binding molecule of the invention is bispecific. For example, in one embodiment, a binding molecule binds to Cripto and another molecule. In one embodiment, a bispecific binding molecule of the present invention may comprise an additional binding site that binds to one or more tumor molecules or molecules associated with tumor cell growth. In one embodiment, for neoplastic disorders, an antigen binding site (i.e. the variable region or immunoreactive fragment or recombinant thereof) of the disclosed polypeptides binds to a selected tumor associated molecule at the site of the malignancy. Given the number of reported molecules associated with neoplasias tumor cell growth, and the number of related antibodies, those skilled in the art will appreciate that the binding sites of the claimed binding molecules may therefore be derived from any one of a number of whole antibodies. More generally, binding sites useful in the present invention may be obtained or derived from any antibody (including those previously reported in the literature) that reacts with a target or marker associated with the selected condition. Further, the parent or precursor antibody, or fragment thereof, used to generate the disclosed polypeptides may be murine, human, chimeric, humanized, non-human primate or primatized. In other preferred embodiments the polypeptides of the present invention may comprise single chain antibody constructs (such as that disclosed in U.S. Pat. No. 5,892,019 which is incorporated herein by reference) having altered constant domains as described herein. Consequently, any of these types of antibodies can be used to obtain a binding site that may be incorporated into a bispecific molecule of the invention.

As used herein, "tumor associated molecules" means any antigen or target molecule which is generally associated with tumor cells, i.e., being expressed the same or to a greater extent as compared with normal cells. More generally, tumor associated molecules comprise any molecule that provides for the localization of immunoreactive antibodies at a neoplastic cell irrespective of its expression on non-malignant cells. Such molecules may be relatively tumor specific and limited in their expression to the surface of malignant cells. Alternatively, such molecules may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma.

In this respect, pan T cell antigens such as CD2, CD3, CD5, CD6 and CD7 also comprise tumor associated molecules within the meaning of the present invention. Still other exemplary tumor associated molecules comprise but not limited to Lewis Y, MAGE-1, MAGE-3, MUC-1, HPV 16, HPV E6 & E7, TAG-72, CEA, L6-Antigen, CD19, CD22, CD37, CD52, HLA-DR, EGF Receptor and HER2 Receptor. In many cases immunoreative antibodies for each of these antigens have been reported in the literature. Those skilled in the art will appreciate that each of these antibodies may serve as a precursor for polypeptides of the invention in accordance with the present invention.

Accordingly, a binding site of the present invention may be derived, generated or fabricated from any one of a number of antibodies that react with tumor associated molecules. In one embodiment the binding site is a synthetic or domain deleted antibodies that is derived using common genetic engineering techniques whereby at least a portion of one or more constant region domains are deleted or altered so as to provide the desired biochemical characteristics such as reduced serum half-life. More particularly, as will be exemplified below, one skilled in the art may readily isolate the genetic sequence corresponding to the variable and/or constant regions of the subject antibody and delete or alter the appropriate nucleotides to provide polypeptides of the invention for use as monomeric subunits in accordance with the instant invention. It will further be appreciated that compatible polypeptides of the invention may be expressed and produced on a clinical or commercial scale using well-established protocols.

Previously reported antibodies that react with tumor associated molecules may be altered as described herein to provide one or more binding sites for a polypeptide of the present invention. Exemplary antibodies that may be used to provide binding sites for the subject polypeptides (or from which binding sites may be derived) include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). In preferred embodiments, the polypeptides of the present invention will bind to the same tumor associated antigens as the antibodies enumerated immediately above. In particularly preferred embodiments, the polypeptides will be derived from or bind the same antigens as 2B8, C2B8, CC49 and C5E10 and, even more preferably, will comprise domain deleted antibodies (i.e., ΔCH2 antibodies).

In a first preferred embodiment, a polypeptide of the invention will bind to the same tumor associated antigen as Rituxan®. Rituxa® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine parent of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., *Blood* 83: 435445 (1994)). Those skilled in the art will appreciate that bispecific binding molecules which bind to Cripto and CD20+ according to the instant disclosure, may be used in conjugated or unconjugated forms to effectively treat patients presenting with CD20+ malignancies. More generally, it must be reiterated that the polypeptides disclosed herein may be used in either a "naked" or unconjugated state or conjugated to a cytotoxic agent to effectively treat any one of a number of disorders.

In other preferred embodiments of the present invention, a bispecific polypeptide of the invention may comprise a binding site from the CC49 antibody (or derived from the CC49 antibody). As previously alluded to, CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., *Proc. Natl. Acad. Sci.* (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be synthetic and used in making a bispecific molecule of the invention.

In addition to the anti-TAG-72 antibodies discussed above, various groups have also reported the construction and partial characterization of domain-deleted CC49 and B72.3 antibodies (e.g., Calvo et al. *Cancer Biotherapy*, 8(1):95-109 (1993), Slavin-Chiorini et al. *Int. J. Cancer* 53:97-103 (1993) and Slavin-Chiorini et al. *Cancer. Res.* 55:5957-5967 (1995). Such constructs may also be included in a bispecific binding molecule of the invention.

In one embodiment, a bispecific binding molecule of the invention binds to the CD23 (U.S. Pat. No. 6,011,138). In a preferred embodiment, a bispecific binding molecule of the invention comprises a binding site that binds to the same epitope as the 5E8 antibody. In another embodiment, a binding molecule of the invention comprises at least one CDR from an anti-CD23 antibody, e.g., the 5E8 antibody.

In another embodiment, a bispecific molecule of the present invention comprises a binding site derived from the C5E10 antibody (or a binding site which binds to the same tumor associated antigen as the C5E10 antibody). As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, bispecific polypeptides (e.g. CH2 domain-deleted antibodies) that specifically bind to the same tumor associated antigen recognized by C5E10 antibodies could be produced and used in a conjugated or unconjugated form for the treatment of neoplastic disorders. In particularly preferred embodiments, the binding molecule will be derived or comprise all or part of the antigen binding region of the C5E10 antibody as secreted from the hybridoma cell line having ATCC accession No. PTA-865. The resulting binding molecule could then be conjugated to a radionuclide as described below and administered to a patient suffering from prostate cancer in accordance with the methods herein.

In another embodiment, a ligand may be included in a binding molecule of the invention, e.g., to impart binding to a particular receptor or a receptor may be incorporated into a binding molecule, e.g., to remove ligands from the circulation. Exemplary ligands and their receptors that may be included in the subject bispecific binding molecules include:

a. Cytokines or Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

b. Adhesion Proteins or Their Receptors

Adhesion molecules are membrane-bound proteins that allow cells to interact with one another. Various adhesion proteins, including leukocyte homing receptors and cellular adhesion molecules, of receptor binding portions thereof, can be incorporated in a binding molecule of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

c. Chemokines or Their Receptors

Chemokines, chemotactic proteins which stimulate the migration of leucocytes towards a site of infection, can also be incorporated into a binding molecule of the invention. Exemplary chemokines include Macrophage inflammatory proteins (MIP-1-α and MIP-1-β), neutrophil chemotactic factor, and RANTES (regulated on activation normally T-cell expressed and secreted).

d. Growth Factors or Growth Factor Receptors

Growth factors or their receptors (or receptor binding or ligand binding portions thereof) or molecules which bind to them may be incorporated in the binding molecule of the invention. Exemplary growth factors include angiopoietin, Vascular Endothelial Growth Factor (VEGF) and its isoforms (U.S. Pat. No. 5,194,596); Epidermal Growth Factors (EGFs); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stem-cell factor (SCF), thrombopoietin (c-Mpl ligand), and the Wnt polypeptides (U.S. Pat. No. 6,159,462).

Exemplary growth factor receptors which may be used include EGF receptors (EGFRs); VEGF receptors (e.g. Flt1 or Flk1/KDR), PDGF receptors (WO 90/14425); HGF receptors (U.S. Pat. Nos. 5,648,273, and 5,686,292); IGF receptors (e.g. IGFR1 and IGFR2) and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)). In another embodiment, both IGFR1 and VEGF are targeted. In yet another embodiment, VLA4 and VEGF are targeted.

Other cell surface receptors and/or their ligands can also be targeted (e.g., the TNF family receptors or their ligands (as described in more detail herein).

e. Hormones

Exemplary growth hormones or molecules which bind to them for use as targeting agents in the binding molecule of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

f. Clotting Factors

Exemplary blood coagulation factors for use as targeting agents in the binding molecules of the invention include the clotting factors (e.g., factors V, VII, VIII, X, IX, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

C. Fusion Proteins

The invention also pertains to binding molecules which comprise one or more immunoglobulin domains. In one embodiment, the fusion proteins of the invention comprise a binding domain (which comprises at least one binding site) and a dimerization domain (which comprises at least one heavy chain portion). For example, in one embodiment, a binding molecule of the invention may comprise at least one humanized B3F6 binding site and a dimerization domain. The subject fusion proteins are bispecific (with one binding site for a first target and a second binding site for a second target). In one embodiment, the subject fusion proteins are multivalent (with two binding sites for the same target).

In one embodiment a fusion protein comprises a B3F6 binding site, at least one heavy chain domain and a synthetic connecting peptide.

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1.990); and Byrn et al., Nature 344:667-670 (1990)); L-selectin (homing receptor) (Watson et al., J. Cell. Biol. 110:2221-2229 (1990); and Watson et al., Nature 349: 164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

In one embodiment, when preparing a fusion proteins of the present invention, nucleic acid encoding a binding domain (e.g., a humanized B3F6 binding domain) will be fused C-terminally to nucleic acid encoding the N-terminus of an immunoglobulin constant domain sequence. N-terminal fusions are also possible. In one embodiment, a fusion protein includes a CH2 and a CH3 domain. Fusions may also be made to the C-terminus of the Fc portion of a constant domain, or immediately N-terminal to the CH1 of the heavy chain or the corresponding region of the light chain.

In one embodiment, the sequence of the ligand or receptor domain is fused to the N-terminus of the Fc domain of an immunoglobulin molecule. It is also possible to fuse the entire heavy chain constant region to the sequence of the ligand or receptor domain. In one embodiment, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. The precise site at which the fusion is made is not critical; particular sites are well known and may be selected in order to optimize the biological activity, secretion, or binding characteristics of the molecule. Methods for making fusion proteins are known in the art.

For bispecific fusion proteins, the fusion proteins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Fusion proteins are taught, e.g., in WO0069913A1 and WO0040615A2. Fusion proteins can be prepared using methods that are well known in the art (see for example U.S. Pat. Nos. 5,116,964 and 5,225,538). Ordinarily, the ligand or receptor domain is fused C-terminally to the N-terminus of the constant region of the heavy chain (or heavy chain portion) and in place of the variable region. Any transmembrane regions or lipid or phospholipids anchor recognition sequences of ligand binding receptor are preferably inactivated or deleted prior to fusion. DNA encoding the ligand or receptor domain is cleaved by a restriction enzyme at or proximal to the 5' and 3'ends of the DNA encoding the desired ORF segment. The resultant DNA fragment is then readily inserted into DNA encoding a heavy chain constant region. The precise site at which the fusion is made may be selected empirically to optimize the secretion or binding characteristics of the soluble fusion protein. DNA encoding the fusion protein is then transfected into a host cell for expression.

III. Synthetic Connecting Peptides

In one embodiment, at least one polypeptide chain of a dimer of the invention comprises a synthetic connecting peptide. In one embodiment, at least two chains of a dimer of the invention comprise a connecting peptide. In a preferred embodiment, two chains of a dimer of the invention comprise a connecting peptide.

In one embodiment, connecting peptides can be used to join two heavy chain portions in frame in a single polypeptide chain. For example, in one embodiment, a connecting peptide of the invention can be used to fuse a CH3 domain (or synthetic CH3 domain) to a hinge region (or synthetic hinge region). In another embodiment, a connecting peptide of the invention can be used to fuse a CH3 domain (or synthetic CH3 domain) to a CH1 domain (or synthetic CH1 domain). In still another embodiment, a connecting peptide can act as a peptide spacer between the hinge region (or synthetic hinge region) and a CH2 domain (or a synthetic CH2 domain).

In another embodiment, a CH3 domain can be fused to an extracellular protein domain (e.g., a VL domain (or synthetic domain), a VH domain (or synthetic domain), a CH1 domain (or synthetic domain), a hinge domain (or synthetic hinge), or to the ligand binding portion of a receptor or the receptor binding portion of a ligand). For example, in one embodiment, a VH or VL domain is fused to a CH3 domain via a connecting peptide (the C-terminus of the connecting peptide is attached to the N-terminus of the CH3 domain and the N-terminus of the connecting peptide is attached to the C-terminus of the VH or VL domain). In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain). In another embodiment, a connecting peptide of the invention can be used to fuse a CH3 domain (or synthetic CH3 domain) to a hinge region (or synthetic hinge region) or portion thereof. In still another embodiment, a connecting peptide can act as a peptide spacer between the hinge region (or synthetic hinge region) and a CH2 domain (or a synthetic CH2 domain).

In one embodiment, a connecting peptide can comprise or consist of a gly/ser spacer. For example, a domain deleted construct having a short amino acid spacer GGSSGGGGSG (SEQ ID No. 8) substituted for the CH2 domain and the lower hinge region (CH2 [gly/ser]) can be used. In another embodiment, a connecting peptide comprises the amino acid sequence IGKTISKKAK (SEQ ID NO: 15).

In another embodiment, connecting peptide can comprise at least a portion of an immunoglobulin hinge region. For example, chimeric hinge domains can be constructed which combine hinge elements derived from different antibody isotypes. In one embodiment, a connecting peptide comprises at least a portion of an IgG1 hinge region. In another embodiment, a connecting peptide can comprise at least a portion of an IgG3 hinge region. In another embodiment, a connecting peptide can comprise at least a portion of an IgG1 hinge region and at least a portion of an IgG3 hinge region. In one embodiment, a connecting peptide can comprise an IgG1 upper and middle hinge and a single IgG3 middle hinge repeat motif.

Because the numbering of individual amino acids in such connecting peptides comprising an amino acid sequence derived from an immunoglobulin hinge region may vary depending upon the length of the connecting peptide, the numbering of amino acid positions in these molecules is given using Kabat numbering see, e.g., Table 2). Table 3 shows naturally occurring hinge sequence for IgG1, IgG3, and IgG4 molecules. Table 2 shows Kabat numbering for portions of these hinge molecules and also shows Kabat numbering for connecting peptide amino acid residues presented in that Table.

In one embodiment, a connecting peptide of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a connecting peptide of the invention. In one embodiment, a connecting peptide of the invention comprises a hinge domain which does not comprise a naturally occurring number of cysteines, i.e., the connecting peptide comprises either fewer cysteines or a greater number of cysteines than a naturally occurring hinge molecule. In a preferred embodiment, incorporation of the connecting peptide into a polypeptide results in a composition in which greater than 50%, 60%, 70%, 80% or 90% of the dimeric molecules present in a form in which the two heavy chain portions are linked via at least one interchain disulfide linkage.

In one embodiment of the invention, a connecting peptide comprises hinge region domain comprising a proline residue at an amino acid position corresponding to amino acid position 243 in the Kabat numbering system (position 230, EU numbering system). In one embodiment, a connecting peptide comprises an alanine residue at an amino acid position corresponding to position 244, Kabat numbering system (position 246, EU numbering system). In another embodiment, a connecting peptide of the invention comprises a proline residue at an amino acid position corresponding to position 245 (Kabat numbering system; position 247, EU numbering system)). In one embodiment, a connecting peptide comprises a cysteine residue at an amino acid position corresponding to position 239, Kabat numbering system (position 226, EU numbering system). In one embodiment, a connecting peptide comprises a serine residue at an amino acid position corresponding to position 239, Kabat numbering system (position 226, EU numbering system). In one embodiment, a connecting peptide comprises a cysteine residue at an amino acid position corresponding to position 242, Kabat numbering system (position 229, EU numbering system). In one embodiment, a connecting peptide comprises a serine residue at an amino acid position corresponding to position 242, Kabat numbering system (position 229, EU numbering system).

In one embodiment, the connecting peptide can be chosen to result in the preferential synthesis of a particular isoform of polypeptide, e.g., in which the two heavy chain portions are linked via disulfide bonds or are not linked via disulfide bonds. For example, as described in the instant examples, the G1/G3/Pro243+[gly/ser] linker (SEQ ID NO: 26), G1/G3/Pro243Ala244Pro245+[gly/ser] linker (SEQ ID NO: 5), Pro243+[gly/ser] linker (SEQ ID NO:33), and Pro243Ala244Pro245+[gly/ser] linker (SEQ ID NO: 32), connecting peptides resulted in the production of only Form A CH2 domain-deleted antibody with no detectable Form B. In contrast, CH2 domain-deleted Cys242Ser:Pro243 (SEQ ID NO: 31), and CH2 domain-deleted Cys242Ser:Pro243Ala244Pro245 (SEQ ID NO: 32), both resulted in a preference for the Form B isoform. These synthetic hinge region connecting peptides would thus be useful for favoring synthesis of Form A or B isoform. This is true for any isotype of antibody, (e.g., IgG1, IgG2, IgG3, or IgG4) based on the high degree of homology among the CH3 domains for all four human isotypes. (Including identical and conserved amino acid residues, IgG1 CH3 domain is 98.13% homologous to IgG2 CH3, 97.20% homologous to IgG3 CH3, and 96.26% homologous to IgG4 CH3). The parentheticals referring to connecting peptides and various binding molecules of the invention represent equivalent terminology unless otherwise indicated.

In one embodiment, a connecting peptide of the invention comprises a hinge region domain followed by a flexible gly/ser linker. Exemplary connecting peptides are shown in Table 2 and in SEQ ID NOs: 5, 25-34. It will be understood that variant forms of these exemplary connecting peptides can be created by introducing one or more nucleotide substitutions, additions or deletions into the nucleotide sequence encoding a connecting peptide such that one or more amino acid substitutions, additions or deletions are introduced into the connecting peptide. For example, mutations may be introduced by standard techniques, such as site-directed mutagenesis and PCR-mediated mutagenesis. Preferably, conservative amino acid substitutions are made at one or more non-essential amino acid residues such that the ability of the connecting peptide to preferentially enhance synthesis of Form A or Form B is not altered. Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Connecting peptides of the invention can be of varying lengths. In one embodiment, a connecting peptide of the invention is from about 15 to about 50 amino acids in length. In another embodiment, a connecting peptide of the invention is from about 20 to about 45 amino acids in length. In another embodiment, a connecting peptide of the invention is from about 25 to about 40 amino acids in length. In another embodiment, a connecting peptide of the invention is from about 30 to about 35 amino acids in length. In another embodiment, a connecting peptide of the invention is from about 24 to about 27 amino acids in length. In another embodiment, a connecting peptide of the invention is from about 40 to about 42 amino acids in length.

Connecting peptides can be introduced into polypeptide sequences using techniques known in the art. For example, in one embodiment, the Splicing by Overlap Extension (SOE) method (Horton, R. M. 1993 Methods in Molecular Biology, Vol 15:PCR Protocols: Current Methods and applications. Ed. B. A. White) can be used. Modifications can be confirmed by DNA sequence analysis. Plasmid DNA can be used to transform host cells for stable production of the polypeptides produced.

In one embodiment, incorporation of one of the subject connecting peptides into a polypeptide yields a composition comprising binding molecules having at least two binding sites and at least two polypeptide chains, wherein at least two of the polypeptide chains comprise a synthetic connecting peptide and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

IV. Expression of Binding Molecules

Following manipulation of the isolated genetic material to provide polypeptides of the invention as set forth above, the genes are typically inserted in an expression vector for introduction into host cells that may be used to produce the desired quantity of polypeptide that, in turn, provides the claimed binding molecules.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of MRNA.

These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above. Preferably, this is effected using a proprietary expression vector of IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the polypeptides of the invention of the instant invention may be expressed using polycistronic constructs such as those disclosed in copending U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the polypeptide (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

V. Separation of Binding Molecules Comprising at Least One Interchain Disulfide Linkage from Those Lacking Interchain Disulfide Linkages In one aspect, the invention pertains to separation of molecules having two heavy chain portions from a mixture, where a fraction of the molecules are present in a form in which the two heavy chain portions are linked via at least one interchain disulfide linkage and a fraction of the molecules comprise heavy chain portions that are not linked via at least one disulfide linkage by hydrophobic interaction chromatography.

Hydrophobic interaction chromatography was first developed following the observation that proteins could be retained on affinity gels which comprised hydrocarbon spacer arms but lacked the affinity ligand. Elution from HIC supports can be effected by alterations in solvent, pH, ionic strength, or by the addition of chaotropic agents or organic modifiers, such as ethylene or propylene glycol. A description of the general principles of hydrophobic interaction chromatography can be found e.g., in U.S. Pat. No. 3,917,527 and in U.S. Pat. No. 4,000,098. HIC in the context of high performance liquid chromatography (HPLC) has been used to separate antibody fragments lacking heavy chain portions (e.g., F(ab')$_2$) from intact antibody molecules in a single step protocol. (Morimoto, K. et al., L. Biochem. Biophys. Meth. 24: 107 (1992)).

The separation method of the invention can be performed on an unpurified population of polypeptides (e.g., culture supernatants or preparations or preparations of polypeptides isolated from prokaryotic inclusion bodies). Alternatively, the instant separation methods can be used on polypeptide mixtures obtained after one or more initial purification steps, e.g., after a preparation comprising forms A and B has been eluted from an affinity matrix.

In one embodiment, the binding molecules subjected to HIC chromatography comprise a connecting peptide of the invention.

In a preferred embodiment, HIC can be applied to mixtures that have been partially purified by other protein purification procedures. The term "partially purified" as used herein includes a protein preparation in which the protein of interest is present in at least 5% by weight, more preferably at least 10% and most preferably at least 45%. Initial or subsequent purification steps can be used to remove, e.g., immunoglobulin aggregates, misfolded species, host cell protein, residue material from preceding chromatographic steps (such as Protein A when employed). In one embodiment, HIC can be performed on polypeptides comprising a connecting peptide of the invention. Accordingly, the application of HIC can also be appreciated in the context of an overall purification protocol. Exemplary purification steps that can be used prior to or subsequent to HIC include: affinity chromatography (for example, PROSEP-A® (BioProcessing Ltd., U.K.) which consists of Protein A covalently coupled to controlled pore glass or Protein A SEPHAROSE® Fast Flow (Pharmacia) or TOYOPEARL 650M Protein A (TosoHaas)). Protein A is preferred for human γ1, γ2, or γ4 heavy chains and protein G for mouse isotypes. Bakerbond ABX™ resin can be used if the molecule comprises a CH3 domain. In addition or alternatively, ion exchange chromatography may be employed. In this regard various anionic or cationic substituents may be attached to matrices in order to form anionic or cationic supports for chromatography. Anionic exchange substituents include diethylaminoethyl (DEAE), quaternary aminoethyl (QAE) and quaternary amine (Q) groups. Cationic exchange substituents include carboxymethyl (CM), sulfoethyl (SE), sulfopropyl (SP), phosphates) and sulfonate (S). Cellulose ion exchange resins such as DE23, DE32, DE52, CM-23, CM-32 and CM-52 are available from Whatman Ltd. Maidstone, Kent, U.K. SEPHADEX®-based and -locross-linked ion exchangers are also known. For example, DEAE-, QAE-, CM-, and SP-SEPHADEXO and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL DEAE-650S or M and TOYOPEARL CM-650S or M are available from Toso Haas Co., Philadelphia, Pa. Because elution from ion exchange supports usually involves addition of salt and because HIC is enhanced under increased salt concentrations, the introduction of a HIC step following an ionic exchange chromatographic step or other salt mediated purification step is preferred. Additional purification protocols may be added including but not necessarily limited to: further ionic exchange chromatography, size exclusion chromatography, viral inactivation, concentration and freeze drying, hydroxylapatite chromatography, gel electrophoresis, dialysis, ethanol precipitation, reverse phase HPLC, chromatography on silica, chromatography on heparin SEQHAROSE™, chromatofocusing, or ammonium sulfate precipitation.

Prior to purification using the subject methods, the composition comprising the mixture of polypeptides to be separated will preferably be placed in a buffer of acidic or approximately neutral pH. This can be done, for example, by adding concentrated buffer, resuspending the sample in the buffer, exchanging the buffer (e.g., using dialysis or ultrafiltration). Alternatively, the pH of the sample buffer can simply be adjusted to be within the desired range.

Hydrophobic interactions are strongest at high ionic strength, therefore, this form of separation is conveniently performed following salt precipitations or ion exchange procedures. Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}<; Ca^{++}<; Mg^{++}<; Li^+<; Cs^+<; Na^+<; K^+<; Rb^+<; NH_4^+$, while anions may be ranked in terms of increasing chaotropic effect as $PO_4^{---}<; SO_4^{--}<; CH_3COOO^-<; Cl^-<; Br^-<; NO_3^-<; ClO_4^-<; SCN^-$ In general, Na, K or $NH_4$ sulfates effectively promote ligand-protein interaction in HIC. Salts may be formulated that influence the strength of the interaction as given by the following relationship: $(NH_4)_2SO_4>; Na_2SO_4>; NaCl>; NH_4Cl>; NaCl>; NaBr>; NaSCN$. In general, salt concentrations of between about 0.75 and about 2M ammonium sulfate or between about 1 and 4M NaCl are useful.

A number of chromatographic supports may be employed in the preparation of HIC columns, the most extensively used are agarose, silica and organic polymer or co-polymer resins. The hydrophobic interaction material is generally a base matrix (e.g., a hydrophilic carbohydrate (such as cross-linked agarose) or synthetic copolymer material) to which hydrophobic ligands (e.g., alkyl or aryl groups) are coupled. The preferred HIC material comprises an agarose resin substituted with phenyl groups. Exemplary HIC material includes: phenyl SEPHAROSE™, FAST FLOW with low or high substitution (Pharmacia LKB Biotechnology, AB, Sweden); phenyl SEPHAROSE™ High Performance column; phenyl or butyl-SEPHAROSE® CL-4B, butyl-SEPHAROSE® FF, octyl-SEPHAROSE® FF and phenyl-SEPHAROSE® FF (Pharmacia LKB Biotechnology AB, Sweden); Fractogel™ EMD Propyl or FRACTOGEL™ EMC Phenyl columns (E. Merck, Germany); MACROPREP™ Methyl or MACRO-PREP™ t-Butyl Supports (Bio-Rad, California); WP HI-Propyl (C3)™ column (J.T. Baker, New Jersey). Exemplary HIC materials are also available from Tosoh Corporation, Tokyo, Japan under the product names TOYOPEARL ether 650, phenyl 650, butyl 650 (Fractogel), ether-5PW-HR, or phenyl-5PW-HR; Miles-Yeda, Rehovot, Israel under the product name alkyl-agarose, wherein the alkyl group contains from 2-10 carbon atoms, and J.T. Baker, Phillipsburg, N.J. under the product name Bakerbond WP-HI-propyl. It is also possible to prepare the desired HIC column using conventional chemistry. (Sa: for example, Er-el. Z. gl all, Biochem. Biophys. Res. Comm. 49:383 (1972) or Ulbrich, V. rd gL Coll. Czech. Chem. Commum. 9:1466 (1964)).

The choice of a particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi orbital interaction with aromatic groups on the protein. Selectively may also be affected by the chemistry of the supporting resin.

Ligand density is an important parameter in that it influences not only the strength of the interaction but the capacity of the column as well. The ligand density of the commercially available phenyl or octyl phenyl gels is on the order of 40 pmoles/ml gel bed. Gel capacity is a function of the particular protein in question as well as pH, temperature and salt type and concentration but generally can be expected to fall in the range of 3-20 mg/ml of gel.

In general, a decrease in temperature decreases the interaction with HIC material. However, any benefit that would accrue by increasing the temperature must also be weighed against adverse effects such an increase may have on the stability of the protein.

In one embodiment, the polypeptides of the invention can be eluted isocratically. In isocratic elution, all compounds begin migration through the column at onset. However, each migrates at a different rate, resulting in faster or slower elution rate. For example, as described in the instant examples, form A can be eluted with the flow through of the column.

In another embodiment, one or more polypeptides of the invention can be bound to the column and eluted, e.g., using stepwise elution or gradient elution. Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene or propylene glycol or (iso)propanol, thereby decreasing the strength of the hydrophobic interactions. Detergents function as displacers of proteins and have been used primarily in connection with the purification of membrane proteins In performing the separation, the polypeptide mixture can be contacted with the HIC material e.g., using a batch purification technique or using a column. Prior to HIC purification it may be desirable to remove any chaotropic agents or very hydrophobic substances, e.g., by passing the mixture through a precolumn.

For example, for batch purification, HIC material is prepared in or equilibrated to the desired starting buffer. A slurry of the MC material is obtained. The polypeptide solution is contacted with the slurry to adsorb at least one of the polypeptides to be separated to the HIC material. The solution containing the polypeptides that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb polypeptides that have bound to the HIC material. In order to elute bound polypeptides, the salt concentration can be decreased.

In one embodiment, the HIC material can be packed in a column. A mixture comprising the polypeptides to be separated can be applied to the column allowing at least one of the polypeptides to be separated to adsorb to the column. The polypeptides that do not adsorb to the column pass through and can be collected. In order to elute bound polypeptides, the salt concentration can be decreased, e.g., in a step-wise fashion or using a salt gradient.

Since form B is more hydrophobic than form A, it adsorbs irreversibly to the stationary phase using approximately 0.7 M (e.g., 0.73M) Ammonium Sulfate/20 mM Sodium Phosphate, pH 4.0 to pH 8.0 as the mobile phase. Form A binds to a lesser extent to the stationary phase under these conditions and is therefore eluted isocratically, i.e. it leaves the column with the flowthrough fraction. Subsequent to the isocratic elution of form A, omitting Ammonium sulfate from the mobile phase desorbs form B.

In an exemplary purification scheme, the HIC material is equilibrated in a buffer comprising a salt concentration yielding a conductivity of from between about 160 to about 110, preferably from between about 140 to about 115, even more preferably from between about 130 or about 120 to about 117 mS/cm. For example, an exemplary starting solution comprises a salt concentration of approximately 1M to 0.7M, e.g., 1M to 0.7M ammonium sulfate. In a preferred embodiment, the solution comprising the mixture of polypeptides to be separated is also brought to the same, or approximately the same conductivity (e.g., using a concentrated stock solution of salt). Under these conditions, Form A is eluted from the column at a conductivity of about 120 mS/cm. In order to elute Form B, a stepwise or linear gradient of reducing ammonium sulfate content can be applied to the column. Form B elutes at a conductivity of approximately 115 to approximately 100 mS/cm.

In one embodiment, the subject purification method yields a composition comprising binding molecules having at least two binding sites and two heavy chain portions, wherein the heavy chain portions lack CH2 domains and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

In one embodiment, the subject purification method yields a composition comprising recombinant binding molecules having at least two binding sites and two heavy chain portions, wherein greater than 99% of the molecules are present in a form in which the two heavy chain portions are linked via at least one interchain disulfide linkage.

In one embodiment, the subject purification method yields a composition comprising binding molecules having at least two binding sites and two heavy chain portions, wherein greater than 95% of the molecules are present in a form in which the two heavy chain portions are linked via at least one interchain disulfide linkage, and wherein the heavy chain portions of the polypeptides are derived from an antibody of the IgG4 isotype.

In one embodiment, the subject purification method yields a composition comprising binding molecules having two light chain portions and two heavy chain portions, wherein the heavy chain portions lack CH2 domains and wherein greater than 80% of the molecules arepresent in a form in which the two heavy chain portions are not linked via at least one interchain disulfide linkage.

In another aspect, the instant invention also provides methods for monitoring the results of purification and/or preferential biosynthesis comprising measuring the relative amounts of Form A and Form B in a composition. Form A and Form B can be measured, e.g., as described herein using non-reducing SDS polyacrylamide gel electrophoresis or mass spectrometry.

VI. Labeling or Conjugation of Binding Molecules

The binding molecules of the present invention may be used in non-conjugated form or may be conjugated to at least one of a variety of effector, i.e., functional, moieties, e.g., to facilitate target detection or for imaging or therapy of the patient. The polypeptides of the invention can be labeled or conjugated either before or after purification, when purification is performed. In particular, the polypeptides of the present invention may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), PEG, or detectable moieties useful in imaging. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, pseudomonas exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the polypeptide and the radioisotope. Particularly preferred chelating agents comprise 1-isothiocycmatobenzyl-3-methyldiothelene triamine-pentaacetic acid ("MX-DTPA") and cyclohexyl diethylen-etriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99m labeled polypeptides may be prepared by ligand exchange processes, by reducing pertechnate ($TcO_4^-$) with stannous ion solution, chelating the reduced technetium onto a Sephadex column and applying the polypeptides to this column, or by batch labeling techniques, e.g. by incubating pertechnate, a reducing agent such as $SnCl_2$, a buffer solution such as a sodium-potassium phthalate-solution, and the antibodies. In any event, preferred radionuclides for directly labeling antibodies are well known in the art and a particularly preferred radionuclide for direct labeling is $^{131}$I covalently attached via tyrosine residues. Polypeptides according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred. Patents relating to chelators and chelator conjugates are known in the art. For instance, U.S. Pat. No. 4,831,175 of Gansow is directed to polysubstituted diethylenetriamine-pentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediamine-tetraacetic acid (EDTA), diethylenetriaminepentaacetic acid (DPTA), 1,4,8,11-tetraazatetradecane, 1,4,8,11-tetraazatet-radecane-1,4,8,11-tetraacetic acid, 1-oxa-4,7,12,15-tetraaza-heptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation in co-pending application Ser. Nos. 08/475,813, 08/475,815 and 08/478,967, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy. It will also be appreciated that, in accordance with the teachings herein, polypeptides may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

As indicated above, a variety of radionuclides are applicable to the present invention and those skilled in the art can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow antibody accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled antibodies. Additionally, internalization of labeled antibody is not required for cell killing, and the local emission of ionizing radiation should be lethal for adjacent tumor cells lacking the target molecule.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the polypeptides of the invention with cytostatic/cytotoxic substances and metal chelates are prepared in an analogous manner.

Many effector moieties lack suitable functional groups to which antibodies can be linked. In one embodiment, an effector moiety, e.g., a drug or prodrug is attached to the antibody through a linking moiety. In one embodiment, the linking moiety contains a chemical bond that allows for the activation of cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking moiety comprises a disulfide bond or a thioether bond. In accordance with the invention, the linking moiety preferably comprises a reactive chemical group. Particularly preferred reactive chemical groups are N-succinimidyl esters and N-sulfosuccinimidyl esters. In a preferred embodiment, the reactive chemical group can be covalently bound to the effector via disulfide bonding between thiol groups. In one embodiment an effector molecule is modified to comprise a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

In one embodiment, a linking moiety may be used to join the effector moiety with the binding molecule. The linking moiety of the invention may be cleavable or non-cleavable. In one embodiment, the cleavable linking moiety is a redox-cleavable linking moiety, such that the linking moiety is cleavable in environments with a lower redox potential, such as the cytoplasm and other regions with higher concentrations of molecules with free sulfhydryl groups. Examples of linking moieties that may be cleaved due to a change in redox potential include those containing disulfides. The cleaving stimulus can be provided upon intracellular uptake of the binding protein of the invention where the lower redox potential of the cytoplasm facilitates cleavage of the linking moiety. In another embodiment, a decrease in pH triggers the release of the maytansinoid cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linking moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, Willner et al., (1993), *Bioconj. Chem.*, 4: 521-7; U.S. Pat. Nos. 4,569,789, 4,631,190, 5,306,809, and 5,665,358). Other exemplary acid-sensitive linking moieties comprise dipeptide sequences Phe-Lys and Val-Lys (King et al., (2002), *J. Med Chem.*, 45: 4336-43). The cleaving stimulus can be provided upon intracellular uptake trafficking to low pH endosomal compartments (e.g. lysosomes). Other exemplary acid-cleavable linking moieties are the moieties that contain two or more acid cleavable bonds for attachment of two or more maytansinoids (King et al, (1999), *Bioconj. Chem.*, 10: 279-88; WO 98/19705).

Cleavable linking moieties may be sensitive to biologically supplied cleaving agents that are associated with a particular target cell, for example, lysosomal or tumor-associated enzymes. Examples of linking moieties that can be cleaved enzymatically include, but are not limited to, peptides and esters. Exemplary enzyme cleavable linking moieties include those that are sensitive to tumor-associated proteases such as Cathepsin B or plasmin (Dubowchik et al, (1999), *Pharm. Ther.*, 83: 67-123; Dubowchik et al., (1998), *Bioorg. Med Chem. Lett.*, 8: 3341-52; de Groot et al., (2000), *J. Med Chem.*, 43: 3093-102; de Groot et al, (1999)m 42: 5277-83). Cathepsin B-cleavable sites include the dipeptide sequences valine-citrulline and phenylalanine-lysine (Doronina et al., (2003), *Nat. Biotech.*, 21(7): 778-84); Dubowchik et al., (2002), *Bioconjug. Chem.*, 13: 855-69). Other exemplary enzyme-cleavable sites include those formed by oligopeptide sequences of 4 to 16 amino acids (e.g., Suc-β-Ala-Leu-Ala-Leu) which recognized by trouse proteases such as Thimet Oliogopeptidase (TOP), an enzyme that is preferentially released by neutrophils, macrophages, and other granulocytes.

In a further embodiment, the linking moiety is formed by reacting a binding molecule of the invention with a linking molecule of the formula:

X—Y—Z wherein:
X is an attachment moiety;
Y is a spacer moiety; and
Z is a effector attachment moeity.

The term "binding molecule attachment moiety" includes moieties which allow for the covalent attachment of the linker to a binding molecule of the invention.

The attachment moiety may comprise, for example, a covalent chain of 1-60 carbon, oxygen, nitrogen, sulfur atoms, optionally substituted with hydrogen atoms and other substituents which allow the binding molecule to perform its intended function. The attachment moiety may comprise peptide, ester, alkyl alkenyl, alkynyl, aryl, ether, thioether, etc. functional groups. Preferably, the attachment moiety is selected such that it is capable of reacting with a reactive functional group on a polypeptide comprising at least one antigen binding site, to form a binding molecule of the invention. Examples of attachment moieties include, for example, amino, carboxylate, and thiol attachment moieties.

Amino attachment moieties include moieties which react with amino groups on a polypeptide, such that a binding molecule of the invention is formed. Amino attachment moieties are known in the art. Examples of amino attachment moieties include, activated carbamides (e.g., which may react with an amino group on a binding molecule to form a linking moiety which comprises urea group), aldehydes (e.g., which may react with amino groups on a binding molecule), and activated isocyanates (which may react with an amino group on a binding molecule to from a linking moiety which comprises a urea group). Examples of amino attachment moieties include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl moiety.

Carboxylate attachment moieties include moieties which react with carboxylate groups on a polypeptide, such that a binding molecule of the invention is formed. Carboxylate attachment moieties are known in the art. Examples of carboxylate attachment moieties include, but are not limited to activated ester intermediates and activated carbonyl intermediates, which may react with a COOH group on a binding moleculeto form a linking moiety which comprises a ester, thioester, or amide group.

Thiol attachment moieties include moieties which react with thiol groups present on a polypeptide, such that a binding molecule of the invention is formed. Thiol attachment moieties are known in the art. Examples of thiol attachment moieties include activated acyl groups (which may react with a sulfhydryl on a binding molecule to form a linking moiety which comprises a thioester), activated alkyl groups (which may react with a sulfhydryl on a binding molecule to form a linking moiety which comprises a thioester moiety), Michael acceptors such as maleimide or acrylic groups (which may react with a sulfhydryl on a binding molecule to form a Michael-type addition product), groups which react with sulfflydryl groups via redox reactions, activated di-sulfide groups (which may react with a sulfhydryl group on a binding molecule to form, for example, a linking moiety which comprises a disulfide moiety). Other thiol attachment moieties include acrylamides, alpha-iodoacetamides, and cyclopropan-1,1-dicarbonyl compounds. In addition, the thiol attachment moiety may comprise a moiety which modifies a thiol on the binding molecule to form another reactive species to which the linking molecule can be attached to form a binding molecule of the invention.

The spacer moiety, Y, is a covalent bond or a covalent chain of atoms which may contain one or more aminoacid residues. It may also comprise 0-60 carbon, oxygen, sulfur or nitrogen atoms optionally substituted with hydrogen or other substituents which allow the resulting binding molecule to perform its intended function. In one embodiment, Y comprises an alkyl, alkenyl, alkynyl, ester, ether, carbonyl, or amide moiety.

In another embodiment, a thiol group on the binding molecule is converted into a reactive group, such as a reactive carbonyl group, such as a ketone or aldehyde. The attachment moiety is then reacted with the ketone or aldehyde to form the desired compound of the invention. Examples of carbonyl reactive attachment moieties include, but are not limited to, hydrazines, hydrazides, O-substituted hydroxylamines, alpha-beta-unsaturated ketones, and $H_2C=CH-CO-NH-NH_2$. Other examples of attachment moieties and methods for modifying thiol moieties which can be used to form binding molecules of the invention are described Pratt, M. L. et al. J Am Chem Soc. May 21, 2003; 125(20):6149-59; and Saxon, E. Science. Mar. 17, 2000; 287(5460):2007-10.

The linking molecule may be any molecule which is capable of reacting with an effector moiety or a derivative thereof to form a binding molecule of the invention. For example, the effector moiety may be linked to the remaining portions of the molecule through a disulfide bond. In such cases, the linking moiety is selected such that it is capable of reacting with an appropriate effector moeity derivative such that the effector moiety is attached to the binding molecule of the invention. As described above, the linking moiety and/or the linker as a whole may be selected that the linker is cleaved in an appropriate environment.

Particularly preferred linker molecules include, for example, N-succinimidyl 3-(2-pyridyldithio)propionate (SPDP) (see, e.g., Carlsson et al., Biochem. J., 173, 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., Eur. J. Biochem., 101, 395-399 (1979)), and N-succinimidyl 4-methyl-4-[2-(5-nitro-pyridyl)-dithio]pentanoate (SMNP) (see, e.g., U.S. Pat. No. 4,563,304) The most preferred linker molecules for use in the inventive composition are SPP, SMCC, and SPDB. In a preferred embodiment, SPDB is used to link an effector moiety to a binding molecule of the invention.

Preferred cytotoxic effector moieties for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine.

Particularly preferred moieties for conjugation are maytansinoids. Maytansinoids were originally isolated from the east African shrub belonging to the genus *Maytenus*, but were subsequently also discovered to be metabolites of soil bacteria, such as *Actinosynnema pretiosum* (see, e.g., U.S. Pat. No. 3,896,111). Maytansinoids are known in the art to include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., J. Med. Chem., 21, 31-37 (1978). Methods for generating maytansinol and analogues and derivatives thereof are described in, for example, U.S. Pat. No. 4,151,042.

Suitable maytansinoids for use as antibody conjugates can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule.

Particularly preferred maytansinoids comprising a linking moiety that contains a reactive chemical group are C-3 esters of maytansinol and its analogs where the linking moiety contains a disulfide bond and the attachment moiety comprises a N-succinimidyl or N-sulfosuccinimidyl ester. Many positions on maytansinoids can serve as the position to chemically link the linking moiety, e.g., through an effector attachment moiety. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol. Most preferably, the maytansinoid used in connection with the inventive composition is $N^{2'}$-deacetyl-$N^{2'}$-(-3-mercapto-1-oxopropyl)-maytansine (DM1) or $N^{2'}$-deacetyl-$N^{2'}$-(4-mercapto-4-methyl-1-oxopentyl)-maytansine (DM4).

Linking moieties with other chemical bonds also can be used in the context of the invention, as can other maytansinoids. Specific examples of other chemical bonds which may be incorporated in the linking moieties include those described above, such as, for example acid labile bonds, thioether bonds, photolabile bonds, peptidase labile bonds and esterase labile bonds. Methods for producing maytansinoids with linking moieties and/or effector attachment moieties are described in, for example, U.S. Pat. Nos. 5,208,020, 5,416,064, and 6,333,410.

The linking moiety (and/or the effector attachment moiety) of a maytansinoid typically and preferably is part of a larger linker molecule that is used to join the antibody to the maytansinoid. Any suitable linker molecule can be used in connection with the invention, so long as the linking molecule provides for retention of the cytotoxicity and targeting characteristics of the maytansinoid and the antibody, respectively. The linking molecule joins the maytansinoid to the antibody through chemical bonds (as described above), such that the maytansinoid and the antibody are chemically coupled (e.g., covalently bonded) to each other. Desirably, the linking molecule chemically couples the maytansinoid to the antibody through disulfide bonds or thioether bonds. Most preferably, the antibody is chemically coupled to the maytansinoid via disulfide bonds.

Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the antibody-toxin construct. Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. An antibody conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting antibody. A potentially attractive variation of this approach would be the attachment of a therapeutic radioisotope to the radiosensitized immunoconjugate, thereby providing the convenience of administering to the patient a single drug.

In one embodiment, a moiety that enhances the stability or efficacy of the polypeptide can be conjugated. For example, in one embodiment, PEG can be conjugated to the polypeptides of the invention to increase their half-life in vivo. Leong, S. R., et al. 2001. *Cytokine* 16:106; 2002; *Adv. in Drug Deliv. Rev.* 54:531; or Weir et al. 2002. Biochem. Soc. Transactions 30:512.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing pro drugs, thiophosphate-containing pro drugs, sulfate containing prodrugs, peptide containing prodrugs, β-lactam-containing prodrugs, optionally substituted phenoxyacetamide-containing prodrugs or optionally substituted phenylacetamide-containing pro drugs, 5-fluorocytosine and other 5-fluorouridine prodrugs that can be converted to the more active cytotoxic free drug. In one embodiment, a cytotoxic agent, such as a maytansinoid, is administered as a prodrug which is released by the hydrolysis of disulfide bonds. Further examples of cytotoxic drugs that can be derivatized into a prodrug form for use in the present invention comprise those chemotherapeutic agents described above.

V. Administration of Polypeptides

Methods of preparing and administering polypeptides of the invention to a subject are well known to or are readily determined by those skilled in the art. The route of administration of the polypeptide of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g., acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Binding molecules of the invention can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma binding molecule or toxin concentration, e.g., 1-1000 μg/ml or 25-300 μg/ml. Alternatively, binding molecules can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the binding molecules of the invention can be administered in unconjugated form. In another embodiment, the polypeptides of the invention can be administered multiple times in conjugated form. In still another embodiment, the binding molecules of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of $^{90}$Y-labeled polypeptides of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not the polypeptides of the invention are used in a conjugated or unconjugated form, it will be appreciated that a major advantage of the present invention is the ability to use these polypeptides in myelosuppressed patients, especially those who are undergoing, or have undergone, adjunct therapies such as radiotherapy or chemotherapy. In other preferred embodiments, the polypeptides (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed antibodies and one or more chemotherapeutic agents. Particularly preferred embodiments of this aspect of the invention will comprise the administration of a toxin conjugated binding molecule, e.g., conjugated to a maytansinoid such as a D4 maytansinoid.

While the polypeptides may be administered as described immediately above, it must be emphasized that in other embodiments conjugated and unconjugated polypeptides may be administered to otherwise healthy patients as a first line therapeutic agent. In such embodiments the polypeptides may be administered to patients having normal or average red marrow reserves and/or to patients that have not, and are not, undergoing adjunct therapies such as external beam radiation or chemotherapy.

However, as discussed above, selected embodiments of the invention comprise the administration of polypeptides to myelosuppressed patients or in combination or conjunction with one or more adjunct therapies such as radiotherapy or chemotherapy (i.e. a combined therapeutic regimen). As used herein, the administration of polypeptides in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated polypeptides could be administered intravenously followed by tumor localized external beam radiation. In yet other embodiments, the polypeptide may be administered concurrently with one or more selected chemotherapeutic agents in a single office visit. A skilled artisan (e.g. an experienced oncologist) would readily be able to discern effective combined therapeutic regimens without undue experimentation based on the selected adjunct therapy and the teachings of the instant specification.

In this regard it will be appreciated that the combination of the polypeptide (either conjugated or unconjugated) and the chemotherapeutic agent may be administered in any order and within any time frame that provides a therapeutic benefit to the patient. That is, the chemotherapeutic agent and polypeptide may be administered in any order or concurrently. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the polypeptide will be administered within 4, 3, 2 or 1 week of any chemotherapeutic agent or treatment. In yet other embodiments the polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppresion and one can easily measure the extent to which myelosuppression is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated polypeptides of the present invention may be used to effectively treat patients having ANCs lower than about 2000/mm$^3$ or platelet counts lower than about 150,000/mm$^3$. More preferably the polypeptides of the present invention may be used to treat patients having ANCs of less than about 1500/mm$^3$, less than about 1000/mm$^3$ or even more preferably less than about 500/mm$^3$. Similarly, the polypeptides of the present invention may be used to treat patients having a platelet count of less than about 75,000/mm$^3$, less than about 50,000/mm$^3$ or even less than about 10,000/mm$^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed polypeptides may be used to treat disorders in patients exhibiting myelosuppression regardless of the cause.

In this regard it will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), ChlVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996).

In one embodiment, a binding molecule of the invention may be administered to a subject who has undergone, is undergoing, or will undergo a surgical procedure, e.g., to remove a primary tumor, a metastasis or precancerous growth or tissue as a preventative therapy.

In another embodiment, a binding molecule of the invention is administered in conjunction with a biologic. Biologics useful in the treatment of cancers are known in the art and a binding molecule of the invention may be administered, for example, in conjunction with such known biologics.

For example, the FDA has approved the following biologics for the treatment of breast cancer: Herceptine (trastuzumab, Genentech Inc., South San Francisco, Calif.; a humanized monoclonal antibody that has antitumor activity in HER2-positive breast cancer); Faslodex® (fulvestrant, AstraZeneca Pharmaceuticals, LP, Wilmington, Del.; an estrogen-receptor antagonist used to treat breast cancer); Arimidex® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); Femara® (letrozole, Novartis Pharmaceuticals, East Hanover, N.J.; a nonsteroidal aromatase inhibitor approved by the FDA to treat breast cancer); and Nolvadex® (tamoxifen, AstraZeneca Pharmaceuticals, LP; a nonsteroidal antiestrogen approved by the FDA to treat breast cancer). Other biologics with which the binding molecules of the invention may be combined include: Avastin™ (bevacizumab, Genentech Inc.; the first FDA-approved therapy designed to inhibit angiogenesis); and Zevalin® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: Avastin™; Erbitux™ (cetuximab, ImClone Systems Inc., New York, N.Y., and Bristol-Myers Squibb, New York, N.Y.; is a monoclonal antibody directed against the epidermal growth factor receptor (EGFR)); Gleevec® (imatinib mesylate; a protein kinase inhibitor); and Ergamisol® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For use in treatment of Non-Hodgkin's Lymphomas currently approved therapies include: Bexxar® (tositumomab and iodine I-131 tositumomab, GlaxoSmithKline, Research Triangle Park, N.C.; a multi-step treatment involving a mouse monoclonal antibody (tositumomab) linked to a radioactive molecule (iodine I-131)); Intron® A (interferon alfa-2b, Schering Corporation, Kenilworth, N.J.; a type of interferon approved for the treatment of follicular non-Hodgkin's lymphoma in conjunction with anthracycline-containing combination chemotherapy (e.g., cyclophosphamide, doxorubicin, vincristine, and prednisone [CHOP])); Rituxan® (rituximab, Genentech Inc., South San Francisco, Calif., and Biogen Idec, Cambridge, Mass.; a monoclonal antibody approved for the treatment of non-Hodgkin's lymphoma; Ontak® (denileukin diftitox, Ligand Pharmaceuticals Inc., San Diego, Calif.; a fusion protein consisting of a fragment of diphtheria toxin genetically fused to interleukin-2); and Zevalin® (ibritumomab tiuxetan, Biogen Idec; a radiolaebeled monoclonal antibody approved by the FDA for the treatment of B-cell non-Hodgkin's lymphomas).

For treatment of Leukemia, exemplary biologics which may be used in combination with the binding molecules of the invention include Gleevec®; Campath®-1H (alemtuzumab, Berlex Laboratories, Richmond, Calif.; a type of monoclonal antibody used in the treatment of chronic Lymphocytic leukemia). In addition, Genasense (oblimersen, Genta Corporation, Berkley Heights, N.J.; a BCL-2 antis ense therapy under development to treat leukemia may be used (e.g., alone or in combination with one or more chemotherapy drugs, such as fludarabine and cyclophosphamide) may be administered with the claimed binding molecules.

For the treatment of lung cancer, exemplary biologics include Tarceva™ (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include Velcade® Velcade (bortezomib, Millennium Pharmaceuticals, Cambridge Mass.; a proteasome inhibitor). Additional biologics include Thalidomid® (thalidomide, Clegene Corporation, Warren, N.J.; an immunomodulatory agent and appears to have multiple actions, including the ability to inhibit the growth and survival of myeloma cells and antiangiogenesis).

Other exemplary biologics include the MOAB IMC-C225, developed by ImClone Systems, Inc., New York, N.Y.

In addition, the claimed binding molecules may be administered in conjunction with vaccines or other agents (e.g., cytokines) to modulate anti-cancer immune responses. For example, Melacine® (Corixa Corporation, Seattle, Wash.) is an allogeneic tumor vaccine that has been reported to have promising results in the treatment of T3N0M0 resected melanoma. GMK® (Progenics Pharmaceutical, Inc., Tarrytown, N.Y.) is a ganglioside antigen administered as an adjuvant phase III agent in patients who are at high risk for melanoma recurrence. Anti-gastrin therapeutic Vaccine® (Aphton Corporation, Miami, Fla.) neutralizes hormones G17 and glyextened and is in phase III clinical trials for patients with colorectal, pancreatic, and stomach cancers. CeaVac® (Titan Pharmaceuticals, Inc., South San Francisco, Calif.) is an anti-idiotype antibody vaccine being studied in colorectal cancer. Finally, Theratope® (Biomira Inc., Edmonton, Alberta, Canada) is a synthetic carbohydrate therapeutic vaccine being investigated as a phase III agent in patients with metastatic breast cancer (Pharmaceutical Research and Manufacturers of America, 2000).

In another embodiment, a binding molecule of the invention may be administered in conjunction with an anti-angiogenesis agent, e.g., Endostatin (an endogenous, tumor-derived, endothelial-specific inhibitor that halts microvascular endothelial cell production); anti-VEGF antibody; thalidomide; or matrix metalloproteinase inhibitors inhibit the synthesis and degradation of the basement membrane of blood vessels).

As previously discussed, the polypeptides of the present invention, immunoreactive fragments or recombinants thereof may be administered in a pharmaceutically effective amount for the in vivo treatment of mammalian disorders. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the polypeptide, immunoreactive fragment or recombinant thereof, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the polypeptides of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VI. Methods of Use

The molecules of the invention can be used for diagnostic or therapeutic purposes. Preferred embodiments of the present invention provide compounds, compositions, kits and methods for the diagnosis and/or treatment of disorders, e.g., neoplastic disorders in a mammalian subject in need of such treatment. Preferably, the subject is a human.

The polypeptides of the instant invention will be useful in a number of different applications. For example, in one embodiment, the subject binding molecules may be used in an assay to detect Cripto in vitro, e.g., using an ELISA assay. Exemplary assays are known in the art, see, e.g., United States Application Number 20040077025.

In another embodiment, the subject binding molecules are useful for detecting the presence of Cripto bearing cells using imaging technology. For such applications, it may be desirable to conjugate the binding molecule to a detectable moiety, e.g., a radiolabel, as described further below.

In another embodiment, the subject binding molecules are useful for reducing or eliminating cells bearing target (e.g., an epitope of Cripto) recognized by a binding molecule of the invention. In another embodiment, the subject binding molecules are effective in reducing the concentration of or eliminating soluble target molecules in the circulation In one embodiment, a binding molecule of the invention reduces tumor size, inhibits tumor growth and/or prolongs the survival time of a tumor-bearing subject. Accordingly, this invention also relates to a method of treating tumors in a human or other animal by administering to such human or animal an effective, non-toxic amount of polypeptide. One skilled in the art would be able, by routine experimentation, to determine what an effective, non-toxic amount of polypeptide would be for the purpose of treating malignancies. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

For purposes of clarification "mammal" refers to any animal classified as a mammal, including humans, domestic and farm animals, and zoo, sports, or pet animals, such as dogs, horses, cats, cows, etc. Preferably, the mammal is human. "Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

In general, the disclosed invention may be used to prophylactically or therapeutically treat any neoplasm comprising a marker that allows for the targeting of the cancerous cells by the binding molecule. In a preferred embodiment, the gbinding molecules of the invention are used to treat solid tumors. Exemplary cancers that may be treated include, but are not limited to, prostate, gastric carcinomas such as colon, skin, breast, ovarian, lung and pancreatic cancer. In another embodiment, the antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated molecules related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (CCL), diffuse large cell lymphoma (DLCL), small lymphocytic (SL) NHL, intermediate grade/follicular NHL, intermediate grade diffuse NHL, high grade immunoblastic NIL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated molecules.

In one embodiment of the invention, molecules are provided which are capable of binding specifically to Cripto and which inhibit growth of tumor cells in a patient, especially where the tumor growth is mediated by the loss or decrease of Activin B signaling. In certain embodiments, the tumor cells are brain, head, neck, prostate, breast, testicular, colon, lung, ovary, bladder, uterine, cervical, pancreatic and stomach tumor cells. In other embodiments, a binding molecule of the invention binds specifically to Cripto and inhibits growth of tumor cells which overexpress Cripto. In one embodiment, the tumor cells are cell lines which overexpress Cripto, such as cell lines derived from brain, breast, testicular, colon, lung, ovary, bladder, uterine, cervical, pancreatic and stomach cancers.

This invention is further illustrated by the following examples which should not be construed as limiting. The contents of all references, patents and published patent applications cited throughout this application are incorporated herein by reference.

Examples

Example 1

Identification of A and B Isoforms

Solutions of antibody molecules comprise two different isoforms. One form, Form A comprises heavy chain molecules that are linked via at least one disulfide linkage. The other form, Form B, comprises heavy chain molecules that are not linked via at least one disulfide linkage. Form B does not appear or appears at a very low frequency in with intact gamma 1 MAbs, such as Rituxan®. However with domain deleted (dd) constructs having a similar hinge, the frequency of Form B is much higher. These forms can be distinguished using denaturing, non-reducing SDS page. In domain deleted antibody preparations, Form A appears as a 120 kDa dimer while Form B appears as a 60 kDa monomer.

Example 2

Identification of Hinge Region Heterogeneity in CH2 Domain Deleted MAb Fragments Hinge domains can be subdivided into three distinct regions: upper, middle, and lower hinge regions (Roux et al. J. Immunol. 1998 161:4083). Polypeptide sequences encompassing these regions for IgG1 and IgG3 hinges are shown in Table 3. The IgG3 hinge middle region contains, in addition to the two conserved cysteine residues, a 15 amino acid. motif that repeats three times. Amino acid sequences from these regions were used to design synthetic IgG1/IgG3 connecting peptides. These consisted of IgG1 upper hinge residues corresponding to positions 226 through 238, an IgG1 middle hinge corresponding to positions 239 through 241, and a single IgG3 middle hinge repeat motif corresponding to positions 241EE through 242 combined with either an added proline at position 243 or an added proline, alanine, proline at positions 243, 244, and 245, respectively (Kabat numbering system), followed by a flexible Gly/Ser spacer (Table 2). In addition, novel connecting peptides were designed consisting of a serine amino acid residue substituted for the cysteine at positions 239 or 242 combined with either an added proline at position 243 or an added proline, alanine, proline at positions 243, 244, and 245, respectively (Kabat numbering system). Pro243Ala244Pro245 and Pro 243 connecting peptides were also made. The amino acid sequence of the parent CH2 domain deleted humanized CC49 connecting peptide beginning at the first residue of the IgG1 hinge (position 226, Kabat numbering system) to the last residue of the hinge/GlySer connecting peptide is shown in Table 2. Also shown are the various connecting peptide designs by alignment to CC49 with positions of the cysteine residues indicated in Kabat numbering system.

TABLE 2

Hinge Region Connecting Peptide Sequences

| Kabat hinge position: | 226 | 227 | 228 | 229 | 230 | 232 | 235 | 236 | 237 | 238 | 239 | 240 | 241 | 241EE | 241FF | 241GG | 241HH | 241II | 241JJ |
|---|---|---|---|---|---|---|---|---|---|---|---|---|---|---|---|---|---|---|---|
| IgG1 hinge sequence (SEQ ID NO: 36) | E | P | K | S | C | D | K | T | H | T | C | P | P | | | | | | |
| IgG4 hinge sequence (SEQ ID NOs.: 37 and 38) | E | S | K | Y | G | | | | | | P | P | C | P | S | | | | |
| IgG3 middle hinge sequence (SEQ ID NO: 35) | | | | | | | | | | | | | | C | P | E | P | K | S |

| Connecting peptide: | Connecting peptide sequences | | | | | | | | | | | | | | | | | | |
|---|---|---|---|---|---|---|---|---|---|---|---|---|---|---|---|---|---|---|---|
| G1 (Seq. ID NO: 25) | E | P | K | S | C | D | K | T | H | T | C | P | P | | | | | | |
| G1/G3/Pro243 (Seq. ID NO: 26) | E | P | K | S | C | D | K | T | H | T | C | P | P | C | P | E | P | K | S |
| G1/G3/Pro243Ala244Pro245 (Seq. ID NO: 27) | E | P | K | S | C | C | K | T | H | T | C | P | P | C | P | E | P | K | S |
| G1/Cys239Ser:Pro243 (Seq. ID NO: 28) | E | P | K | S | C | D | K | T | H | T | S | P | P | | | | | | |
| G1/Cys239Ser:Pro243Ala244Pro245 (Seq. ID NO: 29) | E | P | K | S | C | D | K | T | H | T | S | P | P | | | | | | |
| G1/Cys242Ser:Pro243 (Seq. ID NO: 30) | E | P | K | S | C | D | K | T | H | T | S | P | P | | | | | | |
| G1/Cys242Ser:Pro243Ala244Pro245 (Seq. ID NO: 31) | E | P | K | S | C | D | K | T | H | T | S | P | P | | | | | | |
| G1/Pro243Ala244Pro245 (Seq. ID NO: 32) | E | P | K | S | C | D | K | T | H | T | S | P | P | | | | | | |
| G1/Pro243 (Seq. ID NO: 33) | E | P | K | S | C | D | K | T | H | T | S | P | P | | | | | | |
| G4/G3/Pro243Ala244Pro245 (Seq. ID NO: 34) | E | S | K | Y | G | | | | | | P | P | C | P | S | C | P | E | P | K | S |

| Kabat hinge position: | 241KK | 241LL | 241MM | 241NN | 241OO | 241PP | 241QQ | 241RR | 241SS | 242 | 243 | 244 | 245 |
|---|---|---|---|---|---|---|---|---|---|---|---|---|---|
| IgG1 hinge sequence (SEQ ID NO: 36) | | | | | | | | | | C | P | A | P |
| IgG4 hinge sequence (SEQ ID NOs.: 37 and 38) | | | | | | | | | | C | P | A | P |
| IgG3 middle hinge sequence (SEQ ID NO: 35) | C | | D | | T | | P | P | P | C | P | R | |

| Connecting peptide: | Connecting peptide sequences | | | | | | | | | | | | |
|---|---|---|---|---|---|---|---|---|---|---|---|---|---|
| G1 | | | | | | | | | | C | GGGSSGGGSG | | |
| G1/G3/Pro243 | C | | D | | T | | P | P | P | C | P | R | C | P | GGGSSGGGSG |

TABLE 2-continued

Hinge Region Connecting Peptide Sequences

| | | | | | | | | | | | | | | |
|---|---|---|---|---|---|---|---|---|---|---|---|---|---|---|
| G1/G3/Pro243Ala244Pro245 | C | D | T | P | P | P | C | P | R | C | P | A | P | GGGSSGGGSG |
| G1/Cys239Ser:Pro243 | | | | | | | | | | C | P | | | GGGSSGGGSG |
| G1/Cys239Ser:Pro243 Ala244Pro245 | | | | | | | | | | C | P | A | P | GGGSSGGGSG |
| G1/Cys242Ser:Pro243 | | | | | | | | | | S | P | | | GGGSSGGGSG |
| G1/Cys242Ser:Pro243 Ala244Pro245 | | | | | | | | | | S | P | A | P | GGGSSGGGSG |
| G1/Pro243Ala244Pro245 | | | | | | | | | | C | P | A | P | GGGSSGGGSG |
| G1/Pro243 | | | | | | | | | | C | P | | | GGGSSGGGSG |
| G4/G3/Pro243Ala244Pro245 | | D | T | P | P | P | C | P | R | C | P | A | P | |

TABLE 3

IgG1, IgG3 and IgG4 Hinge Regions

| IgG | Upper Hinge | Middle Hinge | Lower Hinge |
|---|---|---|---|
| IgG1 | EPKSCDKTHT (SEQ ID NO: 17) | CPPCP (SEQ ID NO: 18) | APELLGGP (SEQ ID NO: 19) |
| IgG3 | ELKTPLGDTTHT (SEQ ID NO: 20) | CPRCP (EPKSCDTPPPCPRCP)$_3$ (SEQ ID NO: 21) | APELLGGP (SEQ ID NO: 19) |
| IgG4 | ESKYGPP (SEQ ID NO: 22) | CPSCP (SEQ ID NO: 23) | APEFLGGP (SEQ ID NO: 24) |

Example 3

Construction of Connecting Polypeptides and Preferential Synthesis of Isoforms

Nucleic acid sequences encoding the hinge region connecting peptides shown in Table 2 were introduced into CH2 domain deleted huCC49 gene sequences using the Splicing by Overlap Extension (SOE) method (Horton, R. M. 1993 Methods in Molecular Biology, Vol 15:PCR Protocols: Current Methods and applications. Ed. B. A. White). Correct modifications to the hinge region were confirmed by DNA sequence analysis. Plasmid DNA was used to transform CHO DG44 cells for stable production of antibody protein.

CH2 domain deleted huCC49 antibodies containing the eight designed synthetic connecting peptides indicated in Table 2 were constructed and antibody produced in CHO DG44 cells. Supernatants were collected from isolated cell lines and concentration of antibody in the culture supernatants determined by immunoassay. Supernatants containing antibody ranging from 0 to 30 ng of total antibody protein from each cell line was analyzed by non-reducing SDS-PAGE electrophoresis followed by Western Blot with anti-human kappa HRP conjugated antibody to detect CH2 domain deleted huCC49 Form A and Form B isoforms. Under these conditions, Form A migrates as a single 120 kDa homodimer and Form B as a 60 kDa doublet. Also visible are kappa chain monomer and dimers. Connecting peptides shown in SEQ ID NOs: 5, 26, 32, and 33 were all found to increase the proportion of form A produced. These results show that both the G1/G3/Pro243Ala244Pro245+[Gly/Ser] (SEQ ID NO:5) and G1/G3/Pro243+[Gly/Ser] (SEQ ID NO:26) hinges resulted primarily if not entirely in the production of Form A CH2 domain-deleted huCC49 antibody with little or no detectable Form B. In contrast CH2 domain-deleted huCC49 Cys242Ser:Pro243 (SEQ ID NO:30) and CH2 domain-deleted huCC49 Cys242Ser:Pro243Ala244Pro245 (SEQ ID NO:32) resulted in a moderate to significant preference of the Form B isoform, respectively.

Cell lines containing the Pro243Ala244Pro245+[Gly/Ser] (SEQ ID NO:32) and G1/G3/Pro243Ala244Pro245+[Gly/Ser] (SEQ ID NO:5) connecting peptides introduced into the huCC49 antibody sequence were used for antibody production. The Pro243Ala244Pro245+[Gly/Ser] and G1/G3/Pro243Ala244Pro245+[Gly/Ser] connecting peptides were also introduced into the huCC49 V2 antibody sequence and cell lines generated (The humanized CC49 version 2 sequence is known in the art). Antibody was produced from CHO DG44 cells and purified using methods described in Example 4 below. Yields of the Form A isoform following the Protein G and HIC steps are reported in Table 4. From these results it is clear that the modifications introduced to the hinge region in the CH2 domain deleted antibodies led to the preferential synthesis of the A isoform. Following the HIC purification technique described in Example 4, purified HuCC49 Pro230Ala231Pro232 and HuCC49 V2 Pro230Ala231Pro232 Form A material was achieved at values greater than 98%. HuCC49 G1/G3/Pro243Ala244Pro245 and HuCC49 V2 G1/G3/Pro243Ala244Pro245 Form A materials, purified using only the Protein G column, both eluted essentially as single peaks at ≧96% purity without further HIC purification. All antibodies were examined by size exclusion chromatography and were found to elute as single peaks indicating that there was no significant aggregation or decomposition of antibody product.

Peptide mapping was used to determine the integrity of disulfide bond formation in the heavy chain hinge regions of CH2 domain deleted HuCC49, HuCC49 PAP, and HuCC49 G1/G3/PAP antibodies. Samples of the CH2 domain deleted CC49 antibodies were denatured, reduced and digested with trypsin as follows: aliquots of 150 ug were diluted to 100 ml in HPLC water and denatured in 6M guanidine hydrochloride, 50 mM Tris pH 8.0. The samples were reduced by the addition of 20 mM DTT and incubated for 30 minutes at 37° C. The reduced samples were alkylated with 50 mM iodoacetic acid for 30 minutes at 37° C. The alkylation reaction was quenched by the addition of excess DTT. The reduced and alkylated samples were buffer exchanged into 25 mM TRIS, 20 mM $CaCl_2$, pH 7.5 using PD-10 columns. Trypsin was added to each sample in a 1:15 (w/w) ratio and incubated for 4 hours at 37° C. The digestion was stopped by the addition of trifluoroacetic acid (TFA) to a final concentration of 0.1%. Trypsin digested samples (15 ug) were then analyzed according to chromatographic conditions described below.

Samples of the CH2 domain deleted CC49 antibodies were analyzed by endoproteinase Lys-C digestion. Denatured and reduced samples were prepared by adding a final concentration of 4 M guanidine HCl and 25 mM DTT to 1.5 mg/mL of sample. Non-reduced samples were prepared by adding a final concentration of 4 M guanidine HCl to 1.5 mg/mL of sample. Samples were incubated for 2 hours at 37° C. Digestion buffer (50 mM Tris, pH 7.0 and 0.062 AU/ml endoproteinase Lys-C) was then added to the samples at 1:1 (v/v) and samples were incubated for 15 hours at 37° C. At 15 hours, a second aliquot of enzyme (0.29 mAU: ug Antibody) was added and samples were incubated for an additional 6 hours at 37° C. To quench the reaction, TFA was added at 0.1% final concentration. Non-reduced and reduced endoproteinase Lys-C digested samples (12 ug) were then analyzed according to the procedure described below.

HPLC/mass spectrometry analysis. Samples were analyzed on an Agilent 1100 HPLC system connected to an Agilent MSD single quadrupole mass spectrometer. A reverse phase C18 column (Vydac catalog number 218TP52) was used with an eluant system of water/0.1% TFA (v/v) (Buffer A) and acetonitrile/0.1% TFA (v/v) (Buffer B), at a flow rate of 0.2 mL/minute. A post column "TFA fixative" solution of acetonitrile and acetic acid (1:1 v/v) at 0.1 mL/minute was added to enhance ionization. The column temperature was controlled at 45° C. and the elution profile was monitored at 215 and 280 nm. The total ion chromatogram was monitored in positive ion mode. Samples were injected onto the column and the gradient was held at 0% Buffer B for five minutes. Elution was accomplished with a linear gradient of 0 to 50% Buffer B over 125 minutes, followed by a 75% Buffer B wash over 10 minutes and a 0% Buffer B re-equilibration over 30 minutes.

In the endo Lys-C reduced analysis, fragment (L52-109) was undetected for all samples. This fragment is very hydrophobic and may have not eluted from the column matrix due to strong interactions. The corresponding tryptic fragment (L68-109) was also undetected in all samples. Since these fragments contain a large number of amino acids, the percent amino acid identity was lowered to ~89% identity. In addition, fragment (L68-119) was undetected in the endo Lys-C analysis of G1/G3/PAP bringing the identity down to ~79%.

The endo Lys-C non-reduced analysis provided much better results. Fragment (L52-109) was detected as a disulfide linkage with fragment (L1-24) in all samples. All other disulfide linkages were detected and the total % amino acid identity was ~99% for all samples. The G1/G3/PAP sample showed an additional heavy chain-heavy chain disulfide linkage in fragment (H232-275), below the original (H224-227) CPPC hinge region. The theoretical and observed mass values for the engineered hinge region peptides was measured. The HuCC49ΔCH2 hinge endo Lys-C non-reduced peptide (residues H221-257) had an observed MW of 7419.4, in good agreement with the calculated mass of 7419.4 g/mol for a linked hinge containing two interchain disulfide bridges. The HuCC49ΔCH2 PAP hinge endo Lys-C non-reduced peptide (residues H221-260) had an observed MW of 7949.7 also in good agreement with the calculated mass of 7949.8 g/mol for a linked hinge containing two interchain disulfide bridges. Two hinge non-reduced peptide fragments resulted from digestion of HuCC49ΔCH2 G1/G3/PAP by endo Lys-C due to the presence of the lysine residue at Kabat position 241II in the 15 amino acid γ3 motif. Peptide fragments of residues H221-231 and H232-275 had observed MWs of 2414.3 and 8782.6 in excellent agreement with the calculated masses of 2413.0 and 8782.0 g/mol, respectively. The mass data supports the assertion that the THTCPPCPEPK peptide (residues H221-231) derived from HuCC49ΔCH2 G1/G3/PAP contains two interchain disulfide bridges. Importantly, the peptide comprising residues H232-275 contains at least one interchain disulfide bridge consistent with the notion that the chimeric G1/G3/PAP hinge is participating in the formation of more than two disulfide bridges. These analyses show that HuCC49ΔCH2 PAP hinge forms two heavy chain interchain disulfide bonds. HuCC49ΔCH2 G1/G3/PAP hinge forms at least three heavy chain interchain disulfide bonds but possibly five. It is certain that fragment HuCC49ΔCH2 G1/G3/PAP residues H232-275 contains minimally one interchain disulfide bond, however it is not possible to discriminate mass differences in a hinge region containing three interchain disulfide bonds from one containing a single interchain and two intrachain disulfide bonds.

TABLE 4

The percentage of Form A antibody after affinity chromatography (Protein G) and after HIC purification

| CH2 domain deleted Antibody | % Form A Antibody | |
|---|---|---|
| | After Protein G | After HIC purification |
| HuCC49 (connecting peptide SEQ ID NO: 25) | 60 | 98 |
| HuCC49 PAP (connecting peptide SEQ ID NO: 32) | 83 | 98 |
| HuCC49 V2 PAP (connecting peptide SEQ ID NO: 32) | 90 | 99 |
| HuCC49 G1/G3/PAP (connecting peptide SEQ ID NO: 5) | 98 | Not done |
| HuCC49 V2 G1/G3/PAP (connecting peptide SEQ ID NO: 5) | 96 | Not done |

These data show that novel, engineered synthetic hinge region connecting peptides can be used to preferentially favor the formation of the A or B isoform. These studies also reveal the importance of the cysteine residues at position 242 (Kabat numbering system) in synthesizing the CH2 domain-deleted antibody Form A isoform. Accordingly, in one embodiment, a connecting peptide of the invention comprises a cysteine at at least one of position 239 or 242. Substituting the cysteine at either position 239 or 242 with serine (e.g., using connecting peptides shown in SEQ ID NOs:28, 29, 30, or 31) shifts CH2 domain-deleted antibody biosynthesis to the Form B isoform. The use of connecting peptides which increase the proportion of Form A produced will lead to a beneficial improvement in process, yield and/or stability. These synthetic hinge region connecting peptides are useful for favoring synthesis of CH2 domain deleted antibody Form A isoform for any antibody isotype, e.g., IgG1, IgG2, IgG3, or IgG4, based on the extremely high degree of homology among the CH3 domains for all four human isotypes. Including identical and conserved amino acid residues, IgG1 CH3 domain is 98.13% homologous to IgG2 CH3, 97.20% homologous to IgG3 CH3, and 96.26% homologous to IgG4 CH3.

Example 4

Purification of Form A and Form B from a Monoclonal Antibody Mixture Containing Both Isoforms 10 mL of ddCC49 supernatant was titrated with 1M Tris pH 9.0 to a final pH of 7.5. This material was filtered through a series of Sol-Vac 0.8µ and 0.4µ membranes. A 100 mL XK50 Protein G column was pre-equilibrated with 1×PBS at a flow rate of 80 ml/min. The titrated, filtered supernatant was loaded onto the column at 80 ml/min. Bound protein was washed with the equilibrium buffer for 2 column volumes and then eluted with 100 mM Glycine at pH 3.0. The fractions containing the ddCC49 peak were collected and immediately titrated with 1 M Tris pH 9.0 to a final pH of 7.0.

A Toso Biosep Phenyl 5PW-HR column was pre-equilibrated with 20 mM Phosphate pH 7.2; 1 M Ammonium Sulfate. The Protein G eluate was titrated to 1 M Ammonium Sulfate using a 3.5 M Ammonium Sulfate pH 7.2 stock and loaded at a concentration of 2 mg/ml of gel bed. Bound protein was washed with a 20 mM Phosphate pH 4 or 7.2 Ammonium Sulfate to adjust the conductivity to 116.4 mS/cm. The material eluted from this condition has an apparent molecular weight about 120 kD (Form A) on a non-reducing SDS-PAGE. The remaining bound antibody was further eluted with a linear gradient of reducing Ammonium Sulfate content in the Phosphate buffer. The latter eluted antibody apparently lacks the disulfide linkage between the heavy chains and its molecular weight is about 60 kDa (form B).

Both of the above purified materials can be recaptured by bringing the ammonium sulfate concentration to 1M and reloading it onto the cleaned Phenyl 5PW-HR column. Bound protein is eluted with 20 mM Phosphate pH 7.2 and dialyzed into 1×PBS.

Example 5

Comparison of Stability of Form A and Form B

The biologic activity of Forms A and B (as measured in preliminary experiments e.g., using direct binding or competition studies) revealed that Forms A and B have similar biologic activity.

The stability of Forms A and B was also compared. Purified ddCC49 molecules were concentrated to about 5 mg/ml by Amicon concentrator fitted with YM30 membrane (Millipore). The concentrated materials were equally divided into four portions for each isoforms and each fraction was put into 10K dialysis cassette (Pierce, cat#66410) for 16 h dialysis in the following buffers: 1) 10 mM Sodium Phosphate, pH3; 2) 10 mM Sodium acetate, pH 5; 3) 10 mM Sodium Phosphate, pH 7; and 4) 10 mM Sodium Borate, pH 9. After dialysis, the protein concentration of each solution was adjusted to 3 mg/ml. In addition to the pure A and B isoform solution, a portion of A and B solutions from each pH were mixed to create a mixture containing 50% each isoform. Total of 12 formulations were created (four pH levels times 3 antibody solutions). The solutions were filtered and filled in 3 ml Type-1 glass serum vials (West Pharmaceuticals) with gray butyl stopper.

Three temperatures, 2-8° C., 20-25° C., and 38-42° C. were chosen to store the protein solutions for stability testing. Prior to storage, 500 µl samples were drawn from each formulation for physical and chemical analyses, these zero-time point data were referred to as control. Once in storage, samples were drawn at the following schedule, 2 weeks, 1 month, 2 months and 3 months and submitted for testing immediately.

To evaluate the physical and chemical stability of the two isoforms, the following methods were used: turbidity measured at $OD_{320}$, non-reducing SDS-PAGE, and size-exclusion chromatography.

Non-reducing SDS-PAGE was performed on samples stored at 2-8° C., 20-25° C. and 38-42° C. for various time points. Both A and B form are relatively stable at pH 5 when stored at 2-8° C. However, when formulated at pH 7 and 9, both A and B forms showed degradation as indicated by increasing in number of bands that were smaller than the original major bands (120 kDa for form A and 60 kDa for form B). It was noticed that, particularly for pH 7 and 9 samples stored at low and intermediate temperatures, the intensity and number of bands that were less than 55 kDa were higher in B-isoform than A. This indicated that under these conditions the A-isoform is more stable than B-isoform. However, this seems not to be the case for A-isoform in pH 5 and stored at 20-25° C. This sample seemed to have more fragments than B-isoform. This appears to have been an artifact due to microbial contamination (discussed in more detail below). At high storage temperature, both forms at pH 9 were significantly degraded and there was almost no difference in gel patterns among the samples. Under this condition, trace amount of smear bands showed up at top of the gel which indicated the formation of aggregates. Because aggregates could be dissolved by SDS, the aggregation was investigated using the methods described in the following sections.

Table 5A through Table 5C list the turbidity data for ddCC49 stored at three different temperatures. The turbidity measures both the soluble and non-soluble aggregates and it is based on the amount of light scattered by these particles. When present, aggregates will scatter light and result in an increase in $A_{320}$. As showed in Table 5A-C, the turbidity of ddCC49 molecules stored at 2-8° C. increases as pH increased for both A and B isoforms, with the former being less turbid than the latter. This trend held true for samples stored for less than a month at higher temperatures (20-25° C. and 38-40° C.). As storage time reached 3 months, the turbidity increased significantly for samples at high pH and temperature, and the difference between A and B forms diminished. These results parallel those of SDS-PAGE and indicate that both isoforms are relatively stable (in terms of not forming aggregates) at pH 3 and 5, and that A-isoform is less susceptible to aggregation than the B isoform.

TABLE 5A

Turbidity measured at $A_{320}$ for ddCC49 samples stored at 2-8° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| 0 | 0.030 | 0.038 | 0.044 | 0.056 | 0.034 | 0.042 | 0.046 | 0.066 | 0.036 | 0.042 | 0.051 | 0.061 |
| ½ | 0.029 | 0.029 | 0.046 | 0.045 | 0.030 | 0.038 | 0.048 | 0.058 | 0.034 | 0.033 | 0.043 | 0.055 |
| 1 | 0.033 | 0.039 | 0.035 | 0.055 | 0.033 | 0.035 | 0.044 | 0.059 | 0.032 | 0.040 | 0.039 | 0.066 |
| 2 | 0.042 | 0.022 | 0.042 | 0.044 | 0.039 | 0.037 | 0.055 | 0.067 | 0.042 | 0.024 | 0.040 | 0.058 |
| 3 | 0.035 | 0.047 | 0.051 | 0.050 | 0.038 | 0.041 | 0.066 | 0.081 | 0.027 | 0.048 | 0.051 | 0.065 |

TABLE 5B

Turbidity measured at $A_{320}$ for ddCC49 samples stored at 20-25° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.031 | 0.032 | 0.056 | 0.066 | 0.039 | 0.034 | 0.064 | 0.083 | 0.034 | 0.039 | 0.060 | 0.071 |
| 1 | 0.025 | 0.043 | 0.055 | 0.090 | 0.034 | 0.042 | 0.070 | 0.084 | 0.028 | 0.039 | 0.055 | 0.094 |
| 2 | 0.034 | 0.053 | 0.077 | 0.113 | 0.046 | 0.032 | 0.090 | 0.087 | 0.037 | 0.038 | 0.066 | 0.108 |
| 3 | 0.036 | 0.056 | 0.156 | 0.143 | 0.029 | 0.060 | 0.121 | 0.125 | 0.044 | 0.050 | 0.101 | 0.142 |

TABLE 5C

Turbidity measured at $A_{320}$ for ddCC49 samples stored at 38-42° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.041 | 0.042 | 0.068 | 0.063 | 0.041 | 0.044 | 0.080 | 0.067 | 0.041 | 0.039 | 0.070 | 0.064 |
| 1 | 0.041 | 0.043 | 0.071 | 0.065 | 0.036 | 0.040 | 0.079 | 0.069 | 0.032 | 0.048 | 0.078 | 0.070 |
| 2 | 0.047 | 0.030 | 0.066 | 0.060 | 0.046 | 0.045 | 0.087 | 0.082 | 0.051 | 0.034 | 0.078 | 0.079 |
| 3 | 0.058 | 0.051 | 0.098 | 0.105 | 0.046 | 0.057 | 0.101 | 0.157 | 0.056 | 0.057 | 0.101 | 0.126 |

Size exclusion chromatography (SEC) is a powerful method for revealing the percent of intact molecules and the degraded products (both fragments and soluble aggregates) and is highly reproducible. In Table 5A-C the percent of intact monomer of A-isoform, B-isoform and the mixture stored at different temperatures are listed. For samples stored at 2-8° C., it is clear that Form A has a higher percentage of monomer as compared to Form B, and the mixture of Form A and Form B was somewhere in between. At this storage temperature, both forms were relatively stable at pH 3, 5 and 7 (with pH 5 being the most stable condition) for about three months. However, at pH 9 there was a significant decrease in percentage of monomer for Form B but only a slight decrease for Form A. At elevated temperatures, all samples showed a significant decrease in percent of monomer as storage time increased; the A-isoform outperformed the B-isoform. However there was an exception, the sample of A-isoform in pH 5 stored at room temperature exhibited much more degradation than the B-isoform or the mixture under similar storage conditions. A close examination of this particular A-isoform vial, the data from SDS-PAGE, and SEC of the sample suggested that microbial contamination might have caused this unexpected result. First, both the SEC and SDS-PAGE results indicated that the degradation for this sample was primarily accounted for by a increase in fragmentation, presumably resulting from microbial digestion, otherwise some degree of increase in aggregation would have been expected. Second, the fact that the mixture sample, which contained 50% each of A and B-isoform, showed a better stability profile than B-isoform indicating that a more stable A-isoform must have contributed to the higher percent of monomer. Finally, A-isoform in pH 5 stored at 2-8° C. and 38-42° C. both showed higher percent of monomer than B-isoform under similar conditions. Therefore, intermediate storage temperature should have yielded similar results. Due to the limited amount of sample, an assay for microbial contamination could not be performed.

It was also noted that for both isoforms of IDEC-159 stored in high pH (9) and at 40° C., the percent of monomer reduced to about 30%. Under these severe conditions, the stability differences between the two isoforms disappeared. This SEC result mirrors of the results found using SDS-PAGE. Both results indicate that, although some chemical and physical characteristics differ between the two isoforms, the mechanism and by-products of degradation for both isoforms are similar, if not identical.

In summary, the SEC results indicate that both A and B-isoforms have optimal pH at about 5, and that A-isoform is more stable than B-isoform in terms of retaining higher percent of intact monomer at similar storage conditions.

TABLE 6A

Percent of monomer for ddCC49 samples stored at 2-8° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| 0 | 98.81 | 99.13 | 98.16 | 97.93 | 97.02 | 97.70 | 96.88 | 93.51 | 97.83 | 98.27 | 97.44 | 95.81 |
| ½ | 98.98 | 99.16 | 98.25 | 98.00 | 97.15 | 97.87 | 96.96 | 91.95 | 98.15 | 98.49 | 97.68 | 95.59 |
| 1 | 98.80 | 99.20 | 97.99 | 97.11 | 97.02 | 97.81 | 96.62 | 88.99 | 98.04 | 98.45 | 97.41 | 94.45 |
| 2 | 98.74 | 99.01 | 98.00 | 95.67 | 97.15 | 97.69 | 95.50 | 84.84 | 98.06 | 98.34 | 96.81 | 92.17 |
| 3 | 98.28 | 98.89 | 97.88 | 95.31 | 96.69 | 98.14 | 95.37 | 85.98 | 97.61 | 98.15 | 96.65 | 89.90 |

TABLE 6B

Percent of monomer for ddCC49 samples stored at 20-25° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 97.83 | 99.04 | 97.12 | 93.65 | 95.84 | 97.62 | 93.71 | 79.61 | 96.75 | 98.30 | 95.37 | 87.67 |
| 1 | 96.60 | 96.63 | 95.65 | 88.09 | 94.38 | 97.23 | 90.69 | 72.26 | 95.36 | 97.99 | 93.05 | 80.92 |
| 2 | 93.62 | 92.79 | 93.17 | 80.06 | 91.71 | 96.96 | 85.51 | 66.53 | 92.78 | 97.51 | 89.33 | 73.91 |
| 3 | 92.81 | 89.56 | x | 74.31 | 89.30 | 96.04 | 82.57 | 63.25 | 90.46 | 97.02 | 86.80 | 69.36 |

TABLE 6C

Percent of monomer for ddCC49 samples stored at 38-42° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 86.31 | 97.50 | 85.06 | 66.42 | 79.85 | 94.29 | 69.68 | 63.64 | 82.09 | 95.70 | 76.24 | 63.95 |
| 1 | 78.71 | 95.19 | 73.77 | 51.55 | 66.73 | 89.37 | 54.70 | 50.10 | 68.53 | 92.02 | 62.93 | 49.28 |
| 2 | 66.64 | 91.63 | 60.45 | 38.43 | 60.29 | 81.08 | 42.98 | 37.09 | 61.33 | 85.81 | 51.08 | 36.68 |
| 3 | 57.87 | 86.99 | 52.82 | 30.81 | 43.61 | 74.23 | 36.68 | 29.73 | 46.75 | 80.93 | 44.35 | 30.18 |

Example 6

Preparative Purification of Forms A and B

IDEC-159 (ddCC49) is a CH2 domain deleted monoclonal antibody directed against TAG-72 antigen, which is expressed on the surface of tumors. IDEC-159 contains two isoforms of the antibody, called Form A and Form B. The current cell culture process for IDEC-159 produces an approximate 50:50 ratio of Form A to Form B. The form A isoform is an antibody with a deleted CH2 region in the $F_C$ portion of the heavy chain. In addition to having a deleted CH2 region, Form B also lacks the disulfide bond linkage across the $F_C$ region and is only held together by hydrophobic interactions and salt bridges.

The third and final chromatography step in the IDEC-159 purification process was developed to separate the two isoforms of IDEC-159. The separation is achieved by hydrophobic interaction chromatography (HIC), using a Phenyl TSK-gel 5PW-HR adsorbent. Since Form B is more hydrophobic than Form A, it adsorbs irreversibly to the stationary phase using approximately 0.73 M Ammonium Sulfate/20 mM Sodium Phosphate, pH 4.0-pH 7.0 as the mobile phase. Form A binds to a lesser extent to the stationary phase under these conditions and is therefore eluted isocratically, i.e. it leaves the column with the flowthrough fraction. Subsequent to the isocratic elution of Form A, omitting Ammonium sulfate from the mobile phase desorbs Form B. The following method was used to separate the two isoforms of IDEC-159:

The column was sanitized using ≧3 CVs of 0.5 N NaOH, at ≦150 cm/hr.

The column was equilibrated using ≧5 CVs of 0.73 M Ammonium Sulfate/20 mM Sodium Phosphate, pH 4.0, at ≦150 cm/hr.

The column was loaded with room temperature TMAE Flowthrough that has been adjusted to include 0.43 volumes of 2.5 M Ammonium Sulfate/20 mM Sodium Phosphate, pH 4.0 liquid stock solution, at 5 mg per ml of resin. The antibody was loaded onto the column at pH 4.0, at ≦100 cm/hr. Collection of the antibody started when the outlet O.D. at 280 nm reaches 10 mAU.

The column was washed using 15 CVs of 0.73 M Ammonium Sulfate/20 mM Sodium Phosphate, pH 4.0, at ≦100 cm/hr. Continue antibody collection throughout the 15 CV wash, then the outlet was diverted back to waste.

The column was stripped using ≧5CVs of 20 mM Sodium Phosphate, pH 4.0, at ≦100 cm/hr. 6. The column was cleaned with ≧3 CVs 0.5 N NaOH, at ≦150 cm/hr.

The column was equilibrated with ≧3 CVs of 0.73 M Ammonium Sulfate/20 mM Sodium Phosphate, pH 4.0, at ≦150 cm/hr.

The column was stored in ≧3 CVs of 20% Ethanol, at ≦150 cm/hr.

The separation of the two forms at a preparative scale (5 L column volume, total IDEC-159 load approximately 20 g) has been performed. The first two peaks comprise the isocratic elution of Form A, the second peak shows the eluted Form B, while the third peak contains impurities, which are removed from the stationary phase during cleaning.

The capability of this method to separate Forms A and B at preparative scale was also demonstrated by SDS PAGE. The fractions eluted isocratically using 0.73 M Ammonium Sulfate/20 mM Sodium Phosphate, pH 4.0 (lanes 6 to 8) contain predominantly Form A (purity >90%).

Example 7

Humanization of Monoclonal Antibody CC49

Several changes to the CC49 antibody were made to create a humanized CC49 version 2 (huCC49 V2). To further reduce potential immunogenicity of the humanized CC49 MAb, murine residues present in the antibody were examined and considered for replacement with human framework residues derived from human acceptor sequences LEN for light chain substitutions and 21/28' CL for heavy chain substitutions. (Singer I I et al., 1993. Optimal Humanization of 1B4, an Anti-CD 18 Murine Monoclonal Antibody, is Achieved by Correct Choice of Human V-Region Framework Sequences. J. Immunol. 150:2844-2857. Padlan E A, 1991. Possible Procedure For Reducing the Immunogenicity of Antibody Variable Domains While Preserving Their Ligand-Binding Properties. Molecular Immunol. 28:489-498).

Framework residues considered to be important for preserving the specificity and affinity of the combining site revealed only a few differences. In the heavy chain sequence, the predicted buried residues at positions 69 (leucine) and 93 (threonine) were both substituted with the human residues isoleucine and alanine, respectively. In the light chain sequence, one residue predicted to be mostly buried at position 43 (serine) was substituted with the human residue proline.

Domain deleted forms of the V2 CC49 antibody were made and connecting peptides were inserted into the huCC49.V2 sequence. A CH2 domain-deleted huCC49 V2 containing G1/G3/Pro243Ala244Pro245+[Gly/Ser] hinge connecting peptide was made as was CH2 domain-deleted huCC49 V2.

Example 8

Enhanced Biodistribution Profiles of Antibodies Comprising Novel Connecting Peptides Various forms of domain deleted antibodies (with and without connecting peptides) were tested in a competitive binding assay for their ability to bind to bovine submaxillary mucine, a source of the TAG-72 antigen, by time-resolved flourometric immunoassay using a Wallac 1420 Multilabel Counter Victor V (PerkinElmer). HuCC49 PAP (containing the connecting peptide shown in SEQ ID NO: 32), HuCC49 V2 PAP (containing the connecting peptide shown in SEQ ID NO: 32), HuCC49 G1/G3:PAP (containing the connecting peptide shown in SEQ ID NO: 5), HuCC49 V2 G1/G 3/PAP (containing the connecting peptide shown in SEQ ID NO: 5), and control parent HuCC49 antibodies were evaluated. Relative binding activities for all three hinge engineered antibodies are indistinguishable or within 2-3-fold of the control parent CC49 antibody.

Biodistribution of $^{90}$Y-2-(p-isothiocyanatobenzyl)(p-SCN-Bz)-cyclohexyldiethylenetriaminepentaacetic acid ligand (CHx-DTPA) conjugated HuCC49 V2 PAP (containing the connecting peptide shown in SEQ ID NO: 32) and control parent HuCC49 antibody were evaluated and compared in athymic mice bearing LS-174T human tumor xenografts. Percentage injected dose (% ID) of $^{90}$Y radiolabelled antibody per gram of tumor or normal tissue was determined at 3 and 24 hours and is shown in Table 7.

TABLE 7

| | Blood | Spleen | Kidney | Liver | Tumor |
|---|---|---|---|---|---|
| | | | HuCC49 | | |
| 3 hrs | 20.1 ± 3.5 | 6.1 ± 1.6 | 11.7 ± 1.7 | 10.1 ± 1.8 | 9.3 ± 2.0 |
| 24 hrs | 0.7 ± 0.2 | 9.5 ± 4.0 | 11.0 ± 2.0 | 12.0 ± 1.5 | 12.7 ± 7.1 |
| | | | HuCC49 V2 PAP | | |
| 3 hrs | 24.6 ± 3.0 | 4.6 ± 2.2 | 10.0 ± 1.4 | 8.4 ± 1.0 | 16.1 ± 5.0 |
| 24 hrs | 2.0 ± 0.6 | 7.7 ± 1.8 | 6.7 ± 0.4** | 11.2 ± 2.2 | 21.3 ± 4.8* |

7 mice/group

Data represent mean values +/− standard deviations.
*p < 0.05 unpaired t test compared to 24 hr time point HuCC49 in tumor
**p < 0.001 unpaired t test compared to 24 hr time point HuCC49 in kidney Surprisingly, at the 24 hour time point HuCC49 V2 PAP uptake was significantly higher in the tumor (p<0.05 unpaired t Test) and, conversely, lower in the kidney (p<0.01) than control HuCC49 antibody. When the tumor to organ ratio for these antibodies was compared, the HuCC49 V2 PAP resulted in a higher tumor to organ ratio for all organs except blood.

These results suggest that these novel hinges impart structural changes to antibodies that positively effect tumor localization and decrease uptake by normal organs, such as the kidney. Thus, these novel hinges are particularly useful when incorporated into therapeutic antibodies.

Example 9

Enhanced Biodistribution Profiles of Antibodies Comprising Novel Connecting Peptides: Detailed Time Course This example confirms and extends the results presented in Example 8. The antibodies Human CC49 V2 G1/G3/Pro243Ala244Pro245+[Gly/Ser] (SEQ ID NO: 5) and HuCC49 (gly/ser) were diafiltered and concentrated into low metal 5 mM sodium acetate buffer, pH 5 (LMB) using a pre-rinsed Amicon Centricon 30. Centrifugation of the centricon was performed in a fixed angle rotor at 5000×g held at a temperature of 2-8° C. Each antibody was recovered by adding 50 µl of LMB to the sample reservoir, vortexing briefly, and back-spinning for 10 minutes at 1000×g. The protein concentration was determined using UV Spec analysis at 280 nm using the extinction coefficient of 1.48. Each antibody was then adjusted down to 10.5 mg/ml using LMB.

The antibodies were adjusted to ~pH 8.6 using 1.0 M Boric Acid (pH 8.6, Chelex treated and 0.2 µm filtered). CHx-DTPA (dissolved in 1.0 M Boric Acid) was then added at a molar ratio of 3 chelates to 1 mole of antibody. The amount of Boric acid added was one-tenth the antibody volume. This mixture was then vortexed and incubated for 16 to 18 hours at room temperature. The reaction was stopped by adding the mixture to a new, pre-rinsed Centricon 30 and diafiltered into low metal 5 mM Sodium Acetate, 150 mM Sodium Chloride, pH 5 as per the previous diafiltration. The concentration of each antibody was adjusted to 3 mg/mL.

Female nude mice were inoculated s.c. with LS174T cells suspended in HBSS (Biowhittaker, Cat#10-547F) on the inside of the right thigh. Tumor sizes were measured one day prior to study start. Tumor volumes were calculated by multiplying the length times half of the squared width [L×((W²)/2)]. The mice were grouped to give an average tumor volume of ~200 mm3.

Forty two nude mice were injected with $^{111}$In-labeled CH2 domain deleted antibody at time zero. The study tracked the distribution of the antibody over the course of seven timepoints with each timepoint consisting of six mice. Urine was collected from each mouse by holding the mouse over tared weigh paper and squeezing the bladder. Blood was taken via "eye bleed" (approximately 200 ul per mouse). For each individual mouse, any feces excreted during the blood and urine sampling was collected.

Following the blood collection, the mice were sacrificed by cervical dislocation. Once each of the six mice had been sacrificed the other samples were collected via dissection. Each sample (except for the skin) was rinsed with 3% formalin, blotted dry on paper towel and then weighed. All samples were weighed using tared weigh paper Following the sample collections, the samples were placed into borosilicate test tubes and counted on a gamma counter along with a decay control consisting of a 1:10 dilution of the labeled antibody. The percent radioactivity associated with each organ or tissue relative to the decay control (% injected dose/g tissue or organ) was calculated. The example shows that antibody molecules comprising this novel connecting peptide show decreased accumulation in the kidney, slightly increased accumulation in the blood and significantly increased accumulation at tumor. This profile is consistent with these molecules having increased stability in vivo and enhanced efficacy and safety.

Example 10

Antibodies Comprising Connecting Peptides have Decreased Sensitivity to Reducing Agents The example demonstrates that domain deleted CC49 G1/G3/Pro243Ala244Pro245+[Gly/Ser] (SEQ ID NO: 5) appears more stable toward glutathione (GSH) reduction, as is parent CC49, than domain deleted CC49 with a Gly-Ser hinge linker.

Briefly, 50 ug of ddCC49 (Gly-Ser), ddCC49 G1/G3/Pro243Ala244Pro245+[Gly/Ser] (SEQ ID NO: 5) or parent CC49 were incubated with 0, 1, 5 or 10 mM GSH for one hour at room temperature. Reaction buffers used include 100 mM PBS, pH 7.2 or 100 mM Sodium Acetate, 100 mM NaCl, pH 4.5. GSH-treated antibodies were heated with SDS and applied to a 4-20% gradient SDS-PAGE, non-reducing gel. Applied samples were allowed to migrate through the gel at a constant 120 Volts for 90 minutes at room temperature. Proteins were Coomassie stained and gels dried.

Domain deleted CC49 G1/G3/Pro243Ala244Pro245+[Gly/Ser] (SEQ ID NO:5) appears more stable toward glutathione (GSH) reduction, as is parent CC49, than domain deleted CC49 with a Gly-Ser hinge linker. In addition, 100 mM Sodium Acetate at pH 4.5 further protects domain deleted CC49 G1/G3/Pro243Ala244Pro245+[Gly/Ser] (SEQ ID NO: 5) from GSH reduction compared to 100 mM PBS at pH 7.2. This unexpected observation of decreased sensitivity to reducing agents suggests that the G1/G3/Pro243Ala244Pro245+[Gly/Ser] (SEQ ID NO: 5) hinge design enables the use of chemistries using reducing agents, such as those used to prepare drug conjugates (e.g. SPDP linkers) or techniques for attaching radioisotopes to antibodies (eg. $^{99M}$Tc), while maintaining the physical integrity of the antibody. This advantage with respect to reducing agent sensitivity does not appear to alter pharmacokinetic advantages of CH2-domain deleted constructs (see mouse biodistribution data in Example 9). The decreased sensitivity to reducing agents also may be predictive of increased in vivo stability.

Example 11

Anti-CD20 Antibody Comprising a Connecting Peptide

The hinge region connecting peptide G1/G3/Pro243Ala244Pro245+[Gly/Ser] (SEQ ID NO: 5) was introduced into a CH2 domain-deleted C2B8 antibody as described in Example 3. C2B8 is a chimeric anti-CD20 monoclonal antibody consisting of murine heavy and light chain variable domains fused to human heavy and light chain constant domains, respectively. Correct modifications to the hinge region were confirmed by DNA sequence analysis. Plasmid DNA was used to transform CHO DG44 cells for transient production of antibody protein.

Supernatant was collected from cells producing CH2 domain-deleted C2B8 antibody containing the G1/G3/Pro243Ala244Pro245+[Gly/Ser] connecting peptide and concentration of antibody in the culture supernatants determined by immunoassay. Approximately 3 ng of total antibody protein from the transient cell culture was compared to CH2 domain-deleted huCC49 MAb by non-reducing SDS-PAGE electrophoresis followed by Western Blot with anti-human IgG HRP conjugated antibody to detect CH2 domain deleted huCC49 Form A and Form B isoforms. Under these conditions, Form A migrates as a single 120 kDa homodimer and Form B as a 60 kDa doublet. Incorporation of the connecting peptide shown in SEQ ID NO: 5 was found to substantially increase the proportion of Form A produced. The results demonstrate that the G1/G3/Pro243Ala244Pro245+[Gly/Ser] hinge (SEQ ID NO:5) resulted in the production of essentially all Form A CH2 domain-deleted C2B8 antibody with little or no detectable Form B, demonstrating that the utility of this hinge for producing the Form A isoform is generally applicable to antibodies of varying specificities.

Example 12

Anti-CD23 Antibody Comprising a Connecting Peptide

The hinge region connecting peptide G1/G3/Pro243Ala244Pro245+[Gly/Ser] (SEQ ID NO: 5) was used to construct a CH2 domain-deleted 5E8 (5E8ΔCH2) antibody essentially as described in Example 3. 5E8 is a chimeric anti-CD23 monoclonal antibody consisting of primate heavy and light chain variable domains fused to human heavy and light chain constant domains, respectively. Correct modifications to the hinge region were confirmed by DNA sequence analysis. Nucleic acid and amino acid sequences of 5E8 light chain and heavy chain are known in the art. Plasmid DNA was used to transform CHO DG44 cells for production of antibody protein.

A cell line (1A7) containing the G1/G3/Pro243Ala244Pro245+[Gly/Ser] (SEQ ID NO:5) connecting peptide introduced into the 5E8ΔCH2 antibody sequence was used for antibody production. Antibody was produced and purified using methods described in Example 4 above. 5E8ΔCH2 G1/G3/Pro243Ala244Pro245 antibody, purified using only the Protein G column, eluted essentially as a single peak at ≧97% purity without further HIC purification.

Reduced and non-reduced purified protein samples were analyzed by SDS-PAGE electrophoresis. Under non-reducing conditions, Form A is expected to migrate as a single 120 kDa homodimer and Form B as a 60 kDa doublet. The connecting peptide shown in SEQ ID NO: 5 was found to substantially increase the proportion of Form A produced. This result shows that the G1/G3/Pro243Ala244Pro245+[Gly/Ser] hinge (SEQ ID NO:5) resulted in the production of essentially all Form A 5E8ΔCH2 antibody with little or no detectable Form B (see lane 2), demonstrating that the utility of this hinge for producing the Form A isoform is generally applicable to antibodies of varying specificities. 5E8ΔCH2 G1/G3/Pro243Ala244Pro245 antibody was examined by size exclusion chromatography and found to elute as a single peak indicating that there was no significant aggregation or decomposition of antibody product. 5E8ΔCH2 G1/G3/Pro243Ala244Pro245 antibody was further tested in a FRET (fluorescence resonance energy transfer) competitive binding assay for Cy5-labeled soluble CD23 binding to Eu-labeled 5E8 IgG using a Delphia fluorimeter (Wallac 1420 Multilabel Counter Victor V, PerkinElmer). 5E8ΔCH2 G1/G3/Pro243Ala244Pro245 (containing the connecting peptide shown in SEQ ID NO: 5), and control parent 5E8 IgG antibodies were evaluated in competitive binding assays. Relative binding activity of the hinge engineered antibody was indistinguishable from control parent 5E8 IgG antibody. From these results it is clear that introduction of the hinge region (containing the connecting peptide shown in SEQ ID NO: 5) in the 5E8ΔCH2 antibody led to the preferential synthesis of the A isoform while retaining full binding activity and supports the general utility of the engineered hinges.

Example 13 chB3F6 Antibody Comprising a Connecting Peptide

The hinge region connecting peptide G1/G3/Pro243Ala244Pro245+[Gly/Ser] (SEQ ID NO: 5) was used to construct a CH2 domain-deleted chimeric B3F6 (chB3F6ΔCH2) antibody essentially as described in Example 3. "chB3F6" is a chimeric anti-CRIPTO monoclonal antibody consisting of murine heavy and light chain variable domains fused to human heavy and light chain constant domains, respectively. Correct modifications to the hinge region were confirmed by DNA sequence analysis. Nucleic acid and amino acid sequences of chB3F6 light chain and heavy chain are shown in are shown in FIGS. 1 and 2, respectively. Plasmid DNA was used to transform CHO DG44 cells for production of antibody protein.

A cell line (3C7) containing the G1/G3/Pro243Ala244Pro245+[Gly/Ser] (SEQ ID NO:5) connecting peptide introduced into the chB3F6ΔCH2 antibody sequence was used for antibody production. Antibody was produced and purified using methods described in Example 4 above. ChB3F6ΔCH2 G1/G3/Pro243Ala244Pro245 antibody, purified using only the Protein G column, eluted essentially as a single peak at 97% purity without further HIC purification. Reduced and non-reduced purified protein samples were analyzed by SDS-PAGE electrophoresis. Under these conditions, Form A is expected to migrate as a single 120 kDa homodimer and Form B as a 60 kDa doublet. The connecting peptide shown in SEQ ID NO: 5 was found to substantially increase the proportion of Form A produced. This results show that the G1/G3/Pro243Ala244Pro245+[Gly/Ser] hinge (SEQ ID NO:5) resulted in the production of essentially all Form A chB3F6ΔCH2 antibody with little or no detectable Form B, demonstrating that the utility of this hinge for producing the Form A isoform is generally applicable to antibodies of varying specificities. ChB3F6ΔCH2 G1/G3/Pro243Ala244Pro245 antibody was examined by size exclusion chromatography and found to elute essentially as a single peak ranging from 93-98% monomer indicative of little or no significant aggregation or decomposition of antibody product. ChB3F6ΔCH2 G1/G3/Pro243Ala244Pro245 antibody was further tested in a flow cytometry competitive binding assay with FITC-labeled B3F6 IgG binding to GEO tumor cells, a source of the CRIPTO antigen. Competitive binding of ChB3F6ΔCH2 G1/G3/Pro243Ala244Pro245 (containing the connecting peptide shown in SEQ ID NO: 5), and two control samples of chB3F6 IgG antibodies were evaluated. Relative binding activity of the hinge engineered antibody was indistinguishable from the control parent chB3F6 IgG antibodies. From these results it is clear that introduction of the hinge region (containing the connecting peptide shown in SEQ ID NO: 5) in chB3F6ΔCH2 antibody led to the preferential synthesis of the A isoform while retaining full binding activity and further supports the general utility of the engineered hinges.

Example 14

Preparation of Humanized Forms of the B3F6 Anti-Cripto Antibody

The variable regions of the B3F6 antibody were sequenced. The sequence of the light chain variable regions of the murine B3F6 antibody is provided below:

```
                                                                (SEQ ID NO: 39 )
  1 Df LMTQTPLS LPVSLGDQAS ISCRsSQSiV HSNGNTY1EW YLQKPGQSPK

51 LLiY KvsNRF SGVPDRFSgS GSGTDfTLKI SRVEAEDLGV YYCFqGSHVp

101 LTFGAGTKLE LK
```

The sequence of the heavy chain variable regions of the murine B3F6 antibody is provided below:

```
                                                                (SEQ ID NO: 40)
  1 QVQLQQVGAE LVKPGASVKL SCKaSgyTfT SYWiHWVKQR PGQGLEWIGE

51 NDpSNgRTNY NEKFKNKATL TvDKSSSTAY MHLSSLTSED SAVYYCSrGP

101 NYFYSMDYWG QGTSVTVSS
```

For each of these sequences, the CDR residues are underlined, Canonical residues are indicated in lower case, and unusual canonical residues are indicated in lower case, italicized and bolded.

The complementarity determining regions (CDRs) were classified into canonical classes. CDRs contain the residues most likely to bind antigen and must be retained in the reshaped antibody. CDRs are defined by sequence according to Kabat et al (Kabat, E. A., Wu, T. T., Perry, H. M., Gottesman, K. S. and Foeller, C. (1991) Sequences of Proteins of Immunological Interest. 5$^{th}$ Edition, U.S. Dept. Health and Human Services. U.S. Govt. Printing Office). CDRs fall into canonical classes (Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M. and Poljak, R. J. (1989) Nature 342:877-883). where key residues determine to a large extent the structural conformation of the CDR loop. These residues are almost always retained in the reshaped antibody. The CDRs of the heavy and light chain were classified into canonical classes as follows:

| Light Chain: | | | Heavy Chain: | | |
|---|---|---|---|---|---|
| L1: | 16 residues | Class 4 | H1: | 5 residues | Class 1 |
| L2: | 7 residues | Class 1 | H2: | 17 residues | Class 2 |
| L3: | 9 residues | Class 1 | H3: | 10 residues | No canonical class |

The canonical residues important for these classes are indicated in Table 8. Loop L1 has an F at position 2 whereas canonical residues are V/I. Loop H2 has a V at position 71, whereas canonical residues are A/T/L (although V is canonical for H2 class 1).

TABLE 8

| | | |
|---|---|---|
| L1 | Class 4 | 2(V, I) 25(S) 27b(I, L) 33(L) 71(F) |
| L2 | Class 1 | 48(I) 51(A, T) 52(S, T) 64(G) |
| L3 | Class 1 | 90(Q, N, H) 95(P) |
| H1 | Class 1 | 24(A, V, G), 26(G), 27(F, Y), 29(F), 34(M, W, I), 94(R, K) |
| H2 | Class 2 | 52a(P, T, A) 55(G, S) 71(A, T, L) |
| H3 | No Canonical Class | |

The variable light and heavy chains were compared with the consensus sequences for mouse and human subgroups (Kabat et al. 1991) using the program FASTA and a database of consensus sequences. The variable light chain was found to be a member of mouse subgroup Kappa 2 with a 92.9% identity in 113 aa overlap. An alignment is shown below:

```
Alignment of B3F6 Light Chain against mouse subgroup Kappa 2 consensus
>>moukv2 Length: 113 Aug. 6, 1992 15:04 Type: P C (113 aa)
initn: 654 init1: 654 opt: 700 z-score: 83.4 E( ): 0.24
Smith-Watermanscore: 700; 92.920% identity in 113 aa overlap
              10         20         30         40         50         60
B3F6  L DFLMTQTPLSLPVSLGDQASISCRSSQSIVHSNGNTYLEWYLQKPGQSPKLLIYKVSNRF      (SEQ ID NO: 39)
        X .::::::::::::::::::::::::::::.::::::::::::::::::::::::::::
moukv2 DVVMTQTPLSLPVSLGDQASISCRSSQSLVHSNGNTYLEWYLQKPGQSPKLLIYKVSNRF      (SEQ ID NO: 41)
              10         20         30         40         50         60

70         80         90        100        110
B3F6  L SGVPDRFSGSGSGTDFTLKISRVEAEDLGVYYCFQGSHVP-LTFGAGTKLELK
        ::::::::::::::::::::::::::::::::::::::.::X :::.::::.:
moukv2 SGVPDRFSGSGSGTDFTLKISRVEAEDLGVYYCFQGTHVPPYTFGGGTKLEIK
              70         80         90        100        110
```

The variable heavy chain was found to be a member of mouse subgroup 2B with a 80.5% identity in 128 aa overlap. An alignment is shown below:

```
Alignment of B3F6 Heavy Chain against mouse subgroup 2B consensus
>>mouhv2b Length: 127 Aug. 6, 1992 15:04 Type: P (127 aa)
initn: 664 initi: 592 opt: 653 z-score: 96.8 E( ): 0.043
Smith-Waterman score: 653; 80.469% identity in 128 aa overlap 10         20         30         40         50         60
B3F6  H QVQLQQVGAELVKPGASVKLSCKASGYTFTSYWIHWVKQRPGQGLEWIGENDPSNGRTNY      (SEQ ID NO: 40)
        X::::: :::::::::::::::::::::::::::::.::::::::::::: ::..: :::
mouhv2 QVQLQQPGAELVKPGASVKLSCKASGYTFTSYWMHWVKQRPGQGLEWIGRIDPNSGGTNY      (SEQ ID NO: 42)
              10         20         30         40         50         60

70         80         90        100        110
B3F6  H NEKFKNKATLTVDKSSSTAYMHLSSLTSEDSAVYYCSR----GPN-----YFYSMDYWGQ
        ::::::.:::::::::::::::::.::::::::::::.X   : .      .: .:::::
mouhv2 NEKFKSKATLTVDKSSSTAYMQLSSLTSEDSAVYYCARYYYGGSSXXVYXYWY-FDYWGQ
              70         80         90        100        110

B3F6  H GTSVTVSS
        ::.:::::
mouhv2 GTTVTVSS
              120
```

The variable light chain corresponds to human subgroup Kappa 2 with a 76.3% identity in 114 aa overlap. An alignment is shown below:

```
Alignment of B3F6 Light Chain against human subgroup Kappa 2 consensus
>>humkv2 Length: 114 Aug. 6, 1992 15:04 Type: P C (114 aa)
initn: 566 initl: 383 opt: 571 z-score: 73.2 E( ): 0.88
Smith-Waterman score: 571; 76.316% identity in 114 aa overlap
              10        20        30        40        50
B3F6  L DFLMTQTPLSLPVSLGDQASISCRSSQSIVHS-NGNTYLEWYLQKPGQSPKLLIYKVSNR   (SEQ ID NO: 39)
        :..::::.:::::: :. ::::::::::::: .X:.::.::::::::::::.:::: ::::
humkv2 DIVMTQSPLSLPVTPGEPASISCRSSQSLLHSXDGNNYLNWYLQKPGQSPQLLIYLVSNR   (SEQ ID NO: 43)
              10        20        30        40        50        60

60        70        80        90       100       110
B3FG  L FSGVPDRFSGSGSGTDFTLKISRVEAEDLGVYYCFQGSHVP-LTFGAGTKLELK
        ::::::::::::::::::::::::::::::::::::::.:. . X   :::  :::...:
humkv2 ASGVPDRFSGSGSGTDFTLKISRVEAEDVGVYYCMQALQXPRXTFGQGTKVEIK
             70        80        90       100       110
```

The variable heavy chain corresponds to human subgroup 1 with a 65.1% identity in 129 aa overlap. An alignment is shown below:

```
Alignment of B3F6 Heavy Chain against human subgroup 1 consens
>>humhv1 Length: 129 Aug. 6, 1992 15:04 Type: P C (129 aa)
initn: 348 initl: 274 opt: 532 z-score: 85.5 ( ): 0.18
Smith-Waterman score: 532; 65.116% identity in 129 aa overlap 10        20        30        40        50
B3F6  H QVQLQQVGAELVKPGASVKLSCKASGYTFTSYWIHWVKQRPGQGLEWIGENDP-SNGRTN   (SEQ ID NO: 40)
        X::: : ::::. ::::::::::::::::::::: : ::.: :::::::::. .X .:: ::
humhv1 QVQLVQSGAEVVKKPGASVKVSCKASGYTFTSYAISWVRQAPGQGLEWMGWINPYGNGDTN   (SEQ ID NO: 44)
              10        20        30        40        50        60

60        70        80        90       100       110
B3F6  H YNEKFKNKATLTVDKSSSTAYMHLSSLTSEDSAVYYCSRGPNYF---------YSMDYWG
        : .::......:.: :.::::::.::: :::.::::::.::.:           :  .:::::
humhv1 YAQKFQGRVTITADTSTSTAYMELSSLRSEDTAVYYCARAPGYGSGGGCYRGDYXFDYWG
             70        80        90       100       110       120

B3F6  H QGTSVTVSS
        ::: :::::
humhv1 QGTLVTVSS
```

In one humanization design, the xray structure of the B3F6 Fab complexed with the binding peptide from the antigen was used. The most similar human expressed antibody sequences were selected for use as the antibody frameworks. To find the closest expressed sequences the most homologous expressed human frameworks were searched for in the NCBI NR database and the Kabat database. For heavy and light chain sequences two searches (with CDR masked and unmasked) were performed. The selection of the most suitable expressed sequence includes checking for sequence identity of the canonical and interface residues, as well as checking for the similarity in CDR loop lengths. The source of the antibody is also a determining factor. Previously humanized antibodies are excluded. For the NCBI NR database searches we used BLAST, and for the Kabat database search FASTA was used.

The most suitable expressed light chain was found in the nr database (gi-21669417 (BAC01733); Akahori et al. (unpublished, see NCBI web site)), originating from isolated antibodies from a mixture of tissues, tonsils, umbilical cords, peripheral blood and bone marrow. The alignment is shown below:

```
Alignment between B3F6 Light Chain and human gi-21669417 (BAC01733)
>>BAC01733 (112 aa)
initn: 447 initi: 447 opt: 447
Smith-Waterman score: 447; 61.607% identity in 112 aa overlap 10        20        30        40        50        60
B3F6  L DFLMTQTPLSLPVSLGDQASISCXXXXXXXXXXXXXXXXXWYLQKPGQSPKLLIYXXXXXX   (SEQ ID NO: 39)
         X .:::.:::::: :. :::::                  :::::::::::.:::::.:::
BAC017 DVVMTQSPLSLPVTPGEPASISCRSSQSLLHSNGYNYLDWYLQKPGQSPQLLIYLGSNRA   (SEQ ID NO: 45)
              10        20        30        40        50        60

70        80        90       100       110
B3F6  L XGVPDRFSGSGSGTDFTLKISRVEAEDLGVYYCXXXXXXXXXXFGAGTKLELK
        :::::::::::::::::::::::::::::.::::          .:: :::::.X
BAC017 SGVPDRFSGSGSGTDFTLKISRVEAEDVGVYYCMQALQTPYTFGQGTKLEIK
             70        80        90       100       110
```

The most suitable heavy chain was found in the nr database (gi-14289106 (AAK57792); Salcedo et al. (2002)), originating from a polyclonal set of B-lymphocytes in a benign lymphoproliferation. The alignment is shown below:

```
Alignment between B3F6 Heavy Chain and human gi-14289106
>>gi|14289|061gb|AAK57792.1|zimmunoglobulin heavy chain (120 aa)
initn: 395 initi: 395 opt: 397
Smith-Waterman score: 397; 53.782% identity in 119 aa overlap 10        20        30        40        50        60
B3F6   H QVQLQQVGAELVKPGASVKLSCKASGYTFTXXXXXWVKQRPGQGLEWIGXXXXXXXXXXX  (SEQ ID NO: 40)
         .X:: .  :::. ::::::::.::::::::::     ::..: :::::::.:
gi|142   EVQLVESGAEVKKPGASVKVSCKASGYTFTGYFMHWVRQAPGQGLEWMGRINPNSGGTNY  (SEQ ID NO: 46)
              10        20        30        40        50        60

70        80        90       100       110
B3F6   H XXXXXXKATLTVDKSSSTAYMHLSSLTSEDSAVYYCSRXXXXXXXXXXXWGQGTSVTVSS
          ..::: : : :::::.:: : :.:.:::::.:   .    ::::: ::: X
gi|142   AQKFQGRVTLTRDTSISTAYMELSRLRSDDTAVYYCARLDTAIDAFDIWGQGTMVTVCSN
              70        80        90       100       110       120
```

Both human expressed sequences were searched against the database of germline sequences at NCBI, and this resulted in the following selected germlines: A3*/A19* for the light chain (BAC01733), and VH1-2* for the heavy chain (AAK57792).

Selected human framework residues were selected for backmutation to the corresponding mouse residue. Preference was given to retaining canonical residues, interface packing residues and unusual murine residues, which are close to the binding site. In addition, residues within 6 Å of any of the CDR residues were analyzed closely for potential effects on the conformation of the CDRs.

In one version of the humanized B3F6 light chain, the V at position 2 was changed to an F. The amino acid at this position was identified as important because it interacts with L93 (CDR-L3). This CDR is involved in binding the peptide derived from antigen.

Using this methodology one version of the light chain was made:

```
Light ChainVersion L1 (1 backmutation)
                                    (SEQ ID NO: 47)
DfVMTQSPLS LPVTPGEPAS ISCRSSQSIV HSNGNTYLEW

YLQKPGQSPQ LLIYKVSNRF SGVPDRFSGS GSGTDFTLKI

SRVEAEDVGV YYCFQGSHVP LTFGQGTKLE IK
```

The following amino acid residues were selected for potential backmutation in the humanized B3F6 heavy chain: the M at position 48, the V at position 67, the R at position 71, the T at position 73, the A at position 93 and the C at position 112.

The M at position 48 was determined to be close to CDR-H2, but not close to peptide antigen. It was retained in one version of the humanized heavy chain and backmutated to an I in another version.

The V at position 67 was determined to be close to CDR-H2, but not close to peptide antigen. It was retained in one version of the humanized heavy chain and backmutated to an A in another version.

The R at position 71 was determined to be canonical. It was backmutated to a V in both versions.

The T at position 73 was determined to be close to CDR-H2, but not close to peptide antigen. It was retained in one version of the humanized heavy chain and backmutated to a K in another version.

The A at position 93 was determined to be an interface residue without obvious sidechain contact. It was retained in one version of the humanized heavy chain and backmutated to an S in another version.

The C at position 112 was determined to be an unusual human residue. It was backmutated to an S in both versions. Using this methodology two versions of the heavy chain were made:

```
Heavy Chain Version H1 (6 backmutations)
                                    (SEQ ID NO: 48)
EVQLVESGAE VKKPGASVKV SCKASGYTFT SYWIHWVRQA PGQGLEWiGE NDPSNGRTNY NEKFKNRaTL TvDkSISTAY MELSRLRSDD TAVYYCsRGP NYFYSMDYWG QGTMVTVsS Version H2 (2 backmutations)
                                    (SEQ ID NO: 49)
EVQLVESGAE VKKPGASVKV SCKASGYTFT SYWIHWVRQA PGQGLEWMGE NDPSNGRTNY NEKFKNRVTL TvDTSISTAY MELSRLRSDD TAVYYCARGP NYFYSMDYWG QGTMVTVsS
```

Example 15

Preparation of Additional Humanized Forms of the B3F6 Anti-Cripto Antibody

Using a knowledge based method (searching databases of other humanized antibodies to determine sequence changes that are tolerated) another version of the light chain comprising a backmutation at position 2 and at position 100 was made.

The humanization strategy was based on visual inspection and analysis of V region sequences according to the methods described in Rosok et al (Rosok M J, et al., 1996. J. Biol. Chem. 271: 22611-22618). Canonical determinants, surface residues, and potential contact residues were identified. Potential contact residues were noted and broadly classified according to the structural definition of CDR loops as defined by Chothia et al. (Chothia C and Lesk A M. 1987. J. Mol. Biol. 196: 901-917), sequence hypervariability as defined by Kabat et al. (Kabat E A, Wu T T, Reid-Miller M, Parry H M, and Gottesman K S. 1987. Sequences of Protein of Immunological Interest, U.S. department of Health and Human Services, NIH, Bethesda, Md.), and potential antigen contact residues as defined by MacCallum et al. (MacCallum R M, Martin A C R, and Thorton J M. 1996. J. Mol. Biol. 262: 732-745). Murine CDR loops, according to Kabat numbering and definition, were grafted in their entirety onto the acceptor human framework. Packing residues as defined by Padlan (Padlan E A. 1991. Mol Immunol. 28: 489-498) were identified and an attempt is made to conserve the packing residues in accordance with the strategy described in Singer I I et al. (Singer I I et al. 1993. J. Immunol. 150: 2844-2857). Each residue in the framework sequence was assigned a low, medium, or high "risk position" for antibody humanization as described in Harris and Bajorath (Harris L and Bajorath J. 1995. Protein Science 4: 306-310).

In general, low risk positions were kept human. For many of the nonidentical medium and high risk amino acid positions reference was made to collections of humanized antibodies and whether the inclusion of a human or murine (backmutation) amino acid residue resulted in functional binding activity was considered. In those cases where a substitution is considered an amino acid substitution map (D. Bordo and P. Argos. 1991. J. Mol. Biol. 217: 721-729) to confirm the functional interchangeability of the residues.

Using this methodology, one version of the light chain was made. The sequence of the light chain is set forth below:

```
Light Chain Version L2:
                                      (SEQ ID NO: 50)
DfVMTQSPLS LPVTPGEPAS ISCRSSQSIV HSNGNTYLEW

YLQKPGQSPQ LLIYKVSNRF SGVPDRFSGS GSGTDFTLKI

SRVEAEDVGV YYCFQGSHVP LTFGaGTKLE IK
```

And another version of the heavy chain comprising a back-mutation at positions 1, 48, 71, 81, 82b, and 112 was made: Using this methodology, one version of the heavy chain was made. The sequence of the heavy chain is set forth below:

```
Heavy Chain Version H3:
                                      (SEQ ID NO: 51)
qVQLVESGAE VKKPGASVKV SCKASGYTFT SYWIHWVRQA PGQGLEWiGE NDPSNGRTNY NEKFKNRVTL TvDTSISTAY MhLSsLRSDD TAVYYCARGP NYFYSMDYWG QGTMVTVsS
```

Figure 3:
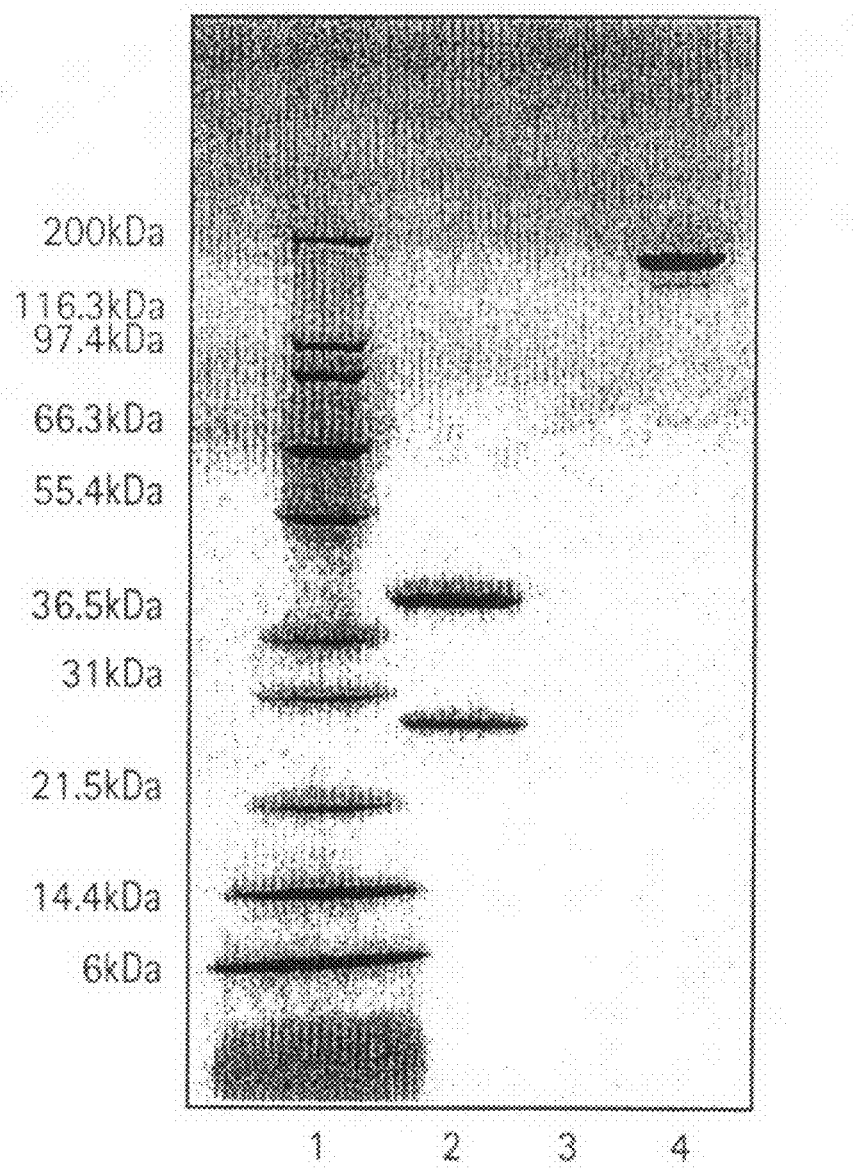
FIG. 3 shows that the inclusion of the G1/G3/Pro243Ala244Pro245+[Gly/Ser] connecting peptide (SEQ ID NO:5) into the CH2 domain-deleted chB3F6 antibody results in the production of essentially all form A antibody with little or no detectable Form B (see lane 4).
Figure 6:
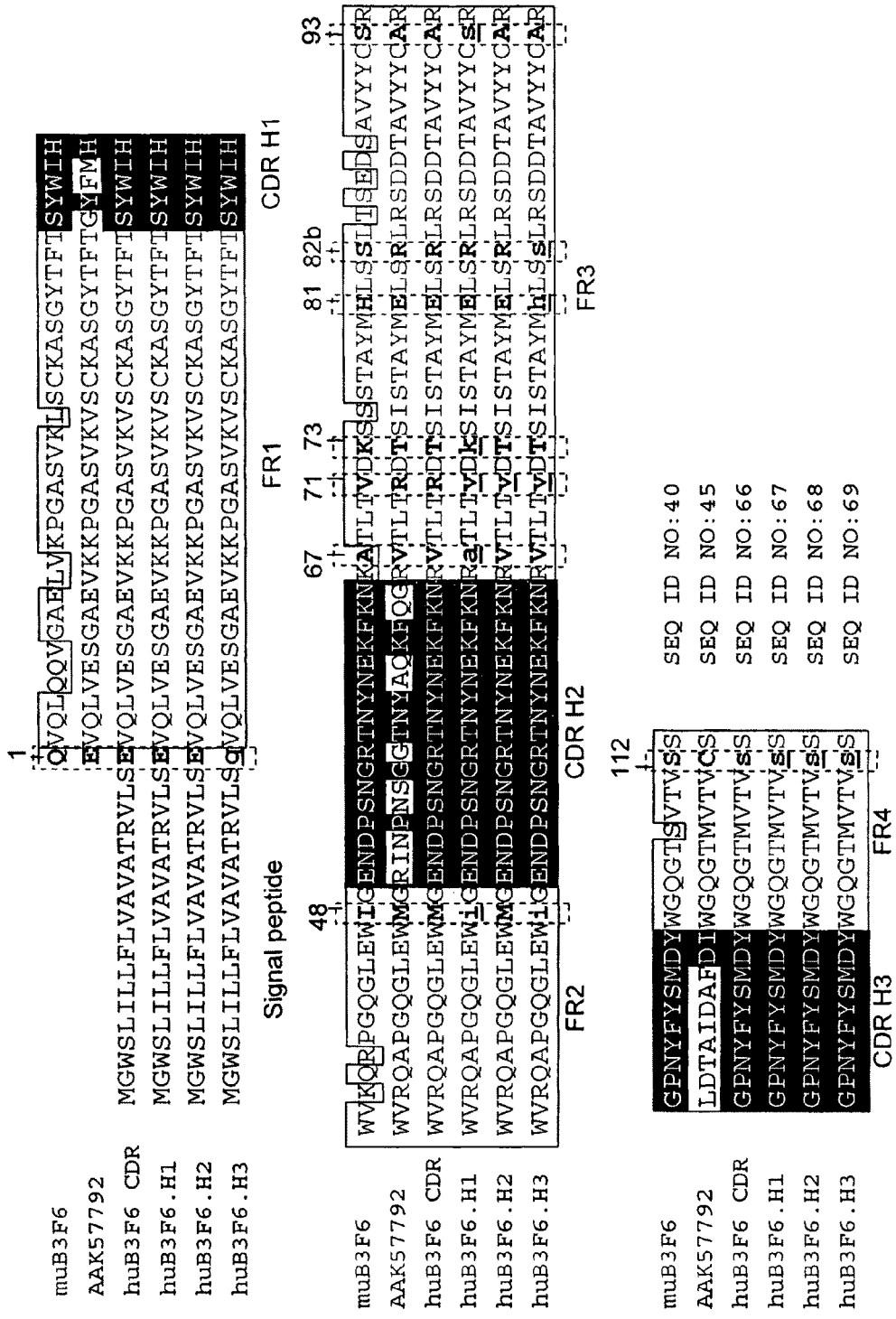
FIG. 6 shows an alignment of the heavy chains of donor murine B3F6 heavy chain region, the human acceptor, and the various humanized forms made. CDR sequences are shaded. The differences in FR amino acid residues between the donor and acceptor are bolded. The backmuations made are indicated in bold and lower case letters. Kabat numbers are indicated along the top of the alignment.

Annotated versions of the CDR grafted humanized B3F6 sequences and those comprising backmutations are shown in FIG. 5 for the light chain and in FIG. 6 for the heavy chain. Kabat numbering of the positions at which backmutations were made is also illustrated.

Example 16

Preparation of Full-length Humanized B3F6 Anti-Cripto Antibodies

Six humanized full-length B3F6 antibodies and six humanized domain deleted B3F6 antibodies were made having the following humanized heavy and light chain combinations:

Full-length Version 1—humanized (hu) B3F6 Light chain version L1/Heavy chain version H1 (L1/H1)
Full-length Version 2—huB3F6 L1/H2
Full-length Version 3—huB3F6 L1/H3
Full-length Version 4—huB3F6 L2/H1
Full-length Version 5—huB3F6 L2/H2
Full-length Version 6—huB3F6 L2/H3

Figure 7:
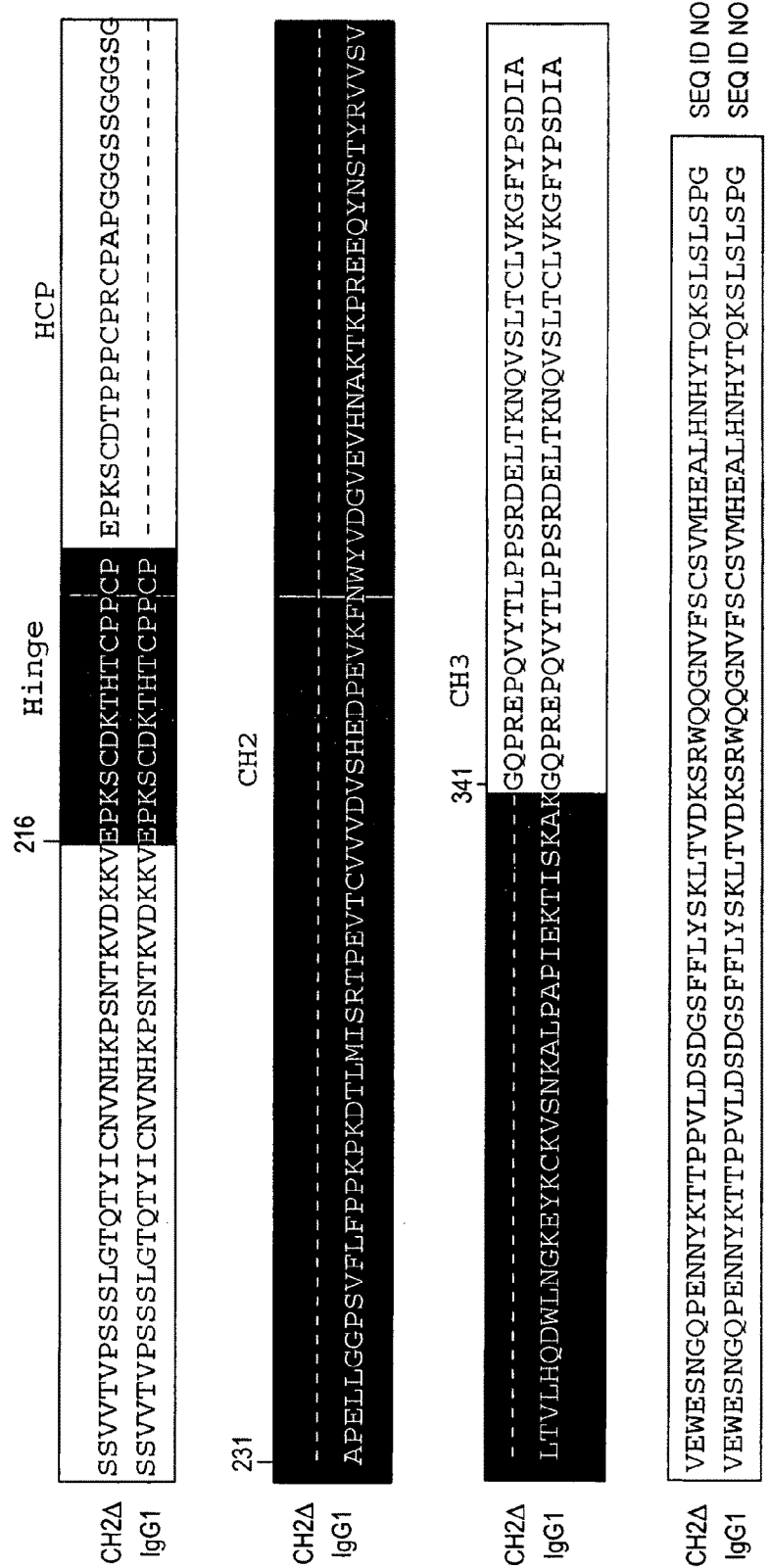
FIG. 7 shows the constant region sequence used to make domain deleted antibodies (comprising a hinge connecting peptide (HCP)) and the full length IgG1 constant region sequence used to make full-length antibodies.
Figure 8:
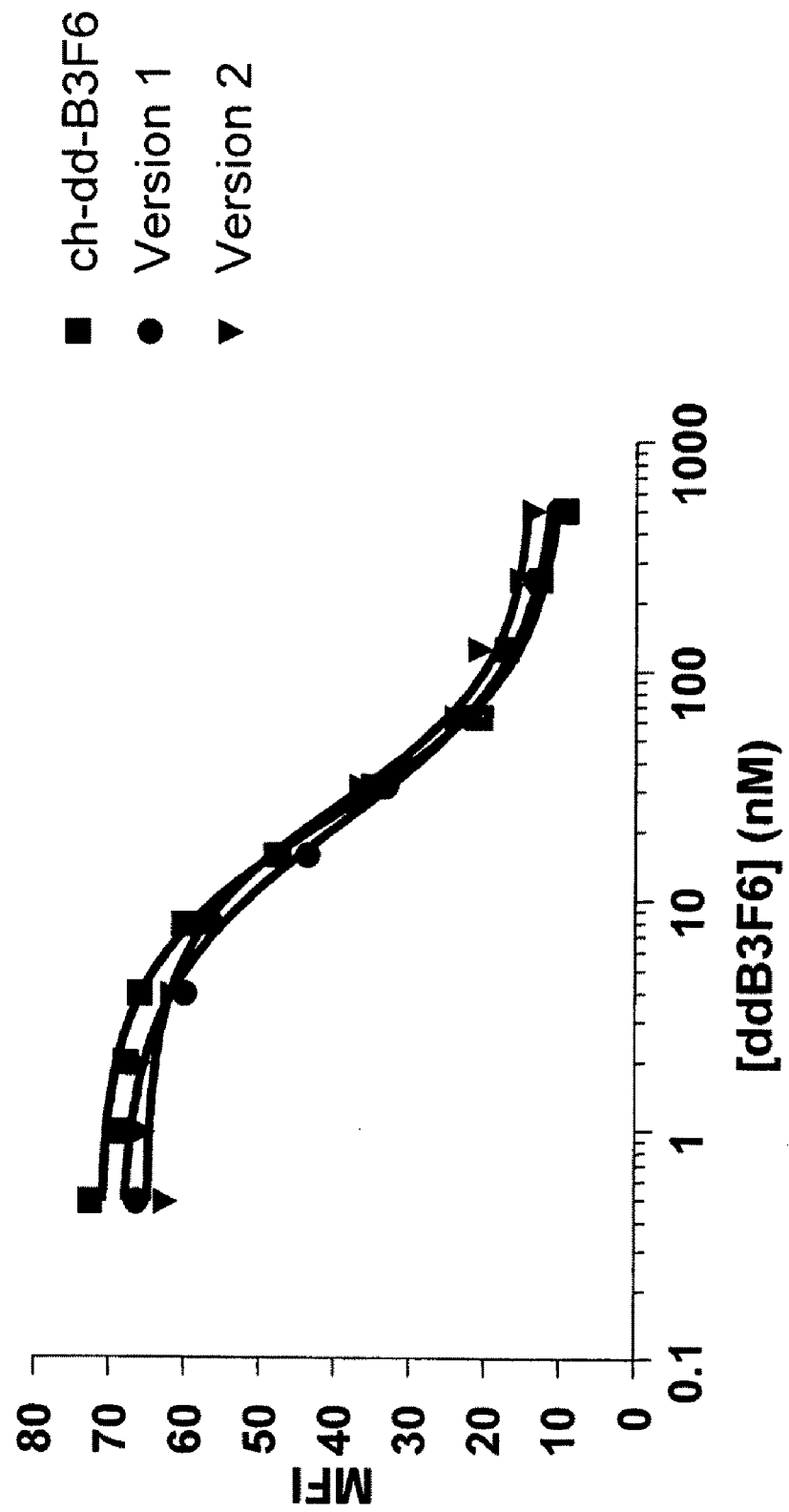
FIG. 8 shows a comparison of the binding of chimeric domain deleted B3F6 with domain deleted humanized B3F6 version 1 and version 2.
Figure 9:
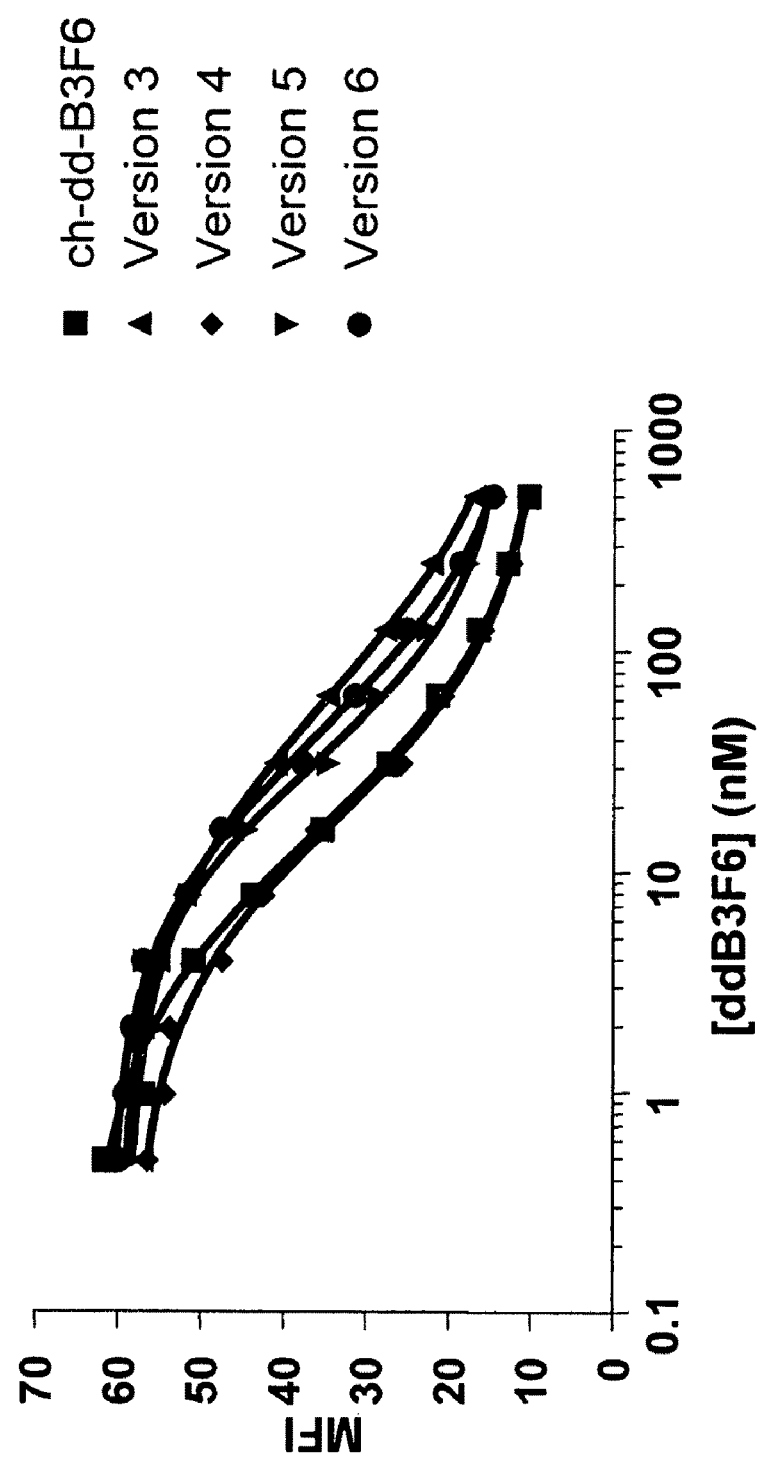
FIG. 9 shows a comparison of the binding of chimeric domain deleted B3F6 with domain deleted humanized B3F6 version 3, version 4, version 5, and version 6.
Figure 10:
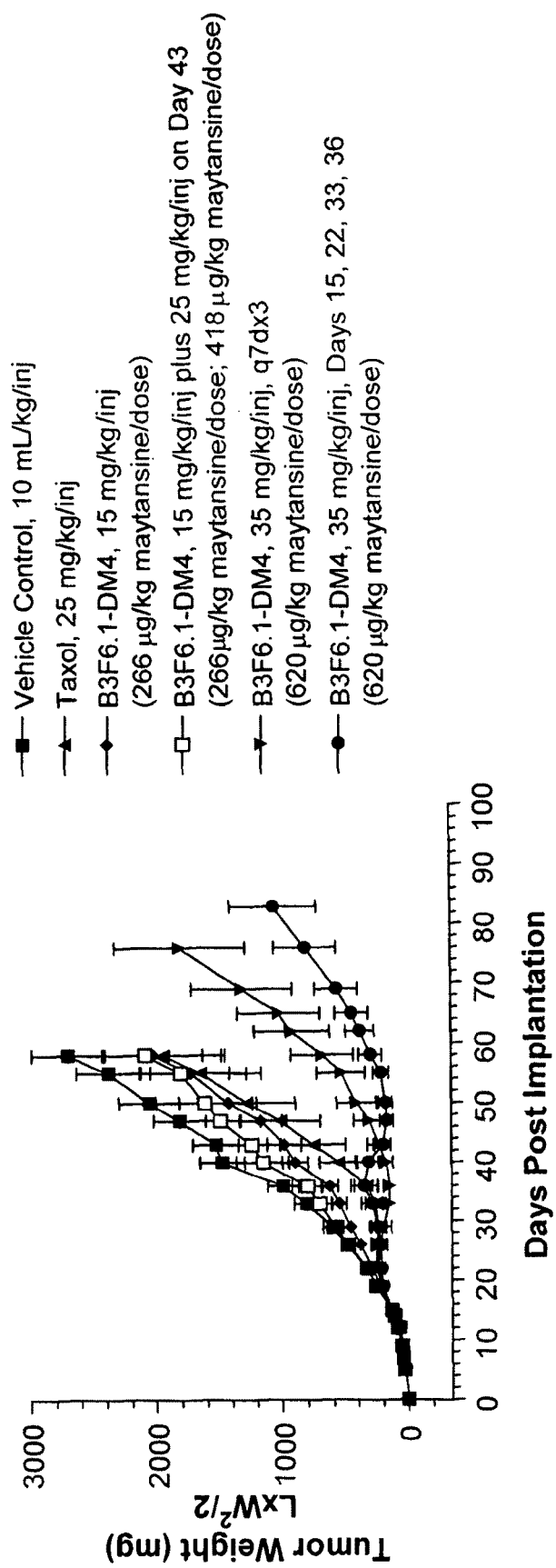
FIG. 10 shows the effect of full-length B3F6 conjugated to DM4 on established BT-474 xenograft tumors in nude mice as measured by change in tumor weight. B3F6.1-DM4 conjugate was administered at 15 mg/kg IV every seven days for three months (q7d×3) plus Day 43 (n=8) or q7d×3 plus 25 mg/kg on Day 43 (n=8), B3 F6.1-DM4 administered at 35 mg/kg IV q7d×3 (n=8) or on Days 15, 22, 33, and 36 (n=8), vehicle (n=16) administered IV q7d×3 and Taxol (n=7) administered IP q4d×3 starting on Day 15. Vertical bars represent standard errors of the means.
Figure 11A:
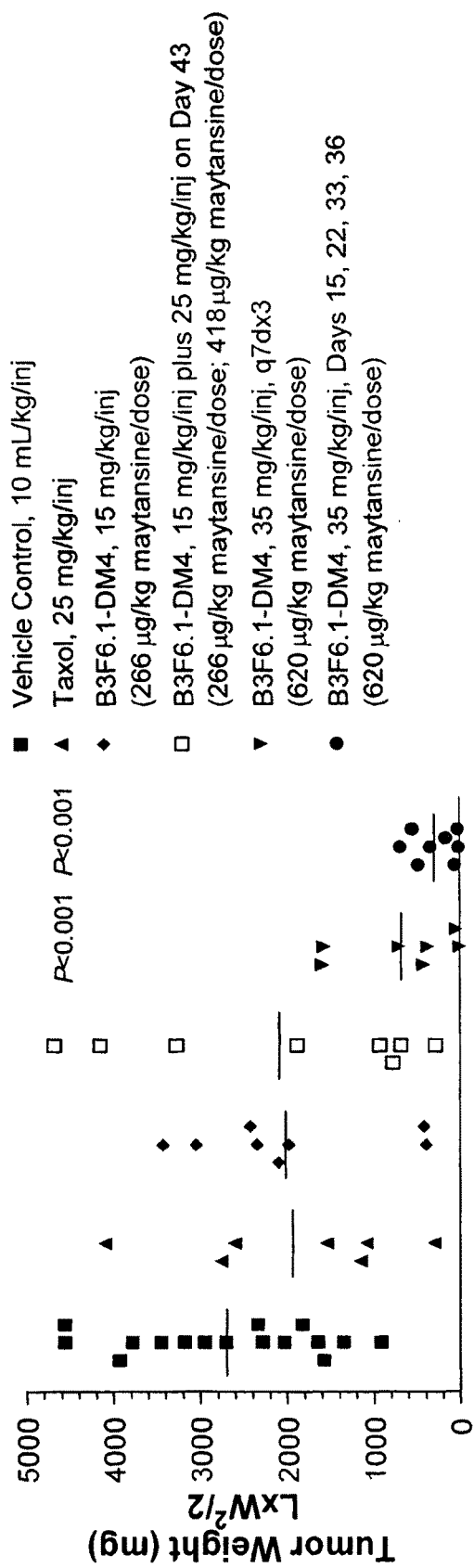
FIG. 11 panels A and B show the effect of full-length B3F6 conjugated to DM4 on BT-474 xenograft tumors in nude mice. The mice bearing established BT-474 human breast tumors were treated with B3F6.1-DM4 at 15 mg/kg IV q7d×3 plus Day 43 (n=8) or q7d×3 plus 25 mg/kg on Day 43 (n=8), B3F6.1-DM4 at 35 mg/kg IV q7d×3 (n=8) or on Days 15, 22, 33, and 36 (n=8), vehicle (n=16) IV q7d×3 and Taxol (n=7) IP q4 d×3 starting on Day 15. Panel A shows individual tumor weights on Day 58. Panel B shows the individual tumor weights of the remaining treatment groups on Day 76. Each point represents the tumor weight of a single mouse, and horizontal bars represent the mean tumor weight for each group.
Figure 11B:
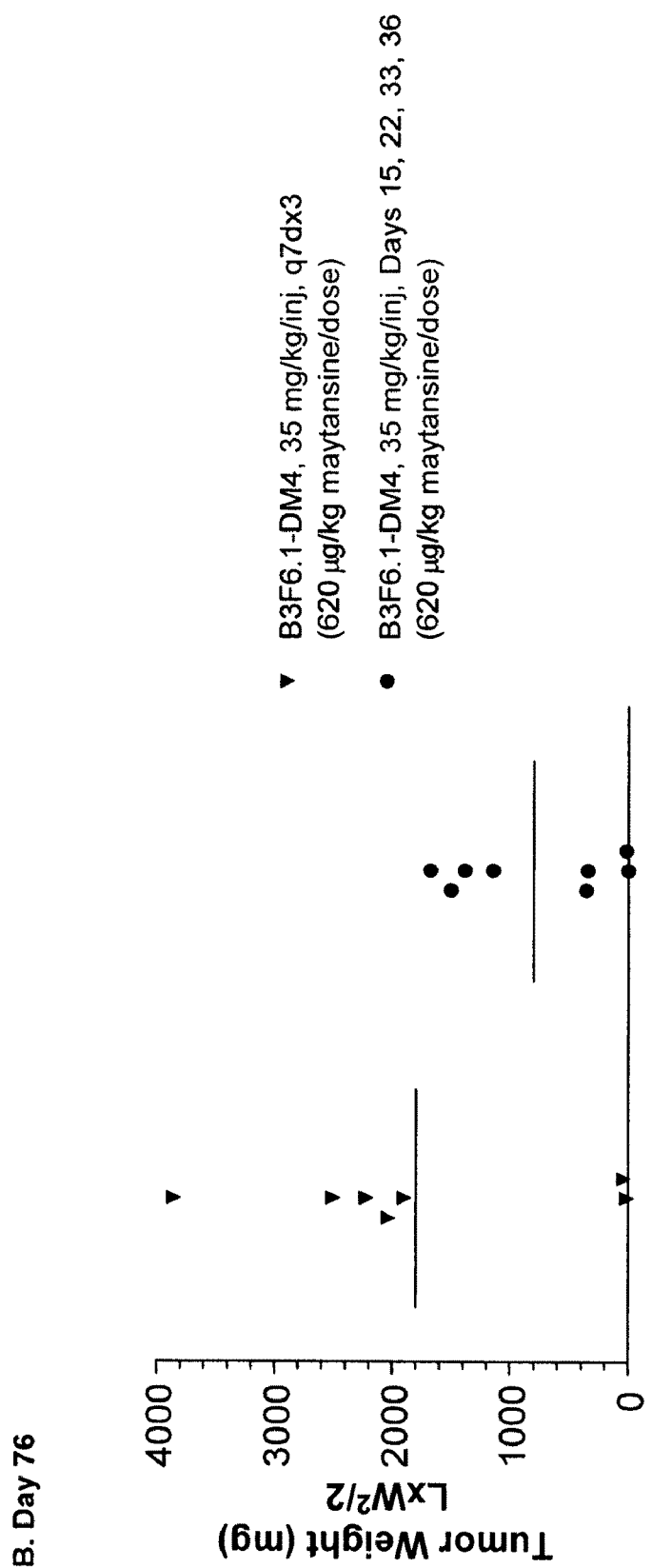
Figure 12:
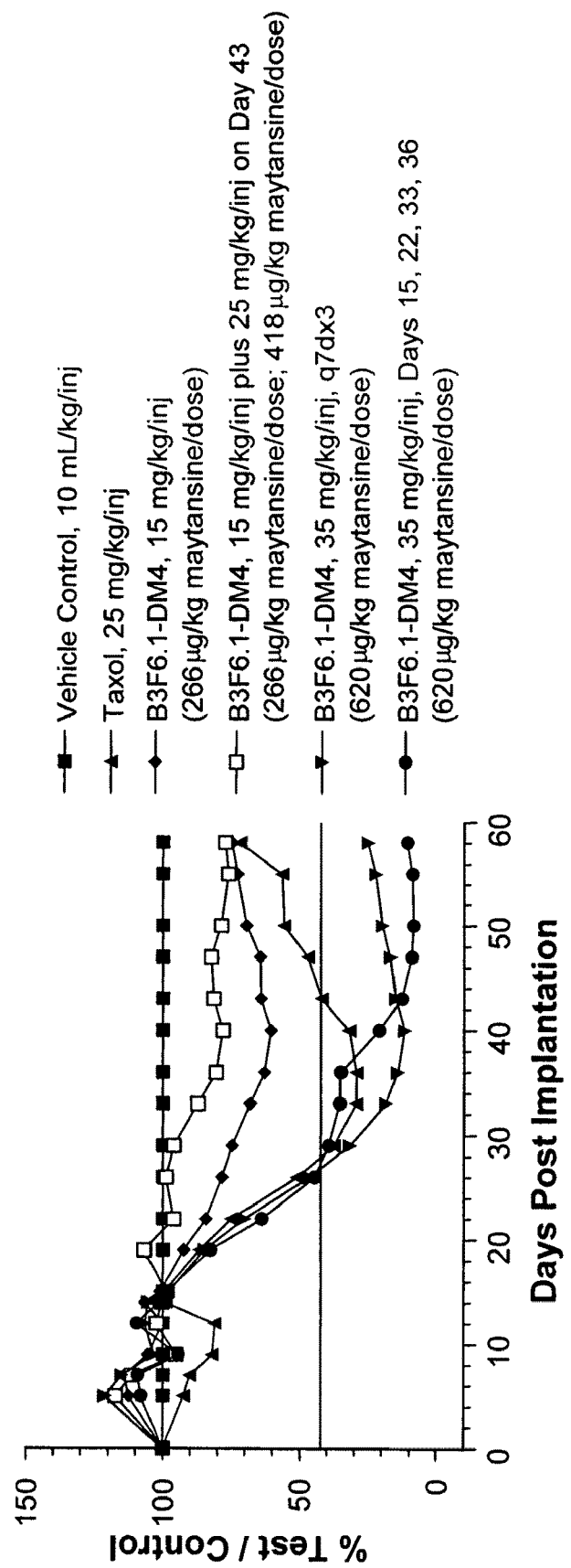
FIG. 12 shows the effect of full-length B3F6 conjugated to DM4 and taxol on established BT-474 xenograft tumors in nude mice. The figure shows a comparison of test group mean tumor sizes as a percentage of the mean vehicle control tumor size. Nude mice bearing established BT-474 human breast tumors were treated with B3F6.1-DM4 at 15 mg/kg IV q7d×3 plus Day 43 (n=8) or q7d×3 plus 25 mg/kg on Day 43 (n=8), B3F6.1-DM4 at 35 mg/kg IV q7d×3 (n=8) or on Days 15, 22, 33, and 36 (n=8), vehicle (n=16) IV q7d×3 and Taxol (n=7) IP q4d×3 starting on Day 15. The horizontal bar represents the National Cancer Institute's criteria for activity (42%).
Figure 13:
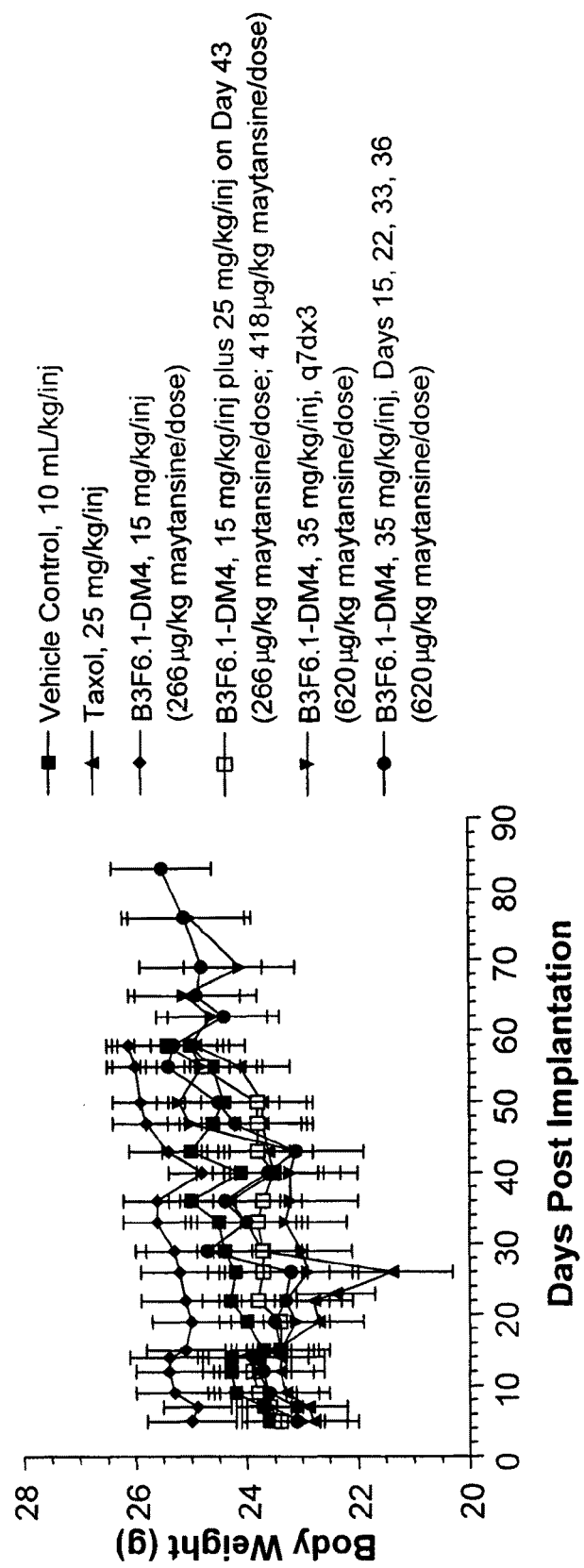
FIG. 13 shows mean body weight of nude mice implanted with BT-474 human breast tumors and treated with full-length B3F6 conjugated to DM4 or taxol. Mice were treated with B3F6.1-DM4 at 15 mg/kg IV q7d×3 plus Day 43 (n=8) or q7d×3 plus 25 mg/kg on Day 43 (n=8), B3F6.1-DM4 at 35 mg/kg IV q7d×3 (n=8) or on Days 15, 22, 33, and 36 (n=8), vehicle (n=16) IV q7d×3 and Taxol (n=7) IP q4d×3 starting on Day 15. Vertical bars represent standard errors of the means.
Figure 14:
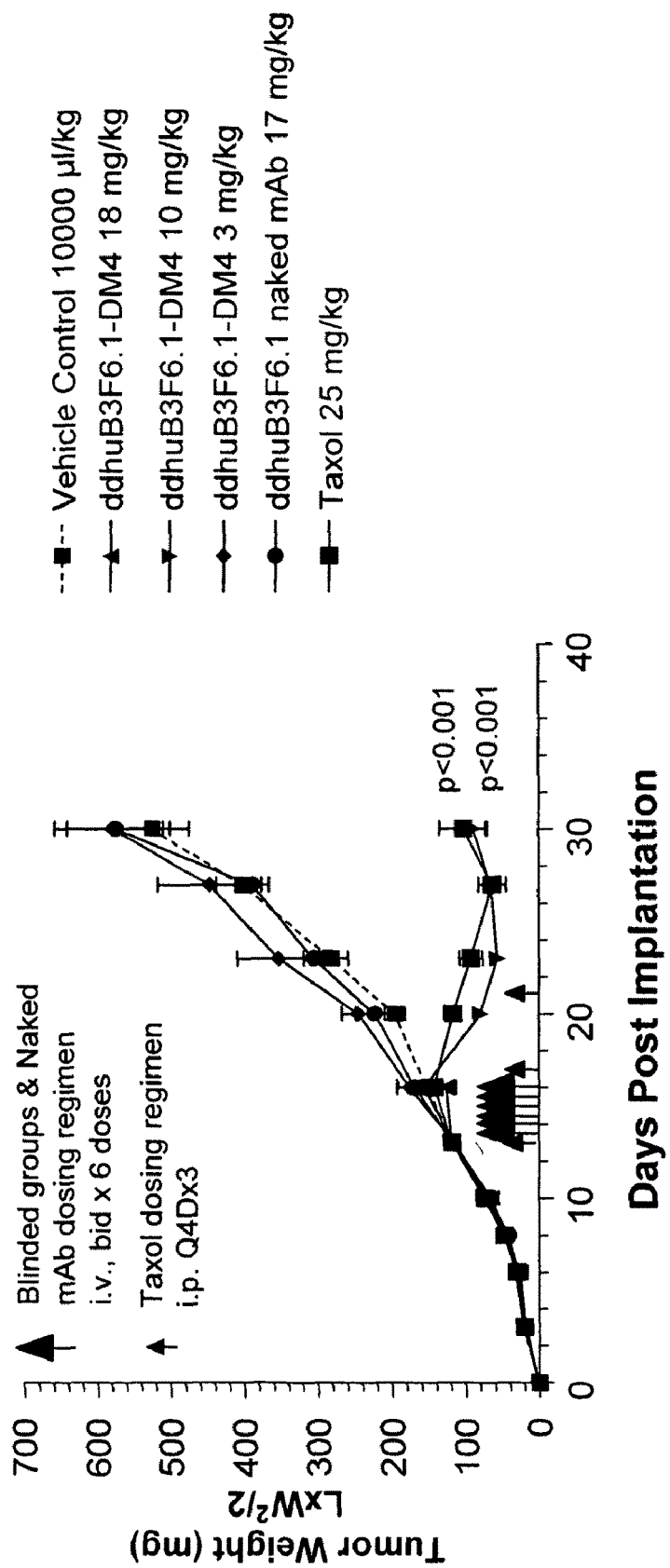
FIG. 14 shows the effect of domain deleted (dd) huB3F6-DM4 on BT-474 breast cancer cells as measured by change in tumor weights. A significant effect was observed with DM-4 conjugated antibody at 18 mg/kg, 10 mg/kg when given 5 doses, and taxol at 25 mg/kg.
Figure 15:
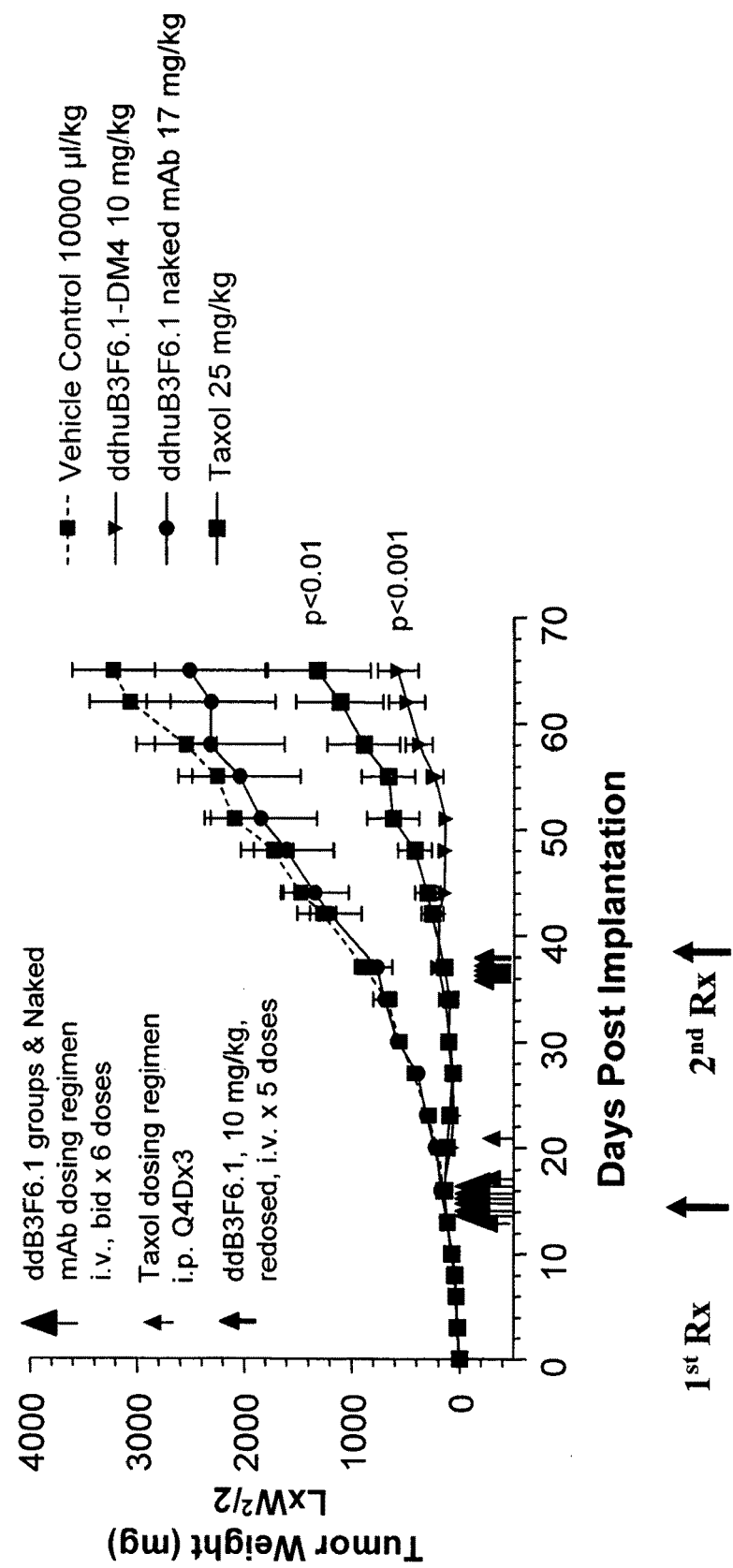
FIG. 15 shows the effect of domain deleted (dd) huB3F6-DM4 on BT-474 cancer cells as measured by change in tumor weights. The animals were redosed after three weeks of regression/stasis. A significant effect was observed with DM-4 conjugated antibody at 10 mg/kg and with Taxol at 25 mg/kg.
Figure 16:
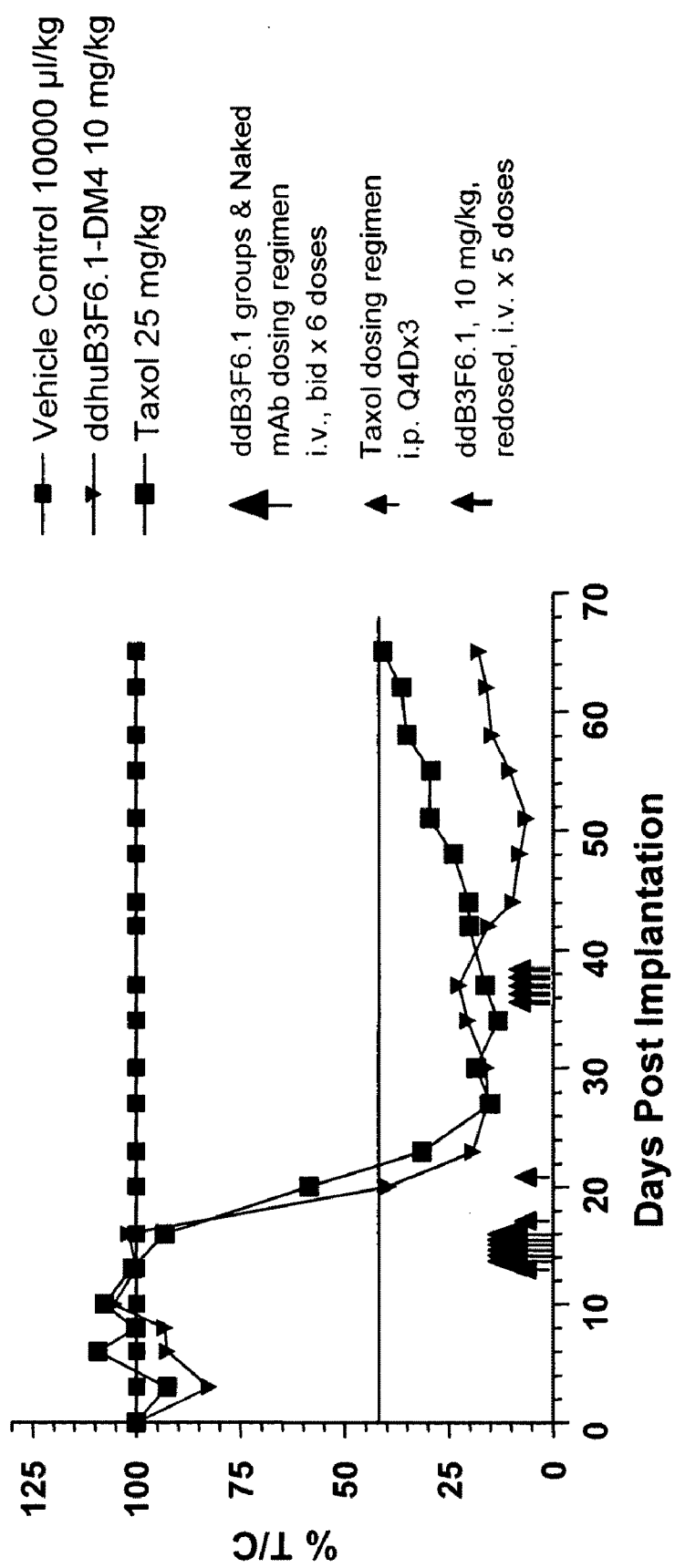
FIG. 16 shows the effect of domain deleted (dd) huB3F6-DM4 on BT-474 cancer cells. The tumor weight is shown as a percentage of test tumor weight/vehicle control. Both Taxol and 10 mg/kg huB3F6-DM4 reduced tumor weight by 50% or greater.
Figure 17:
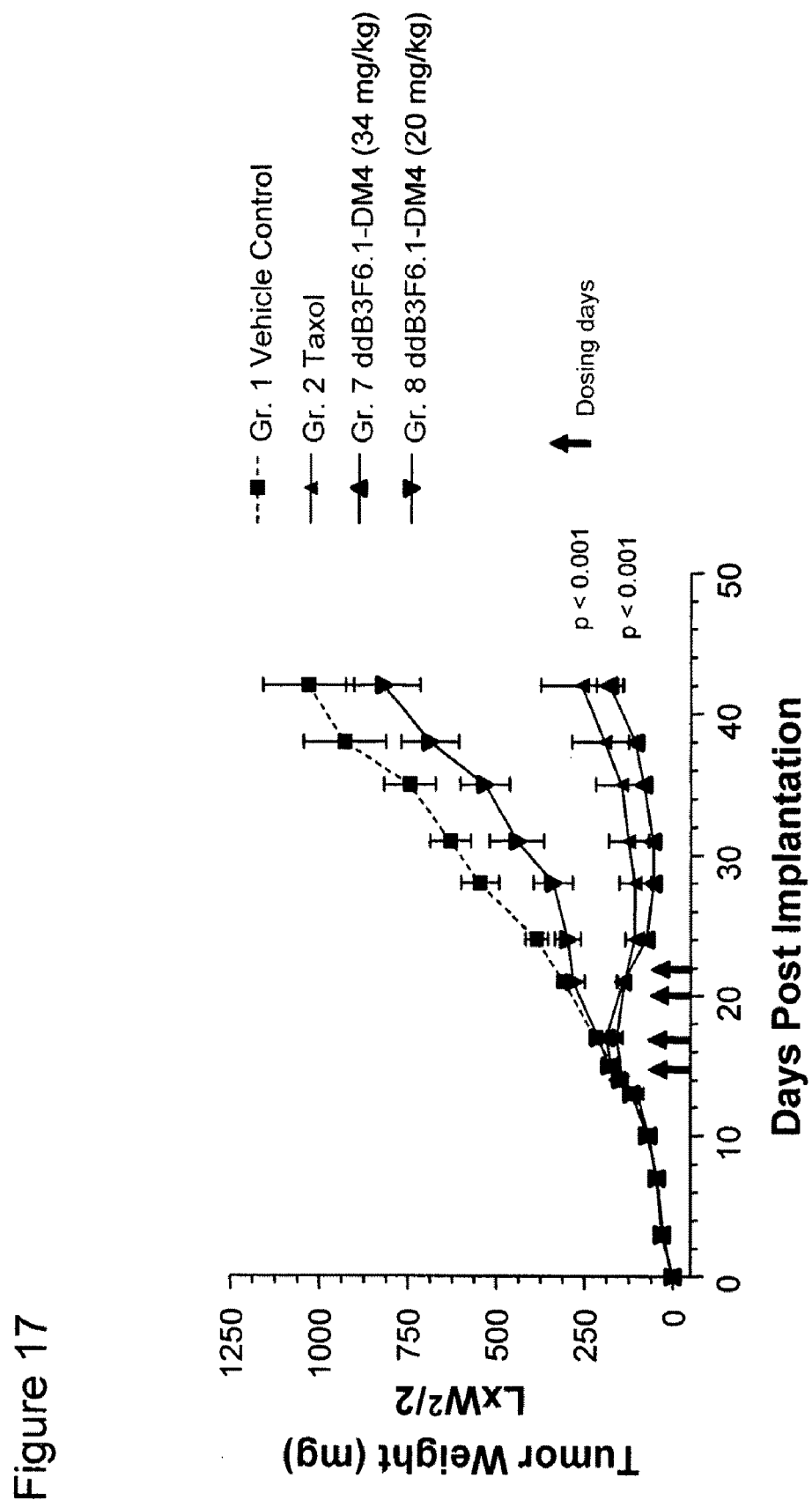
FIG. 17 shows the effect of domain deleted (dd) huB3F6-DM4 on BT-474 cancer cells as measured by a change in tumor weights. The animals were dosed on Monday, Wednesday, Friday, and Monday. ⅞ animals remained in group 7.
Figure 18:
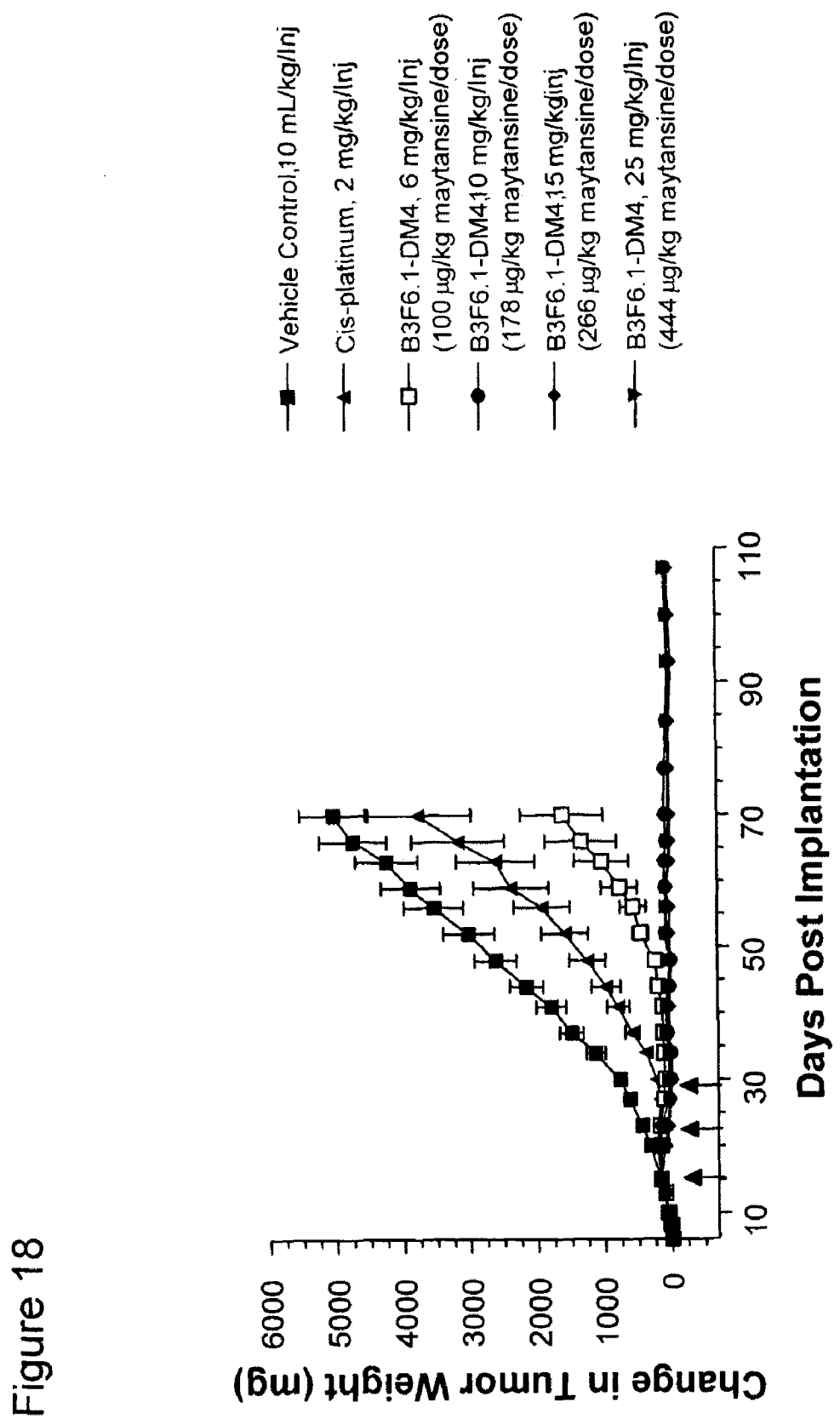
FIG. 18 shows the effect of full-length B3F6 conjugated to DM4 or Cis-platinum on established NCCIT xenograft tumors in nude mice as shown by change in tumor weight. B3F6.1-DM4 at 6 (n=8), 10 (n=8), 15 (n=8) and 25 (n=8) mg/kg was administered IV q7d×3 (as indicated by arrows), vehicle (n=16) administered IV q7d×3, and cis-platinum (n=8) administered SC 2 mg/kg 3×/wk×6 starting on Day 15. Vertical bars represent standard errors of the means.
Figure 19A:
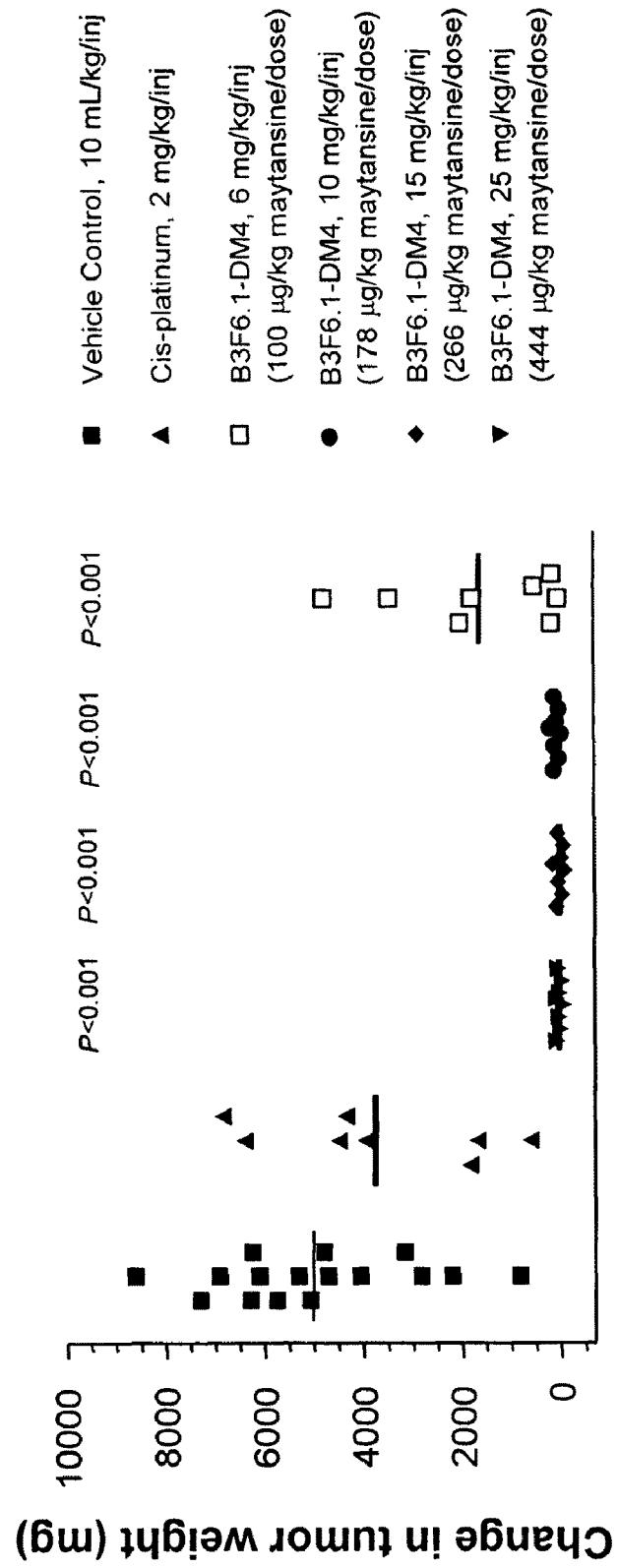
FIG. 19 panels A and B show the effect of full-length B3F6.1-DM4 on tumors in nude mice in a scatter plot. Nude mice bearing established NCCIT human testicular tumors were treated with B3F6.1-DM4 at 6 (n=8), 10 (n=8), 15 (n=8), and 25 (n=8) mg/kg IV q7d×3, vehicle (n=16) IV q7d×3, and cis-platinum (n=8) SC 3×/wk×4 starting on Day 15. Panel A shows individual tumor weights on Day 70. Panel B shows the individual tumor weights of the remaining treatment groups on Day 107. Each point represents the tumor weight of a single mouse, and bars represent the mean tumor weight for each group.
Figure 19B:
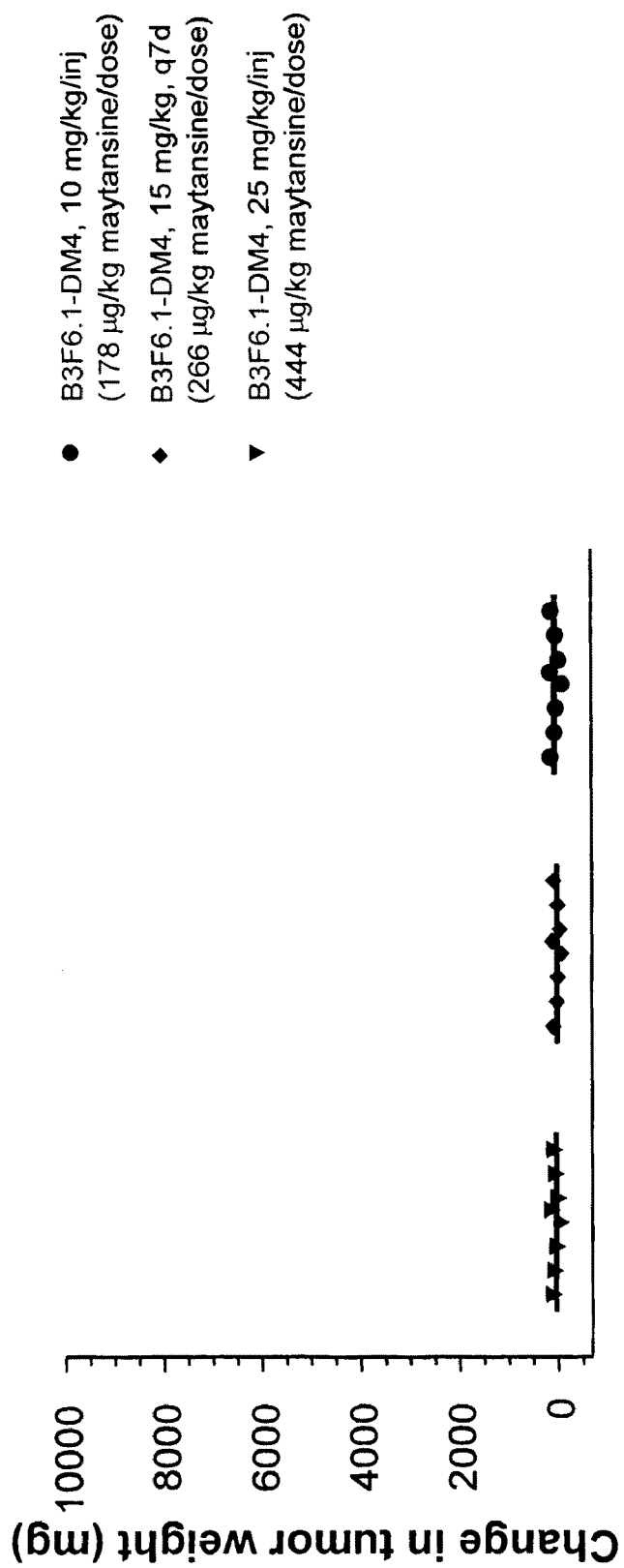
Figure 20:
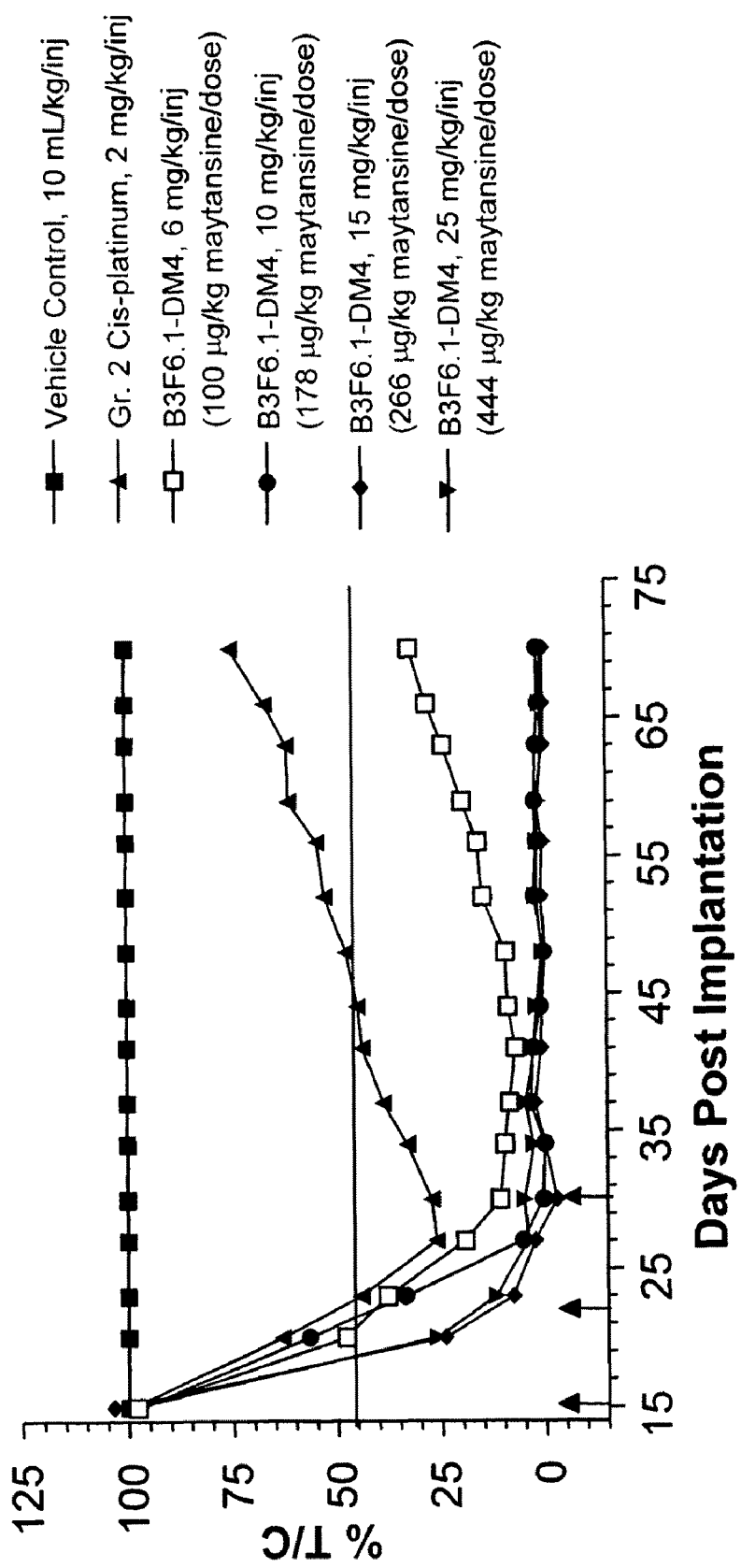
FIG. 20 shows the effect of full-length B3F6 conjugated to DM4 or cis-platinum on established NCCIT xenograft tumors in nude mice. The figure shows a comparison of test group mean tumor sizes as a percentage of the mean vehicle control tumor size. Nude mice bearing established NCCIT human testicular tumors were treated with B3F6.1-DM4 at 6 (n=8), 10 (n=8), 15 (n=8), and 25 (n=8) mg/kg IV q7d×3, vehicle (n=16) IV q7d×3, and cis-platinum (n=8) SC 3×/wk×4 starting on Day 15. The bar indicates the National Cancer Institute's criteria for activity (42%).
Figure 21:
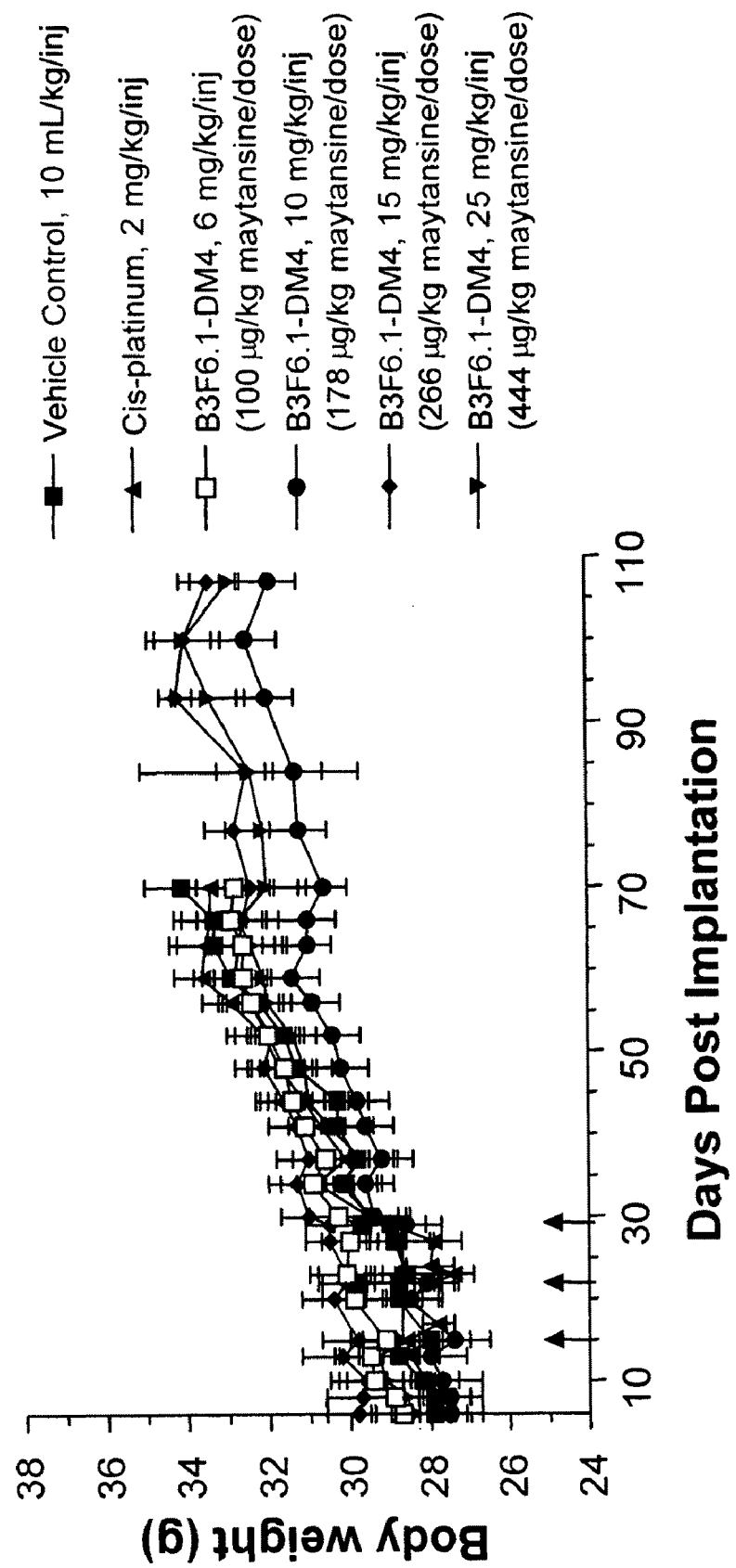
FIG. 21 shows the mean body weight of mice implanted with NCCIT xenograft tumors and treated with full-length B3F6 conjugated to DM4 or cis platinum. The mice were treated with B3F6.1-DM4 at 6 (n=8), 10 (n=8), 15 (n=8), and 25 (n=8) mg/kg IV q7d×3, vehicle (n=16) IV q7d×3, and cis-platinum (n=8) SC 3×/wk×4 starting on Day 15. Vertical bars represent standard errors of the means.
Figure 22A:
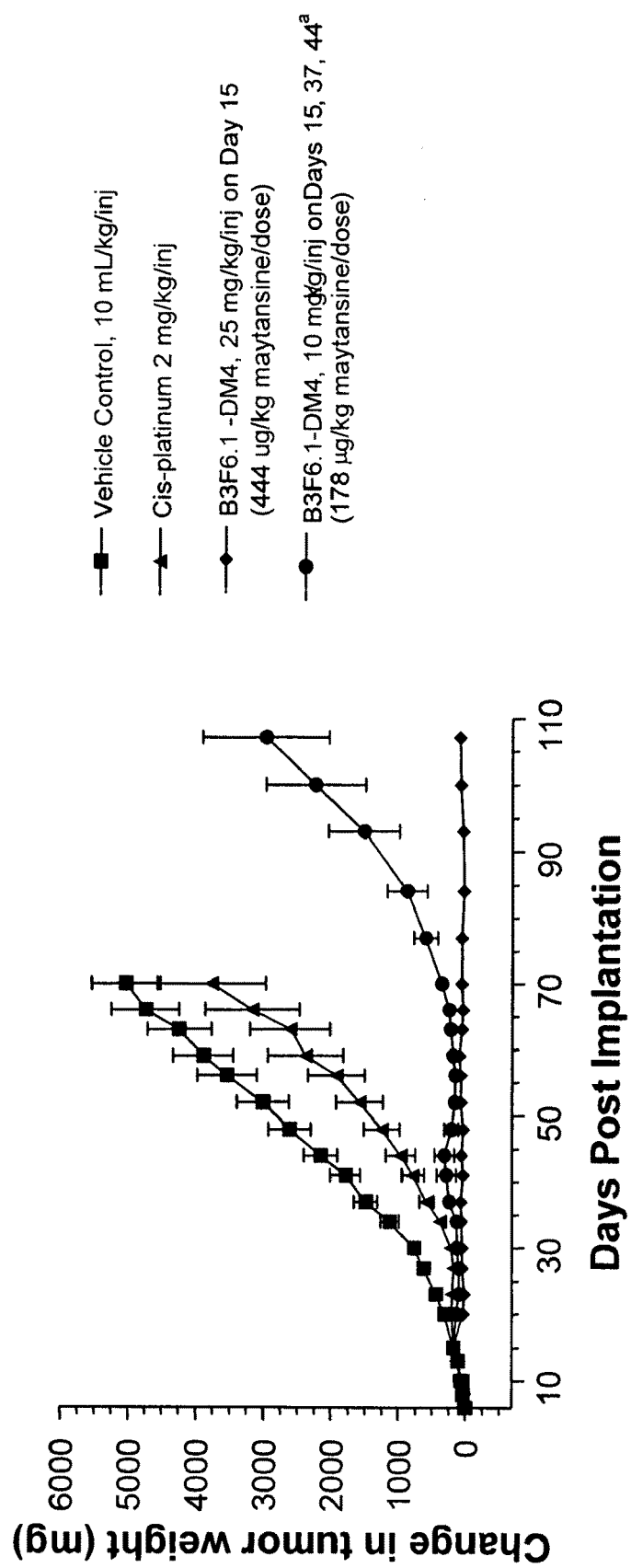
FIG. 22 panels A and B show the effect of full-length B3F6 conjugated to DM4 dosed on Day 15 and upon regrowth or cis-platinum on established NCCIT xenograft tumors in nude mice as demonstrated by change in tumor weight. B3F6.1-DM4 was administered at 25 (n=8) mg/kg IV once on Day 15, B3F6.1-DM4 at 10 (n=8) mg/kg IV administered on Days 15, 37, and 44$^a$, vehicle (n=16) administered IV q7d×3, and cis-platinum (n=8) administered SC 2 mg/kg 3×/wk×6 starting on Day 15. Vertical bars represent standard errors of the means. Panel A shows the combined data for all mice dosed at 10 mg/kg. Panel B shows the data for the mice (n=5) dosed at 10 m/kg on Day 15 and 37 separated out from the data for mice (n=3) dosed at 10 mg/kg on Day 15, 37, and 44.
Figure 22B:
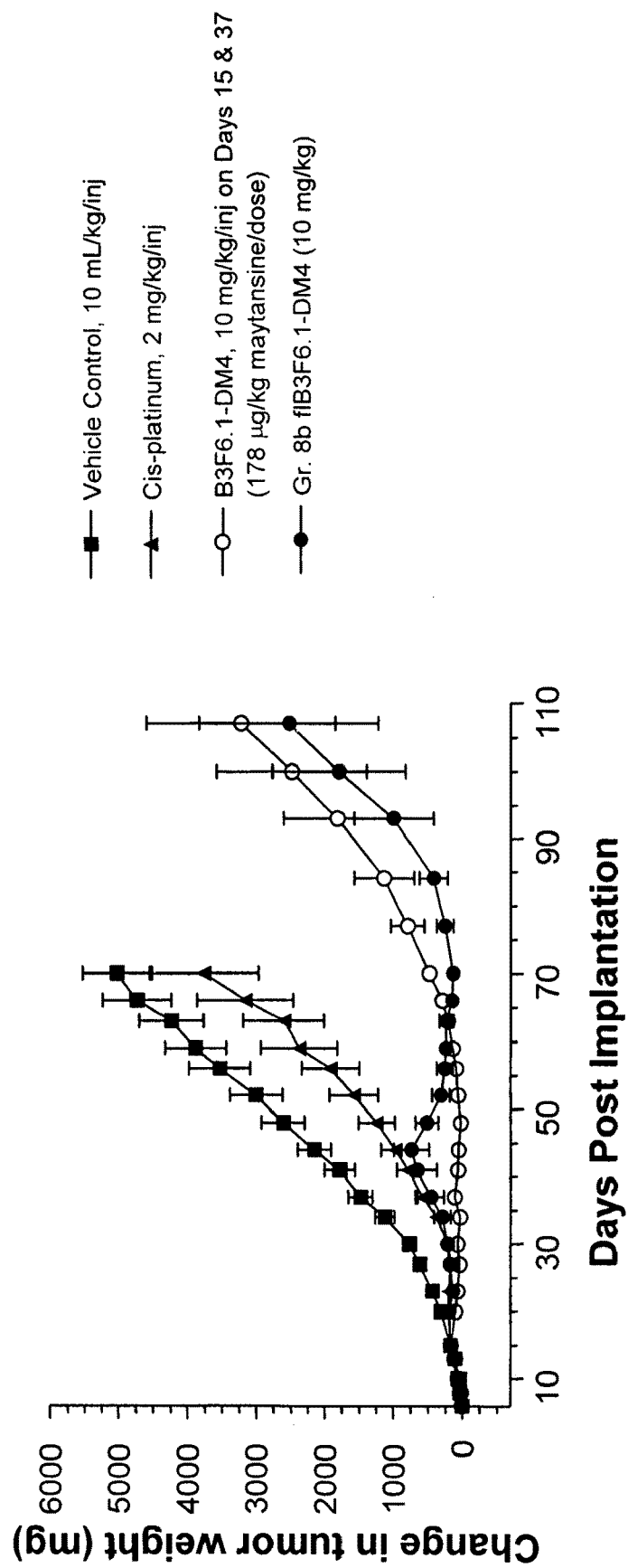

The amino acid sequence of the IgG1 heavy chain constant region that was used to make the full-length antibody molecules is shown in FIG. 7.

The complete amino acid sequences of the CDR grafted B3F6 light chain and versions L1 and L2 are shown below:

```
CDR-grafted B3F6 light chain
                                      (SEQ ID NO: 52)
DVVMTQSPLSLPVTPGEPASISCRSSQSIVHSNGNTYLEWYLQKPGQSPQ

LLIYKVSNRFSGVPDRFSGSGSGTDFTLKISRVEAEDVGVYYCFQGSHVP

LTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC huB3F6 L1
                                      (SEQ ID NO: 53)
DFVMTQSPLSLPVTPGEPASISCRSSQSIVHSNGNTYLEWYLQKPGQSPQ

LLIYKVSNRFSGVPDRFSGSGSGTDFTLKISRVEAEDVGVYYCFQGSHVP

LTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC huB3F6 L2
                                      (SEQ ID NO: 54)
DFVMTQSPLSLPVTPGEPASISCRSSQSIVHSNGNTYLEWYLQKPGQSPQ

LLIYKVSNRFSGVPDRFSGSGSGTDFTLKISRVEAEDVGVYYCFQGSHVP

LTFGAGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

The complete amino acid sequences of the CDR grafted B3F6 heavy chain and versions H1, H2, and H3 for the full length antibodies made are shown below:

```
CDR-grafted full-length B3F6 heavy chain
                                      (SEQ ID NO: 55)
EVQLVESGAEVKKPGASVKVSCKASGYTFTSYWIHWVRQAPGQGLEWMGE

NDPSNGRTNYNEKFKNRVTLTRDTSISTAYMELSRLRSDDTAVYYCARGP

NYFYSMDYWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG huB3F6 H1
                                      (SEQ ID NO: 56)
EVQLVESGAEVKKPGASVKVSCKASGYTFTSYWIHWVRQAPGQGLEWIGE

NDPSNGRTNYNEKFKNRATLTVDKSISTAYMELSRLRSDDTAVYYCSRGP

NYFYSMDYWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV
```

-continued

```
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG huB3F6 H2
                                         (SEQ ID NO: 57)
EVQLVESGAEVKKPGASVKVSCKASGYTFTSYWIHWVRQAPGQGLEWMGE
NDPSNGRTNYNEKFKNRVTLTVDTSISTAYMELSRLRSDDTAVYYCARGP
NYFYSMDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG huB3F6 H3
                                         (SEQ ID NO: 58)
QVQLVESGAEVKKPGASVKVSCKASGYTFTSYWIHWVRQAPGQGLEWIGE
NDPSNGRTNYNEKFKNRVTLTVDTSISTAYMHLSSLRSDDTAVYYCARGP
NYFYSMDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG
```

From stable bulk cultures, the full-length version 2 humanized antibody (comprising the version 1 light chain and the version 2 heavy chain) produced the highest amount of antibody and had a comparable binding affinity to the parent mouse antibody.

Example 17

Preparation of Domain Deleted Humanized B3F6 Anti-Cripto Antibodies

Six humanized CH2 domain deleted B3F6 antibodies were made having the following humanized heavy and light chain combinations:

Domain deleted (dd) Version 1—humanized domain deleted B3F6 light chain version 1/heavy chain version 1 (L1/H1)
ddVersion 2—huddB3F6L1/H2
ddVersion 3—huddB3F6L1/H3
ddVersion 4—huddB3F6L2/H1
ddVersion 5—huddB3F6L2/H2
ddVersion 6—huddB3F6L2/H3

The amino acid sequence of the heavy chain constant region that was used to make the domain deleted antibody molecules is shown in FIG. 7.

The complete amino acid sequences of the CDR grafted B3F6 light chain and light chain versions L1 and L2 used for making domain deleted antibodies are shown below:

```
CDR-grafted B3F6 light chain
                                         (SEQ ID NO: 52)
DVVMTQSPLSLPVTPGEPASISCRSSQSIVHSNGNTYLEWYLQKPGQSPQ
LLIYKVSNRFSGVPDRFSGSGSGTDFTLKISRVEAEDVGVYYCFQGSHVP
LTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC huB3F6 L1
                                         (SEQ ID NO: 53)
DFVMTQSPLSLPVTPGEPASISCRSSQSIVHSNGNTYLEWYLQKPGQSPQ
LLIYKVSNRFSGVPDRFSGSGSGTDFTLKISRVEAEDVGVYYCFQGSHVP
LTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC huB3F6 L2
                                         (SEQ ID NO: 54)
DFVMTQSPLSLPVTPGEPASISCRSSQSIVHSNGNTYLEWYLQKPGQSPQ
LLIYKVSNRFSGVPDRFSGSGSGTDFTLKISRVEAEDVGVYYCFQGSHVP
LTFGAGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC
```

The complete amino acid sequences of the CDR grafted B3F6 heavy chain and versions H1, H2, and H3 used for making domain deleted antibodies are shown below:

```
CDR-grafted CH2 domain-deleted B3F6 heavy chain.
                                         (SEQ ID NO: 59)
EVQLVESGAEVKKPGASVKVSCKASGYTFTSYWIHWVRQAPGQGLEWMGE
NDPSNGRTNYNEKFKNRVTLTRDTSISTAYMELSRLRSDDTAVYYCARGP
NYFYSMDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPEPKSCDTPPPCPRCPAPG
GGSSGGGSGGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPG huB3F6 H1
                                         (SEQ ID NO: 60)
EVQLVESGAEVKKPGASVKVSCKASGYTFTSYWIHWVRQAPGQGLEWIGE
NDPSNGRTNYNEKFKNRATLTVDKSISTAYMELSRLRSDDTAVYYCSRGP
NYFYSMDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPEPKSCDTPPPCPRCPAPG
```

-continued
GGSSGGGSGGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPG huB3F6 H2
(SEQ ID NO: 61)
EVQLVESGAEVKKPGASVKVSCKASGYTFTSYWIHWVRQAPGQGLEWMGE

NDPSNGRTNYNEKFKNRVTLTVDTSISTAYMELSRLRSDDTAVYYCARGP

NYFYSMDYWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPEPKSCDTPPPCPRCPAPG

GGSSGGGSGGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPG huB3F6 H3
(SEQ ID NO: 62)
QVQLVESGAEVKKPGASVKVSCKASGYTFTSYWIHWVRQAPGQGLEWIGE

NDPSNGRTNYNEKFKNRVTLTVDTSISTAYMHLSSLRSDDTAVYYCARGP

NYFYSMDYWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPEPKSCDTPPPCPRCPAPG

GGSSGGGSGGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPG

The binding activity of six versions of the domain deleted antibodies (not including the CDR grafted antibodies) was tested. Briefly, GEO human colon adenocarcinoma cells were grown in DMEM, 10% FBS with 2 mM glutamine, 0.5 mM sodium pyruvate, penicillin/streptomycin, and non-essential amino acids. Cells were removed from the flask using PBS, 20 mM EDTA, centrifuged at 1200 rpm for 3 min, and resuspended in PBS, 0.02% azide, 0.1% BSA. Humanized or chimeric antibodies at various concentrations were mixed with a final concentration of 5 nM murine B3F6 in polypropylene V-bottom plates. One million GEO cells were added to each plate and the cells were incubated with antibodies at 4 degrees C. for two hours. Cells were washed with FACS buffer three times and incubated with a 1:500 dilution of anti-murine IgG phycoerythrin conjugate for one hour at 4 degrees C. Cells were washed once more, fixed in 3% formaldehyde, and run on a FACScalibur intstrument. The mean fluorescence intensity (MFI) was plotted against the humanized or chimeric antibody concentration. The $IC_{50}$ was determined by a four-parameter fit. In each experiment, the $IC_{50}$ for each humanized antibody was compared to the chimeric antibody in that experiment. The results are shown in Table 9 below:

TABLE 9

| Antibody | $IC_{50}$ (nM) |
|---|---|
| chimeric dd-B3F6 (experiment 1) | 23 |
| dd-B3F6 Version 1 | 21 |
| dd-B3F6 Version 2 | 26 |
| chimeric dd-B3F6 (experiment 2) | 15 |
| dd-B3F6 Version 3 | 63 |
| dd-B3F6 Version 4 | 18 |

TABLE 9-continued

| Antibody | $IC_{50}$ (nM) |
|---|---|
| dd-B3F6 Version 5 | 32 |
| dd-B3F6 Version 6 | 43 |

Example 18

Humanized B3F6 Antibody Conjugated to a Toxin is Effective in Inhibiting the Growth of Human Breast Cancer Cells in an in vivo Model The following materials and methods were used in this example:

Mice

One hundred forty (140) female athymic nude mice (Harlan Sprague Dawley, Madison, Wis.) were started on the study at ten weeks of age. Animals were acclimated to the laboratory for at least five days prior to implantation of the tumor. Housing was in ventilated cage racks, and food and water were allowed ad libitum.

Tumor Model

BT-474 tumors were obtained from cryopreserved solid tumor fragments from a serially passaged in vivo donor line established at Biogen Idec (cryo reg #0141, established originally from cells obtained from the American Tissue Type Collection (Manassas, Va.)). Tumor fragments were removed from cryopreservation and serially passaged SC in vivo for 3 generations in female athymic nude mice prior to implantation for this study. Bacterial cultures were performed on samples of the tumor tissue that was implanted into the mice. Bacteriology cultures were negative for bacterial contamination at both 24 and 48 hours post implant.

On Day −1, the mice were implanted with BioMedics animal ID chips (Model IMI-1000; Seaford, Del.) SC on the left flank. On Day 0, tumors from eight donor animals were harvested, debrided of necrotic tissue, minced, and a 3 mm$^3$ fragments of the BT-474 tumors were implanted SC into the right flank area of each mouse. Tumor size and body weight measurements were recorded at least twice weekly beginning on Day 5. When the tumors measured a minimum of 100 mg (Day 15), mice were randomized to treatment and control groups (see Table 10) based on tumor size and excluding tumors with non-progressive growth.

TABLE 10

Control and Test Treatment Groups

| Agent | Dose/injection | Equivalent dose of maytansine (µg/kg) | Route | Schedule | # of mice |
|---|---|---|---|---|---|
| Vehicle control | 10 ml/kg | 0 | IV[a] | q7d × 3 | 16 |
| B3F6.1-DM4 | 15 mg/kg | 266 | IV | q7d × 3 plus Day 43 | 8 |
| B3F6.1-DM4 | 15 mg/kg | 266 | IV | q7d × 3 | 8 |
| | 25 mg/kg | 418 | IV | Day 43 | |
| B3F6.1-DM4 | 35 mg/kg | 620 | IV | q7d × 3 | 8 |
| B3F6.1-DM4 | 35 mg/kg | 620 | IV | Days 15, 22, 33, 36 | |
| Taxol | 25 mg/kg | | IP[b] | q4d × 3 | |

[a]intravenous
[b]intraperitoneal

Test Articles and Positive Chemotherapeutic Agent

Maytansin DM4 conjugations (2000-67 3.5 D/A, 6 mg/ml and 2000-79, 3.3 D/A, 5.5 mg/ml) were prepared at ImmunoGen, Inc (Cambridge, Mass.) with ImmunoGen's Tumor Activated Prodrug (TAP) technology. In all experiments, B3F6 antibodies were conjugated with an average of 3-4 DM4 molecules per antibody. As an example of the amount of DM4 delivered, a 23 mg/kg dose of B3F6-DM4 conjugate antibody with an average of 3DM4/mAb would correspond to approximately 350 ug/kg of DM4. Clinical grade Taxol™ (paclitaxel injection, NDC 0015-3476-30) was obtained from Bristol-Myers Squibb (Lot No 4L83460, exp. November 2007).

Study Groups and Treatment Regimens

Study groups and treatment regimens are described in Table 10. The vehicle control (10 mM citrate buffer, pH 5.5, 135 mM sodium chloride) was administered IV once per week for three doses (q7dx3) and Taxol™ was administered IP every 4 days for 3 doses (q4dx3). B3F6.1-DM4 at 15 mg/kg was administered IV q7dx3 plus and additional dose on Day 43 or q7dx3 plus a dose at 25 mg/kg on Day 43. B3F6.1-DM4 at 35 mg/kg was administered IV q7dx3 or on Days 15, 22, 33, and 36. All treatments commenced on Day 15.

Evaluation of Anticancer Activity

Tumor measurements were determined using digital calipers. Body weights and tumor size measurements were recorded on Day 0 and were continued twice weekly until the termination of the study. The formula to calculate volume for a prolate ellipsoid was used to estimate tumor volume (mm$^3$) from two-dimensional tumor measurements: Tumor Volume (mm$^3$)=(Length×Width$^2$)÷2. Assuming unit density, volume was converted to weight (i.e., one mm$^3$=one mg).

On Day 58, the groups treated with vehicle control, Taxol, and B3F6.1-DM4 at 15 mg/kg/inj were euthanized. Tumor weights and body weights continued to be captured from the remaining groups weekly. The group treated with B3F6.1-DM4 at 35 mg/kg/inj q7dx3 was euthanized on Day 76. The group treated with B3F6.1-DM4 at 35 mg/kg/inj on Days 15, 22, 33 and 36 was euthanized on Day 83, when the study was terminated.

Statistical Analysis

Student's t test was performed on mean tumor weights at the end of each study to determine whether there were any statistically significant differences between each treatment group and the vehicle control group.

There was a 98% tumor take-rate following the implantation, and mice within a tight range of size were selected to initiate the treatments. The tumor growth in the vehicle control group was well within the typical range we see with this model. Taxol produced a response consistent with this model, resulting in significant (P<0.05) inhibition of tumor growth from Day 26 to Day 50. On Day 58, the groups treated with vehicle control, Taxol, and B3F6.1-DM4 at 15 mg/kg/inj were euthanized. Tumor weights and body weights continued to be captured from the remaining groups weekly. The group treated with B3F6.1-DM4 at 35 mg/kg/inj q7dx3 was euthanized on Day 76. The group treated with B3F6.1-DM4 at 35 mg/kg/inj on Days 15, 22, 33 and 36 was euthanized on Day 83, when the study was terminated.

FIGS. 10-13 show the effect of two doses (15 and 35 mg/kg/inj) of B3F6.1-DM4 dosed IV on various regimens on change in tumor weight, % Test/Control (% T/C), and body weight in athymic nude mice bearing established BT-474 xenograft tumors. B3F6.1-DM4 at 15 mg/kg/inj dosed IV q7dx3 plus and additional dose on Day 43 significantly (P<0.05) inhibited tumor growth from Day 33 to Day 47, but no longer showed significant inhibition when this group was terminated on Day 58. The other cohort treated with B3F6.1-DM4 at 15 mg/kg/inj, dosed IV q7dx3 and at 25 mg/kg/inj on Day 43, showed no significant inhibition of tumor growth throughout the study. Both dosing regimens of B3F6.1-DM4 at 35 mg/kg/inj resulted in statistically significant (P<0.001) inhibition of tumor growth from Day 29 to Day 58 when the Vehicle Control group was terminated.

The % T/C for both cohorts treated with B3F6.1-DM4 at 35 mg/kg/inj dropped below the NCI criteria for activity of 42% by Day 29 and remained below this level throughout the study. The % T/C of the cohorts treated with B3F6.1-DM4 at 15 mg/kg never went below 42%.

Clinical Observations

Several mice treated with B3F6.1-DM4 experienced mild coryneoform bacterial infections of the skin. This bacteria resides on the skin and is considered an opportunistic infection that can occur if the animal is stressed. Most of the mice treated with B3F6.1-DM4 at 35 mg/kg/inj developed infections by Day 29 and all infections resolved (except in No. 33) by Day 43.

One mouse treated with Taxol experienced weight loss due to technical failure during administration of Taxol. Taxol is known to cause GI toxicity and care must be taken when administering this cytotoxic agent IP. Administration of SC fluids did not improve the condition of the mouse, and it was euthanized on Day 26, three days after receiving its last dose of Taxol, per IACUC guidelines regarding weight loss (euthanasia when weight loss exceeds 20%). The data for this animal are excluded from the graphs and statistical anyalysis.

One mouse treated with B3F6.1-DM4, 35 mg/kg/inj q7dx3 experienced weight loss beginning on Day 26. The weight loss continued until the mouse had to be euthanized on Day 43, 14 days after receiving its last dose of B3F6.1-DM4, per IACUC guidelines. Necropsy revealed clear subcutaneous fluid in the chest. It is not known if the weight loss was treatment related, as only one other mouse in this group experienced slight weight loss. However, No. 35 also experienced a coryneoform bacterial infection, which may have resulted in slight body weight loss.

On Day 50, one mouse in the vehicle control group was euthanized, per IACUC guidelines, when its tumor had reached a weight greater than 20% of its body weight. Another mouse in the vehicle control group was euthanized on Day 50 due to a severe ulceration of the tumor and body weight loss. Tumor weights for these mice were carried forward in the data for the remainder of the study.

Example 19

Humanized Domain Deleted B3F6 Antibody Conjugated to a Toxin is Effective in Inhibiting the Growth of Breast Cancer Cells in an in vivo Model The following materials and methods were used in this example:

Animals:

135 athymic nude female mice from Harlan Sprague Dawley (Madison, Wis.) were started on the study at 6-7 weeks of age. Animals were acclimated to the lab for at least 5 days prior to implantation of tumor. Animals individually implanted with animal ID chips prior to implantation of the tumor. 8 animals were included in the test group and 20 animals in the vehicle control group.

Tumor:

The BT-474 in-vitro cell line was originally obtained from the NCI Tumor Repository. A serial transplanted in-vivo donor line (from Biogen Idec cryo reg #0141 (without estrogen supplementation) was established at Biogen Idec and transplanted for 4 generations in athymic nude female mice prior to implantation into this study. Animals implanted with a 3 mm$^3$ fragment of tissue/mouse subcutaneously into the right flank area.

Treatments were initiated when tumors reach a minimum size of 100 mgs. Animals were randomized into the following test and control groups:

TABLE 11

| Group # | Treatment** | # of Mice |
|---|---|---|
| 1. | Vehicle Control, 0.2 ml/mouse, iv., 2x/day for 5 doses (20 mM citrate buffer, pH 5.5, 135 mM sodium chloride) | 16 |
| 2. | Positive chemotherapeutic agent, Taxol, 25.0 mg/kg/inj. i.p. q4dx3 | 8 |
| 3. | ddB3F6.1 - DM4, 18.0 mg/kg/inj, i.v., 2x/day for 5 doses (3.5 DM4/mAb) | 8 |
| 4. | ddB3F6.1 - DM4, 10.0 mg/kg/inj, i.v., 2x/day for 5 doses (3.5 DM4/mAb) | 8 |
| 5. | ddB3F6.1 - DM4, 3.0 mg/kg/inj, i.v., 2x/day for 5 doses (3.5 DM4/mAb) | 8 |
| 6. | ddB3F6.1 naked mAb, 18.0 mg/kg/inj, iv., 2x/day for 5 doses | 8 |

Note:
**Doses are based upon the 23 mg/kg dose = 3 drugs/mAb providing animals with 350 ug/kg of maytansine (MTD).

The Testing Schedule was:

Day −1: Animal ID chips were inplanted and initial body weights recorded.

Day 0: Tumors were harvested, implanted and mice were randomized. Bacterial cultures were run on the tumor.

Day 4: Tumor size measurements were recorded for staging tumors and continue either daily or every other day until staging day.

Mice with tumors measuring a minimum size of 100 mgs were selected. Mice were randomized and body weights recorded. Treatments were administered as a single i.v. dose. Positive control agent was administered i.p. on a q4dx3 schedule.

Body weights and tumor measurements recorded on staging day and continued 2 times weekly until the termination of the study.

The data in FIGS. 14-17 show that domain deleted B3F6 was effective in reducing tumor weight in mice treated with certain concentrations of the domain deleted molecule.

Example 20

Humanized B3F6 Antibody Conjugated to a Toxin is Effective in Inhibiting the Growth of Human Testicular Cancer Cells in an In Vivo Model In the following Example, anti-Cripto humanized IgG1 monoclonal antibody (mAb) B3F6 (also referred to as B3F6.1) was conjugated with DM4, a derivative of the cytotoxic agent maytansine, (B3F6.1-DM4). This conjugate was evaluated for evidence of anticancer activity in male athymic nude mice bearing established, subcutaneously (SC) implanted xenografts of the NCCIT human testicular carcinoma. Cohorts of animals were treated with B3F6.1-DM4 mAb intravenously (IV) at 6, 10, 15 and 25 mg/kg/injection (equivalent to 100, 178, 266 and 444 ug/kg maytansine respectively) once per week for three doses (q7dx3) or at 25 and 10 mg/kg/injection on Day 15 and subsequent days dependent on tumor re-growth, a vehicle control IV q7dx3, or cis-platinum (positive chemotherapeutic control) at 2 mg/kg/injection SC three times per week for 6 doses (3x/wkx6). Treatments were initiated on Day 15 when the tumors reached a minimum change in size of 100 mg.

The results indicate that tumor growth in the vehicle control group was well within acceptable limits for this model. Cis-platinum produced a significant (P<0.05) inhibition of tumor growth, consistent with this model, from Day 20 to Day 66. B3F6.1-DM4 dosed q7dx3 produced a regression of the tumors at 10 (P<0.001), 15 (P<0.001) and 25 mg/kg/inj (P<0.001) beginning on Day 20 and remained regressed until study termination on Day 107. B3F6.1-DM4 at 6 mg/kg/inj q7dx3 regressed tumors from Day 20 to Day 44 and significantly (P<0.001) inhibited growth of the tumors until the group was terminated on Day 70. B3F6.1-DM4 dosed once on Day 15 at 25 mg/kg produced regression of the tumors throughout the study (P<0.001). B3F6.1-DM4 dosed once on Day 15 at 10 mg/kg caused initial regression of the tumors (P<0.001). Additional doses of 10 mg/kg given on days 37 and 44 resulted in regression (P<0.01) of tumors that had begun to grow back. In conclusion, B3F6.1-DM4 at the tested dose regimens was highly efficacious against established xenografts of the NCCIT testicular carcinoma.

The following Materials and Methods were used in this Example

Mice

One hundred fifty (150) male athymic nude mice (Harlan Sprague Dawley, Madison, Wis.) were started on the study at seven to eight weeks of age. Animals were acclimated to the laboratory for at least five days prior to implantation of the tumor. Housing was in ventilated cage racks, and food and water were allowed ad libitum.

Tumor Model

NCCIT cells were obtained from the American Tissue Type Collection (Manassas, Va.). The cell line was passed in vitro 4 times prior to implantation. Cells were grown in vitro in RPMI-1640+10% fetal bovine serum (FBS) media without antibiotics (5% $CO_2$). Bacterial cultures were performed on aliquots of the cell homogenate preparation that was implanted into the mice. Bacteriology cultures were negative for bacterial contamination at both 24 and 48 hours post implant.

On Day −1, the mice were implanted with BioMedics animal ID chips (Model IMI-1000; Seaford, Del.) subcutaneously on the left flank. An inoculum of 5×10$^6$ NCCIT cells in 200 L RPMI-1640 without serum (25%) plus Matrigel (75%) was implanted SC into the right flank area on Day 0. Tumor size and body weight measurements were recorded at least twice weekly beginning on Day 6. On Day 15, mice with tumors with a minimum increase in tumor weight of 100 mg and a maximum increase of 244 mg, excluding tumors with non-progressive growth, were randomized to treatment and control groups (see Table 12). Change in tumor weight since the first tumor measurement (Day 6) was used to assess tumor growth, rather than actual tumor weight, to account for the volume of Matrigel in the inoculum.

Test Articles and Positive Chemotherapeutic Agent

DM4 conjugations (2000-67, 6.0 mg/ml) were prepared at ImmunoGen, Inc (Cambridge, Mass.) with ImmunoGen's Tumor Activated Prodrug (TAP) technology. Vehicle Control and B3F6.1-DM4 mAb dosing solutions (Lot No 11155-104, formulation, notebook: LC 11155-104) were provided by Ling Ling Chen at Biogen Idec. Clinical grade Platinol-AQ (cisplatin injection, NDC 0015-3221-22) was obtained from Bristol-Myers Squibb (Lot No 2C65556, exp. Mar. 2003).

Study Groups and Treatment Regimens

Study groups and treatment regimens are described in Table 12. B3F6.1-DM4 has a half-life of 3.9 days in athymic nude mice. B3F6.1-DM4 mAbs were administered intravenously (IV) either once per week for three doses (q7d×3) or on Day 15 and on subsequent days dependent on tumor re-growth. The vehicle control (10 mM citrate buffer, pH 5.5, 135 mM sodium chloride) was administered IV q7d×3 and cis-platinum was administered SC three times per week for six doses (3×/wk×6). All treatments commenced on Day 15. Table 12 Shows Control and Test Treatment Groups Control and Test Treatment Groups

| Agent | Dose/ injection | Equivalent dose of maytansine (ug/kg) | Route | Schedule | # of mice |
|---|---|---|---|---|---|
| Vehicle control | 10 ml/kg | 0 | IV[a] | q7d × 3 | 16 |
| B3F6.1-DM4 | 6 mg/kg | 100 | IV | q7d × 3 | 8 |
| B3F6.1-DM4 | 10 mg/kg | 178 | IV | q7d × 3 | 8 |
| B3F6.1-DM4 | 15 mg/kg | 266 | IV | q7d × 3 | 8 |
| B3F6.1-DM4 | 25 mg/kg | 444 | IV | q7d × 3 | 8 |
| B3F6.1-DM4 | 10 mg/kg | 100 | IV | Day 15, Day 37, Day 44 | 8 |
| B3F6.1-DM4 | 25 mg/kg | 444 | IV | Day 15 | 8 |
| cis-platinum | 2 mg/kg | | SC[b] | 3×/wk × 6 | 8 |

All treatments started on Day 15
[a]intravenous
[b]subcutaneous

Evaluation of Anticancer Activity

Tumor measurements were determined using digital calipers. Body weights and tumor size measurements were recorded on Day 6 and were continued at least twice weekly until the termination of the study. The formula to calculate volume for a prolate ellipsoid was used to estimate tumor volume ($mm^3$) from two-dimensional tumor measurements: Tumor Volume ($mm^3$)=(Length×Width$^2$) divided by 2. Assuming unit density, volume was converted to weight (i.e., one $mm^3$=one mg).

Change in tumor weight since the first measurement (Day 6) was used to assess tumor growth, rather than actual tumor weight, to account for the volume of Matrigel in the inoculum.

On Day 70, the groups treated with vehicle control, cis-platinum, and B3F6.1-DM4 at 6 mg/kg/inj were euthanized. The remaining groups continued to be followed until Day 107 when the study was terminated.

Statistical Analysis

Student's t test was performed on mean tumor weights at the end of each study to determine whether there were any statistically significant differences between each treatment group and the vehicle control group.

Late in the study, some mice in the vehicle control group were euthanized, per IACUC guidelines, when their tumors had reached a weight greater than 20% of their body weight. The final tumor weights from these mice were carried forward in the data until study termination.

There was a 95% tumor take-rate following the implantation, and mice with tumors within a tight range of change in tumor weight on Day 15 were selected to initiate treatments. The tumor growth in the vehicle control group was well within the typical range seen in this model. Cis-platinum produced a response consistent with the model resulting in significant inhibition (P<0.05) of tumor growth from Day 20 to Day 66. On Day 70, the groups treated with vehicle control, cis-platinum, and B3F6.1-DM4 at 6 mg/kg/inj were euthanized. The remaining groups continued to be followed until Day 107 when the study was terminated.

FIGS. 18-21 show the effect of four doses (6, 10, 15 and 25 mg/kg/inj) of B3F6.1-DM4 dosed q7d×3 or cis-platinum dosed 3×/wk×6 on change in tumor weight, % Test/Control, and body weight in athymic nude mice bearing established NCCIT xenograft tumors. B3F6.1-DM4 dosed q7d×3 produced a regression of the tumors at 10 (P<0.01), 15 (P<0.001) and 25 mg/kg (P<0.001) from Day 20 to Day 70 (the day that the Vehicle Control group was terminated). Tumors in these groups remained regressed until study termination on Day 107. B3F6.1-DM4 at 6 mg/kg/inj dosed q7d×3 regressed tumors from Day 20 to Day 44. After Day 44, many tumors in this group began to re-grow, however, tumor growth was significantly (P<0.01) inhibited through Day 70 when the group was terminated.

The % T/C for B3F6.1-DM4 at 6 and 10 mg/kg/inj dropped below the NCI criteria for activity of 42% on Day 23 and remained below this level throughout the study. The % T/C for the 25 mg/kg/inj group dropped below 42% by Day 20 and remained less than 10% from Day 23 throughout the study.

FIGS. 22-25 show the effect of B3F6.1-DM4, 25 mg/kg/inj, dosed once on day 15 dosed, B3F6,1, 10 mg/kg/inj, dosed on Day 15 and subsequently upon tumor re-growth (Day 37 & 44), or Cis-platinum dosed 3×/wk×6 on change in tumor size, % Test/Control, and body weight in athymic nude mice bearing established NCCIT xenograft tumors. B3F6.1-DM4, 25 mg/kg/inj dosed once on Day 15 produced regression (P<0.001) of the tumors from Day 20 to Day 70 (the day that the Vehicle Control group was terminated). The tumors in this group remained regressed until study termination on Day 107. B3F6.1-DM4 dosed once on Day 15 at 10 mg/kg caused initial regression of the tumors (P<0.001). Additional doses of 10 mg/kg given on Day 37 and 44 resulted in regression (P<0.01) of tumors that had begun to grow back.

The % T/C for B3F6.1-DM4 at 10 and 25 mg/kg/inj dropped below the NCI criteria for activity of 42% by Day 20 and remained below this level throughout the study.

Several mice treated with B3F6.1-DM4 experienced mild to moderate coryneoform bacterial infections of the skin that resolved within a few days of onset. This bacteria resides on the skin and is considered an opportunistic infection that can occur if the animal is stressed. Two mice treated with B3F6.1-DM4 at 25 mg/kg/inj, q7d×3, two mice treated with 25 mg/kg/inj on Day 15 only, and one mouse treated with 15 mg/kg/inj, q7d×3 showed signs of infection from Days 20-23. One mouse treated with 25 mg/kg/inj, q7d×3 showed signs of a mild infection on Day 30.

On Day 52, one mouse treated with B3F6.1-M4, 25 mg/kg/inj once on Day 15 presented with a distended abdomen and the bladder could not be expressed. The mouse was euthanized and necropsy revealed a bladder stone.

Example 21

Humanized B3F6 Inhibits the Growth of CLAU-6 Human Lung Cancer Cells In an In Vivo Model The purpose of this study was to determine the efficacy of B3F6.1-DM4 conjugated mAb on the growth of Calu-6 xenograft tumors when treatment is initiated on an established, preformed tumor mass.

The following Materials and Methods were used in this Example:

Mice

One hundred sixty (160) female athymic nude mice (Harlan Sprague Dawley, Madison, Wis.) were started on the study at eight to nine weeks of age. Animals were acclimated to the laboratory for at least five days prior to implantation of the tumor. Housing was in ventilated cage racks, and food and water were allowed ad libitum.

Tumor Model

Calu-6 cells were obtained from the American Tissue Type Collection (Manassas, Va.). The cell line was passed in vitro 11 times prior to implantation. Cells were grown in vitro in RPMI-1640+10% fetal bovine serum (FBS) media without antibiotics (5% $CO_2$). Bacterial cultures were performed on aliquots of the tumor homogenate preparation that was implanted into the mice. Bacteriology cultures were negative for bacterial contamination at both 24 and 48 hours post implant.

On Day −1, the mice were implanted SC with BioMedics animal ID chips (Model IMI-1000; Seaford, Del.) subcutaneously on the left flank. An inoculum of $5 \times 10^6$ Calu-6 cells in 200 μL RPMI-1640 without serum was implanted SC into the right flank area on Day 0. Tumor size and body weight measurements were recorded at least twice weekly beginning on Day 4. When the tumors measured a minimum of 100 mg, the mice were randomized to treatment and control groups (see Table 13).

Test Articles and Positive Chemotherapeutic Agent

DM4 conjugations (2000-79 3.3 D/A, 5.5 mg/ml) were prepared at ImmunoGen, Inc (Cambridge, Mass.) with ImmunoGen's Tumor Activated Prodrug (TAP) technology. Vehicle Control and B3F6.1-DM4 mAb dosing solutions (Lot# 10878-49, formulation, notebook: AC 10878-49) were provided by Anne Cheung at Biogen Idec. Clinical grade Camptosar™ (irinotecan injection, NDC 0009-7529-01) was obtained from Pharmacia and Upjohn (Lot No. 76KDP, exp. July 2006 for first 7 doses, and Lot No. 46MFH, exp. August 2007 for last 3 doses).

Study Groups and Treatment Regimens

Study groups and treatment regimens are described in Table 13. B3F6.1-DM4 has a half-life of 3.9 days in athymic nude mice and all B3F6.1-DM4 mAbs were administered IV either on Day 13, 17, and 21 or once per week for three doses (q7d×3). The vehicle control (10 mM citrate buffer, pH 5.5, 135 mM sodium chloride) was administered q7d×3 and the irinotecan was administered IP on Day 13-14, 17-21, and 24-26. The dosing regimen of the vehicle control group paralleled the dosing of treatment groups not relevant to this report and first treatments were given on Day 14. Treatments of B3F6.1-DM4 and irinotecan commenced on Day 13.

TABLE 13

Control and Test Treatment Groups

| Agent | Dose/ injection | Equivalent dose of maytansine (ug/kg) | Route | Schedule | # of mice |
|---|---|---|---|---|---|
| Vehicle control | 10 ml/kg | 0 | IV[a] | 3×/wk × 4 | 16 |
| B3F6.1-DM4 | 10 mg/kg | 167 | IV | Day 13, Day 17, Day 21 | 8 |
| B3F6.1-DM4 | 20 mg/kg | 334 | IV | Day 13, Day 17, Day 21 | 8 |
| B3F6.1-DM4 | 15 mg/kg | 251 | IV | Q7d × 3 | 8 |
| B3F6.1-DM4 | 30 mg/kg | 502 | IV | Q7d × 3 | 8 |
| irinotecan | 10 mg/kg | | IP[b] | Day 13-14, 17-21 | |

[a]intravenous
[b]intraperitoneal

Evaluation of Anticancer Activity

Tumor measurements were determined using digital calipers. Body weights and tumor size measurements were recorded on Day 4 and were continued twice weekly until the termination of the study. The formula to calculate volume for a prolate ellipsoid was used to estimate tumor volume ($mm^3$) from two-dimensional tumor measurements:

Tumor Volume ($mm^3$)=(Length×$Width^2$)÷2. Assuming unit density, volume was converted to weight (i.e., one mm 3=one mg).

Statistical Analysis

Student's t test was performed on mean tumor weights at the end of each study to determine whether there were any statistically significant differences between each treatment group and the vehicle control group.

Antitumor Activity

There was a 90% tumor take-rate following the implantation, and mice within a tight range of size were selected to initiate the treatments. Irinotecan produced a significant (P<0.001) inhibition of tumor growth, consistent with this model, from Day 20 until Day 45 when the group was terminated.

FIGS. 26-29 show the effect of two doses (10 and 20 mg/kg/inj) of B3F6.1-DM4 dosed IV on Day 13, 17, and 21 or irinotecan dosed on Day 13-14, 17-21, and 24-26 on change in tumor weight, final tumor weight, % Test/Control, and body weight in athymic nude mice bearing established Calu-6 xenograft tumors. B3F6.1-DM4 produced a significant inhibition of tumor growth at both doses for the following durations:

10 mg/kg on Days 24 to 45 (P<0.01 Days 24, 35-38 and 45; P<0.001 Days 27-32 and 41)

20 mg/kg on Days 24 to 45 (P<0.001)

The % T/C reached NCI criteria of activity below 42% at 20 mg/kg/inj on Days 32 to 45.

FIGS. 30-33 show the effect of two doses (15 and 30 mg/kg/inj) of B3F6.1-DM4 dosed IV q7d×3 or irinotecan dosed on Day 13-14, 17-21, and 24-26 on change in tumor weight, final tumor weight, % Test/Control, and body weight in athymic nude mice bearing established Calu-6 xenograft tumors. B3F6.1-DM4 produced a significant inhibition of tumor growth at both doses for the following durations:

15 mg/kg on Days 32 to 45 (P<0.01 Days 32-35 and 45; P<0.001 Days 38-41)

30 mg/kg on Days 24 to 45 (P<0.01 Day 24, P<0.001 Days 27-45)

The % T/C reached NCI criteria of activity below 42% at 30 mg/kg Days 32 to 45.

One mouse in the B3F6.1-DM4 at 10 mg/kg/inj, was found dead on Day 32 post implantation, 11 days after receiving its last dose of B3F6.1-DM4. The animal displayed no signs of toxicity post dosing and none of the other animals in the group displayed any ill health.

All mice in the group B3F6.1-DM4, 30 mg/kg/inj group experienced coryneoform bacterial infections of the skin that resolved several days after the last dose of B3F6.1-DM1 was administered. This bacteria resides on the skin and is considered an opportunistic infection that can occur if the animal is stressed. All animals in this group experienced 5-15% weight loss during dosing, but both the weight loss and infection resolved once dosing ceased. One mouse in this group also experienced a secondary staph infection of the pinna on the R ear that resolved within several days.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated binding molecule comprising:
   (a) a light chain, which comprises the light chain variable region (VL) sequence of SEQ ID NO: 47; and
   (b) a heavy chain, which comprises the heavy chain variable region (VH) sequence of SEQ ID NO: 49,
   wherein the binding molecule binds specifically to a human Cripto antigen.

2. The binding molecule of claim 1, wherein the light chain comprises the amino acid sequence of SEQ ID NO: 53 and the heavy chain comprises the amino acid sequence of SEQ ID NO: 57 or SEQ ID NO: 61.

3. The binding molecule of claim 1, comprising a heavy chain constant region of the γ1 isotype.

4. The binding molecule of claim 1, wherein the heavy chain comprises a constant region sequence of SEQ ID NO:71.

5. The binding molecule of claim 1, wherein said VL or VH is fused to a constant region derived from an antibody of an isotype selected from the group consisting of IgG1, IgG2, IgG3, and IgG4.

6. The binding molecule of claim 5, wherein said constant region comprises a CH3 domain.

7. The binding molecule of claim 5, wherein said constant region comprises a CH1 domain and a hinge region.

8. The binding molecule of claim 1, wherein said binding molecule is conjugated to an agent.

9. The binding molecule of claim 8, wherein said agent is a cytotoxin.

10. The binding molecule of claim 9, wherein said cytotoxin is selected from the group consisting of a radionuclide, a biotoxin, an enzymatically active toxin, a cytostatic agent, a prodrug, an immunologically active ligand, a cytokines, an alkylating agent, an antimetabolilte, an anti-proliferative agent, a tubulin binding agent, a hormone, and a hormone antagonist.

11. The binding molecule of claim 8, wherein said agent is a maytansinoid.

12. The binding molecule of claim 11, wherein said maytansinoid is DM4.

13. An isolated antibody comprising a light chain and a heavy chain, wherein said light chain comprises SEQ ID NO: 53 and said heavy chain comprises SEQ ID NO: 57, wherein said antibody specifically binds to human Cripto.

14. The antibody of claim 13, wherein said antibody is conjugated to DM4.

15. A binding molecule comprising a VH and a VL, wherein said VL comprises an amino acid sequence of SEQ ID NO: 47 and the VH comprises the three CDRs of SEQ ID NO: 12, SEQ ID NO: 13, and SEQ ID NO: 14, wherein said binding molecule specifically binds to human Cripto.

16. The binding molecule of claim 15, wherein said VL is fused to a constant region derived from a human kappa or lambda sequence.

17. The binding molecule of claim 16, wherein said constant region comprises a human subgroup kappa 2 sequence.

18. The binding molecule of claim 17, wherein said VL and said constant region together comprises an amino acid sequence of SEQ ID NO: 53.

19. The binding molecule of claim 15, wherein said binding molecule is conjugated to an agent.

20. The binding molecule of claim 19, wherein said agent is a maytansinoid.

21. The binding molecule of claim 20, wherein said maytansinoid is DM4.

22. A binding molecule comprising a VH and a VL, wherein said VH comprises an amino acid sequence of SEQ ID NO: 49 and the VL comprises the three CDRs of SEQ ID NO: 9, SEQ ID NO: 10, and SEQ ID NO: 11, wherein said binding molecule specifically binds to human CRIPTO.

23. The binding molecule of claim 22, wherein said VH is fused to a constant region derived from an antibody of an isotype selected from the group consisting of IgG1, IgG2, IgG3, and IgG4.

24. The binding molecule of claim 23, wherein said constant region comprises a CH3 domain.

25. The binding molecule of claim 23, wherein said constant region comprises a CH1 domain and a hinge region.

26. The binding molecule of claim 23, wherein said VH and said constant region together comprises SEQ ID NO: 57.

27. The binding molecule of claim 22, wherein said binding molecule is conjugated to an agent.

28. The binding molecule of claim 27, wherein said agent is a maytansinoid.

29. The binding molecule of claim 28, wherein said maytansinoid is DM4.

* * * * *